US012527834B2

(12) United States Patent
Satchi-Fainaro et al.

(10) Patent No.: US 12,527,834 B2
(45) Date of Patent: Jan. 20, 2026

(54) POLYAMINATED POLYGLUTAMIC ACID-CONTAINING COMPOUNDS AND USES THEREOF FOR DELIVERING OLIGONUCLEOTIDES

(71) Applicant: Ramot at Tel-Aviv University Ltd., Tel-Aviv (IL)

(72) Inventors: Ronit Satchi-Fainaro, Tel-Aviv (IL); Anna Scomparin, Tel-Aviv (IL); Dina Polyak, Beer-Sheva (IL); Adva Krivitsky, Bnei-Zion (IL); Shay Eliyahu, Ramat-Gan (IL); Hadas Gibori, Ramot Meir (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 428 days.

(21) Appl. No.: 15/764,429

(22) PCT Filed: Sep. 30, 2016

(86) PCT No.: PCT/IL2016/051071
§ 371 (c)(1),
(2) Date: Mar. 29, 2018

(87) PCT Pub. No.: WO2017/056095
PCT Pub. Date: Apr. 6, 2017

(65) Prior Publication Data

US 2018/0318428 A1 Nov. 8, 2018

Related U.S. Application Data

(60) Provisional application No. 62/234,819, filed on Sep. 30, 2015.

(51) Int. Cl.

| | |
|---|---|
| ***A61K 47/00*** | (2006.01) |
| ***A61K 31/16*** | (2006.01) |
| ***A61K 31/7088*** | (2006.01) |
| ***A61K 38/00*** | (2006.01) |
| ***C08G 69/10*** | (2006.01) |
| ***C08G 69/48*** | (2006.01) |
| ***C12N 15/113*** | (2010.01) |

(52) U.S. Cl.
CPC .............. *A61K 38/00* (2013.01); *A61K 31/16* (2013.01); *A61K 31/7088* (2013.01); *C08G 69/10* (2013.01); *C08G 69/48* (2013.01); *C12N 15/113* (2013.01); *C12N 15/1137* (2013.01); *C12N 2310/14* (2013.01); *C12N 2310/141* (2013.01); *C12N 2320/31* (2013.01); *C12N 2320/32* (2013.01); *C12Y 207/11001* (2013.01)

(58) Field of Classification Search
CPC .... A61K 38/00; A61K 31/7105; A61K 47/60; A61K 47/6935; A61K 47/50
See application file for complete search history.

(56) References Cited

U.S. PATENT DOCUMENTS

2012/0093762 A1 4/2012 Chivakula et al.

FOREIGN PATENT DOCUMENTS

| | | |
|---|---|---|
| JP | 59-071690 | 4/1984 |
| WO | WO 2012/051457 | 4/2012 |
| WO | WO 2012/051458 | 4/2012 |
| WO | WO 2012/051459 | 4/2012 |
| WO | WO 2017/056095 | 4/2017 |

OTHER PUBLICATIONS

Krivitsky et al., Structure-function correlation of aminated poly(alpha)glutamate as siRNA nanocarriers, Biomacromolecules, vol. 17, pp. 2787-2800. (Year: 2016).*
Krivitsky et al., AMphiphilic poly(alpha)glutamate polymeric micelles for systemic administration of siRNA to tumors, Nanomedicine: Nanotechnology, biology, and Medicine, vol. 14, pp. 303-315. (Year: 2018).*
Pan et al., Cellular uptake and transfection activity of DNA complexes based on poly(ethylene glycol)-poly-(L-glutamine) copolymer with PAMAM G2, Journal of Materials Chemistry B, vol. 1, pp. 5114-5127. (Year: 2013).*
Yu et al., Pharmacokinetics, biodistribution and in vivo efficacy of cisplatin loaded poly(L-glutamic acid)-g-methoxy poly(ethylene glycol) complex nanoparticles for tumor therapy, Journal of Controlled Release, vol. 205, pp. 89-97. (Year: 2015).*
International Preliminary Report on Patentability Dated Apr. 12, 2018 From the International Bureau of WIPO Re. Application No. PCT/IL2016/051071. (7 Pages).
International Search Report and the Written Opinion Dated Jan. 12, 2017 From the International Searching Authority Re. Application No. PCT/IL2016/051071. (11 Pages).
Basha et al. "Influence of Cationic Lipid Composition on Gene Silencing Properties of Lipid Nanoparticle Formulations of SiRNA in Antigen-Presenting Cells", Molecular Therapy, 19(12): 2186-2200, Advance Online Publication Oct. 4, 2011.
Ben-Shushan et al. "Overcoming Obstacles in MicroRNA Delivery Towards Improved Cancer Therapy", Drug Delivery and Translational Research, 4(1): 38-49, Published Online Jun. 22, 2013.

(Continued)

*Primary Examiner* — Dana H Shin

(57) ABSTRACT

Polymers useful for associating therewith oligonucleotides and for delivering the oligonucleotides into a cell, conjugates comprising these polymers and an oligonucleotide associated therewith, and compositions comprising same are provided. Also provided are uses of these conjugates in, for example, gene therapy, and particularly gene silencing. The disclosed polymers feature a PGA backbone, and amine-terminated pendant groups attached to at least 40% of the backbone units, and optionally further comprise alkyl pendant groups and/or other nitrogen-containing pendant groups attached to other one or more portions of the backbone units. The disclosed polymers can be cross-linked or can form a part of a block-copolymer.

12 Claims, 66 Drawing Sheets
(28 of 66 Drawing Sheet(s) Filed in Color)
Specification includes a Sequence Listing.

(56) References Cited

OTHER PUBLICATIONS

Boussif et al. "A Versatile Vector for Gene and Oligonucleotide Transfer Into Cells in Culture and In Vivo: Polyethylenimine", Proc. Natl. Acad. Sci. USA, 92: 7297-7301, Aug. 1995.
Jeong et al. "SiRNA Conjugate Delivery Systems", Bioconjugate Chemistry, 20(1): 5-14, Published on Web Nov. 17, 2008.
Li "Poly(L-Glutamic Acid)—Anticancer Drug Conjugates", Advanced Drug Delivery Reviews, 54(5): 695-713, Sep. 13, 2002.
Maeda et al. "Tumor Vascular Permeability and the EPR Effect in Macromolecular Therapeutics: A Review", Journal of Controlled Release, 65(1-2): 271-284, Mar. 1, 2000.
McCaskill et al. "Efficient Biodistribution and Gene Silencing in the Lung Epithelium Via Intravenous Liposomal Delivery of SiRNA", Molecular Therapy—Nucleic Acids, 2: e96-1-e96-10, Published Online Jun. 4, 2013.
Nori et al. "Intracellular Targeting of Polymer-Bound Drugs for Cancer Chemotherapy", Advanced Drug Delivery Reviews, 57: 609-636, Available Online Dec. 24, 2004.
Ofek et al. "In Vivo Delivery of Small Interfering RNA to Tumors and Their Vasculature by Novel Dendritic Nanocarriers", The FASEB Journal, 24(9): 3122-3134, Sep. 2010.
Rozema et al. "Dynamic PolyConjugates for Targeted In Vivo Delivery of SiRNA to Hepatocytes", Proc. Natl. Acad. Sci. USA, PNAS, 104(32): 12982-12987, Aug. 7, 2007.
Salva et al. "Local Delivery of Chitosan/VEGF SiRNA Nanoplexes Reduces Angiogenesis and Growth of Breast Cancer In Vivo", Nucleic and Therapeutics, 22(1): 40-48, 2012.
Satchi-Fainaro et al. "Polymer Therapeutics for Cancer: Current Status and Future Challenges", Advances in Polymer Science, 193: 1-65, Published Online Nov. 10, 2005. & Polymer Therapeutics II: Polymer as Drugs, Conjugates and Gene Delivery Systems.
Shi et al. "A High-Efficiency Panchromatic Squaraine Sensitizer for Dye-Sensitized Solar Cells", Angewandte Chemie, 123(29): 6749-6751, 2011.
Szokan et al. Enzymatic Hydrolysis of Basis Derivativesof Glutamyl Peptides. Part II, Annales Universitatis Scientiarum Budapestinensis de Rolando Eötvös Nominatae, Sectio Biologica, 18-19: 73-79, Dec. 31, 1977. p. 74.
Tiram et al. "Interfering Cancer With Polymeric SiRNA Nanocarriers", Journal of Biomedical Nanotechnology, 9: 1-17, 2013.
Vezhelyev et al. "Proton-Sponge Coated Quantum Dots for SIRNA Delivery and Intracellular Imaging", Journal of the American Chemical Society, JACS, 130: 9006-9012, Published on Web Jun. 21, 2008.
Wu et al. "MicroRNA Delivery by Cationic Lipoplexes for Lung Cancer Therapy", Molecular Pharmceutics, 8(4): 1381-1389, Jun. 7, 2011.
Wu et al. "Therapeutic Delivery of MicroRNA-29b by Cationic Lipoplexes for Lung Cancer", Molecular Therapy—Nucleic Acids, 2: e84-1-e84-10, Published Online Apr. 16, 2013.
York et al. "Rational Design of Targeted Cancer Therapeutics Through the Multiconjugation of Folate and Cleavable SiRNA to RAFT-Synthesized (HPMA-s-APMA) Copolymers", Biomacromolecules, 11(2): 505-514, Published on Web Jan. 5, 2010.
Zhao et al. "Salt-Induced Stability and Serum-Resistance of Polyglutamate Polyelectrolyte Brushes/Nuclear Factor-KB P65 SiRNA Polyplex Enhance the Apoptosis and Efficacy of Doxorubicin", BioMacromolecules, 14(6): 1777-1786, Apr. 25, 2013.

* cited by examiner

A

B

C

D

E

F

G

H

I

J K L M N O P

R

T

Q

S

V

U

W

Y

X

FIG. 27A
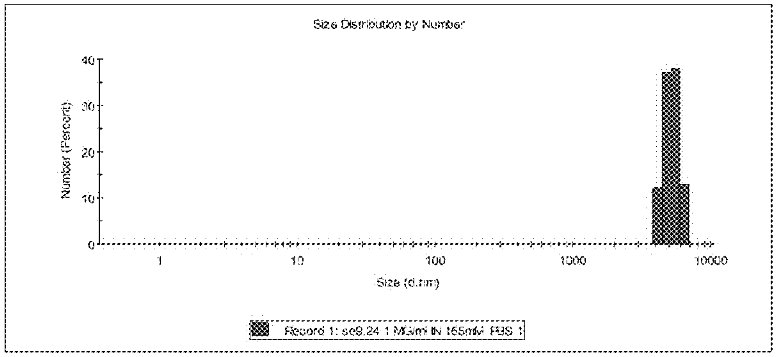
FIG. 27B
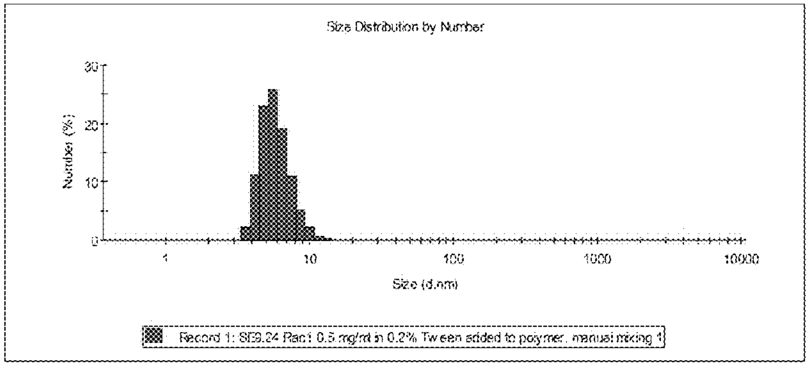
FIG. 27C
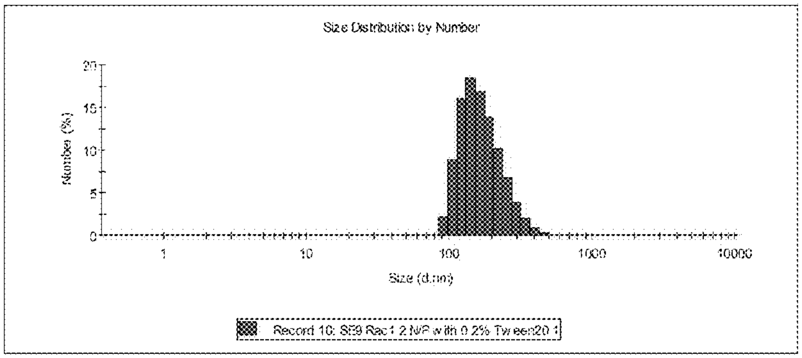
FIG. 27D
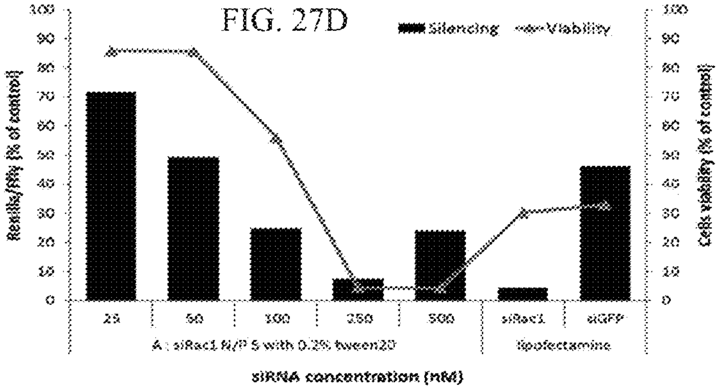
| N/P ratio | formulation | Hydrodynamic diameter [nm] | PDI |
|---|---|---|---|
| 5 | Dissolved in 150 mM PBS | 5218 ± 663.3 | 1.0 |
| 5 | Polymer dissolved in 0.2% Tween complexed to siRNA | 5.9 ± 1.501 | 0.323 |
| 2 | Polymer dissolved in 0.2% Tween complexed to siRNA | 173.3 ± 60.51 | 0.213 |
FIG. 27E FIG. 30A
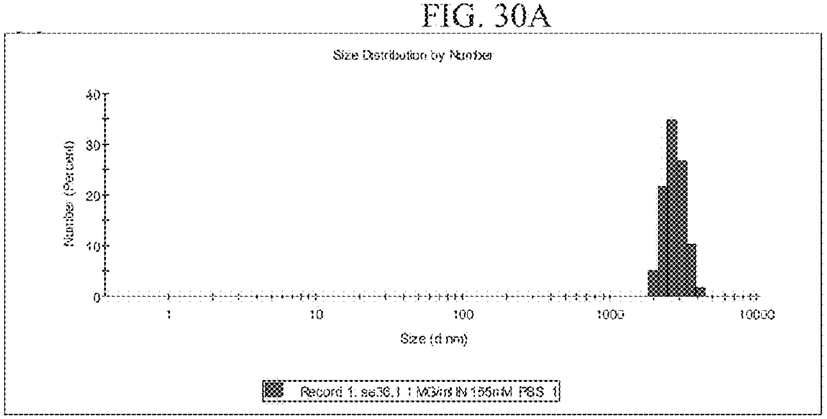
FIG. 30B
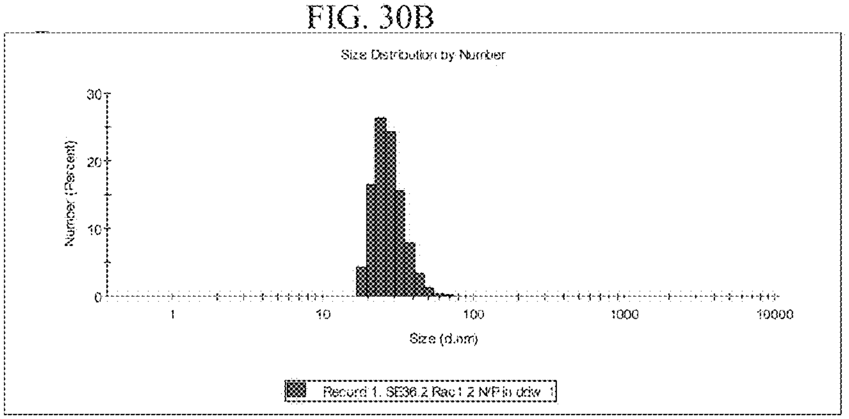
FIG. 30C
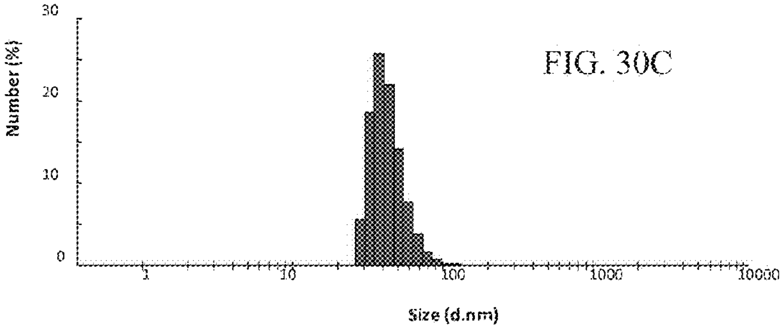
| N/P ratio | formulation | Hydrodynamic diameter [nm] | PDI |
|---|---|---|---|
| 2 | Dissolved in 150 mM PBS | 2786 ± 454.9 | 1.0 |
| 2 | Assembled by microfluidic system in water | 28 ± 7 | 0.471 |
| 1.5 | Assembled by microfluidic system in 5% glucose | 43 ± 12 nm | 0.127 |
FIG. 30D

| Hydrodynamic diameter (nm) | PDI | Zeta potential (mV) |
|---|---|---|
| 189.79 ± 11 | 0.05 | 4.68 ± 3 |

FIG. 54A
```
3' ugUUGGUCGAUU-C-UGUGACGGu 5' hsa-miR-34a     SEQ ID NO:1
     |:|||  ||| | | ||||||
5' uuAGCCA--UAAUGUAAACUGCCu 3' MYC (NM_002467)  SEQ ID NO:2
123                       144
```
FIG. 54B
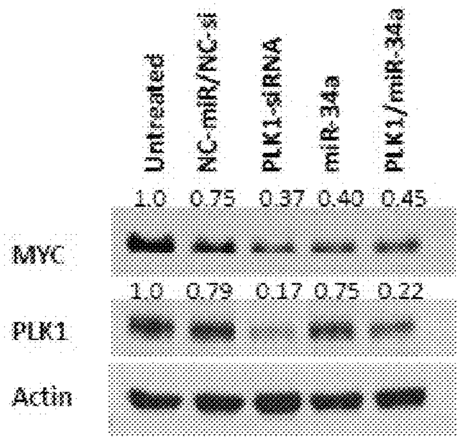
FIG. 54C
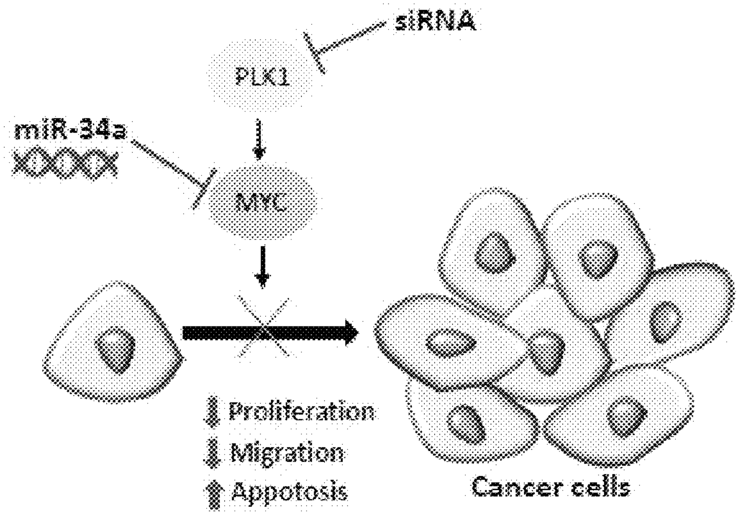

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Hsa-miR 34a nucleic acid sequence

<400> SEQUENCE: 1
uguuggucga uucugugacg gu 22

<210> SEQ ID NO 2
<211> LENGTH: 22
<212> TYPE: DNA
<213> ORGANISM: Artificial Sequence
<220> FEATURE:
<223> OTHER INFORMATION: Homo sapiens MYC proto-oncogene partial nucleic acid sequence (123-144)

<400> SEQUENCE: 2
uuagccauaa uguaaacugc cu 22

POLYAMINATED POLYGLUTAMIC ACID-CONTAINING COMPOUNDS AND USES THEREOF FOR DELIVERING OLIGONUCLEOTIDES

RELATED APPLICATIONS

This application is a National Phase of PCT Patent Application No. PCT/IL2016/051071 having International filing date of Sep. 30, 2016, which claims the benefit of priority under 35 USC § 119 (e) of U.S. Provisional Patent Application No. 62/234,819 filed on Sep. 30, 2015. The contents of the above applications are all incorporated by reference as if fully set forth herein in their entirety.

FIELD AND BACKGROUND OF THE INVENTION

The present invention, in some embodiments thereof, relates to therapy and, more particularly, but not exclusively, to novel functionalized PGA-based polymeric carriers and to uses thereof for conjugating thereto, and delivering, oligonucleotides, and in the treatment of medical conditions treatable by oligonucleotides, for example, medical conditions treatable by gene therapy such as gene silencing.

The gene silencing activity of small interfering RNAs (siRNAs) and microRNAs (miRNAs) has been recognized as an efficient strategy in therapy, due to their ability to knock-down the expression of disease-causing genes with a known sequence. Various medical applications to siRNA/miRNA have been suggested, including, for example, treatment of viral infections, neurodegenerative disorders and cancer. Increasing evidences point out to post-transcriptional gene silencing as a potential leading approach in cancer therapy.

siRNA and miRNA are short sequences of double-stranded RNA that reach the cell cytoplasm either by exogenous double-stranded RNA transfection or by processing of nuclear endogenous transcripts respectively. Both cases result in RNA interference (RNAi), which is the process of sequence-specific, post-transcriptional gene silencing following either RNA degradation or translation arrest.

The two separate mechanisms of action end up in a common pathway: cytoplasmic long dsRNA that was exogenously introduced is cleaved by the enzyme dicer to a 21-23 nucleotides sequence and incorporated into the RNA-induced silencing complex (RISC), where the sense strand is degraded. The anti-sense strand then leads the complex to the complementary mRNA and induces its degradation.

FIG. 1 (Background art) presents a schematic illustration of RNA interference by miRNA and siRNA [taken from Scomparin et al. *Biotechnology advances,* 33, 1294-1309 (2015)].

As shown therein, cytoplasmic long double-stranded RNAs are cleaved to siRNA by Dicer. Pri-miRNAs are transcribed in the nucleus, and are processed by Drosha to create pre-miRNAs which are transported to the cytoplasm. Pre-miRNAs are then cleaved by Dicer into mature miRNAs. Both mature miRNAs and siRNAs are incorporated into the RISC complex, that eliminates the sense strand and induce Watson-Crick base pairing (full or partial) with target mRNA. As a consequence gene silencing occurs either by mRNA degradation or by repression of the translation.

One difference between the two mechanisms is in the degree of complementation: while siRNA binds to only one perfect match and therefore can degrade only one mRNA specific sequence, miRNA recognizes partially complementary sequences, leading to arrest of translation of several mRNAs.

Research involving multiple human cancers has shown a connection between miRNA downregulation, tumorigenesis and poor cellular differentiation. Other studies have demonstrated the ability of exogenous synthetic miRNA/siRNA to reduce cell-viability in cancerous tissue cultures and to inhibit growth and metastasis of tumor xenografts in mice models.

The potential of silencing a specific oncogene for cancer therapy has been demonstrated by targeting vascular endothelial growth factor (VEGF). It has been shown that Chitosan-VEGF siRNA nanoplexes that were injected intratumoraly in a rat mammary cancer model resulted in a marked reduction in tumor growth [Salva, E., et al., Nucleic Acid Ther, 2012. 22(1): p. 40-8].

Other examples include cationic liposomes that were used to deliver miR-29b and miR-133b, which are potential tumor-suppressors and key regulators of CDK6, DNMT3B, and MCL1 to non-small cell lung cancer (NSCLC) cells. Successful delivery of those miRNAs significantly reduced cell growth both in vitro and in a xenograft murine model [Wu, Y., et al., Mol Ther Nucleic Acids, 2013. 2: p. e84; Wu, Y., et al., Mol Pharm, 2011. 8(4): p. 1381-9].

Another attempt to use a tumor-suppressor miRNA for cancer treatment is the ongoing phase I study with miR-34a (MRX34), which is given intravenously to patients with unresectable primary liver cancer or metastatic cancer with liver involvement (see, www(dot)clinicaltrials(dot)gov/ct2/show/NCT01829971). miR-34a is a transcriptional target of p53 that was found to down regulate MYCN, BCL2, SIRT1, SFRP1, CAMTA1, NOTCH1, JAG1, CCND1, CDK6, and E2F3, and its expression resulted in a reduction of cellular proliferation, metastasis and resistance to chemotherapy [Zenz, T., et al., Blood, 2009. 113 (16): p. 3801-8; Hermeking, H., Cell Death Differ, 2010. 17 (2): p. 193-9].

SiRNAs/miRNAs gene silencing-based therapeutic approaches have encountered pharmacokinetic limitations. Injectable RNAi therapeutics (parenteral administration) have faced fundamental delivery problems including aggregation in aqueous media, very short in vivo circulation time (ti/2 ranging from seconds to minutes), fast renal clearance, high immunogenicity and non-specific body distribution. For both locally administered as well as parenteral therapeutics, additional drawbacks include poor intracellular uptake (due to its high molecular weight and negative charge), poor ability to escape from the endosome and the need for cytoplasmic localization in order for the siRNA/miRNA to be active.

In order to increase the in vivo stability of the siRNA/miRNA, chemical modifications have been introduced on the oligonucleotides backbone. These include mainly 2'F, 2'O-Me and 2'H substitutions that were found to reduce cytokines production and to increase stability and specificity [Kenski, D. M., et al., Mol Ther Nucleic Acids, 2012. 1: p. e5; Esau, C. C., 2008. 44(1): p. 55-60; C. C. Esau, Inhibition of microRNA with antisense oligonucleotides. *Methods* 44, 55-60 (2008); published online EpubJan (10.1016/j.ymeth.2007.11.001)].

Several non-viral RNA delivery approaches have been developed, most being based on cationic lipids or polymeric carriers that can electrostatically interact with the negatively-charged RNA [Wu et al., 2011 (supra); Ofek, P., et al., FASEB J, 2010. 24(9): p. 3122-34; Basha, G., et al., Mol Ther, 2011. 19(12): p. 2186-200]. Most delivery systems are based upon electrostatic interactions between positively charged polymers, dendrimers or liposomes and the negatively charged siRNA. The resulting supramolecular structure forms polyplexes or lipoplexes. Other methods include encapsulation into the core of a nanoparticle, or chemical conjugation to a polymer.

FIG. 2 (Background art) depicts representative delivery vehicles that are described in the art as usable for siRNA/miRNA delivery [modified from Ben-Shushan, D., et al., Drug Delivery and Translational Research, 2014 February; 4(1):38-49].

The different structures such as linear, branched or globular, can form different assemblies when bound to the RNA such as RNAi entrapped in liposomes, core and shell particles, and polyplexes where the RNAi is complexed with polymers.

Several studies use conjugation of RNAi to a polymeric chain or the combination of RNAi conjugation with its subsequent assembly into supramolecular structures. See, Tiram, G., et al., Journal of Biomedical Nanotechnology, 2014. 10: p. 50-66, Ofek et al., 2010 (supra); McCaskill, J., et al., Mol Ther Nucleic Acids, 2013. 2: p. e96; Shi, J., et al., Angew Chem Int Ed Engl, 2011. 50(31): p. 7027-31; York, A. W., F. Huang, and C. L. McCormick, Biomacromolecules, 2010, 11(2): p. 505-14; and Jeong, J. H., et al., *Bioconjug Chem,* 2009. 20(1): p. 5-14. Some examples include CALAA-01, a nano-sized cyclodextrin based siRNA-delivery system consisting of a mixture with siRNA and adamantane-coupled PEG stabilizers some of which carry a transferrin transferrin ligand. This delivery system targets RRM2, a gene involved in DNA replication; and Dynamic PolyConjugates (DPC), which is a polymer functionalized with N-acetyl-galactosamine (NAG) ligand for hepatocyte targeting and linked to siRNA with a disulfide bond for reductive release [Rozema et al. (2007) *Proc Natl Acad Sci USA,* 104, 12982-7]. The basis of the system is an endosomolytic backbone that is reversibly masked with PEG and the targeting moiety, but once in the endosome, goes through selective activation at the acidic environment, to release its cargo to the cytoplasm.

Polymer therapeutics can address many of the problems arisen by the administration of naked siRNA/miRNA. In the case of polymer-RNAi polyplexes, the RNAi can be electrostatically bound to proteins, polysaccharides, or synthetic polymers. Normally, polymer-RNAi polyplexes achieve tumor specific targeting by the enhanced permeability and retention (EPR) effect. The impaired hyperpermeable angiogenic tumor vessels allow preferential extravasation of circulating macromolecules, and once in tumor interstitium, they are retained there by poor intra-tumoral lymphatic drainage [Maeda et al., *J Control Release* 65, 271-284 (2000); R. Satchi-Fainaro et al., in *Polymer therapeutics II: Polymers as drugs, Conjugates and Gene Delivery Systems*, R. Satchi-Fainaro, R. Duncan, Eds. (Springer, 2006), vol. 193, pp. 1-65]. In order to improve targeting specificity, the polymer can be conjugated to a moiety of interest, for example antibodies, peptides or sugars which target disease-related antigens or receptors [A. Nori and J. Kopecek, *Adv Drug Deliv Rev* 57, 609-636 (2005)]. In order to ensure cytoplasmic localization, polyaminated polymers are used as proton sponges: a large number of weak conjugate bases (with buffering capabilities at pH 5-6), lead to proton absorption in acid organelles and the consequent osmotic pressure across the organelle membrane. That further causes swelling and burst of the acidic compartments and release of their contents to the cytoplasm [M. V. Yezhelyev et al. *Journal of the American Chemical Society* 130, 9006-9012 (2008); Boussif et al. *Proceedings of the National Academy of Sciences of the United States of America* 92, 7297-7301 (1995)].

Poly(α)glutamic acid is a synthetic polymer, which is non-immunogenic, nontoxic, and biodegradable by cathepsin B, an enzyme that is highly expressed in most tumor tissues. PGA was shown to be safe at the required doses in clinical trials, when bound to the chemotherapeutic drug Paclitaxel. PGA is composed of naturally-occurring L-glutamic acid linked together through amide bonds rather than non-degradable C—C backbone. PGA is usually prepared from poly(γ-benzyl-L-glutamate) by removing the benzyl protecting group with the use of hydrogen bromide.

A sequential copolymer of protected PGA may be synthesized by peptide coupling reactions. For the preparation of high-molecular-weight homopolymers and block or random copolymers of protected PGA, tri-ethylamine-initiated polymerization of the N-carboxyanhydride (NCA) of γ-benzyl-L-glutamate is the most frequently used method [Pan, H. and Kopecek, J., *Multifunctional Water-Soluble Polymers for Drug Delivery, in Multifunctional Pharmaceutical Nanocarriers*, M. Ferrari, Editor 2008, Springer. p. 81-142].

Additional background art includes JP Patent No. JP 59071690; WO 2012/051459; WO 2012/051458; WO 2012/051457; U.S. Patent Application Publication No. 2012/0093762; Zhao et al., Biomacromolecules 2013, 14, 1777-1786; and ISSN:0365-088X.

SUMMARY OF THE INVENTION

The present inventors have now devised and successfully prepared, characterized and practiced, novel delivery vehicles for transporting oligonucleotides to cells. The present inventors have contemplated utilizing the pendant free γ-carboxyl group in the repeating L-glutamic acid units in PGA for providing functionality for attachment of various amine-containing units, to which RNA can be associated.

The delivery vehicles described herein include PGA-based polymers and co-polymers, featuring side chains (pendant groups) terminating with various amine-containing moieties.

According to an aspect of some embodiments of the present invention there is provided a polymeric compound, also referred to herein interchangeably as a polymer, composed of a plurality of BU(1), a plurality of BU(2), a plurality of BU(3), a plurality of BU(4), a plurality of BU(5), a plurality of BU(6), a plurality of BU(7) and/or a plurality of BU(8), as described herein. According to another aspect of some embodiments of the present invention there is provided a conjugate comprising a polymer as described herein in any of the respective embodiments, being in association with an oligonucleotide.

According to an aspect of some embodiments of the present invention there is provided a polymer represented by Formula I*:

Formula I*

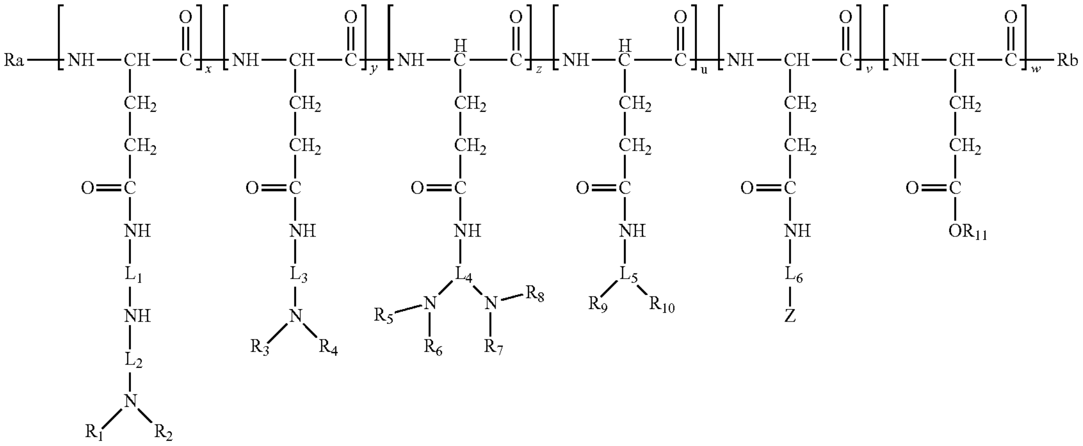

wherein:

x, y, z, u, v and w each independently represents the mol % of the respective backbone unit, such that x+y+z+u+v+w=100 mol %, wherein x+y+z+u+v≥40 mol %;

Ra is an N-terminus group;

Rb is a C-terminus group;

$L_1$, $L_2$, $L_3$ and $L_6$ is each independently a linear (non-branched) linking moiety;

$L_4$ and $L_5$ are each independently a branched linking moiety;

$R_1$-$R_{11}$ are each independently selected from H, alkyl and cycloalkyl; and Z is a nitrogen-containing heterocyclic moiety, provided that at least one of x, y and z is other than 0, and provided that:

(i) x is at least 40 mol %, y is lower than 40 mol %, and at least one of $R_1$ and $R_2$ is other than H; or (ii) when u is other than 0, at least one of $R_9$ and $R_{10}$ is an alkyl being more than 3 carbon atoms in length, and at least one of x, y, z and v is other than 0; or (iii) when v is other than 0, u is other 0; or (iii) z is greater than 40 mol %.

According to some of any of the embodiments described herein, x ranges from 50 to 100 mol %, or from 60 to 100 mol %, or from 70 to 100 mol %.

According to some of any of the embodiments described herein, each of $R_1$ and $R_2$ is alkyl.

According to some of any of the embodiments described herein, the alkyl is methyl.

According to some of any of the embodiments described herein, $R_3$ and $R_4$ are each H.

According to some of any of the embodiments described herein, u is at least 40 mol %.

According to some of any of the embodiments described herein, u ranges from 40 to 50 mol %.

According to some of any of the embodiments described herein, y is other than 0.

According to some of any of the embodiments described herein, y ranges from 60 to 50 mol % respectively.

According to some of any of the embodiments described herein, $R_9$ is H and $R_{10}$ is the alkyl.

According to some of any of the embodiments described herein, each of $R_9$ and $R_{10}$ is the alkyl.

According to some of any of the embodiments described herein, the alkyl is 5 to 10, or 5 to 8, or 6 to 8, carbon atoms in length.

According to some of any of the embodiments described herein, v is at least 20, or at least 30 mol %.

According to some of any of the embodiments described herein, v is other than 0 and u is at least 20, or at least 30 mol %.

According to some of any of the embodiments described herein, v is other than 0, and at least one of x, y and z is other than 0.

According to some of any of the embodiments described herein, y is other than 0.

According to some of any of the embodiments described herein, y ranges from 40 to 60 mol %.

According to some of any of the embodiments described herein, Z is a nitrogen-containing heteroaryl.

According to some of any of the embodiments described herein, the linear linking moiety is a substituted or unsubstituted alkylene.

According to some of any of the embodiments described herein, the branched linking moiety is Rc-CRd-Rf, wherein Rd is H or alkyl; and Rc and Rf are each independently an alkylene or absent.

According to some of any of the embodiments described herein, the polymer is selected from Polymer F, Polymer I, Polymer K, Polymer M, Polymer O, Polymer P, and Polymer T, as described herein.

According to an aspect of some embodiments of the present invention there is provided a polymer represented by Formula II:

Formula II

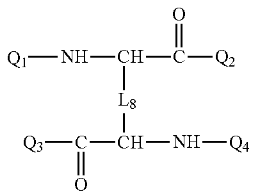

wherein:

$Q_1$ and $Q_4$ are each independently selected from an N-terminus group, and a polymeric chain comprising a plurality of one or more of BU(1), BU(2), BU(3), BU(4), BU(5), BU(6) and BU(7) backbone units; and $Q_2$ and $Q_3$ are each independently selected from an C-terminus group and a polymeric chain comprising a plurality of one or more of BU(1), BU(2), BU(3), BU(4), BU(5), BU(6) and BU(7) backbone units, as described herein in any of the respective embodiments and any combination thereof, provided that at least one of $Q_1$, $Q_2$, $Q_3$ and $Q_4$ comprises a plurality of one or more of BU(2), BU(3), BU(4), and BU(6) backbone units.

According to some of any of the embodiments described herein, a total mol % of the BU(2), BU(3), BU(4), and BU(6) backbone units in the $Q_1$, $Q_2$, $Q_3$ and/or $Q_4$ is at least 40%.

According to some of any of the embodiments described herein, a mol % of the BU(8) ranges from 1 to 20%.

According to an aspect of some embodiments of the present invention there is provided a polymer comprising a plurality of backbone units selected from BU(1), BU(2), BU(3), BU(4), BU(5), and/or BU(6), and a plurality of BU(7) backbone units, as described herein in any of the respective embodiments and any combination thereof, provided that at least 40 mol % of the backbone units are selected from BU(2), BU(3), BU(4), and/or BU(6).

According to some of any of the embodiments described herein, the polymer is arranged as a block-copolymer comprising at least one block comprising a plurality of BU(1), BU(2), BU(3), BU(4), BU(5), and/or BU(6), and at least one block comprising the BU(7) backbone units.

According to some of any of the embodiments described herein, a total mol % of the BU(2), BU(3), BU(4), BU(5), and/or BU(6) is at least 60%.

According to some of any of the embodiments described herein, a polymer as described herein in any of the respective embodiments and any combination thereof is for associating therewith an oligonucleotide.

According to some of any of the embodiments described herein, a polymer as described herein in any of the respective embodiments and any combination thereof is for delivering the oligonucleotide to a cell.

According to some of any of the embodiments described herein, a polymer as described herein in any of the respective embodiments and any combination thereof, when in association with the oligonucleotide, for transfecting a cell.

According to an aspect of some embodiments of the present invention there is provided a conjugate (polyplex) comprising the polymer as described herein in any of the respective embodiments and any combination thereof and an oligonucleotide associated therewith.

According to some of any of the embodiments described herein, the oligonucleotide is associated with the polymer via electrostatic interactions.

According to some of any of the embodiments described herein, the electrostatic interactions are between terminal amine groups of the polymer and phosphate groups of the oligonucleotide.

According to some of any of the embodiments described herein, a ratio between a number of the terminal amine groups and a number of the phosphate groups ranges from 15:1 to 1:1, or from 10:1 to 1:1, or from 5:1 to 1:1.

According to some of any of the embodiments described herein, the oligonucleotide is an RNA oligonucleotide.

According to some of any of the embodiments described herein, the RNA oligonucleotide is selected from a messenger RNA (mRNA), a micro RNA (miRNA), a small interfering RNA (siRNA) and a tiny noncoding RNA (tnRNA).

According to an aspect of some embodiments of the present invention there is provided a conjugate as described herein in any of the respective embodiments and any combination thereof for delivering the oligonucleotide into a cell.

According to an aspect of some embodiments of the present invention there is provided a conjugate as described herein in any of the respective embodiments and any combination thereof for use in transfecting a cell.

According to an aspect of some embodiments of the present invention there is provided a conjugate as described herein in any of the respective embodiments and any combination thereof for use in gene therapy or in gene silencing, or for use in the manufacturing of a medicament for use in gene therapy or gene silencing, or for treating medical conditions in which gene therapy or gene silencing is beneficial.

According to an aspect of some embodiments of the present invention there is provided a pharmaceutical composition comprising the conjugate as described herein in any of the respective embodiments and any combination thereof and a pharmaceutically acceptable carrier.

According to some of any of the embodiments described herein, the carrier is an aqueous carrier.

According to some of any of the embodiments described herein, the carrier further comprises a dispersing agent.

According to some of any of the embodiments described herein, the conjugate is in a form of a plurality of particles dispersed in the carrier.

According to some of any of the embodiments described herein, an average particle size (diameter) of the particles is lower than 1 micron, or lower than 500 nm or lower than 300 nm, or lower than 200 nm.

According to some of any of the embodiments described herein, the PDI of the particles is lower than 1, or lower than 0.5, or lower than 0.3.

According to an aspect of some embodiments of the present invention there is provided a pharmaceutical composition comprising a pharmaceutically acceptable carrier and a conjugate which comprises a polymer represented by Formula I, as described herein in any of the respective embodiments and any combination thereof.

According to some of any of the embodiments described herein, the carrier further comprises a surfactant.

According to some of any of the embodiments described herein, the composition is prepared by means of a microfluidic system.

According to some of any of the embodiments described herein, the carrier comprises a polyethyleneglycol (PEG).

According to some of any of the embodiments described herein, the polymer is selected from Polymers A-Y, as described herein.

According to some of any of the embodiments described herein, the polymer is selected from Polymer A, Polymer B, Polymer F, Polymer I, Polymer K, Polymer M, Polymer O, Polymer P, and Polymer T.

According to some of any of the embodiments described herein, the carrier is an aqueous carrier.

According to some of any of the embodiments described herein, the carrier comprises glucose.

According to some of any of the embodiments described herein, the oligonucleotide is associated with the polymer via electrostatic interactions.

According to some of any of the embodiments described herein, the oligonucleotide is an RNA oligonucleotide, as described herein.

According to some of any of the embodiments described herein, the composition is for delivering the oligonucleotide into a cell.

According to some of any of the embodiments described herein, the composition is for transfecting a cell.

According to some of any of the embodiments described herein, the composition is for use in gene therapy or in gene silencing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and tables. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
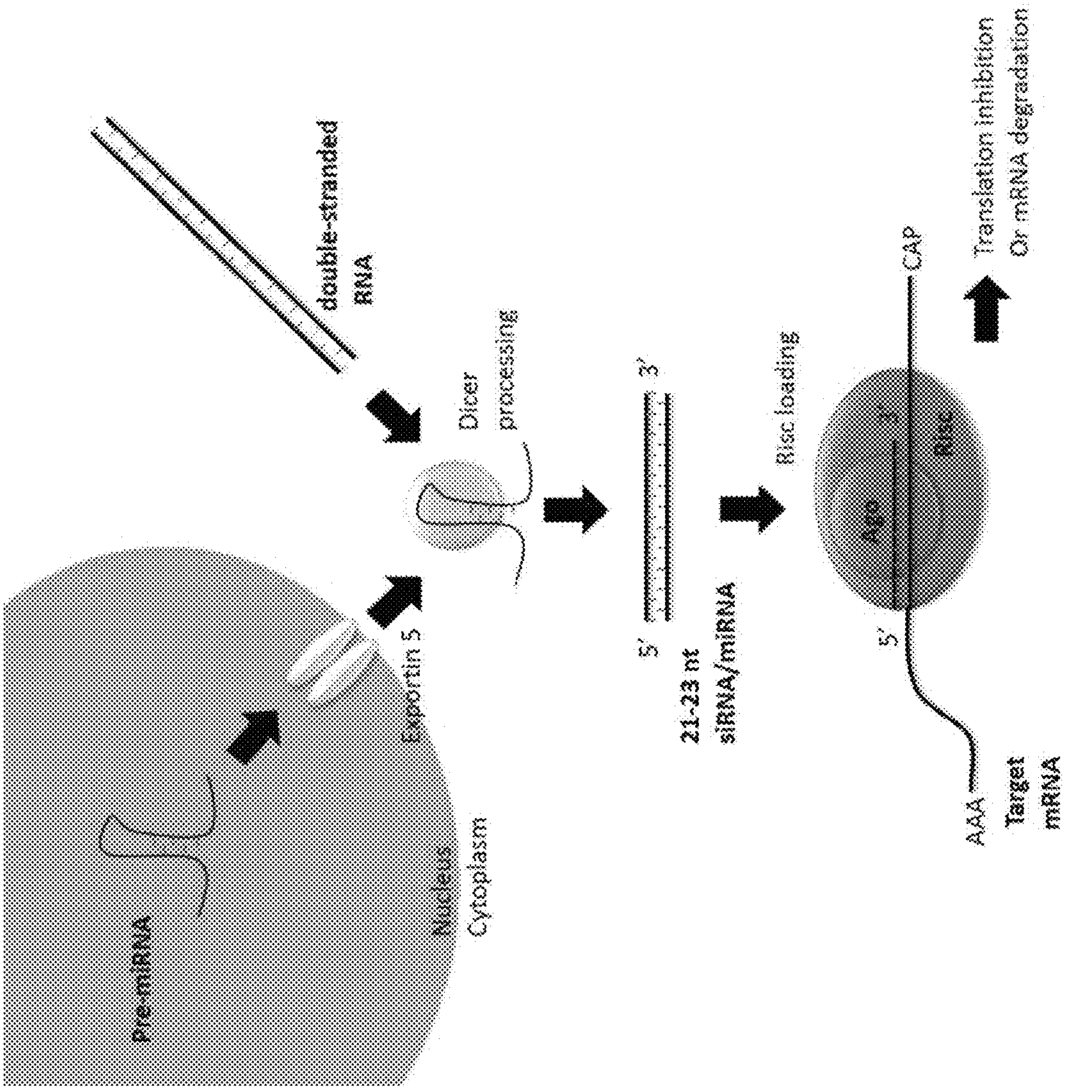
FIG. 1 (BACKGROUND ART)

FIG. 1 (Background art) presents a schematic illustration of RNA interference by miRNA and siRNA.

Figure 2:
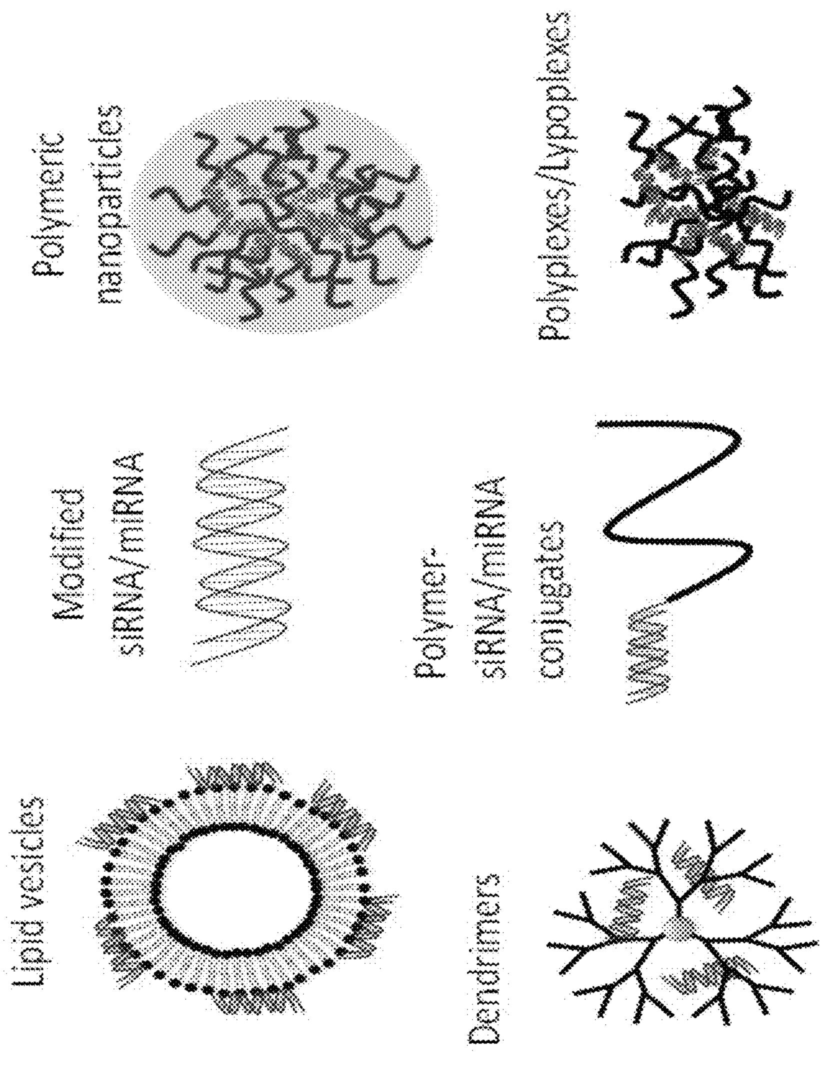
FIG. 2 (BACKGROUND ART)

FIG. 2 (Background art) depicts representative delivery vehicles that are described in the art as usable for siRNA/miRNA delivery.

Figure 3:
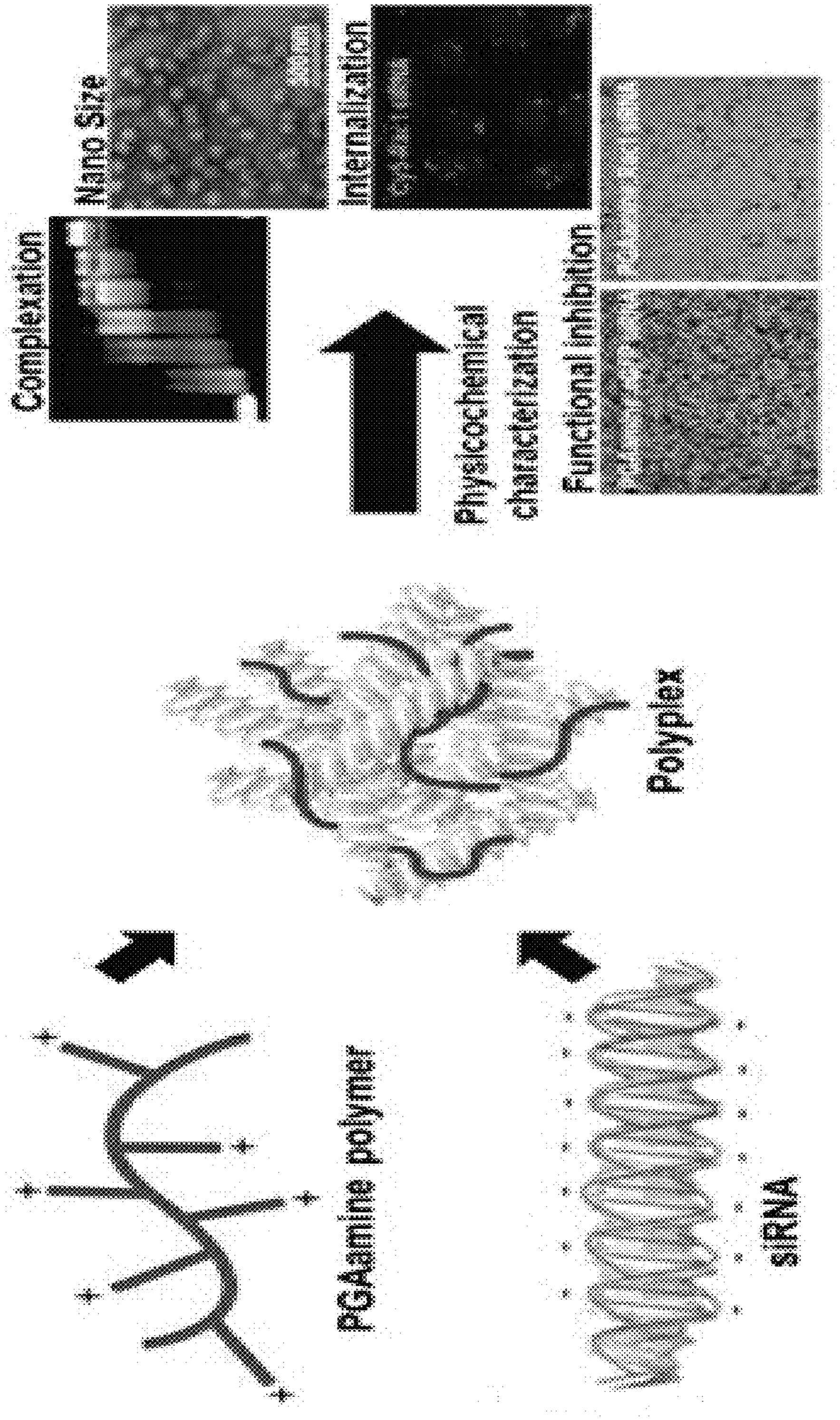

FIG. 3 is a schematic illustration presenting the underlying basis of some embodiments of the present invention.

Figure 4:
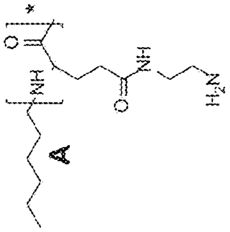
Figure 4:
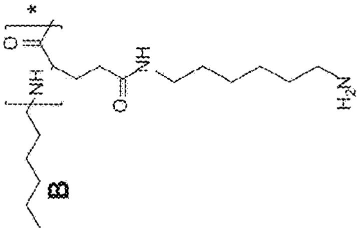
Figure 4:
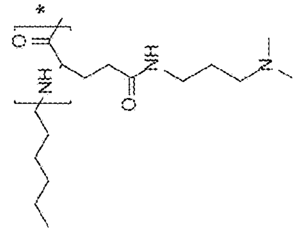
Figure 4:
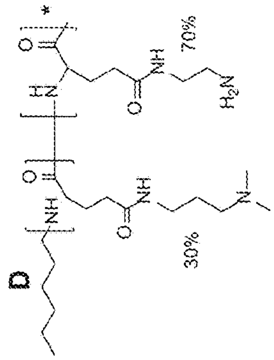
Figure 4:
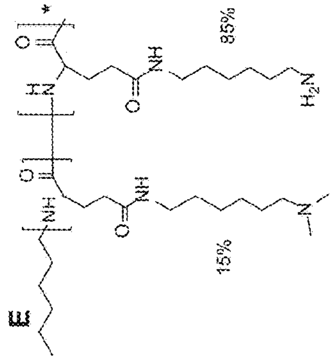
Figure 4:
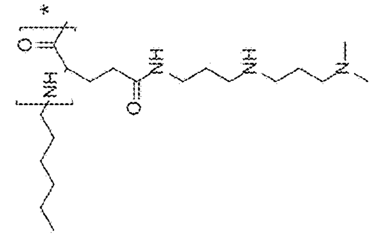
Figure 4:
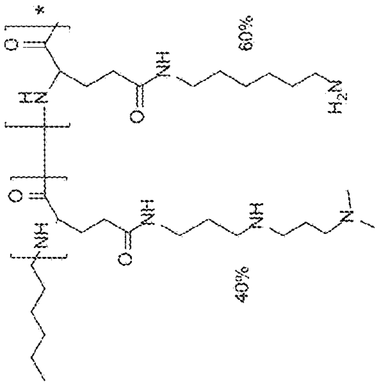
Figure 4:
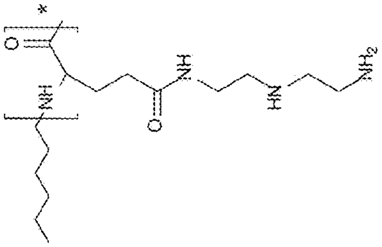
Figure 4:
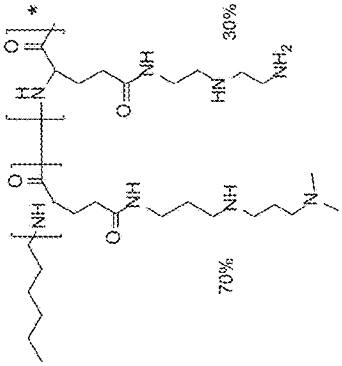

FIG. 4 presents the chemical structures of exemplary polymers according to some embodiments of the present invention, comprising BU(2) and/or BU(3) backbone units and featuring as pendant groups alkylene amines, optionally interrupted by a secondary amine, and terminating by primary and/or tertiary amine (PGAamines A-I; Group I polymers).

Figure 5:
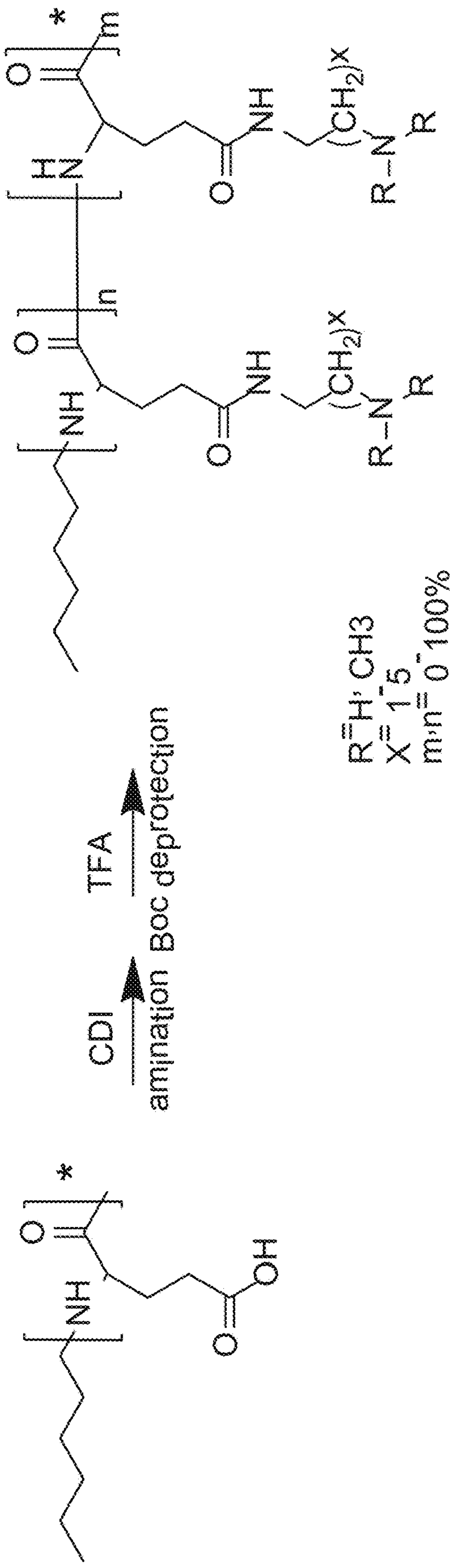

FIG. 5 presents a general synthesis mechanism, according to some embodiments of the present invention, of conjugation of an aminating agent to the PGA backbone via the pending carboxylic groups, carried out by CDI coupling reagent and the subsequent acidic Boc deprotection of the Boc-protected primary terminal amine group (Synthesis of Group I polymers).

Figure 6:
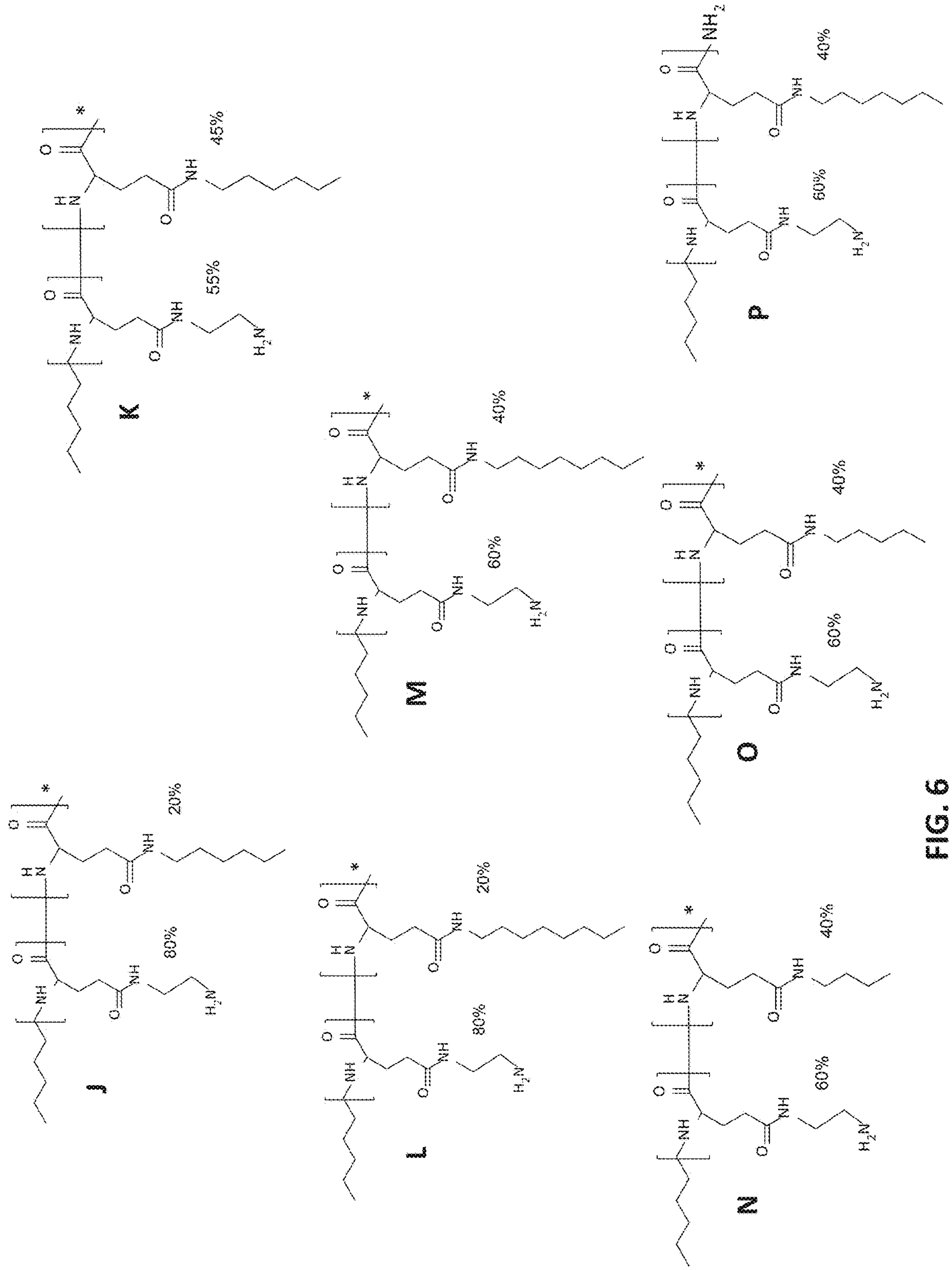

FIG. 6 presents the chemical structures of exemplary polymers according to some embodiments of the present invention, comprising BU(3) and BU(5) backbone units and featuring as pendant groups alkylene amines terminating by a primary amine and linear alkyls (PGAamines J-P; Group II polymers).

Figure 7:
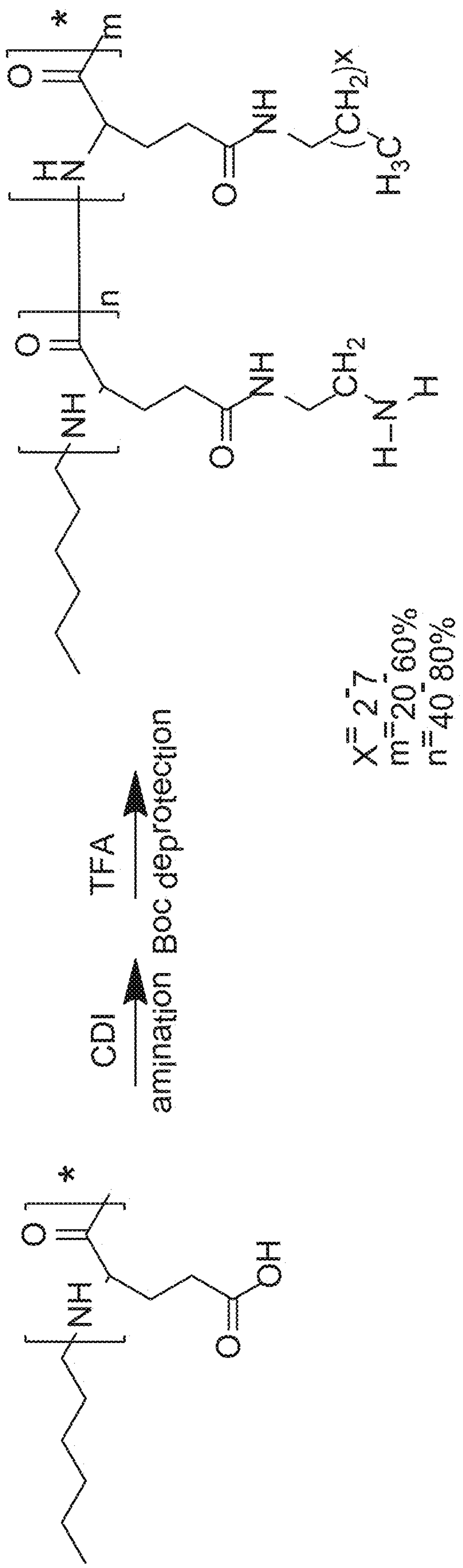

FIG. 7 presents a general synthesis mechanism, according to some embodiments of the present invention, of conjugation of aminating and alkylating agents to the PGA backbone via the pending carboxylic groups, carried out by CDI coupling reagent and the subsequent acidic Boc deprotection of the Boc-protected primary terminal amine group (Synthesis of Group II polymers).

Figure 8:
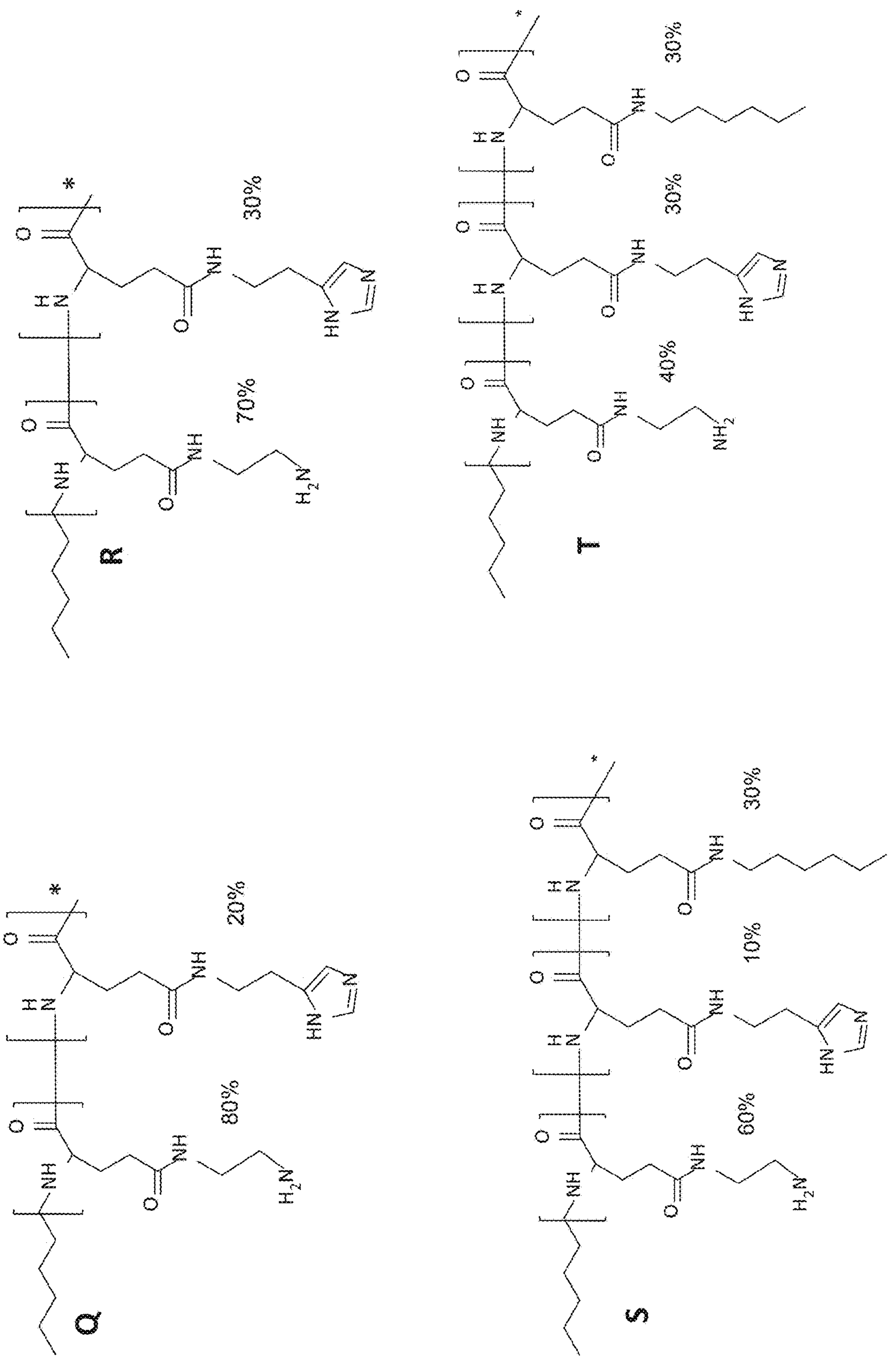

FIG. 8 presents the chemical structures of exemplary polymers according to some embodiments of the present invention, comprising BU(3) and BU(6) backbone units (Q and R), and BU(3), BU(6) and BU(5) backbone units (S and T) and featuring as pendant groups alkylene amines terminating by primary amine and alkylenes terminating by imidazole (PGA amines Q-T; Group III polymers).

Figure 9:
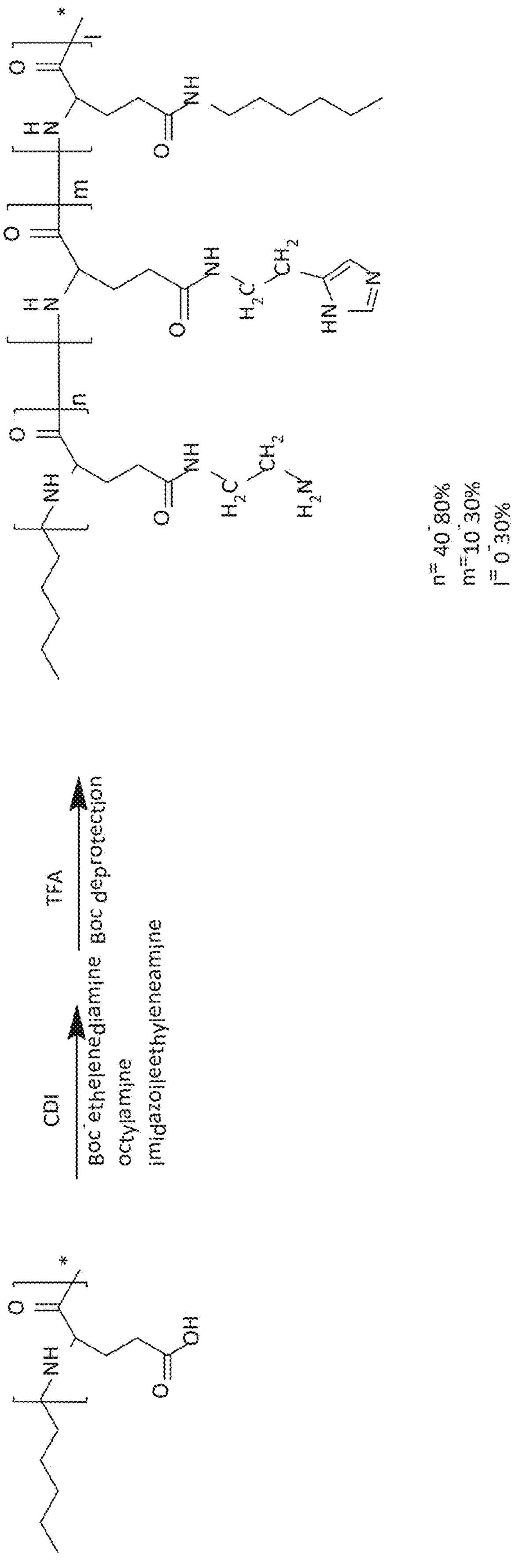

FIG. 9 presents a general synthesis mechanism, according to some embodiments of the present invention, of conjugation of an aminating agent and an imidazole-containing agent to the PGA backbone via the pending carboxylic groups, carried out by CDI coupling reagent and the subsequent acidic Boc deprotection of the Boc-protected primary terminal amine group (Synthesis of Group III polymers).

Figure 10:
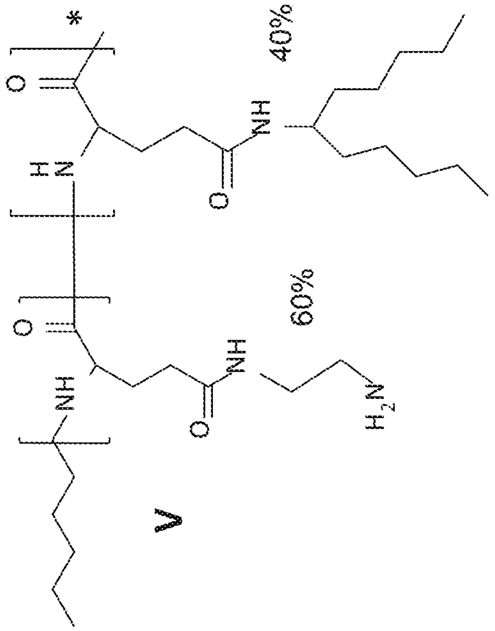
Figure 10:
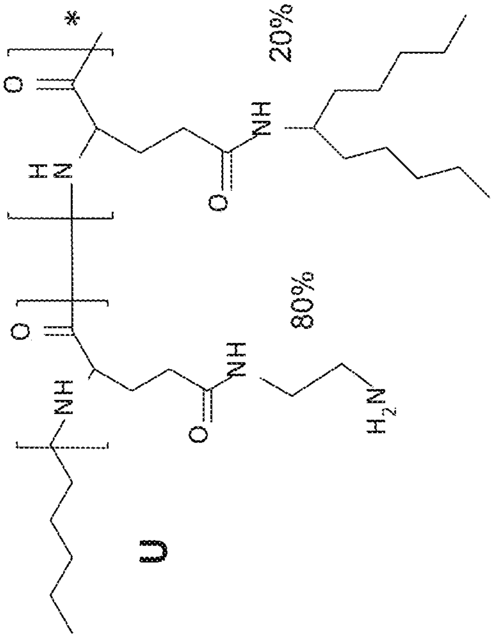
Figure 10:
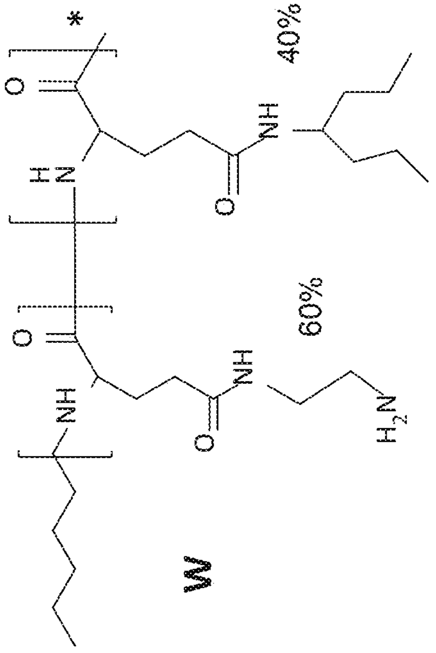

FIG. 10 presents the chemical structures of exemplary polymers according to some embodiments of the present invention, comprising BU(3) and BU(5) backbone units and featuring as pendant groups alkylene amines terminating by a primary amine and branched alkyls (PGAamines U-W; Group IV polymers).

Figure 11:
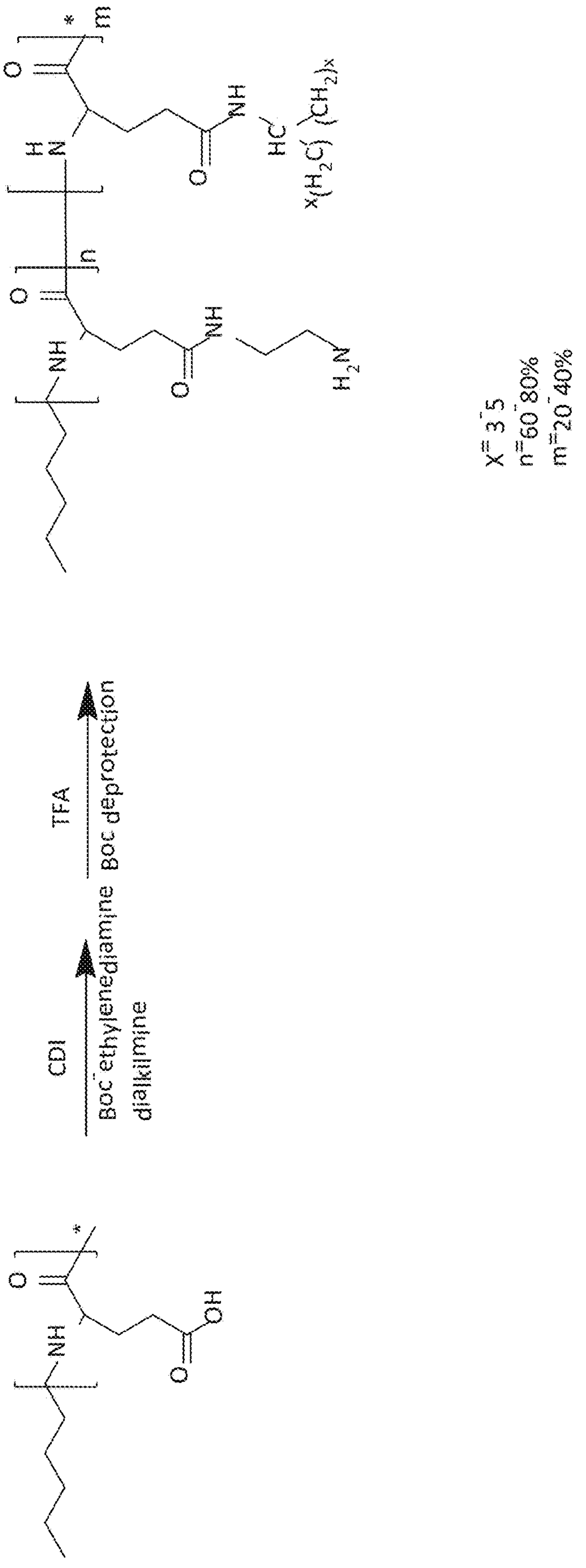

FIG. 11 presents a general synthesis mechanism, according to some embodiments of the present invention, of conjugation of aminating and branched-alkyl agents to the PGA backbone via the pending carboxylic groups, carried out by CDI coupling reagent and the subsequent acidic Boc deprotection of the Boc-protected primary terminal amine group (Synthesis of Group IV polymers).

Figure 12:
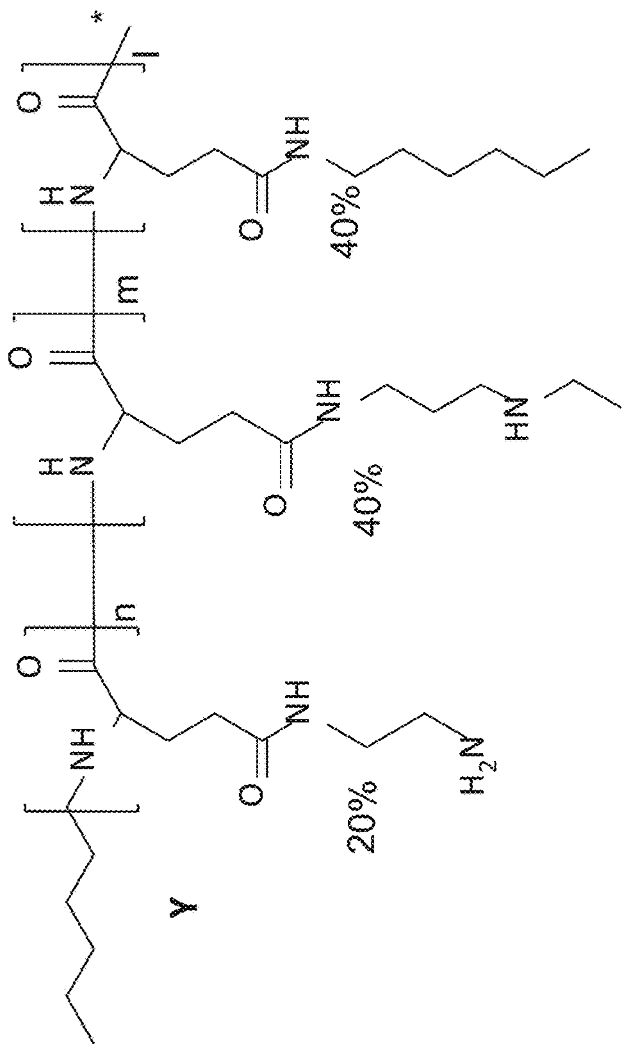
Figure 12:
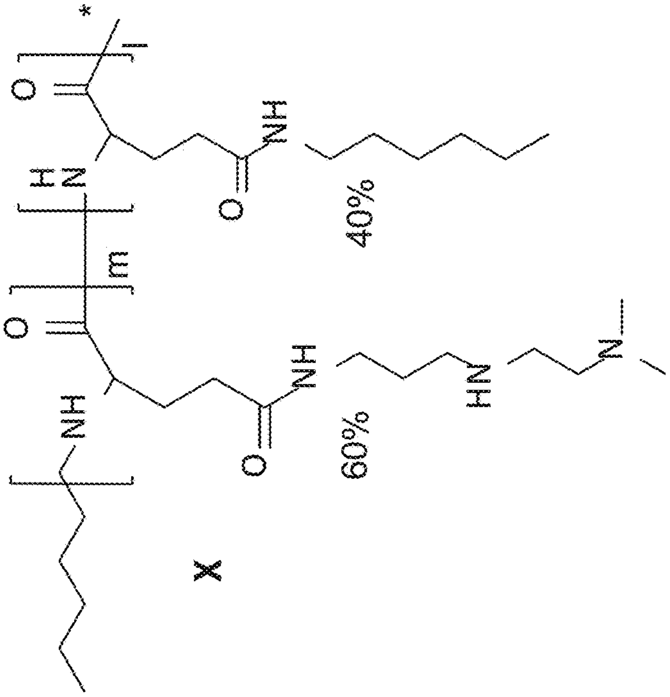

FIG. 12 presents the chemical structures of exemplary polymers according to some embodiments of the present invention, comprising BU(3) and/or BU(2) backbone units which comprise a secondary amine and BU(5) backbone units and featuring as pendant groups alkylene amines terminating by a primary and a secondary or tertiary amine and linear alkyls (PGAamines X and Y; Group V polymers).

Figure 13:
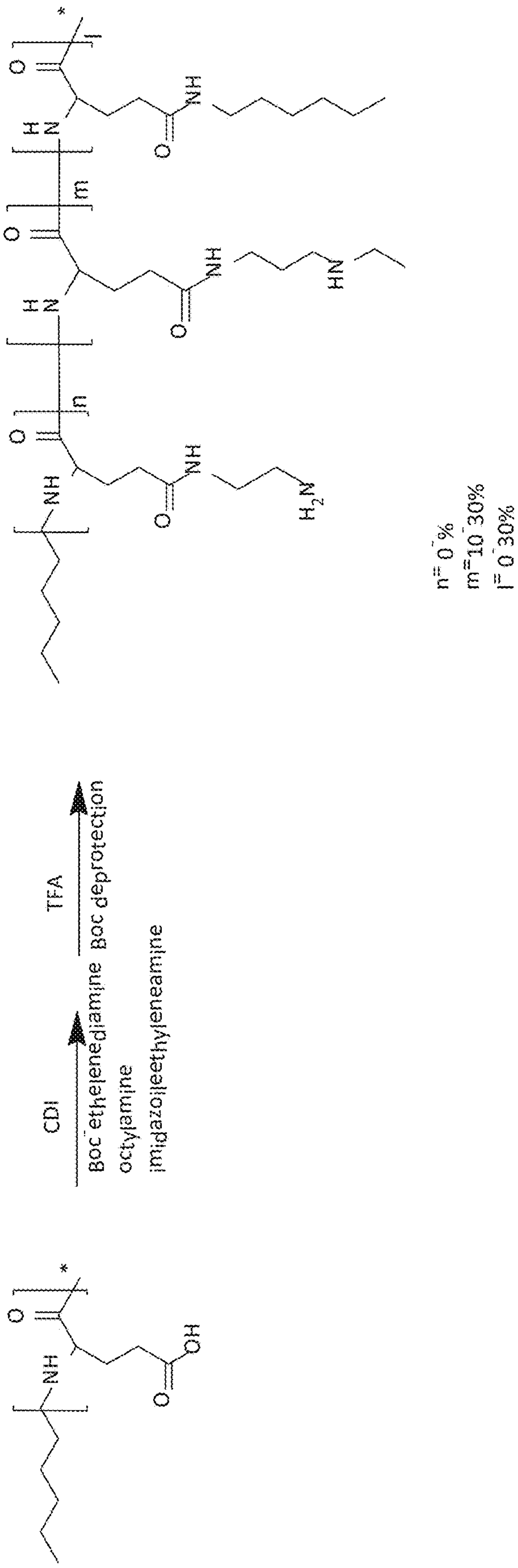

FIG. 13 presents an exemplary synthetic pathway of conjugation of an aminating agent that bears a secondary amine, an aminating agent that bears a primary amine and an alkylating agent to the PGA backbone via the pending carboxylic groups, carried out by CDI coupling reagent and the subsequent acidic Boc deprotection of the Boc-protected primary terminal amine group (Synthesis of PGAamine Y).

Figure 14:
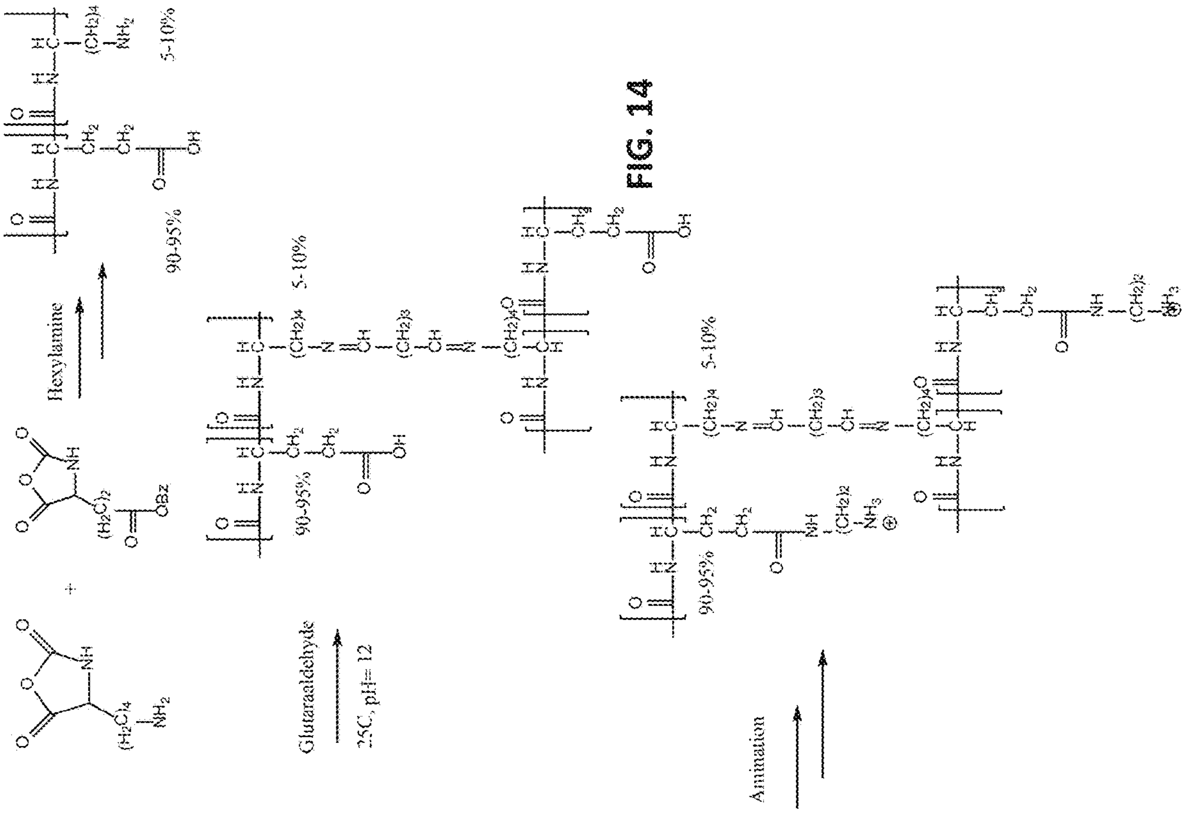

FIG. 14 presents an exemplary synthetic pathway of a cross-linked co-polymer-lysine$_{(10\%)}$-γ-ethylenediamine-L-polyglutamate$_{(90\%)}$ according to some embodiments of the present invention (Polymer CL1).

Figure 15:
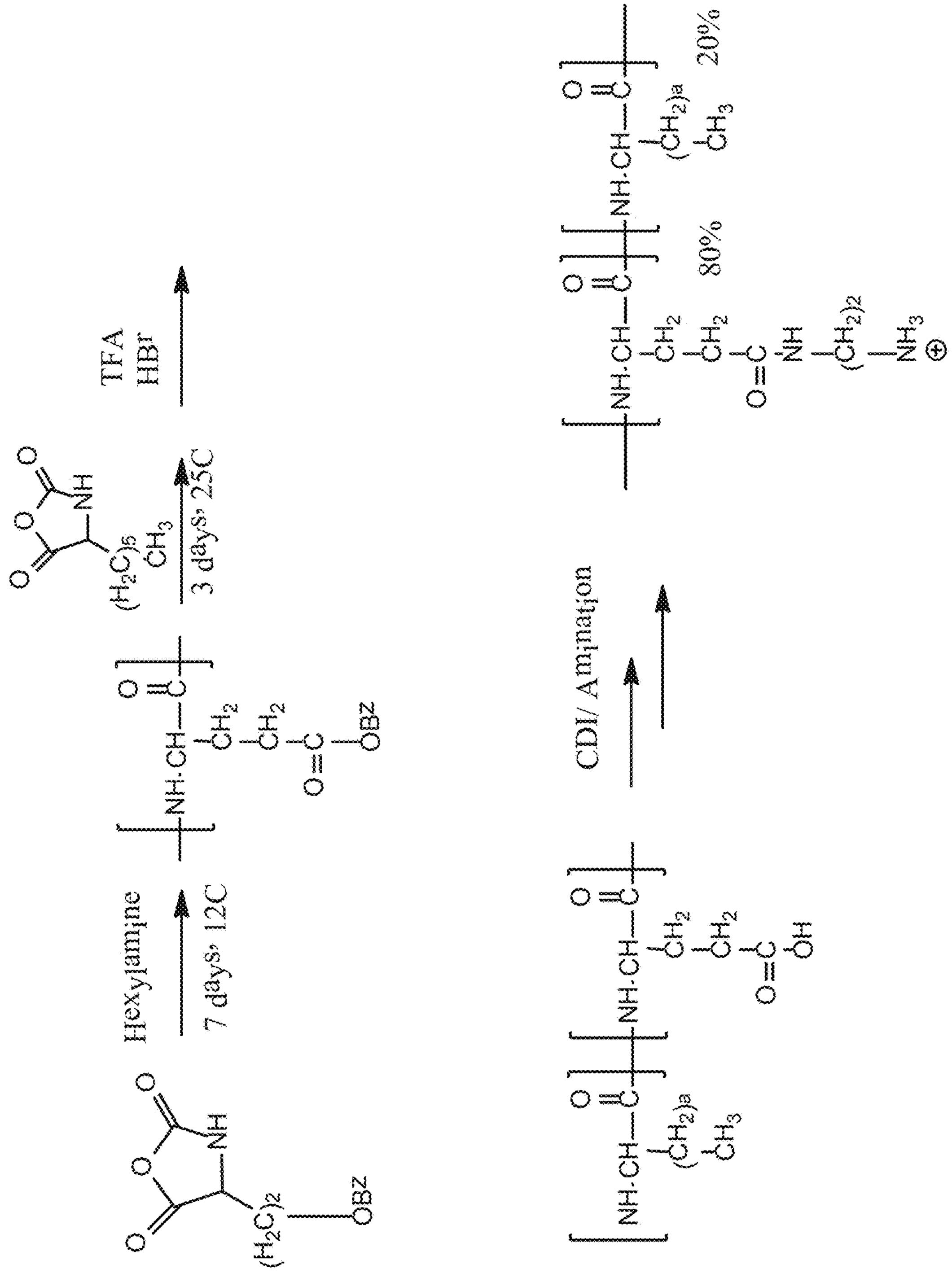

FIG. 15 presents an exemplary synthetic pathway of α-hexyl-amino acid-PGAamine block copolymer according to some embodiments of the present invention (Copolymer BL1).

Figure 16A:
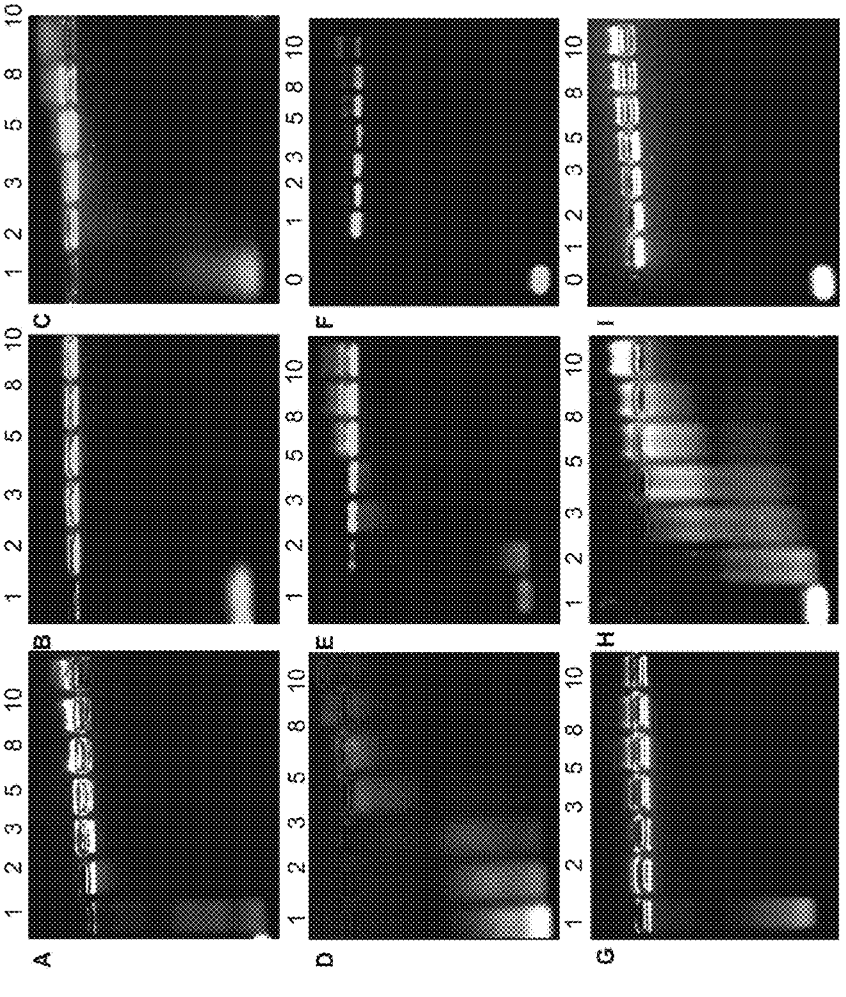
Figure 16B:
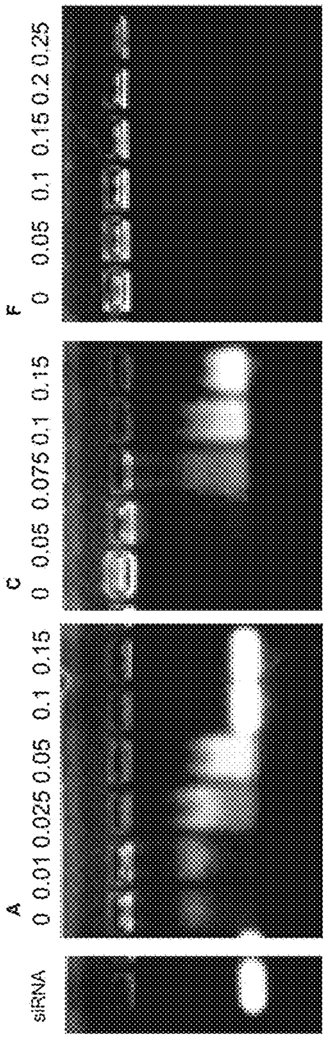
Figure 17:
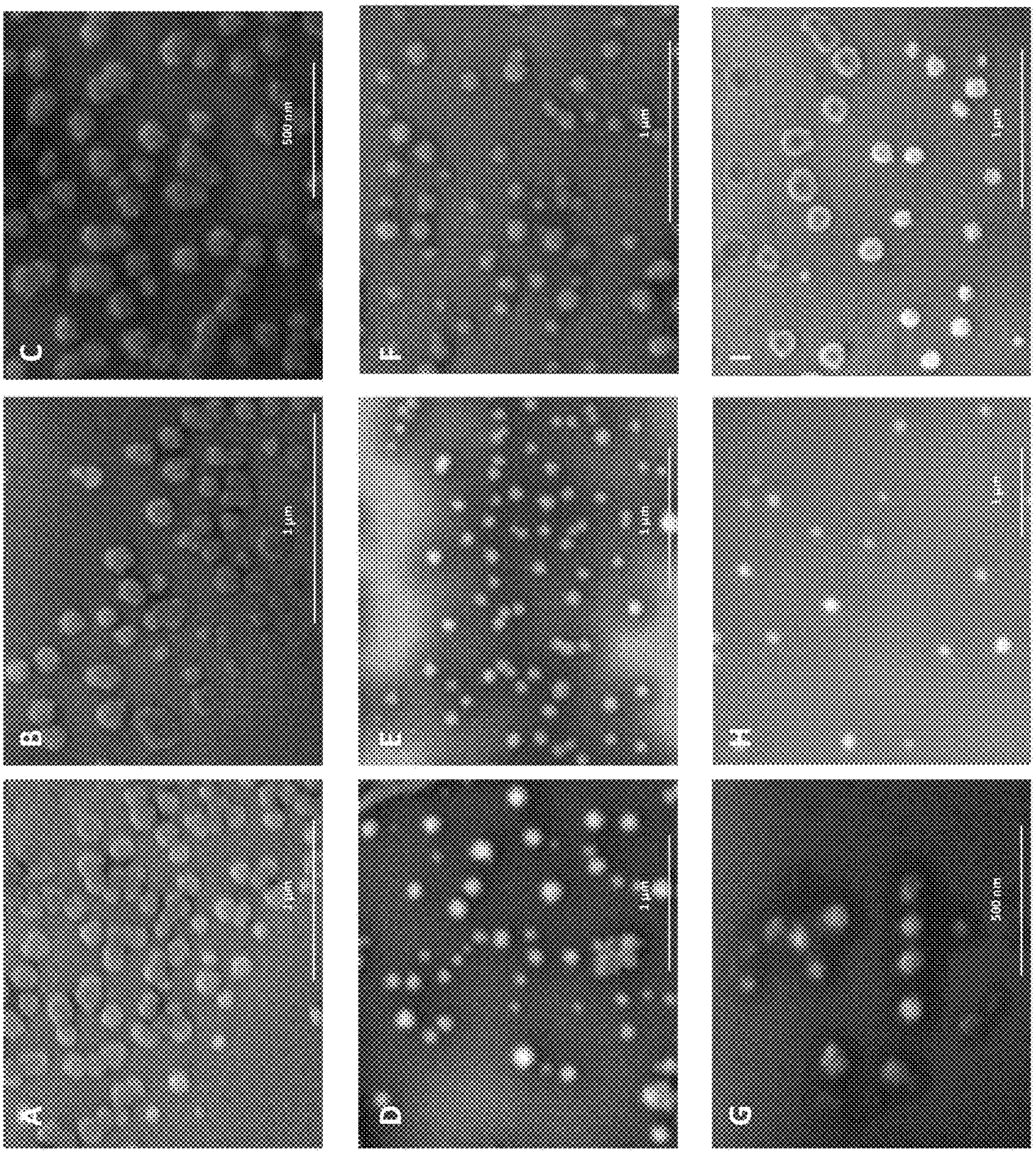

FIGS. 16A-B present a characterization of the electrostatic interaction between PGAamine amination derivatives and siRNA. FIG. 16A presents electrophoresis mobility shift analysis of Polymers A-I complexed with Rac1 siRNA at the indicated nitrogen/phosphorus (N/P) ratios. Each polymer was incubated with 50 pmol of Rac1 siRNA for 30 minutes at room temperature in RNase free water. The samples were loaded on ethidium bromide-stained 2% agarose gel, supplied with voltage of 100 volts for 30 minutes and inspected under UV light. FIG. 16B presents data obtained in the heparin displacement assay performed on Polyplexes A, C, and F at N/P ratio of 5. The international heparin units per sample of 50 pmol siRNA are specified above the gel images. FIG. 17 presents SEM images of exemplary Polymers A-I polyplexed with Rac1 siRNA and forming nano-scaled aggregates at high concentration.

Figure 18A:
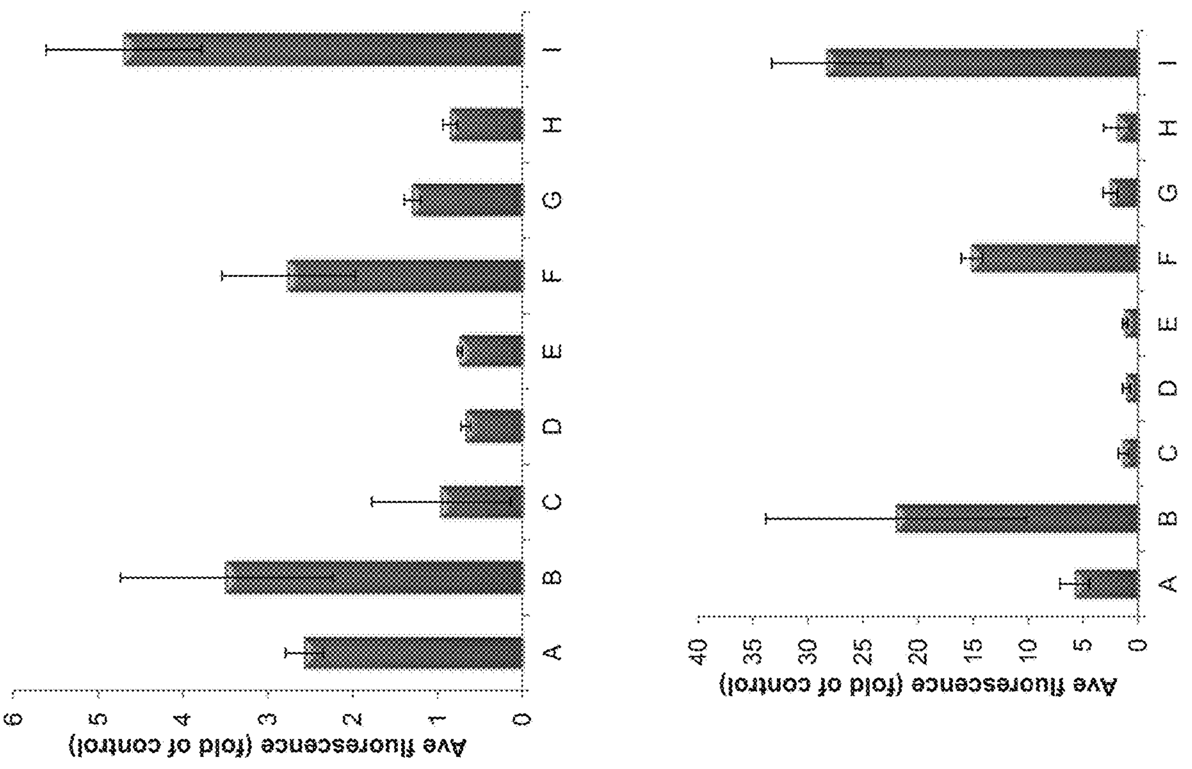
Figure 18B:
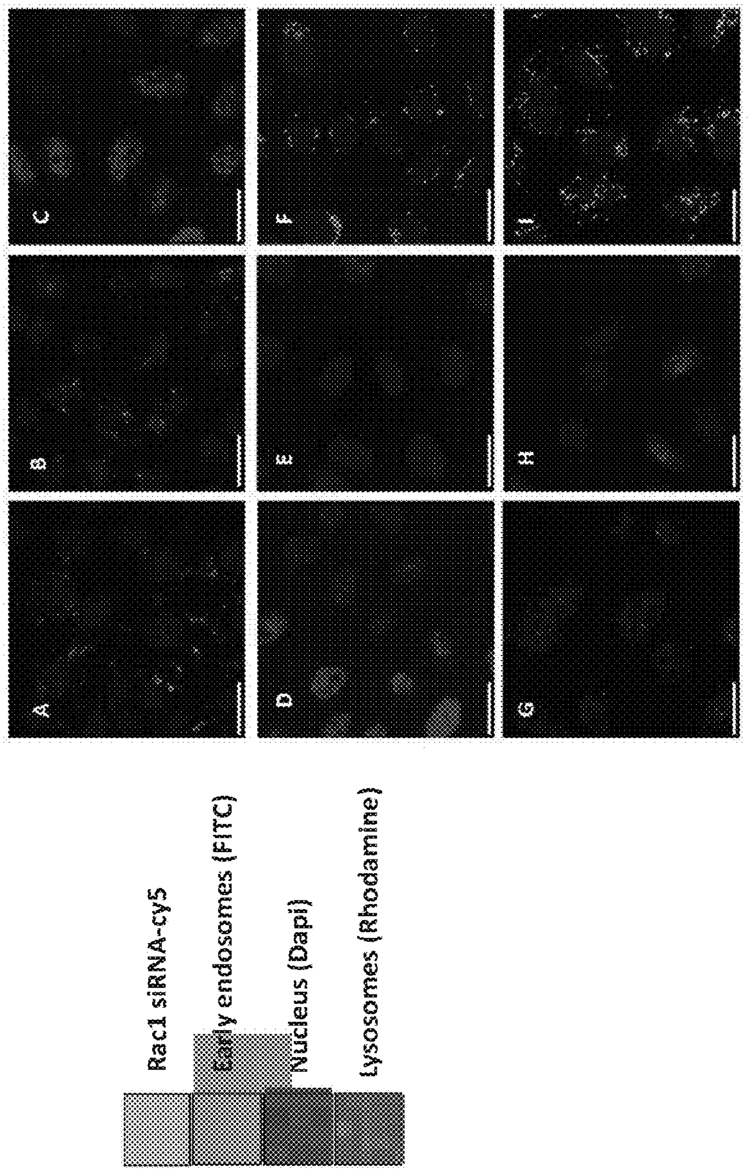
Figure 18C:
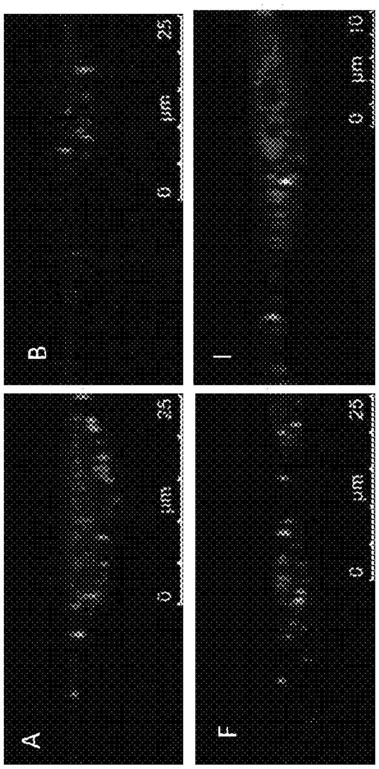

FIGS. 18A-C present a cell internalization of exemplary PGAamine:siRNA polyplexes according to some embodiments of the present invention (PGAamine:Cy5-Rac1 siRNA polyplexes). HeLa and SKOV-3 cells were treated with Polyplexes A-I composed of PGAamine A-I and Cy5-Rac1 siRNA, respectively, at N/P ratios 5 (for A, C, D, E, F, G, H, I) and 10 (for B) at 100 nM concentration for 4 hours. FIG. 18A presents a relative Cy5 fluorescence in HeLa (Upper panel) and SKOV3 (Lower panel) cells, indicating high intensity in cells treated with A, B, F and I polyplexes, as obtained by FACS analysis. Bars represent average ±SD of 3 repeats. FIG. 18B presents confocal images indicating the appearance of Cy5-Rac1 siRNA clusters inside HeLa cells that were treated with polyplexes A, B, F and I. Scale bar=20 μm. FIG. 18C presents Z-sectioning of HeLa cells treated with polyplexes A, B, F, and I illustrating the Cy5-Rac1 siRNA clusters are located at the same sections with early endosomes and lysosomes (green and red) locating the Cy5-Rac1 siRNA intracellulary.

Figure 19A:
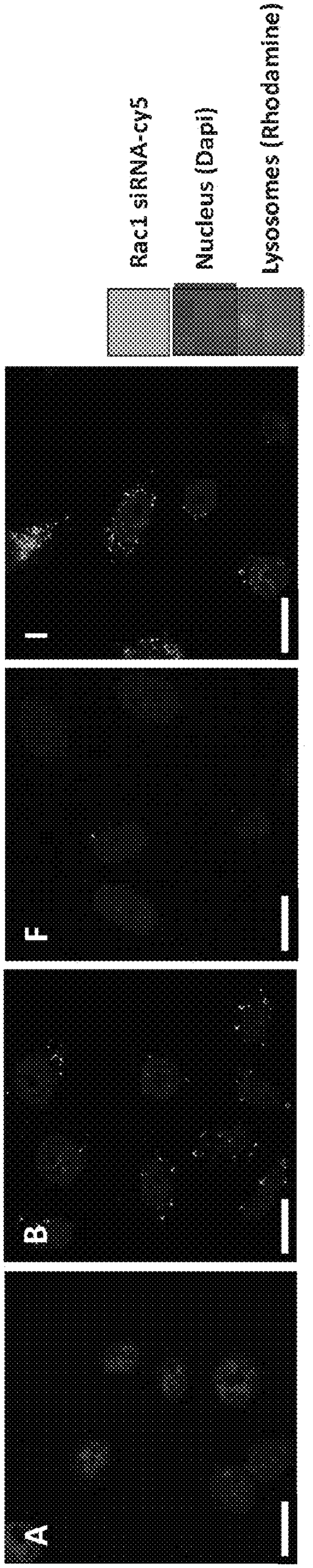
Figure 19B:
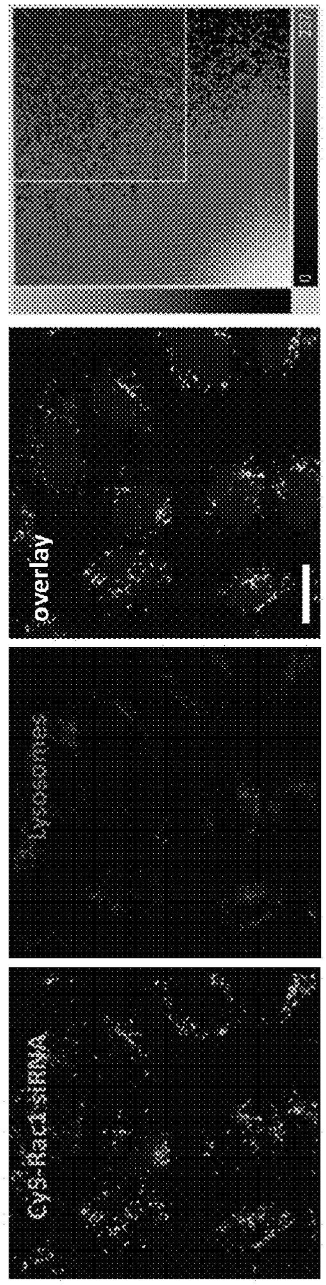
Figure 19C:
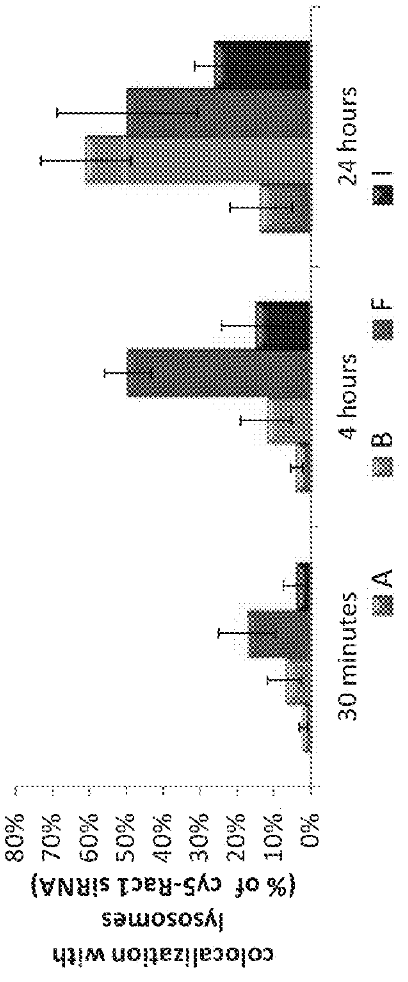

FIGS. 19A-C present data showing the intracellular localization and trafficking of exemplary PGAamine:siRNA polyplexes according to some embodiments of the present invention (A, B, F and I polyplexes). FIG. 19A are images showing that ammonium chloride blocks cellular internalization of A and F polyplexes. HeLa cells were treated with polyplexes A, B, F and I at 100 nM concentration and ammonium chloride at 2 mM concentration for 4 hours. Scale bar=20 μm. FIG. 19B present representative Confocal images of HeLa cells treated with I polyplex for 4 hours, indicating 15% co localization with lysosomes. Scale bar=20 μm. FIG. 19C show the quantification of co-localization extent of the indicated polyplexes with lysosomes indicating time dependent accumulation in lysosomes.

Figure 20A:
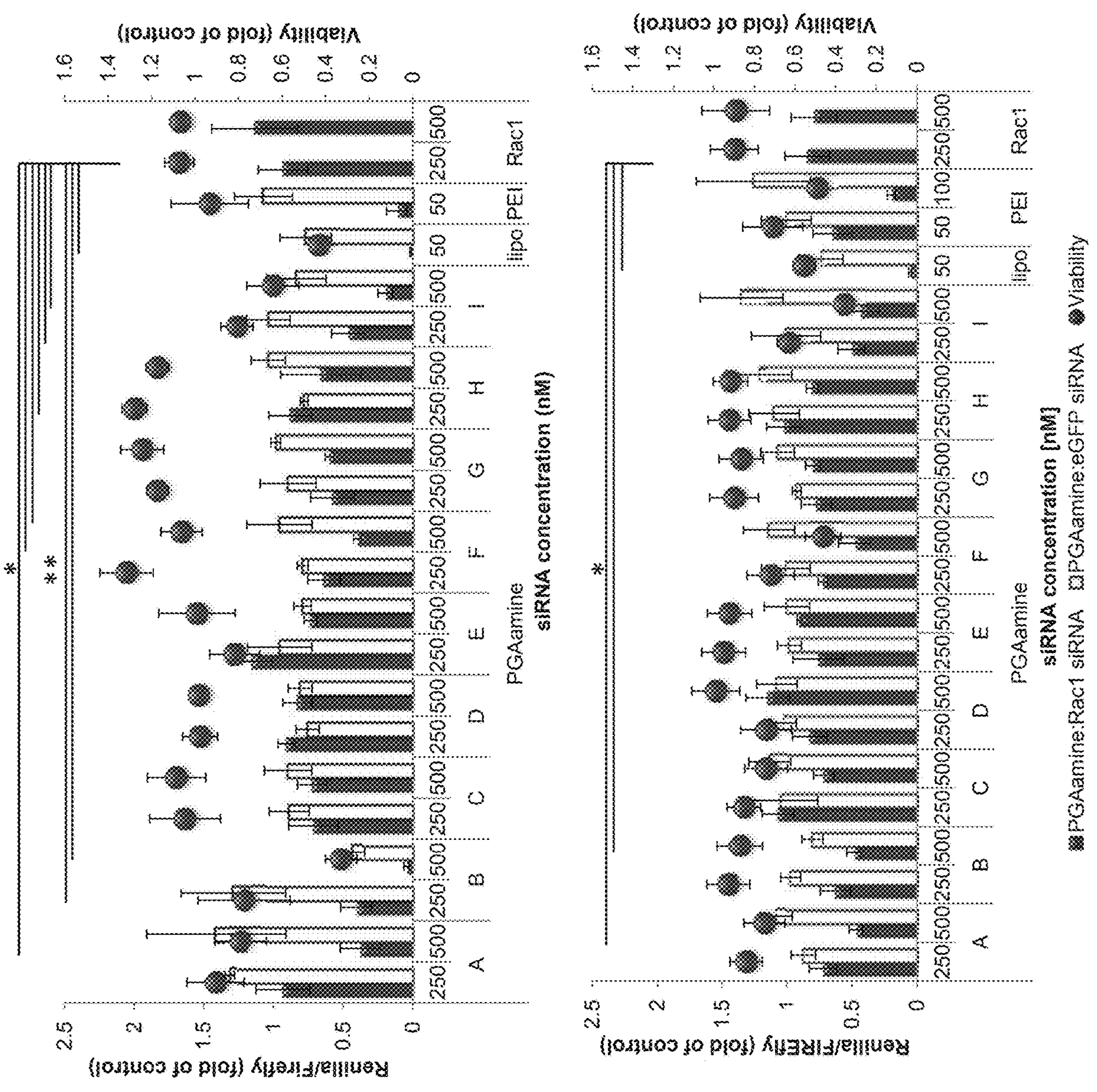
Figure 20B:
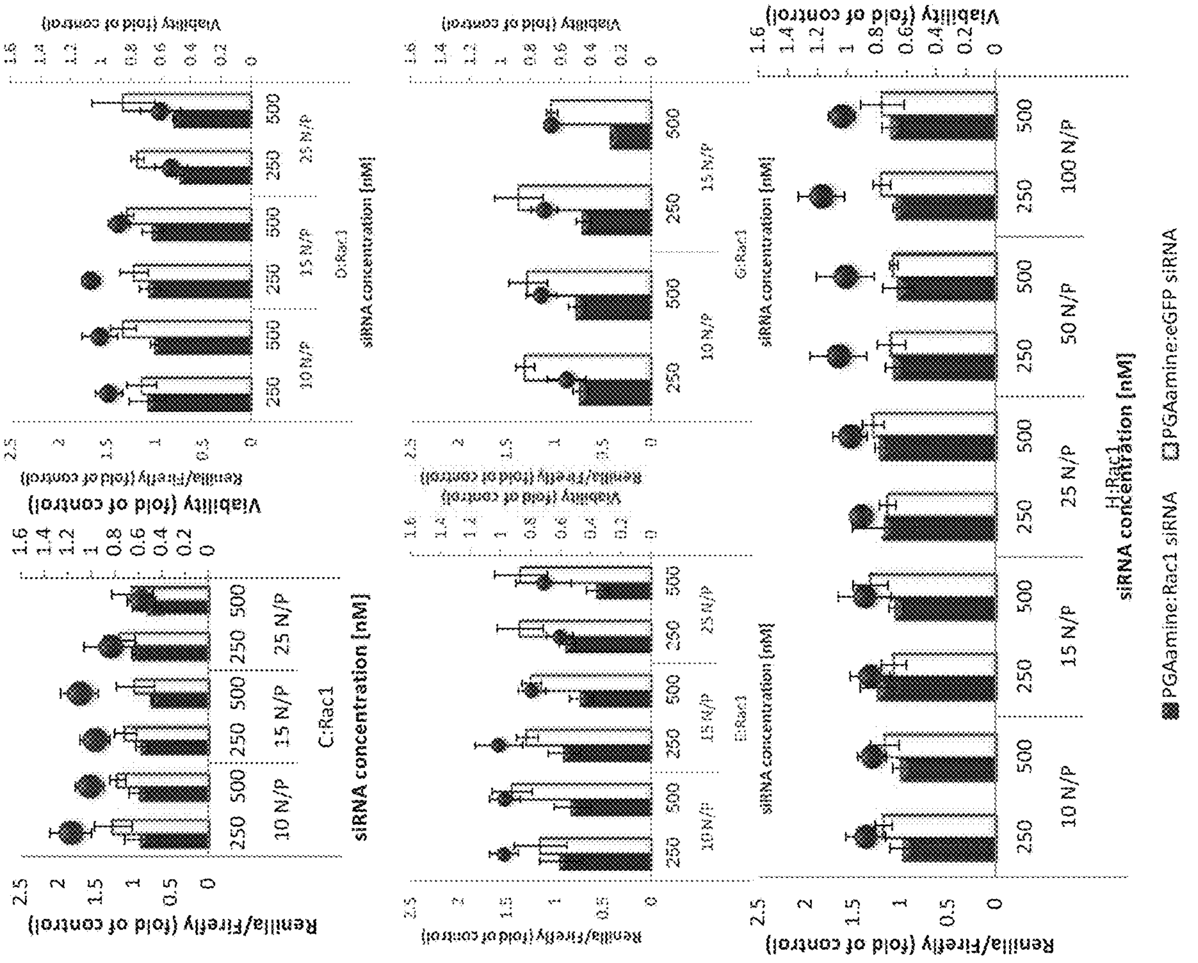
Figure 20C:
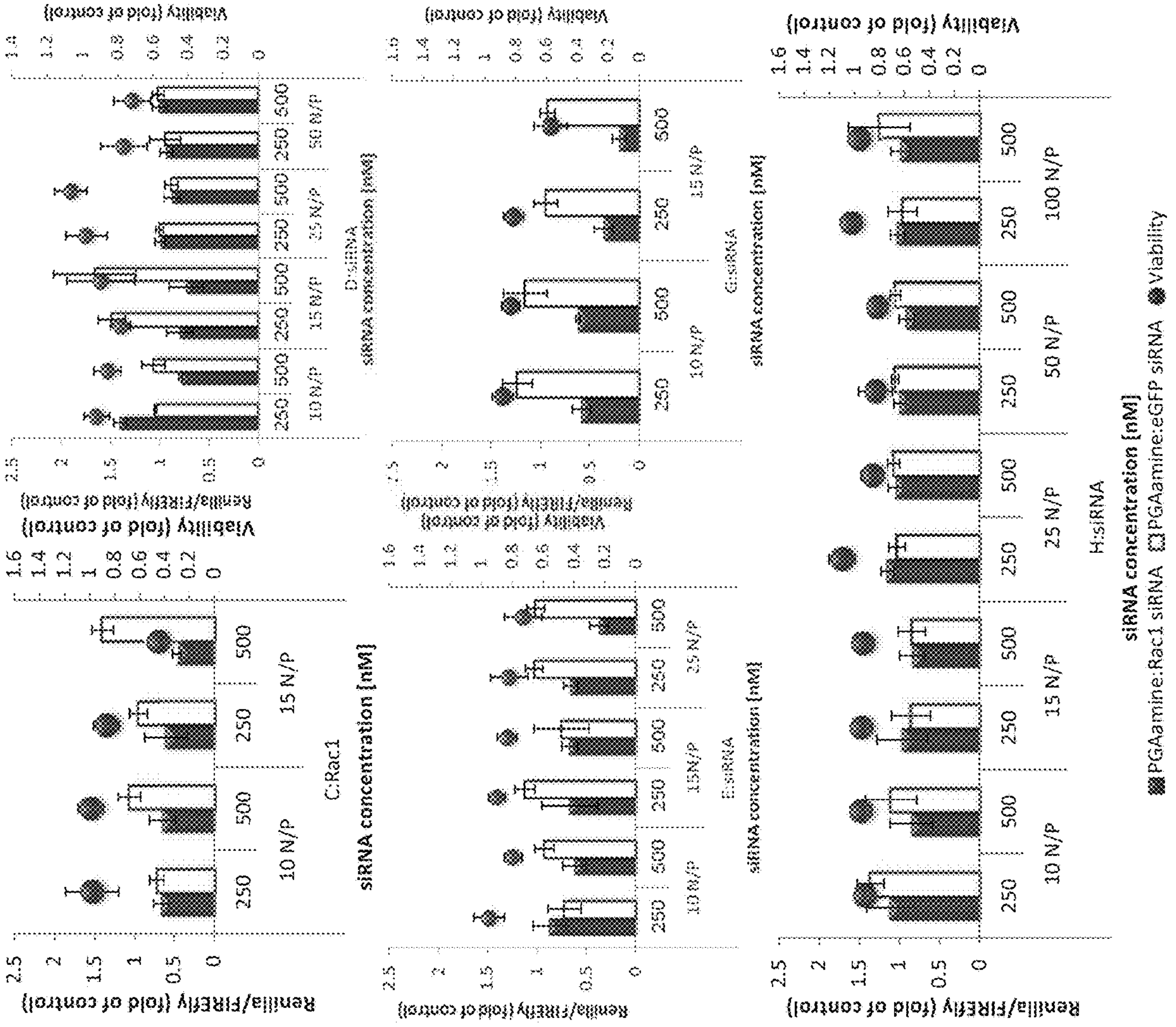

FIGS. 20A-C present data demonstrating the silencing activity of exemplary PGAamine:siRNA polyplexes according to some embodiments of the present invention. FIG. 20A presents the silencing activity and in vitro toxicity values of polyplexes A, C, D, E, F, G, H and I at N/P ratio of 5 and polyplex B at N/P ratio of 10, as indicated by dual luciferase reporter assay (bars) and MTT assay (circles) respectively, performed on HeLa (upper panel) and SKOV-3 (lower panel) culture cells. Results are representative of 3 repeats. Bars represent the average ±SD of 4 wells. Statistical significance of silencing activities: $^{**}p<0.001$, $^{*}p<0.05$. FIG. 20B presents a silencing activity and in vitro toxicity values of polyplexes C,D,E,G and H at 10-100 N/P ratios, as indicated by dual luciferase reporter assay (bars) and MTT assay (circles) respectively, performed on HeLa cells. FIG. 20C presents the silencing activity and in vitro toxicity values of polyplexes C,D,E,G and H at 10-100 N/P ratios, as indicated by dual luciferase reporter assay (bars) and MTT assay (circles) respectively, performed on SKOV-3 cells.

Figure 21A:
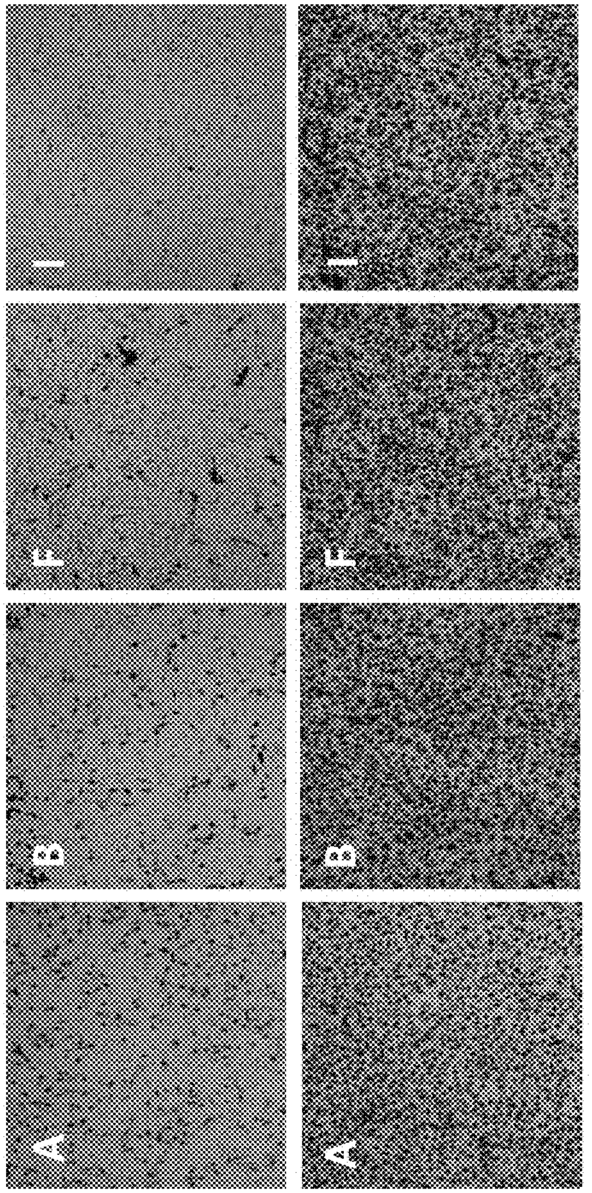
Figure 21B:
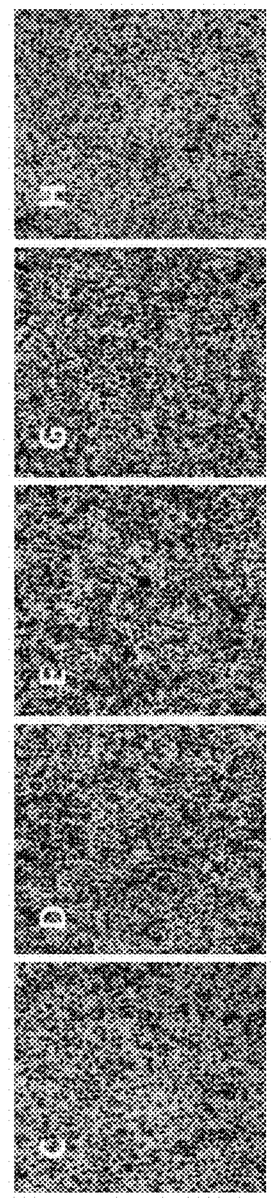
Figure 21C:
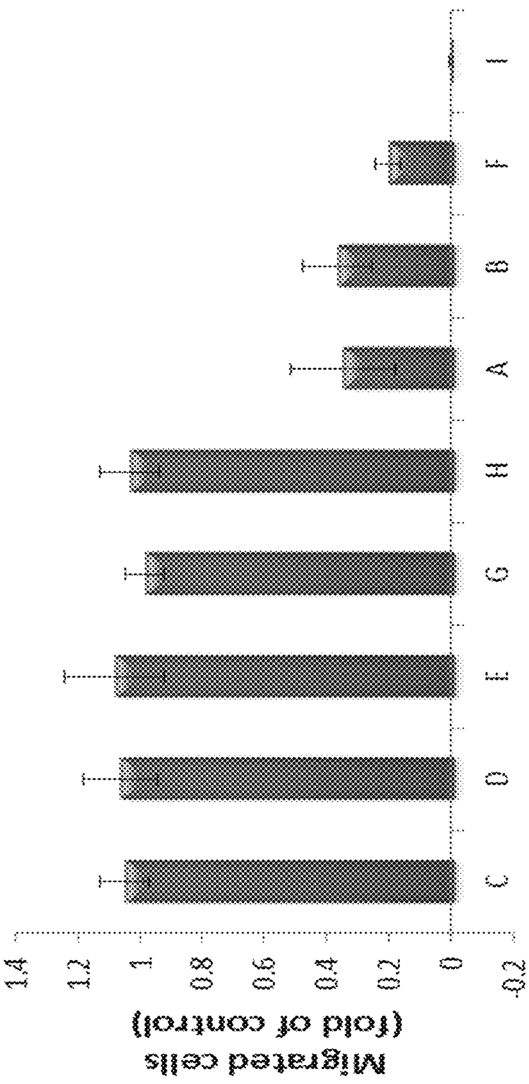

FIGS. 21A-C present the transwell migration of SKOV-3 cells towards 20% FBS-containing RPMI medium following treatment with: PGAamine:Rac1 siRNA polyplexes A, B, F and I at 500 nM concentration and 5, 10, 5 and 5 N/P ratios respectively (FIG. 21A, upper panel) or PGAamine:EGFP siRNA polyplexes A, B, F and I at 500 nM concentration and 5, 10, 5 and 5 N/P ratios respectively (FIG. 21A, lower panel); and PGAamine:Rac1 siRNA polyplexes C, D, E, G and H at 500 nM concentration and 5 N/P ratio (FIG. 21B). FIG. 21C presents a graph summarizing migration rates of PGAamine:Rac1 siRNA polyplexes A-I at 500 nM concentration and 5 N/P ratio (for polyplexes A, C, D, E, F, G, H and I) or 10 N/P ratio (for polyplex B).

Figure 22B:
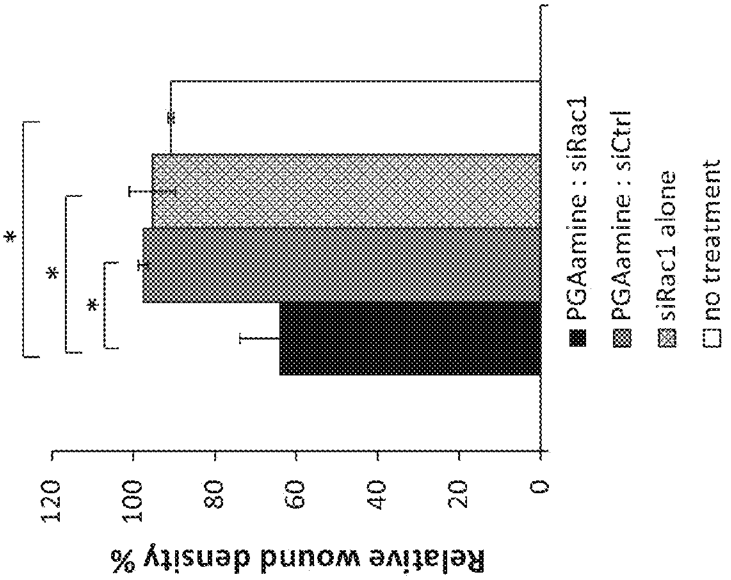
Figure 22A:
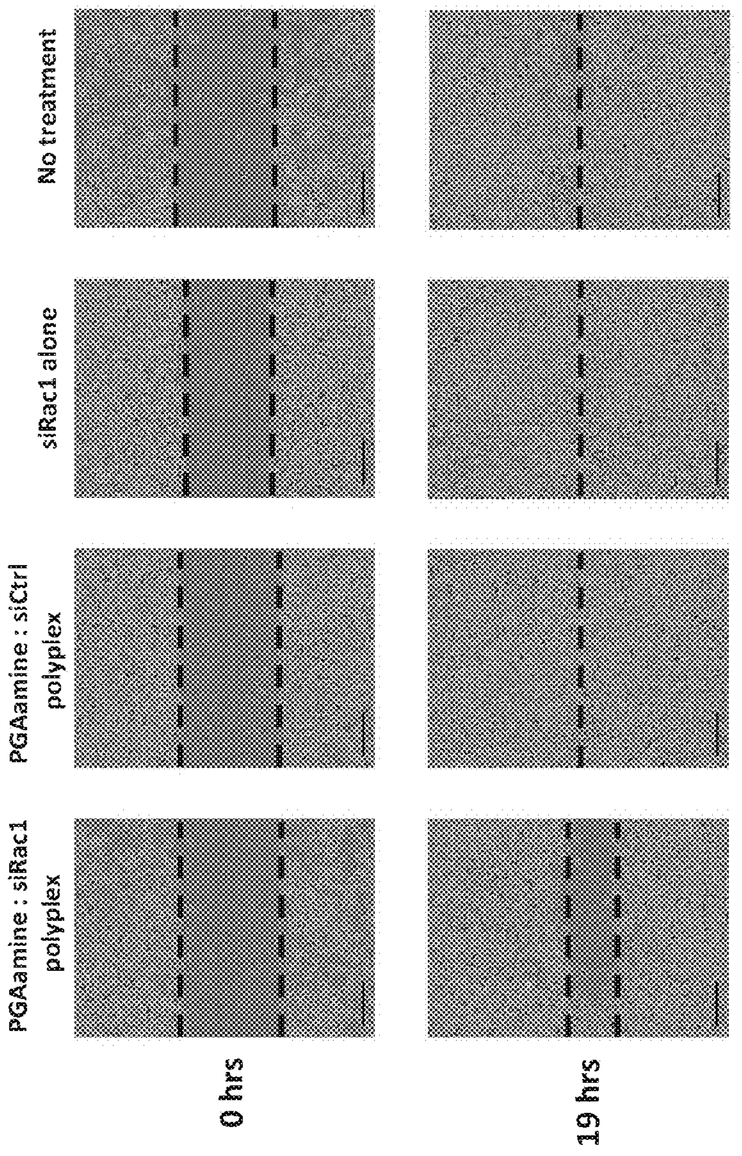

FIGS. 22A-B present the functional efficacy of exemplary PGAamine:siRac1 polyplex as demonstrated via the inhibition of cellular migration and wound healing abilities in SKOV-3 cells. FIG. 22A presents representative images of SKOV-3 cells treated with PGAamine:siRac1 polyplex, PGAamine:siCtrl polyplex, siRac1 alone or left untreated, at 0 and 19 hours in in vitro scratch assay. Phase contrast images taken by IncuCyte ZOOM™ CellPlayer using 10× objective (scale bar represents 300 μm). The dotted lines define the areas lacking cells. FIG. 22B show quantification of gap closure by SKOV-3 cells 19 hours after scratch performed and treatments applied. Statistical significance was determined using one-sided ANOVA and Holm-Sidak post hoc test. $^{*}p<0.01$, $^{**}p<0.001$.

Figure 23B:
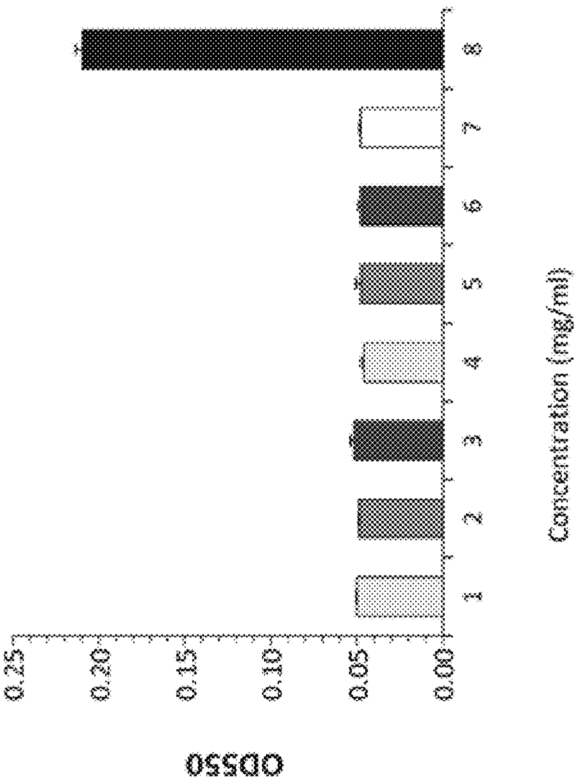
Figure 23A:
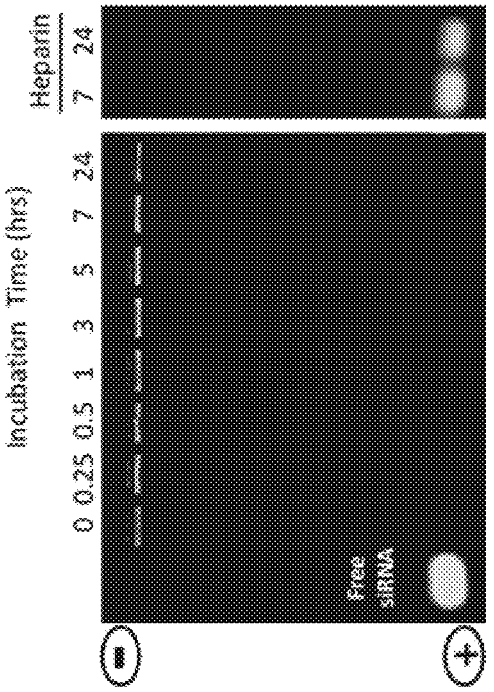
Figure 23C:
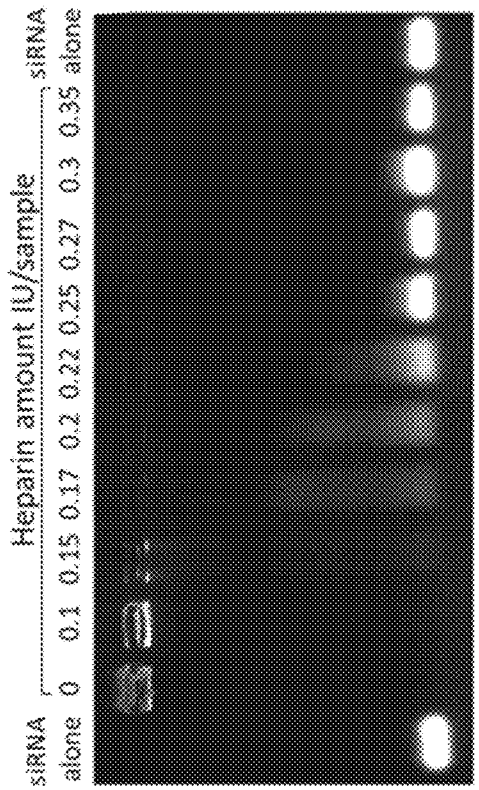

FIGS. 23A-C present data demonstrating the biocompatibility of PGAamine A:Rac1 siRNA. Exemplary PGAamine:siRac1 polyplexes show plasma stability without hemolysis or immune response activation. FIG. 23A presents an image of siRac1 complexed with PGAamine incubated with 100% plasma at the indicated time points. Following plasma incubation, the samples were mixed with heparin sulfate. The complex exhibited high plasma stability up to 24 hours. In FIG. 23B, data obtained for hemolysis of RBC, isolated from whole rat blood, following treatment with PGAamine:siRac1 polyplex, and examined by the quantification of the hemoglobin released from lysed cells, is presented. Levels of hemoglobin as measured by colorimetric assay ($\lambda_{Abs}$=550 nm) following 1 hour incubation of the RBC with siRac1-polyplex, in in vivo-equivalent concentrations, were similar to the levels of hemoglobin released in negative control samples (dextran or PBS). FIG. 23C shown that displacement of siRNA from the polyplex occurs with rising amount of heparin in the sample.

Figure 24A:
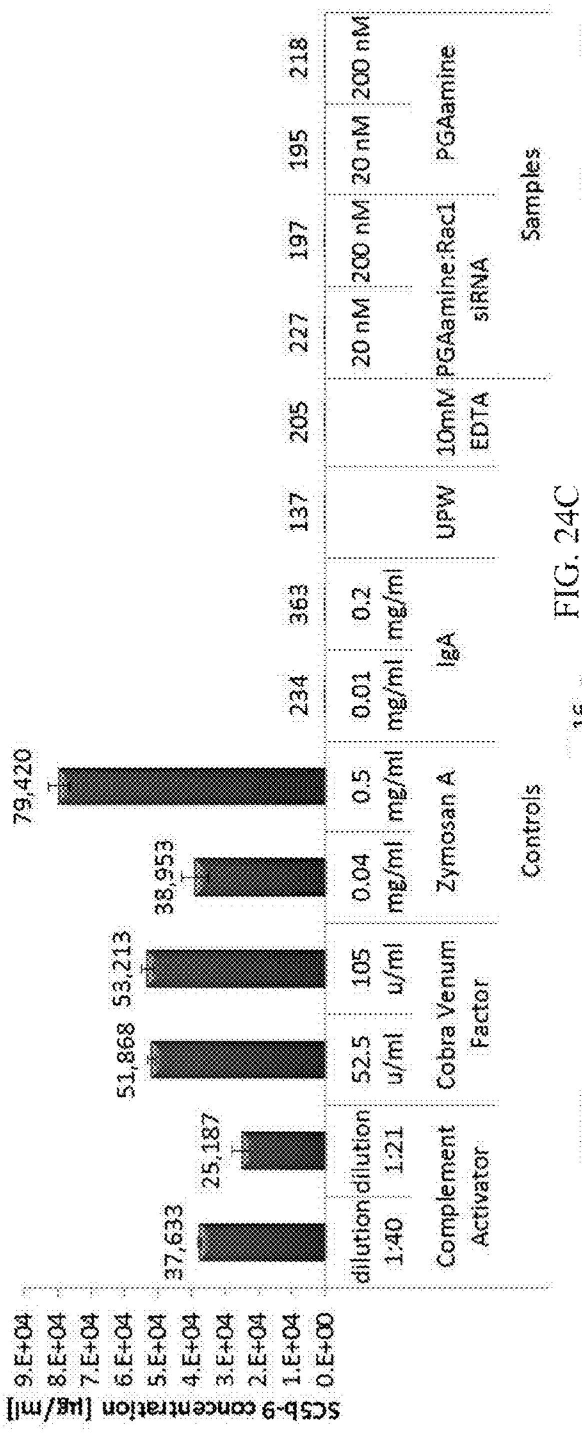
Figure 24B:
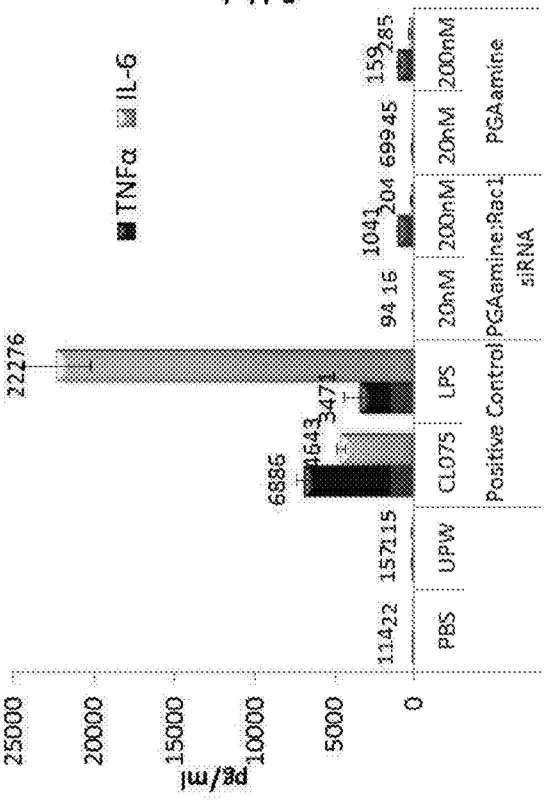
Figure 24C:
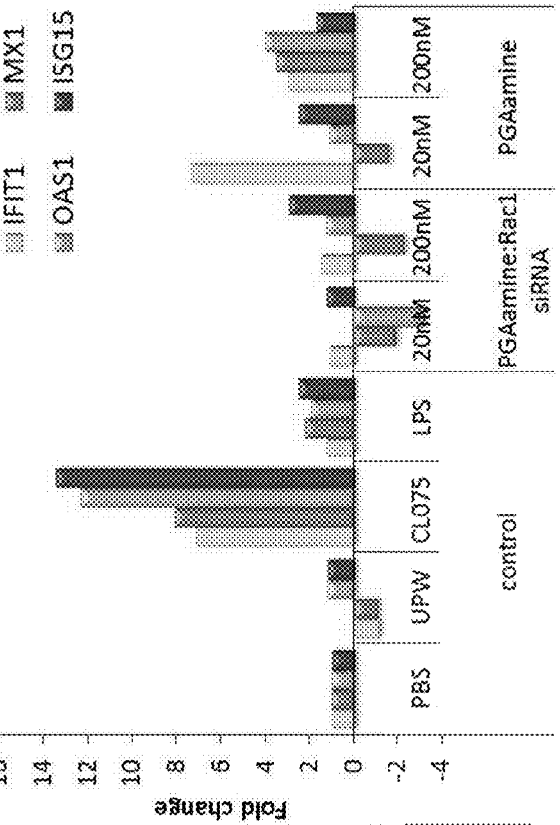

FIGS. 24A-C present data showing measurement of PGAamine A:Rac1 siRNA polyplex-mediated immune response. PGAamine A:Rac1 siRNA 5 N/P ratio polyplexes do not induce complement activation, although moderate induction in cytokines secretion and IFN responsive genes is shown. FIG. 24A is a bar graph demonstrating the low levels of SC5b-9 final complex of the compliment system following treatment with PGAamine A:Rac1 siRNA 5 N/P ratio polyplexes or PGAamine alone. FIG. 24B is a bar graph showing cytokines secretion following 24 hours incubation of PBMCs with PGAamine A polymer alone or with PGAamine A:Rac1 siRNA 5 N/P ratio polyplexes. FIG. 24C is a bar graph showing the levels of IFN responsive inflammatory genes following 24 hours incubation of PBMCs with PGAamine A polymer or with PGAamine A:Rac1 siRNA 5 N/P ratio polyplexes.

Figure 25A:
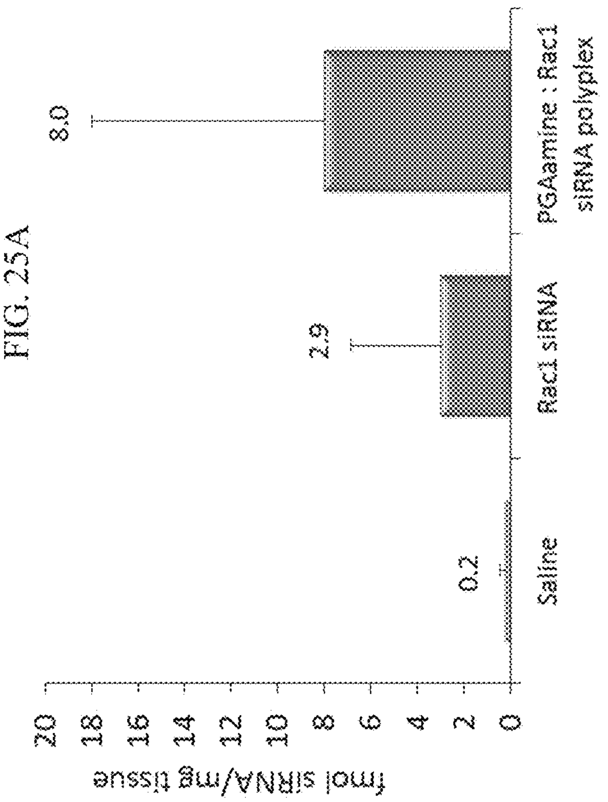
Figure 25B:
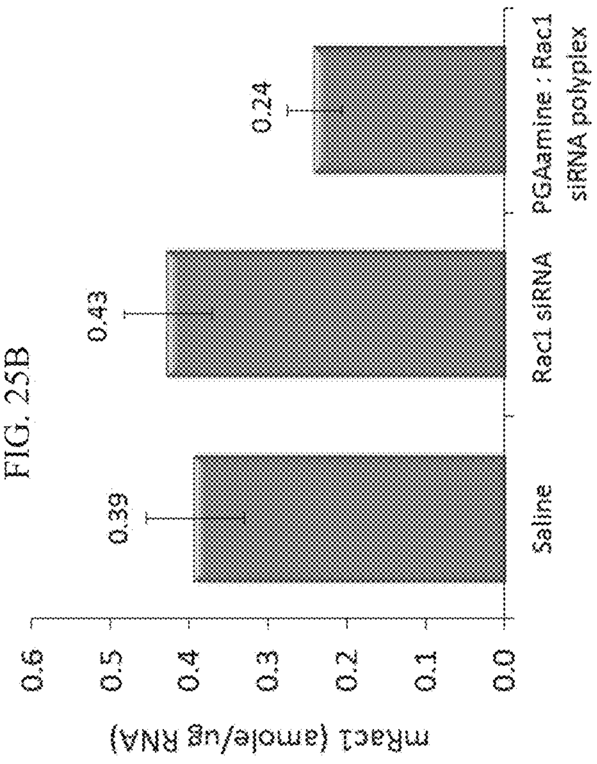
Figure 25C:
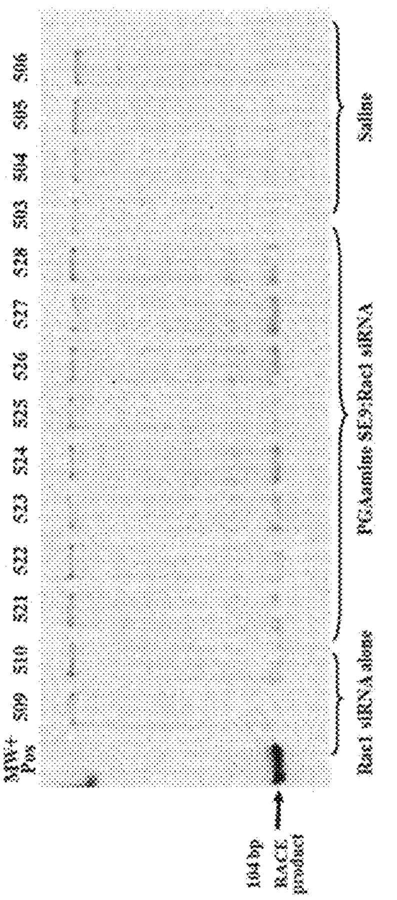
Figure 25D:
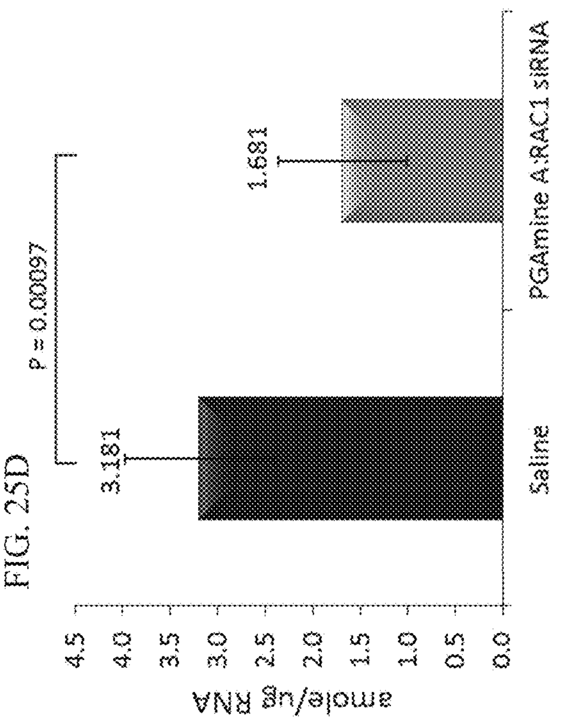

FIGS. 25A-D demonstrate the activity of PGAamine:siRNA polyplex as evaluated following IP or IV administration in human and murine in vivo models. FIG. 25A is a bar graph showing that Rac1 siRNA polyplex displayed 8-fold increase in accumulation in SKOV-3 tumors inoculated intraperitonealy in nu/nu mice following treatment with A:Rac1 siRNA 5 N/P ratio polyplexes compared to saline-treated mice. FIG. 25B is a bar graph showing that IP treatment with A:Rac1 siRNA 5 N/P ratio polyplexes resulted in 38% Rac1 mRNA knockdown in SKOV-3 human ovarian carcinoma tumors inoculated intraperitonealy in nu/nu mice. FIG. 25C presents results of RACE assay showing increased level of mRNA cleavage products resulting from siRNA silencing. FIG. 25D is a bar graph showing that IV treatment with A:Rac1 siRNA 5 N/P ratio polyplexes resulted in 46% Rac1 mRNA knockdown in LLC cells inoculated SC into C57 mice.

Figure 26A:
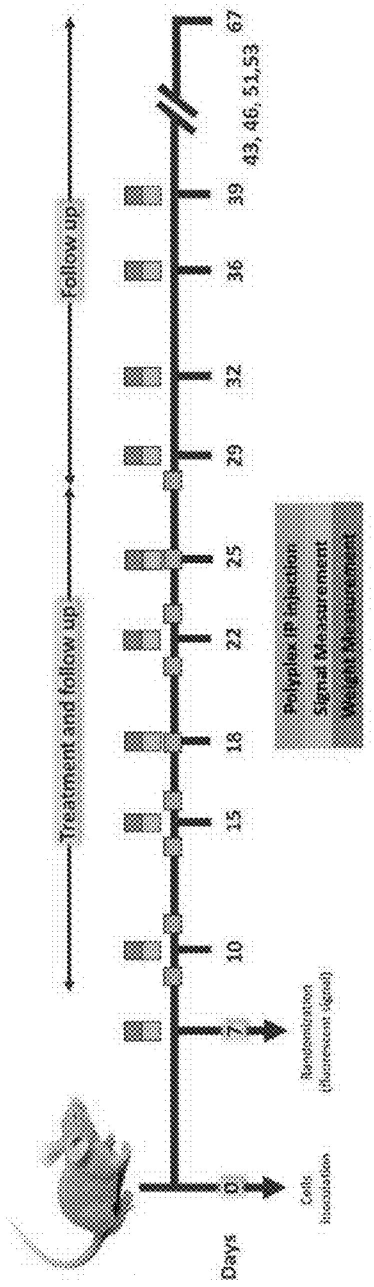
Figure 26B:
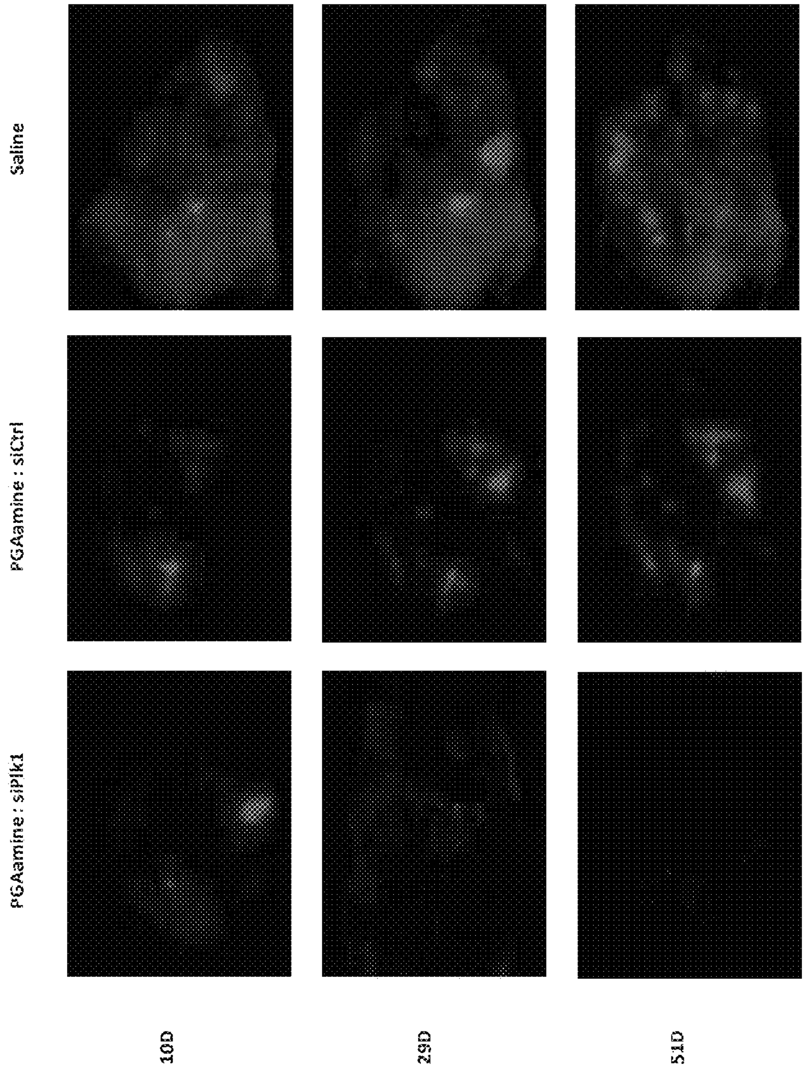
Figure 26D:
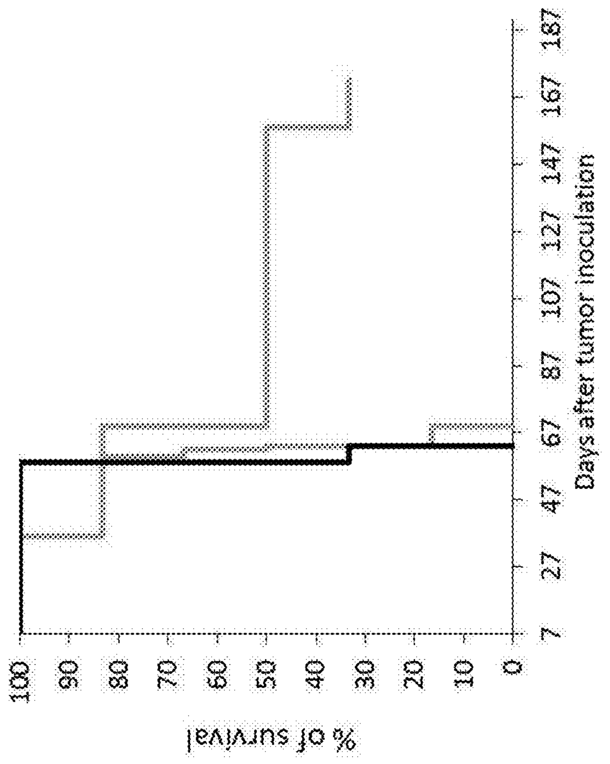
Figure 26C:
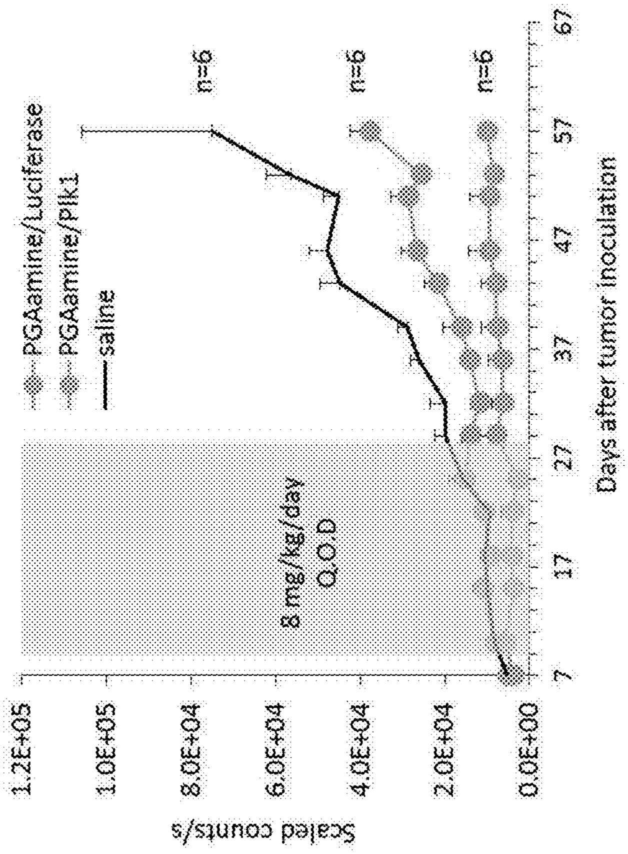

FIGS. 26A-D present the anti-cancer efficacy of PGAamine A:Plk1 siRNA polyplexes in SKOV-3 mCherry-labeled orthotopic tumor bearing nu/nu mice. FIG. 26A presents the mode of operation and treatment regimen for orthotopic ovarian carcinoma treated with IP injected polyplexes. FIG. 26B presents representative images of fluorescently-labeled IP ovarian tumors over the course of treatment period. FIG. 26C are plots showing the progression of mCherry-labeled SKOV-3 tumors following 9 every other day treatments with PGAamine:siPlk/siLuciferase polyplexes (8 mg/kg) or saline (n=6), as was measured by intravital non-invasive fluorescence imaging system. Plk1 siRNA complexed with PGAamine polymer inhibited the growth of ovarian tumors for 30 days after the last injection resulting in 87% inhibition of tumor growth compared to saline-treated mice and 73% inhibition of tumor growth compared to siCtrl-treated mice (p=0.005). Data in tumor volume graph represents mean±s.e.m. FIG. 26D presents Kaplan-Meier survival plot for all treated groups. Fifty percents of mice treated with PGAamine:siPlk polyplex survived 150 days and after that, 33% of mice survived 180 days after the first treatment (siPlk1-treated mice vs. siCtrl treated micep=0.027, siPlk1 treated mice vs. saline treated mice p=0.015, up to day 57).

FIGS. 27A-E present data obtained for a formulation of A:Rac1 siRNA polyplexes. FIG. 27A shows a hydrodynamic diameter of non-formulated A:Rac1 siRNA 5 N/P ratio polyplex as measured by zetasizer ZS. FIG. 27B shows a hydrodynamic diameter distribution of A:Rac1 siRNA 5 N/P ratio polyplex formulated with 0.2% (molar ratio) Tween®20 as measured by zetasizer ZS. FIG. 27C shows a hydrodynamic diameter distribution of A:Rac1 siRNA 2 N/P ratio polyplex formulated with 0.2% (molar ratio) Tween®20 as measured by zetasizer ZS. FIG. 27D shows in-vitro activity of A:Rac1 siRNA 5 N/P ratio polyplex formulated with 0.2% (molar ratio) Tween®20. FIG. 27E presents a table summarizing the N/P ratio, formulation, obtained hydrodynamic diameter and PDI of A:Rac1 siRNA polyplexes.

Figure 28:
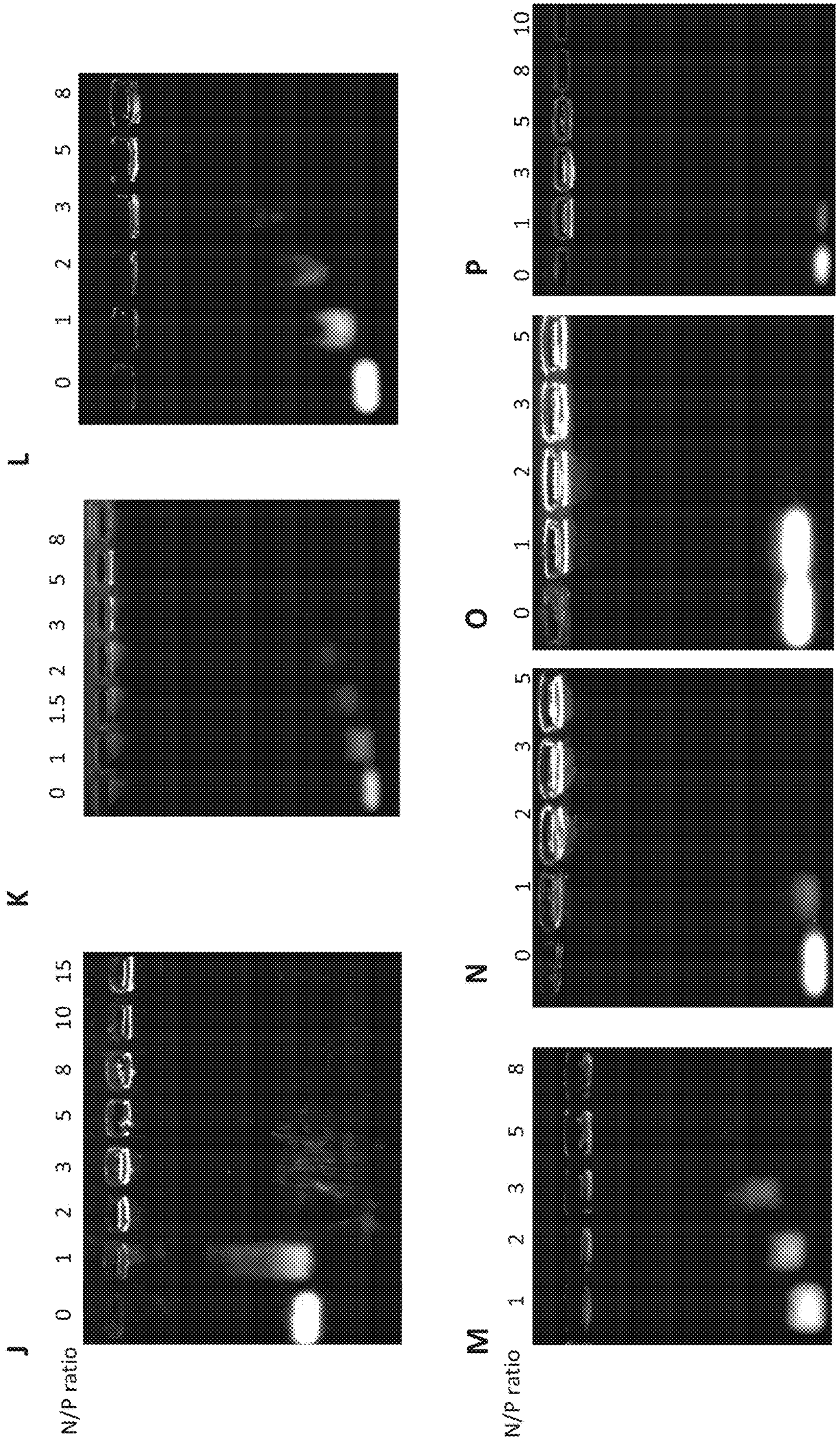

FIG. 28 presents electrophoresis mobility shift analysis of exemplary alkylated PGA amine polymers J-P complexed with Rac1 siRNA at the indicated nitrogen/phosphorus (N/P) ratios. Each polymer was incubated with 50 pmol of Rac1 siRNA for 30 minutes at room temperature in RNase free water. The samples were loaded on ethidium bromide-stained 2% agarose gel, supplied with voltage of 100 volts for 30 minutes and inspected under UV light.

Figure 29:
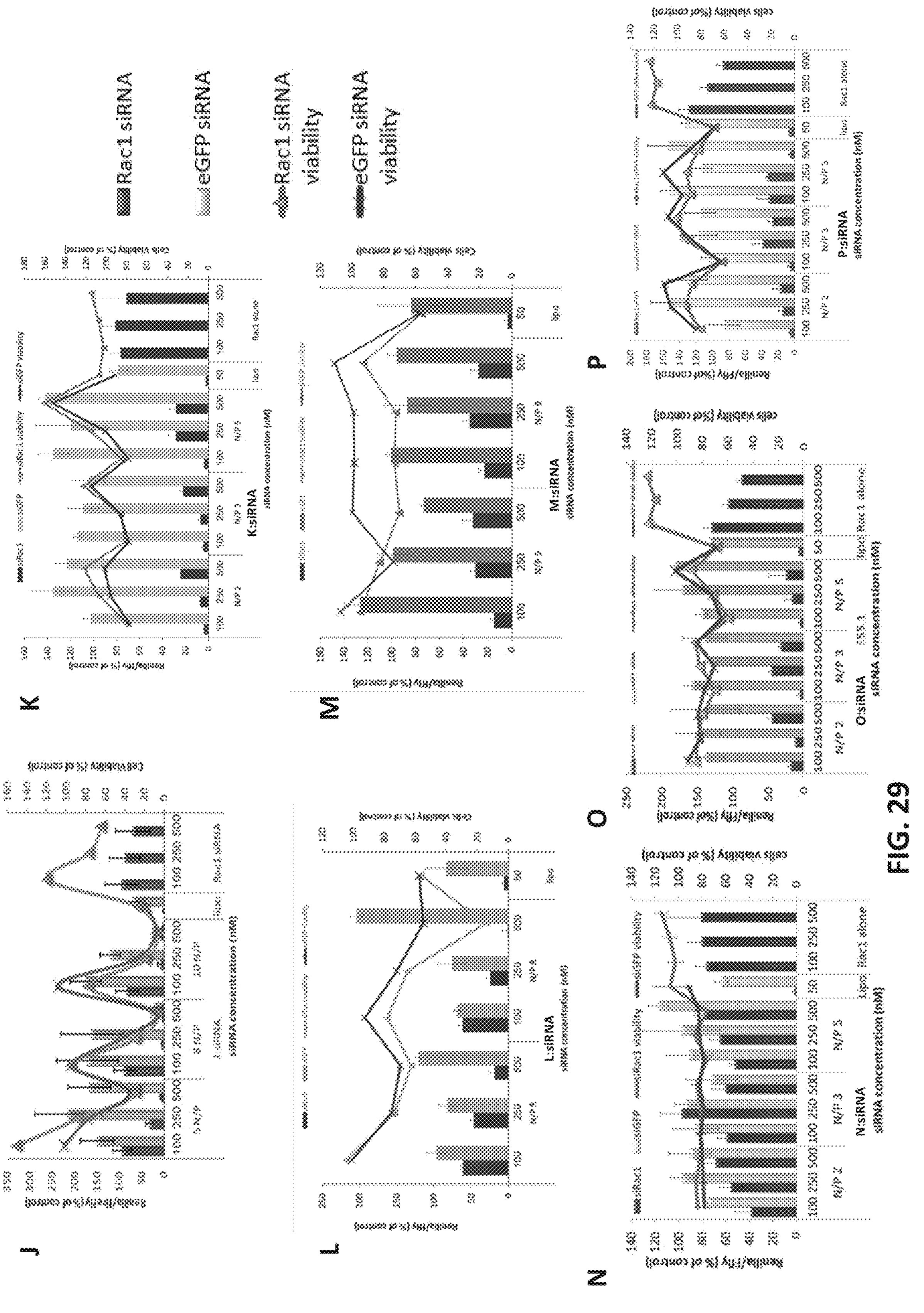

FIG. 29 presents the silencing activity and in vitro toxicity values of exemplary alkylated PGA amine polymers J-P complexed with Rac1 siRNA as indicated by dual luciferase reporter assay (bars) and MTT assay (lines) respectively.

FIGS. 30A-D present data obtained for a formulation of K:Rac1 siRNA polyplexes. FIG. 30A presents the hydrodynamic diameter of non-formulated K:Rac1 siRNA 2 N/P ratio polyplex as measured by zetasizer ZS. FIG. 30B presents the hydrodynamic diameter distribution of K:Rac1 siRNA 2 N/P ratio polyplex assembled in water by a microfluidic system as measured by zetasizer ZS. FIG. 30C presents the hydrodynamic diameter distribution of K:Rac1 siRNA 1.5 N/P ratio polyplex assembled by microfluidic system in 5% (weight/volume) glucose, as measured by zetasizer ZS. FIG. 30D presents a table summarizing the N/P ratios, formulation, obtained hydrodynamic diameters and PDI of K:Rac1 siRNA polyplexes.

Figure 31A:
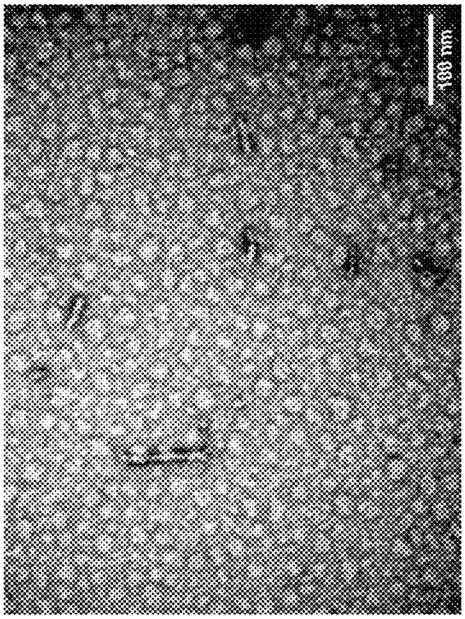
Figure 31B:
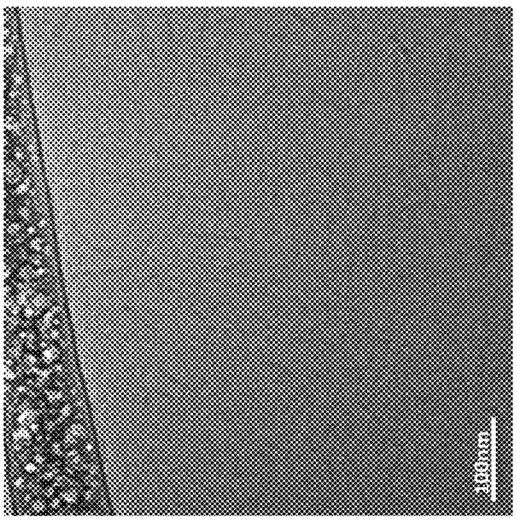
Figure 31C:
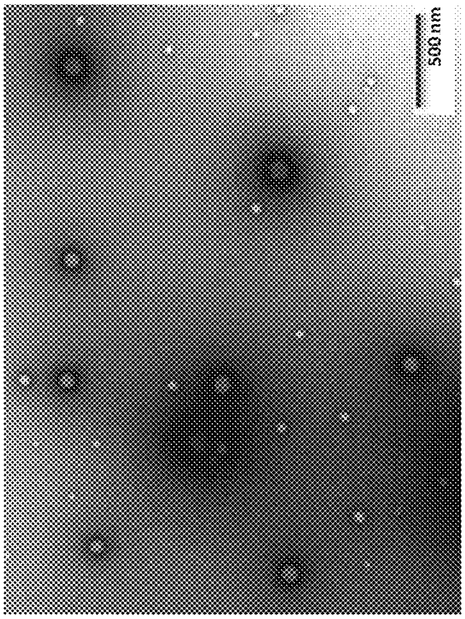
Figure 31D:
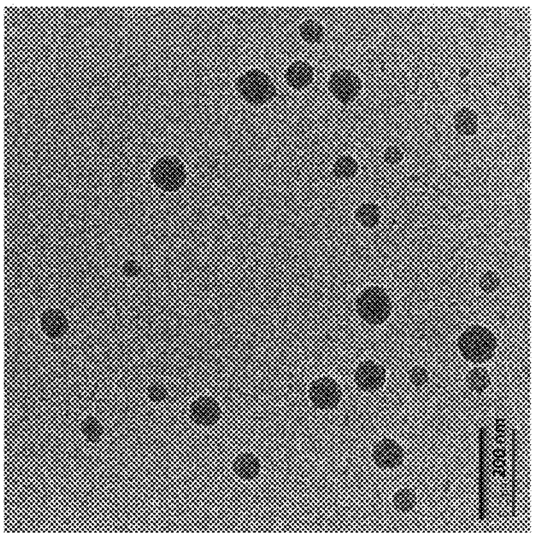

FIGS. 31A-D present a characterization of PGAamine K vs. K:siRNA 1.5 N/P nanoparticles. FIG. 31A is a TEM image of PGAamine polymer indicating rod shaped particles bearing about 5 nm width. FIG. 31B is a Cryo-TEM image of PGAamine polymer showing rod-shaped particles with similar about 5 nm width. FIG. 31C is a TEM image of PGAamin:siRNA polyplexes indicating average diameter of 50±25 nm. FIG. 31D is a Cryo-TEM image of PGAamine:siRNA polyplexes demonstrating average diameter of 60±30 nm.

Figure 32:
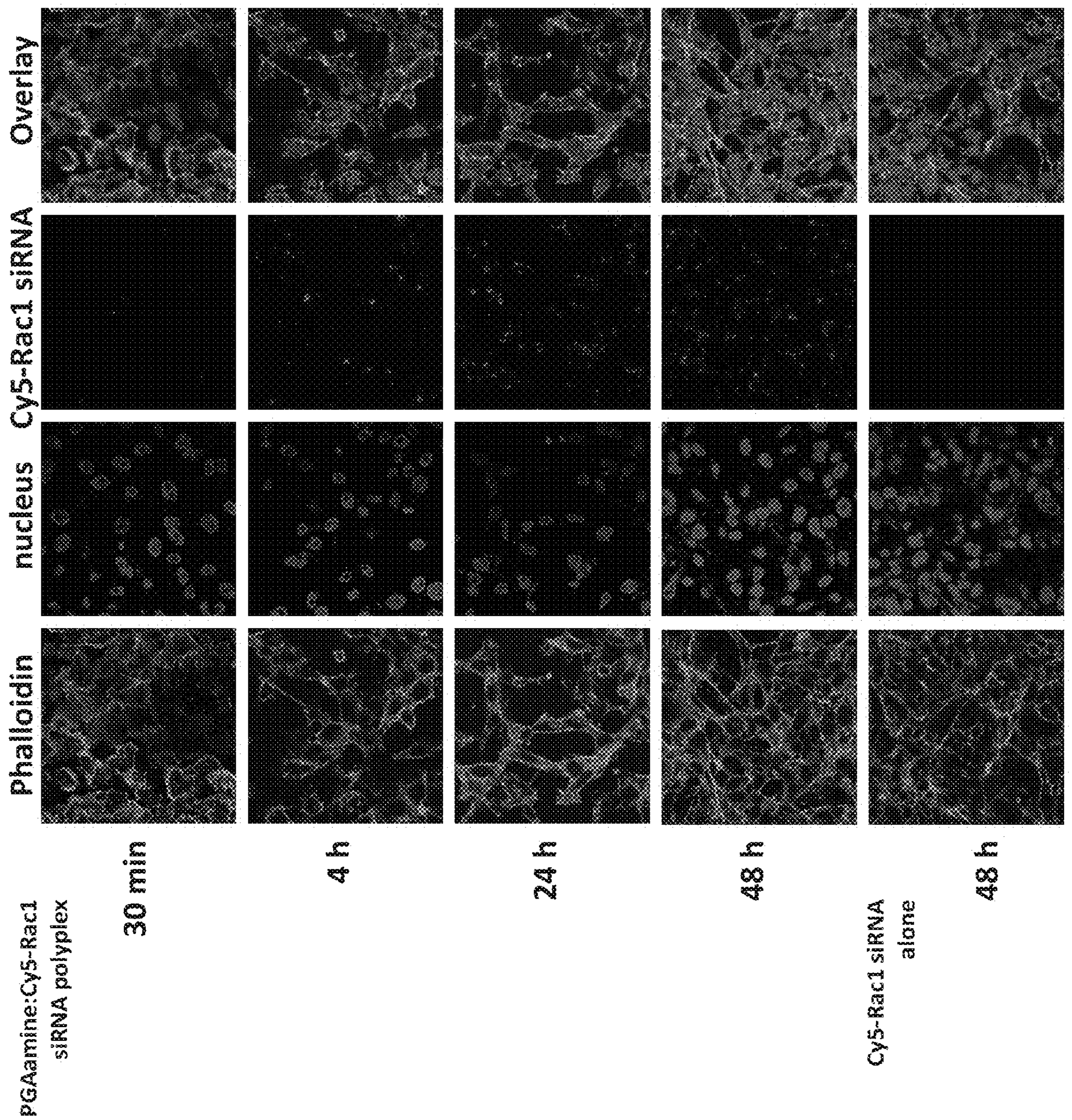

FIG. 32 presents images the cell internalization of PGAamine:Cy5-Rac1 siRNA polyplexes. MDA-MB-231 cells were treated with PGAamine:Cy5-Rac1 siRNA polyplexes at 100 nM concentration for 30 minutes to 48 hours. Time course internalization is indicated by the appearance of Cy5 clusters inside the cells following 4 hours of treatment and the gradual increase in stains over time up to 48 hours. No Cy5 signal was shown in cells treated with naked Cy5-Rac1 siRNA demonstrating the naked siRNA could not internalize to cells.

Figure 33A:
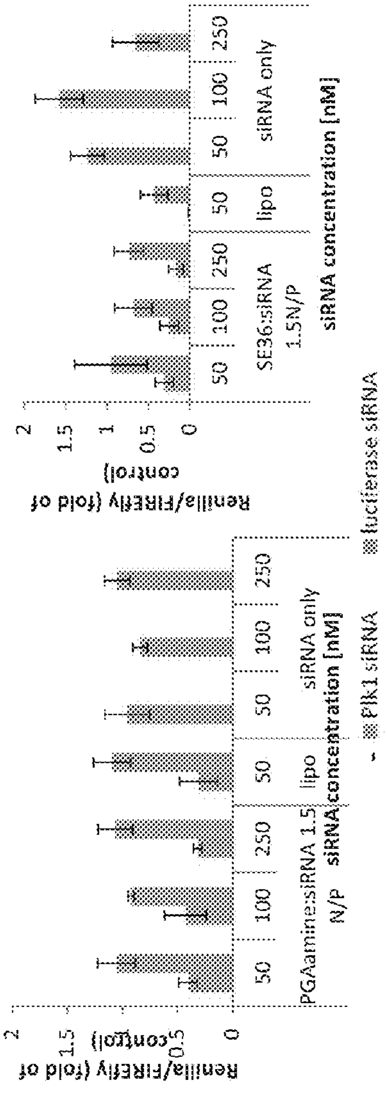
Figure 33B:
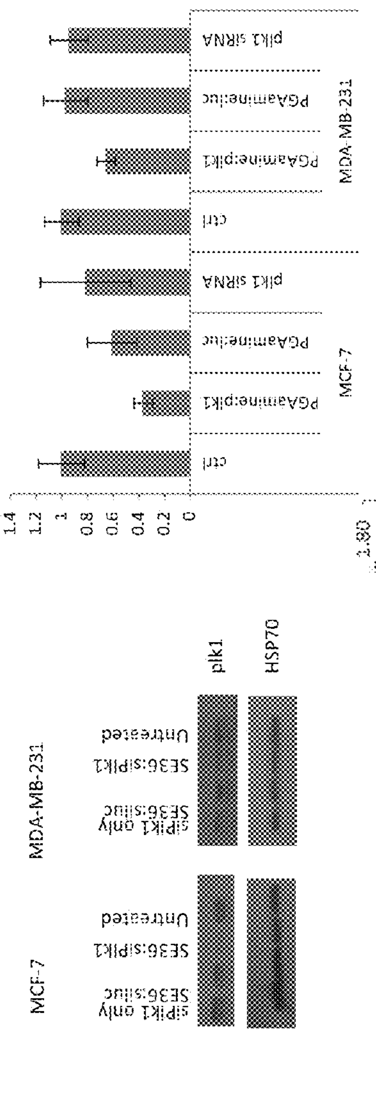
Figure 33C:
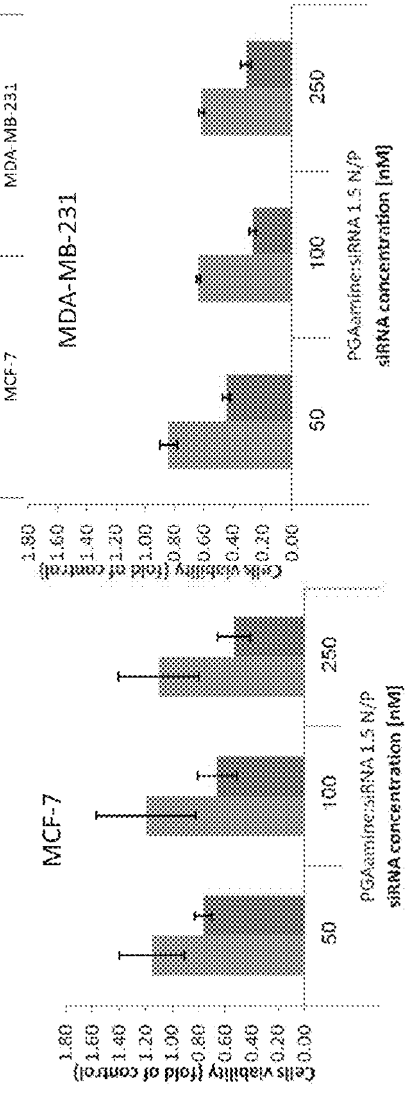

FIGS. 33A-C presents data demonstrating the in vitro activity of SE36 (PGAamine K):siRNA polyplexes on MDA-MB-231 and MCF-7 mammary adenocarcinoma cells. FIG. 33A are bar graphs showing data obtained in a dual luciferase assay of Plk1 siRNA polyplexes. FIG. 33B present a Western blot and corresponding bar graph of MDA-MB-231 and MCF-7 cells performed on cells treated for 48 hours. FIG. 33C are bar graphs showing the viability of MCF-7 and MDA-MB-231 cells treated with SE36:Plk1 or luciferase siRNA polyplexes for 72 hours.

Figure 34A:
Figure 34B:
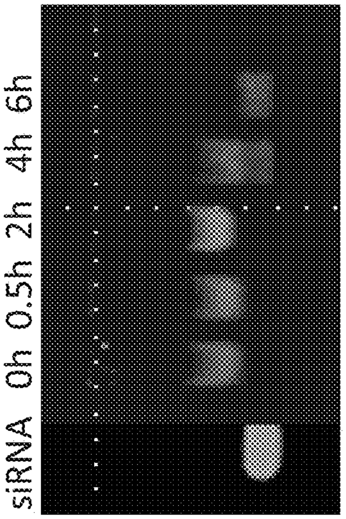
Figure 34C:
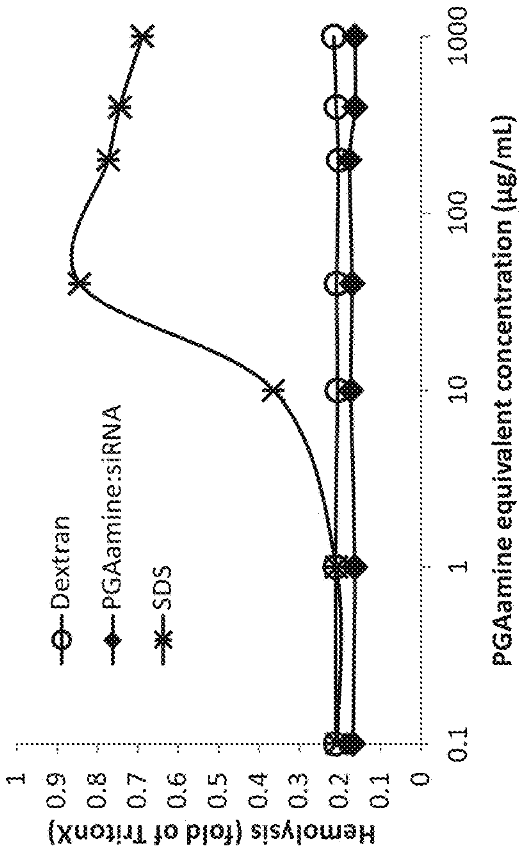

FIGS. 34A-C present the stability and toxicity of SE36 (PGAamine K):siRNA polyplexes at 1.5 N/P ratio. FIG. 34A presents data obtained in a Heparin displacement assay. The international heparin units per sample of 50 pmol siRNA are specified above the gel images. FIG. 34B presents the stability of polyplexes following incubation in 100% serum for the time course specified above the gel. FIG. 34C presents plots showing red blood cell lysis following incubation with PGAamine:siRNA 1.5 N/P ratio polyplexes, SDS (positive control) and dextran (negative control). Results are normalized to hemoglobin released following incubation with tritonX. Data represents mean±SD.

Figure 35A:
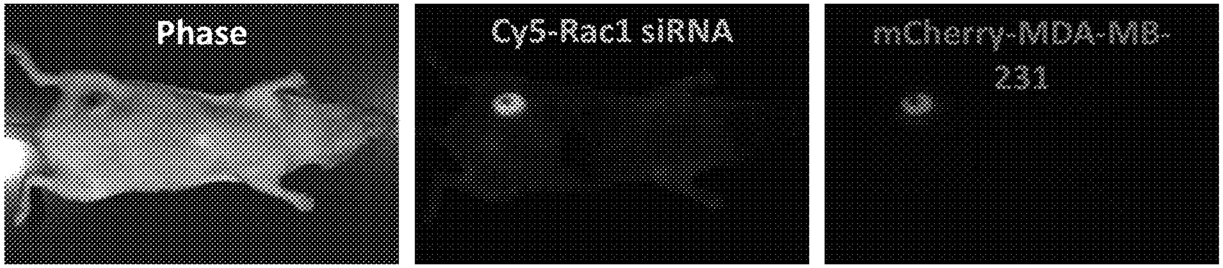
Figure 35B:
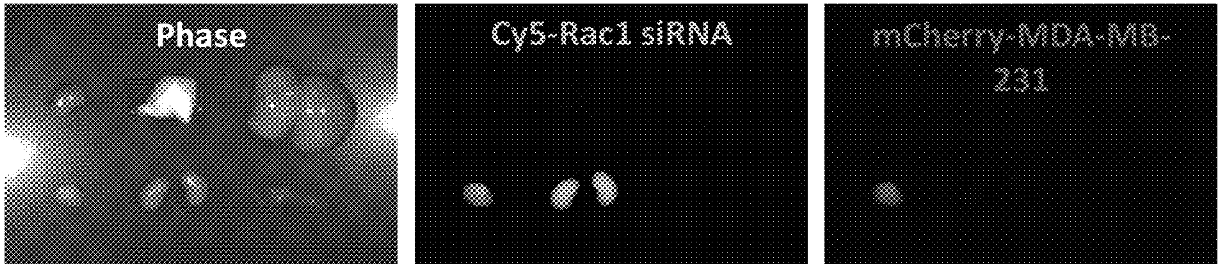
Figure 35C:
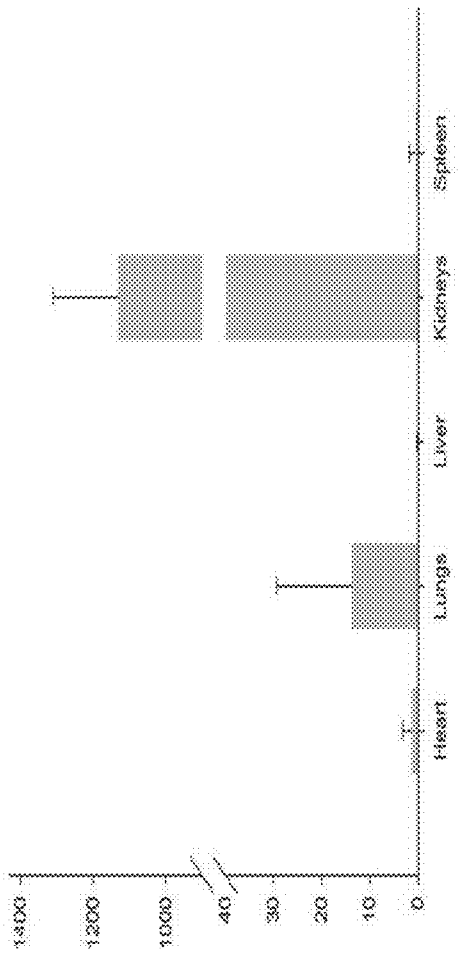
Figure 35D:
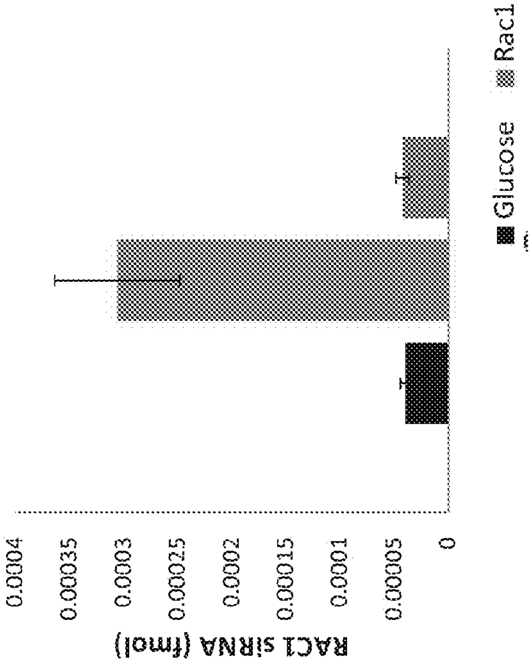
Figure 35E:
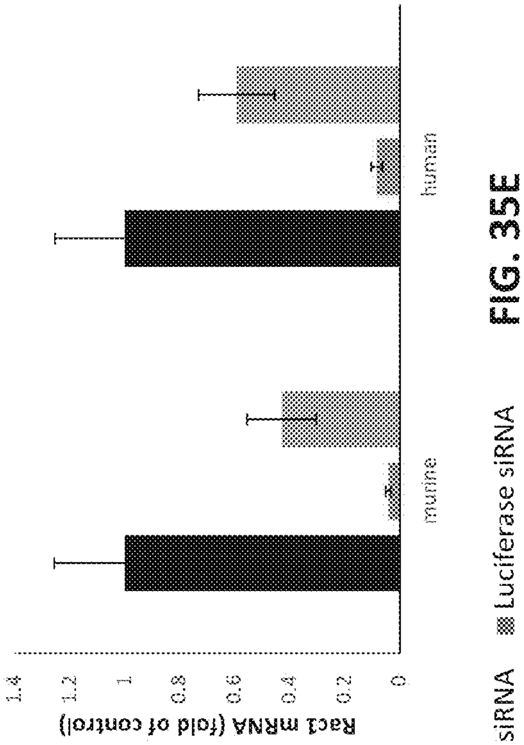

FIGS. 35A-E present representative images of mammary MDA-MB-231 tumor bearing nu/nu mouse 24 hours following IV administration of 1.5 mg/kg PGAamine K:Cy5-Rac1 siRNA polyplexes (FIG. 35A); of organs resection of the same mouse which revealed high Cy5 fluorescence obtained from kidneys (FIG. 35B); a bar graph presenting quantification of the signals obtained from the organs of 5 mice 24 hours from a single IV injection (FIG. 35C); and bar graphs showing siRNA levels in tumors of mice treated with PGAamine K:Plk11siRNA at 1.5 mg/kg siRNA dose for 3 sequential days, 24 hours from last injection, n=5, ave ±SD (FIG. 35D); and murine (left) and human (right) Rac1 mRNA levels in tumors of mice treated with PGAamine K:Rac1siRNA at 1.5 mg/kg siRNA dose for 3 sequential days, 24 hours from last injection, n=5, ave ±SD (FIG. 35E).

Figure 36A:
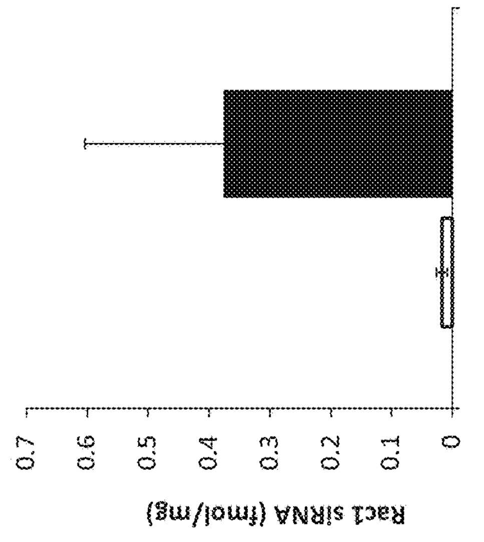
Figure 36B:
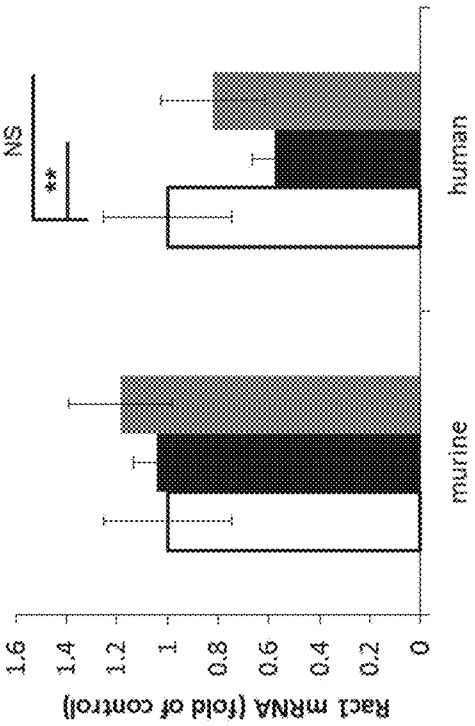
Figure 36C:
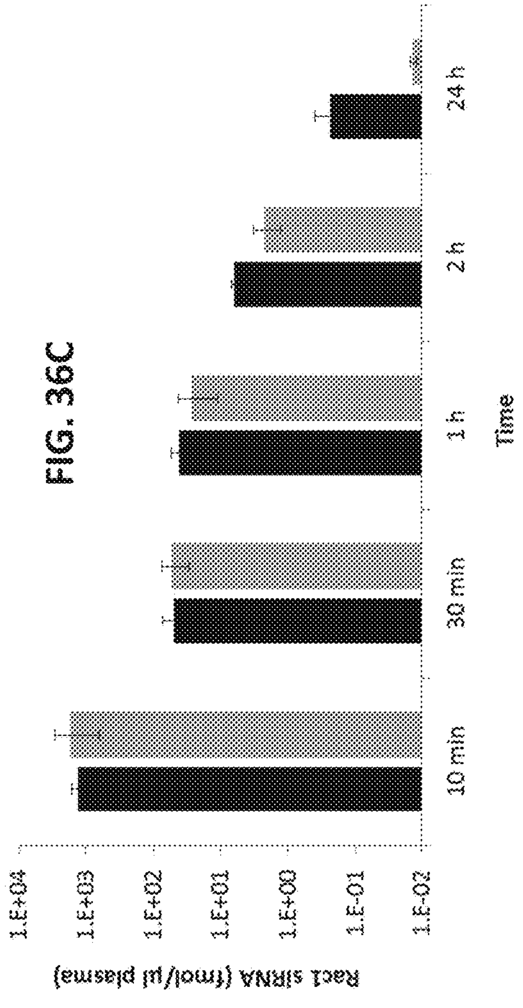

FIGS. 36A-C present data showing that PGAamine K:siPlk polyplexes selectively accumulated in A549 SC tumors and non-significantly silenced human Rac1 mRNA to ~0.7 fold. FIG. 36A is a bar graph showing siRNA levels in tumors of mice treated with PGAamine K:Plk11 siRNA (black) at 4 mg/kg siRNA dose or PBSx1 (white) for 3 sequential days, 24 hours from last injection. n=5, ave ±SD. FIG. 36B is a bar graph showing human and murine Rac1 mRNA levels in tumors of mice treated with PGAamine:Plk11 siRNA (black), Rac1 siRNA alone (gray) (4 mg/kg siRac1 concentration) or PBSx1 (white) for 3 sequential days, 24 hours from last injection. n=5, ave ±SD. <0.01. FIG. 36**C is a bar graph showing blood levels of Rac1 siRNA following single IV injection of PGAamine K:siRac (black) or Rac siRNA alone (gray) at 4 mg/kg siRNA dose to tumor bearing athymic nude mice (n=4).

Figure 37:
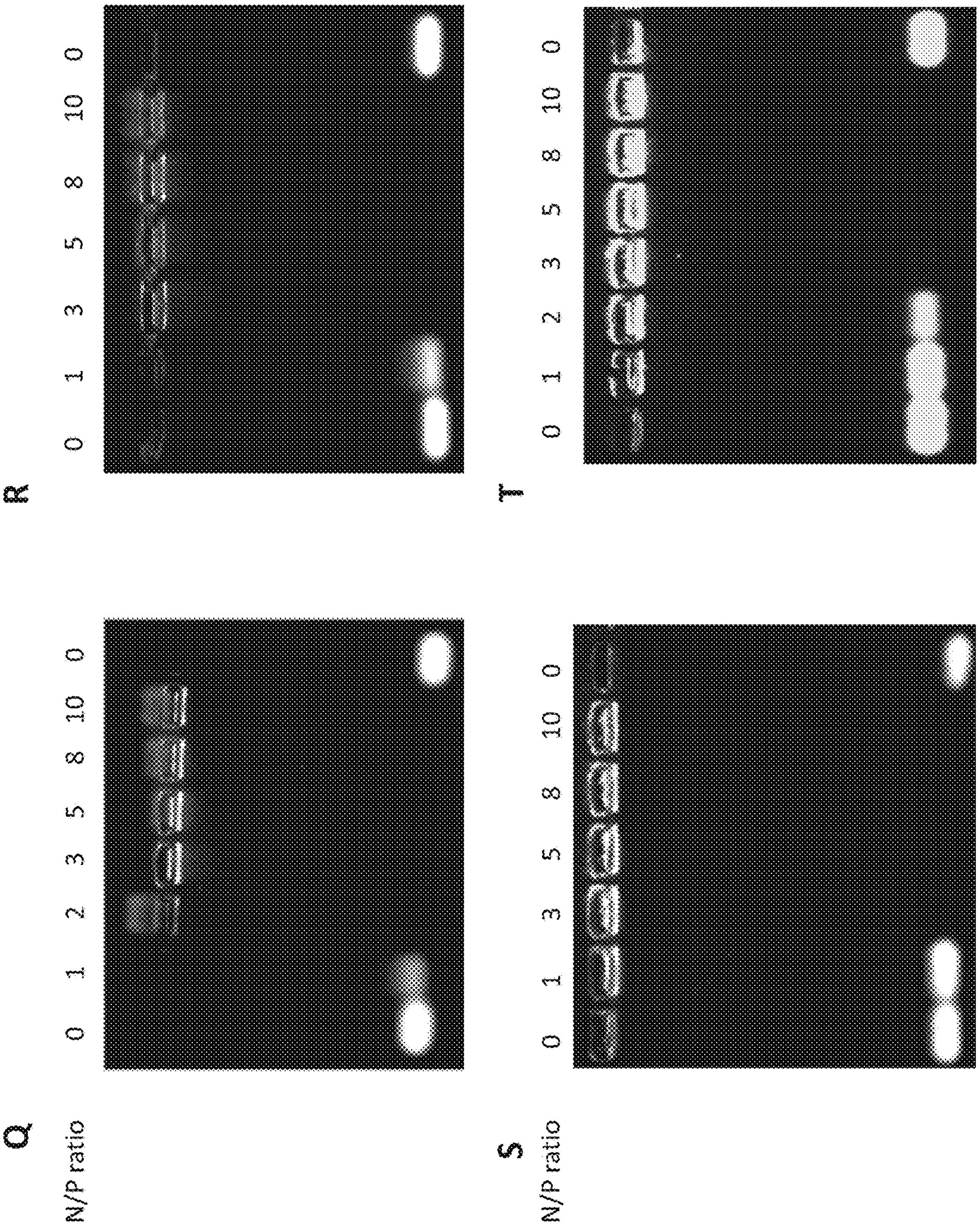

FIG. 37 presents data showing the electrophoresis mobility shift analysis of polymers Q-T complexed with Rac1 siRNA at the indicated nitrogen/phosphorus (N/P) ratios. Each polymer was incubated with 50 pmol of Rac1 siRNA for 30 minutes at room temperature in RNase free water. The samples were loaded on ethidium bromide-stained 2% agarose gel, supplied with voltage of 100 volts for 30 minutes and inspected under UV light.

Figure 38:
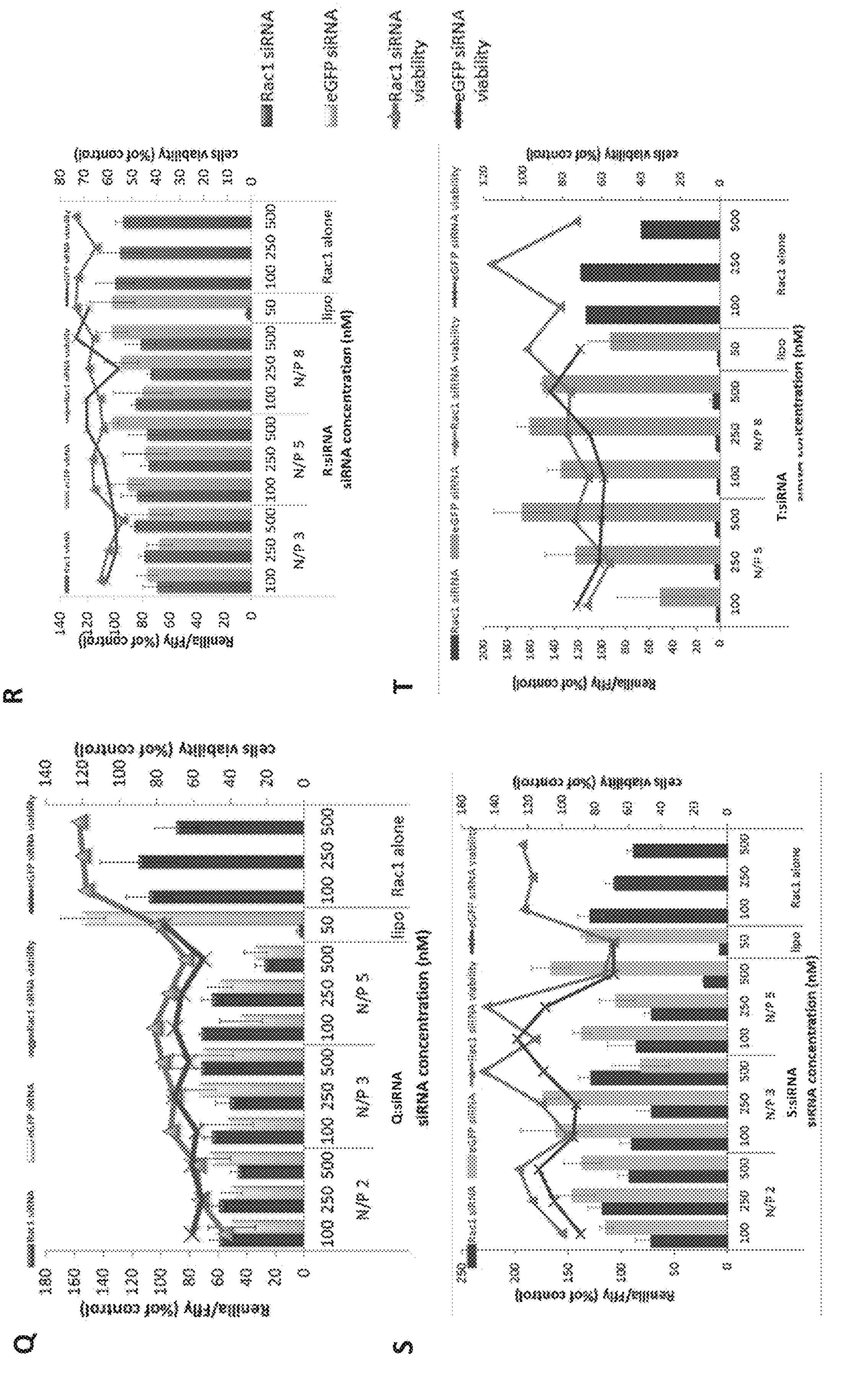

FIG. 38 presents the silencing activity and in vitro toxicity values of PGAamines Q-T:Rac1 siRNA polyplexes as indicated by dual luciferase reporter assay (bars) and MTT assay (lines) respectively.

Figure 39:
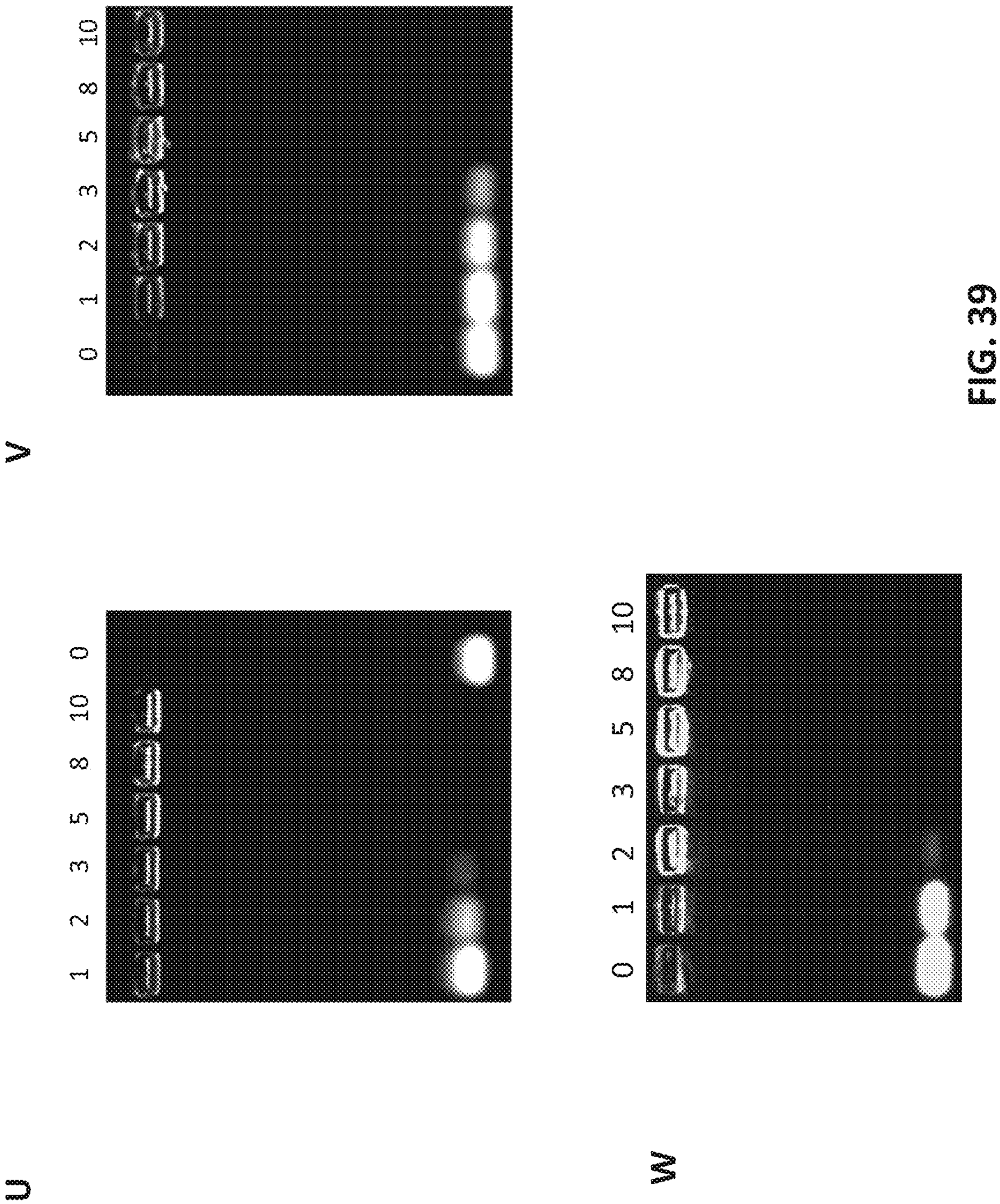

FIG. 39 presents electrophoresis mobility shift analysis of polymers U-W complexed with Rac1 siRNA at the indicated nitrogen/phosphorus (N/P) ratios. Each polymer was incubated with 50 pmol of Rac1 siRNA or miR-34a for 30 minutes at room temperature in RNase free water. The samples were loaded on ethidium bromide-stained 2% agarose gel, supplied with voltage of 100 volts for 30 minutes and inspected under UV light.

Figure 40:
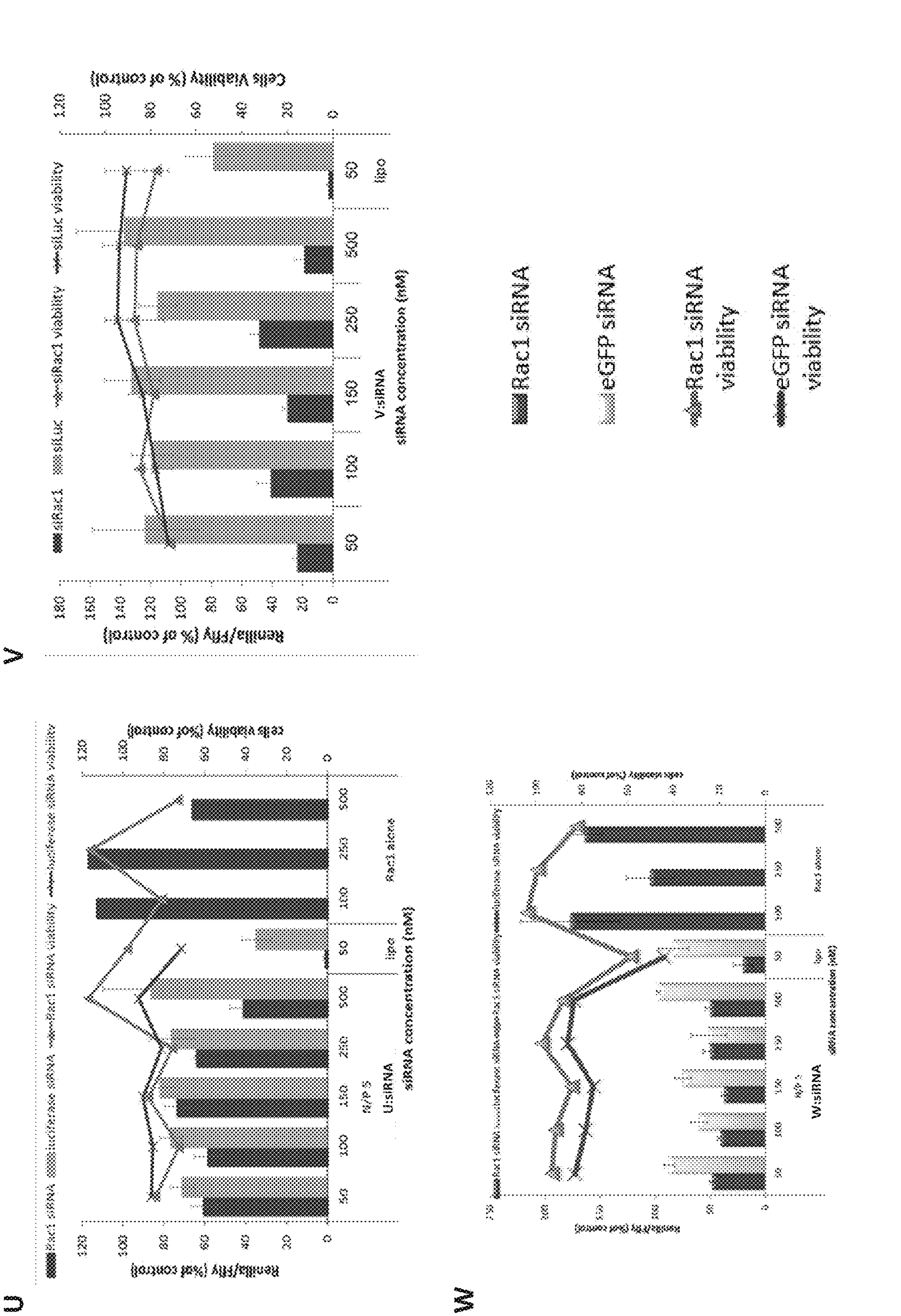

FIG. 40 presents the silencing activity and in vitro toxicity values of PGAamines U-W:Rac1 siRNA polyplexes as indicated by dual luciferase reporter assay (bars) and MTT assay (lines) respectively.

Figure 41:
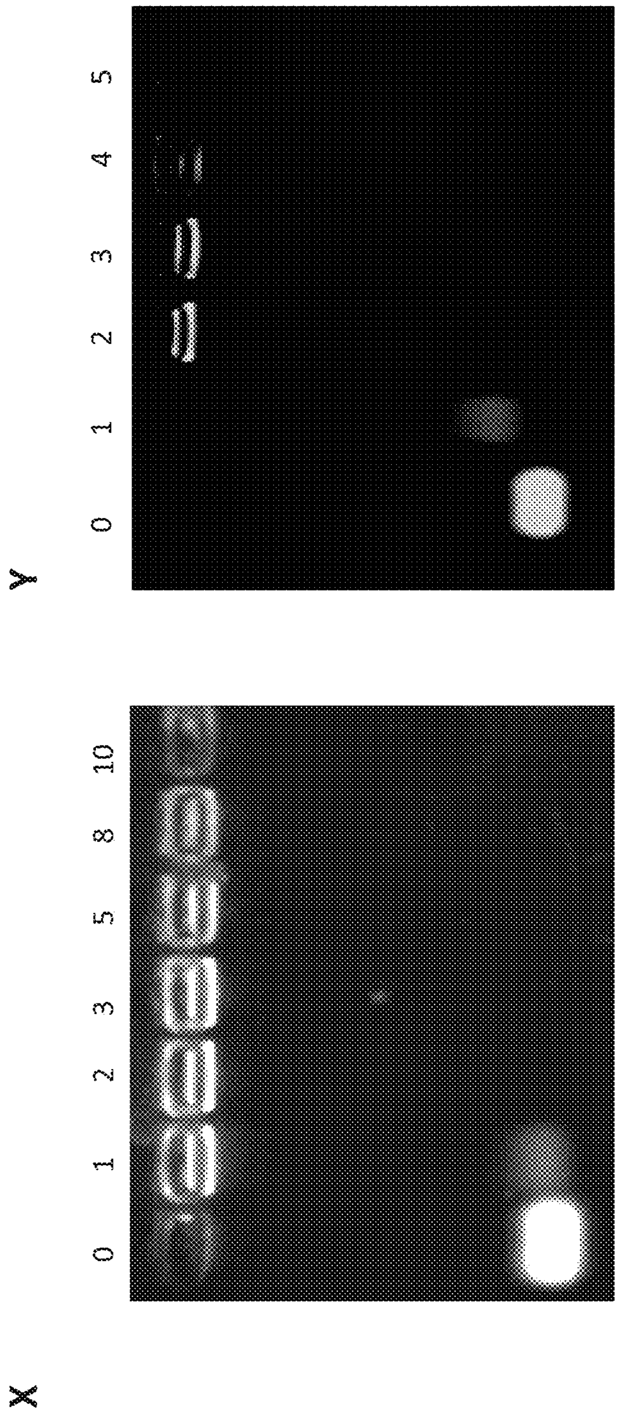

FIG. 41 presents electrophoresis mobility shift analysis of polymers X and Y complexed with Rac1 siRNA at the indicated nitrogen/phosphorus (N/P) ratios. Each polymer was incubated with 50 pmol of Rac siRNA for 30 minutes at room temperature in RNase free water. The samples were loaded on ethidium bromide-stained 2% agarose gel, supplied with voltage of 100 volts for 30 minutes and inspected under UV light.

Figure 42:
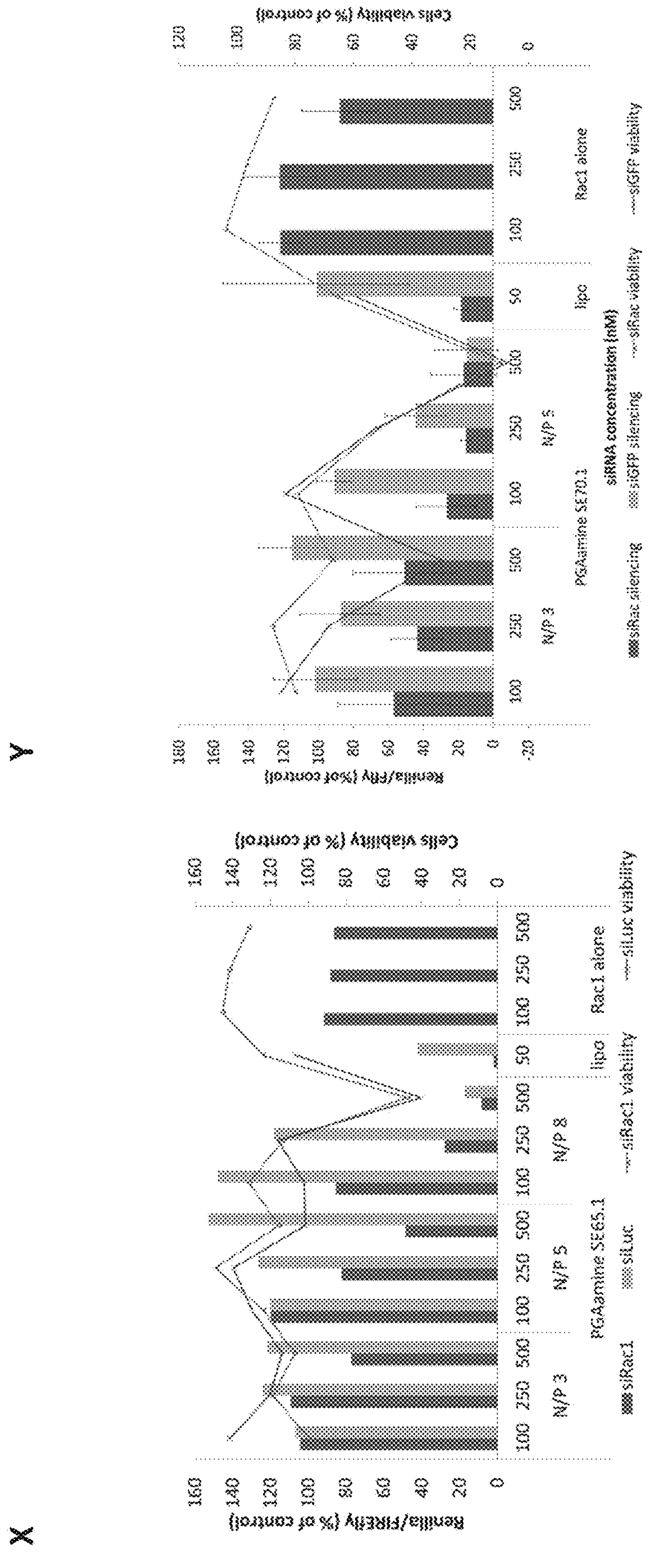

FIG. 42 presents the silencing activity and in vitro toxicity values of X-Y:Rac1 siRNA polyplexes as indicated by dual luciferase reporter assay (bars) and MTT assay (lines) respectively.

Figure 43A:
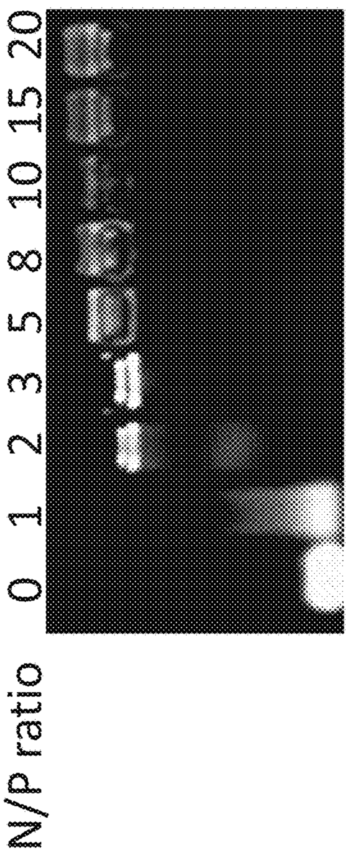
Figure 43B:
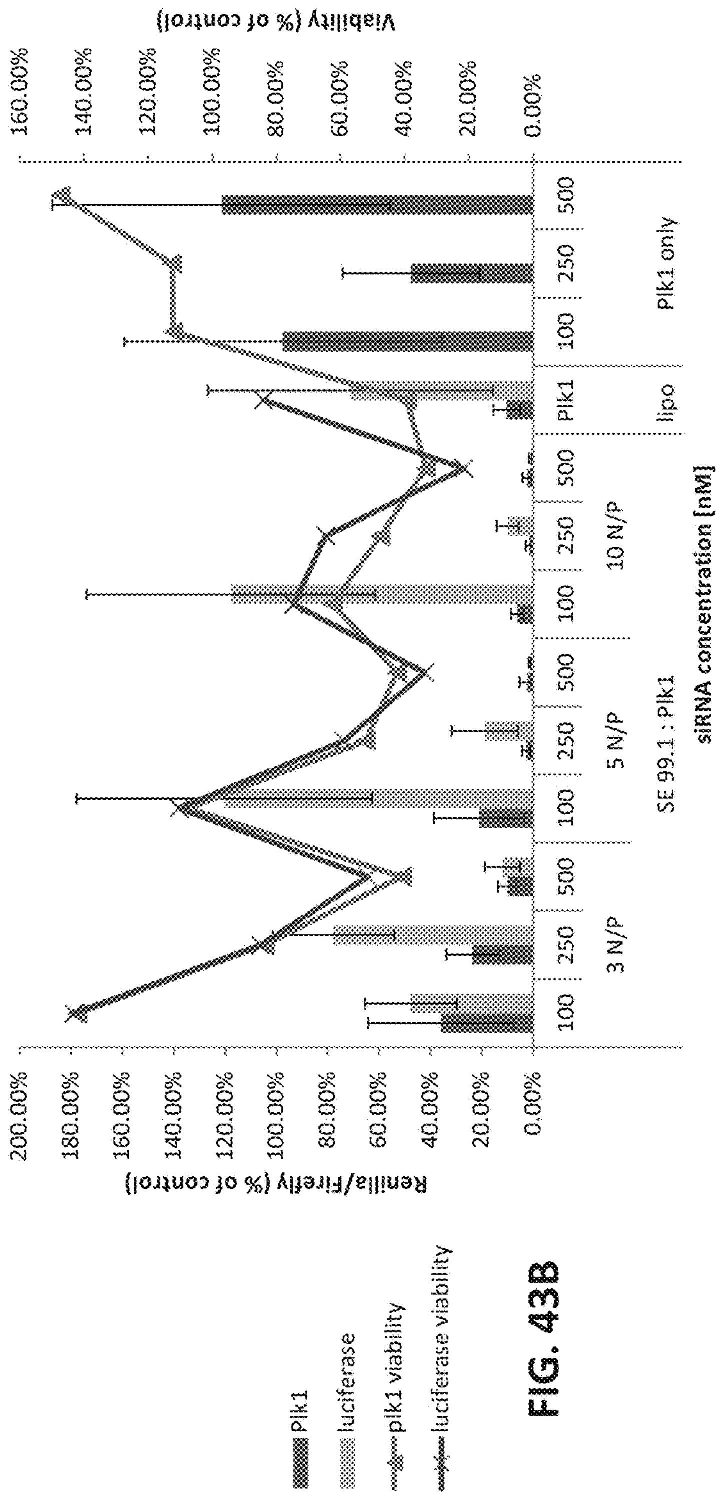

FIGS. 43A-B present data demonstrating the electrostatic interaction between cross linked co-polymer-lysine$_{(10\%)}$-γ-ethylenediamine-L-polyglutamate$_{(90\%)}$ (Polymer CL1) and siRNA and the silencing activity of exemplary polyplexes composed of cross linked co-polymer-lysine$_{(10\%)}$-γ-ethylenediamine-L-polyglutamate$_{(90\%)}$ (Polymer CL1) and Rac1 siRNA according to some embodiments of the present invention. FIG. 43A presents the electrophoresis mobility shift analysis of polymer CL1 complexed with siRNA at the indicated nitrogen/phosphorus (N/P) ratios. FIG. 43B presents the silencing activity and in vitro toxicity values of Polymer CL1:Rac1 siRNA polyplexes as indicated by dual luciferase reporter assay (bars) and MTT assay (lines) respectively.

Figure 44:
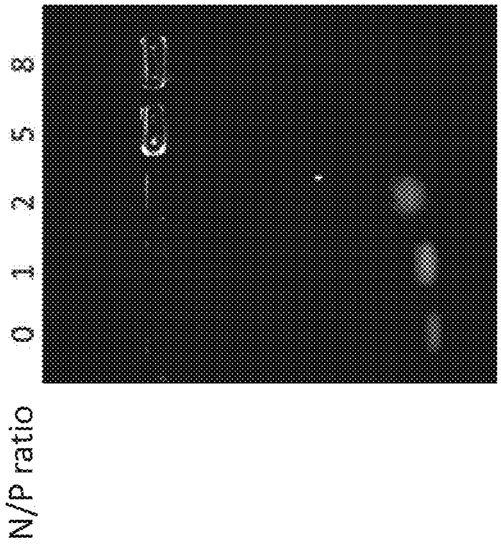

FIG. 44 presents data demonstrating the electrostatic interaction between α-hexyl-amino acid-PGAamine block copolymer and siRNA according to some embodiments of the present invention. Electrophoresis mobility shift analysis of Co-polymer BL1 complexed with siRNA at the indicated nitrogen/phosphorus (N/P) ratios.

Figure 45A:
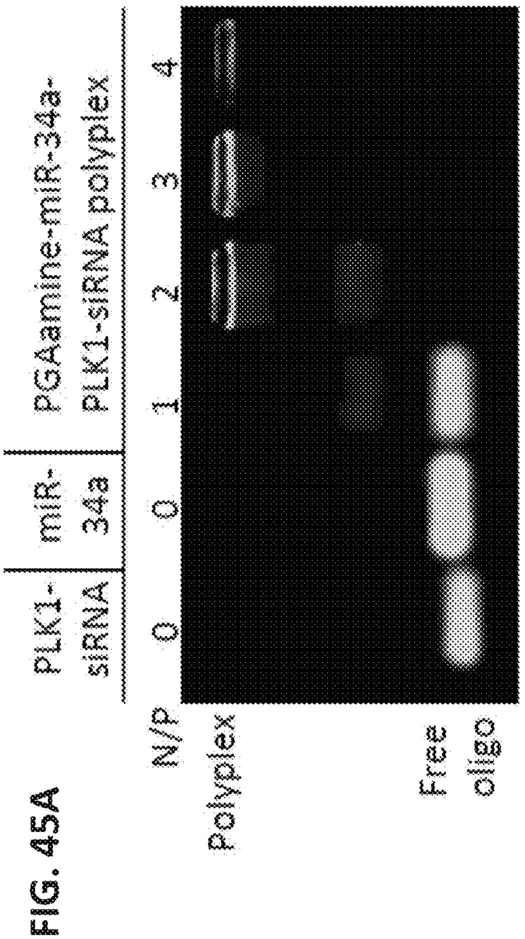
Figure 45B:
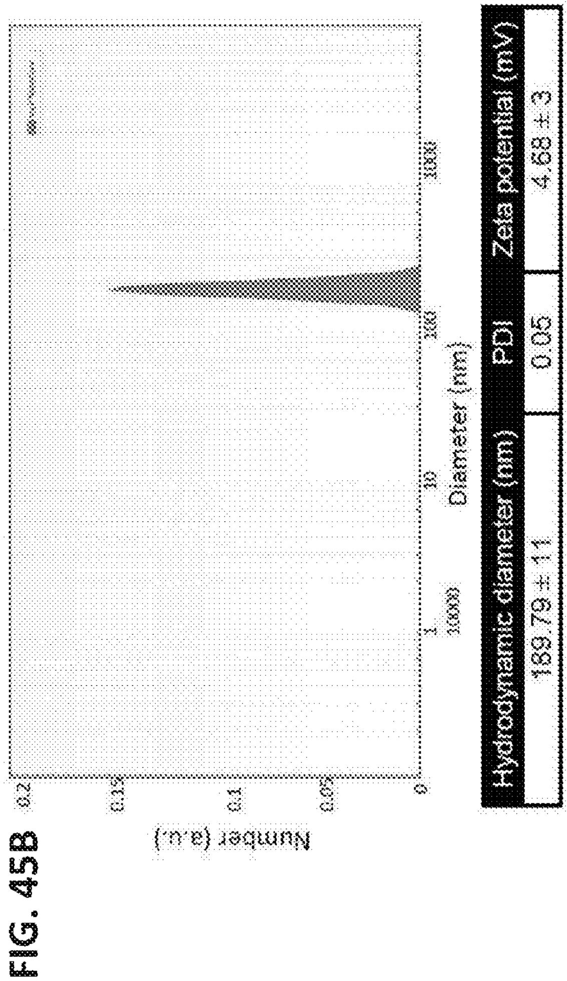
Figure 45C:
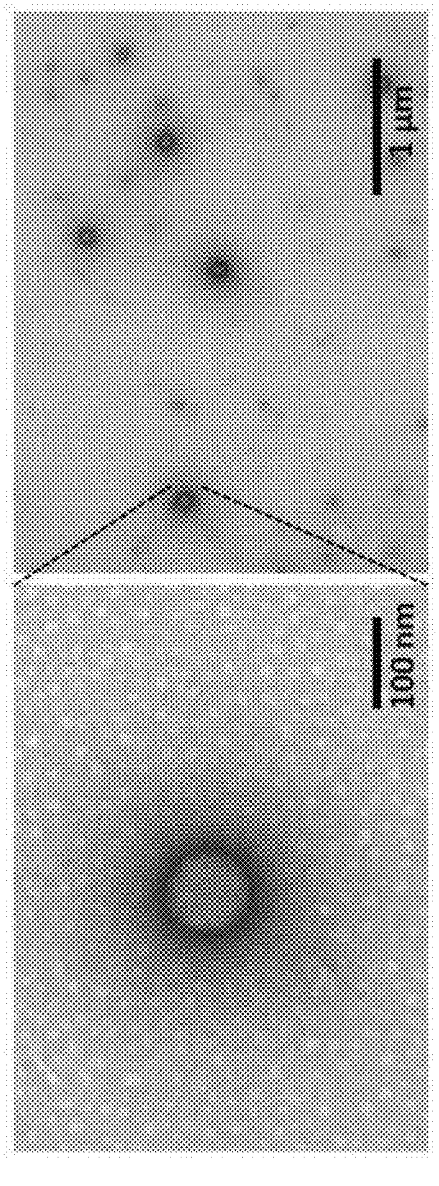
Figure 45D:
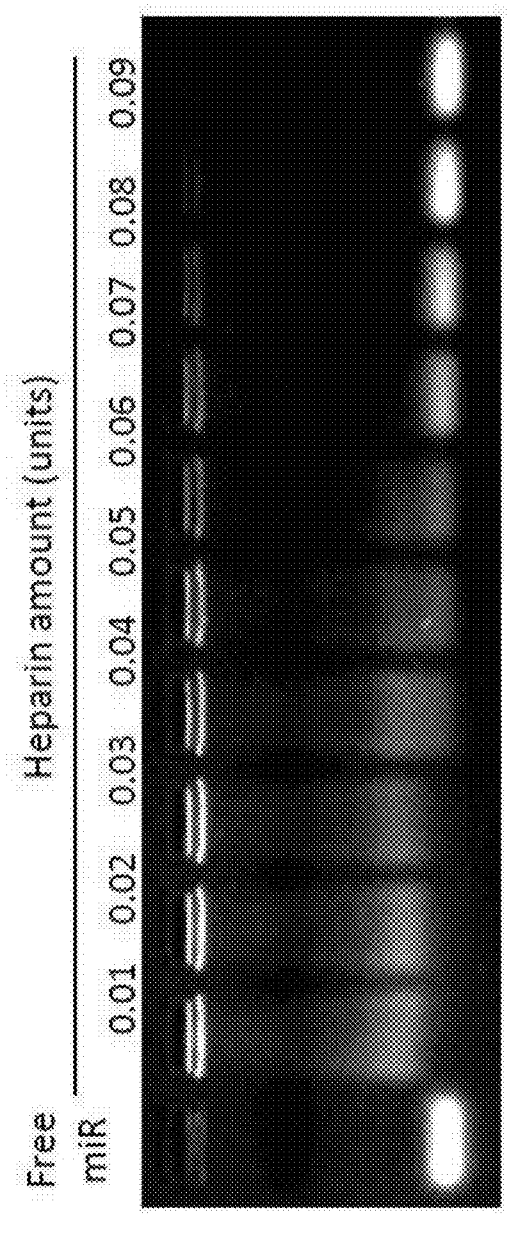

FIGS. 45A-D present some physico-chemical characterization of PGAaine-miR-34a-PLK1-siRNA polyplexes. FIG. 45A presents polyplex formation of PGAamine and miR-34a-PLK1-siRNA at several N/P ratios using EMSA. Different amounts of polymer were incubated with miR and siRNA (total 50 pmol) for 20-30 minutes at room temperature in ultra-pure water and samples were loaded on 2% agarose gel. FIG. 45B presents the hydrodynamic diameter and surface charge of the polyplex at N/P ratio 2 measured by particle size analyzer and Zetasizer, respectively. FIG. 45C presents TEM images of the polyplex. FIG. 45D presents miR-34a release from the polyplex was obtained in vitro by the polyanion heparin displacement assay.

Figure 46A:
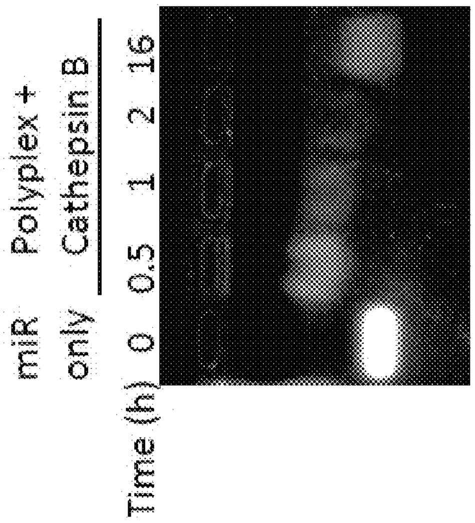
Figure 46B:
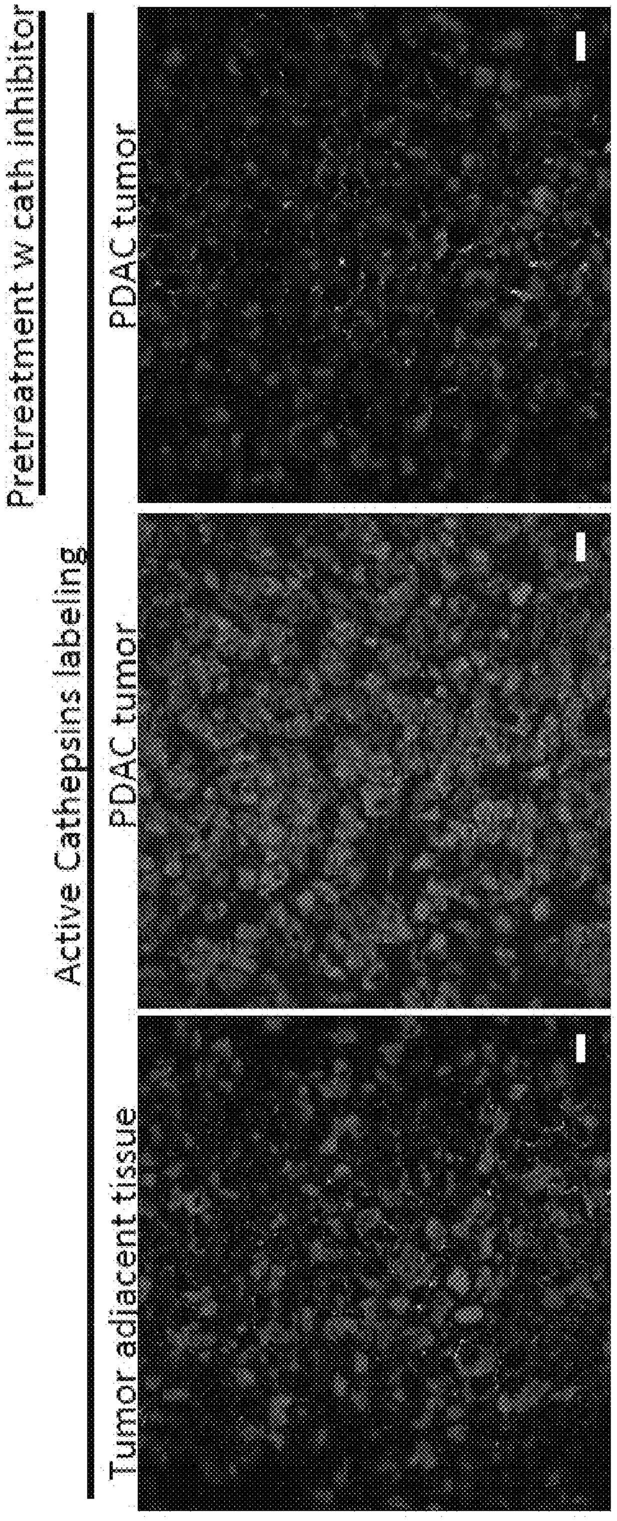

FIGS. 46A-B presents miR-34a release from the polyplex by cathepsin B cleavage of the PGA backbone (FIG. 46A); and direct labeling of active cathepsins in PDAC tumor and normal adjacent tissue (FIG. 46B). Frozen sections were fixed on slides, incubated with 1 μM near infrared fluorescence (NIRF) cathepsin activated-based probe (in red), stained with DAPI (in blue) and imaged with fluorescent microscope. For specificity of staining, slides were treated with non-labeled cathepsin inhibitor (GB111-$NH_2$, 5 μM) before incubation with the NIRF cathepsin activated-based probe (right image). Scale bar=10 μm.

Figure 47A:
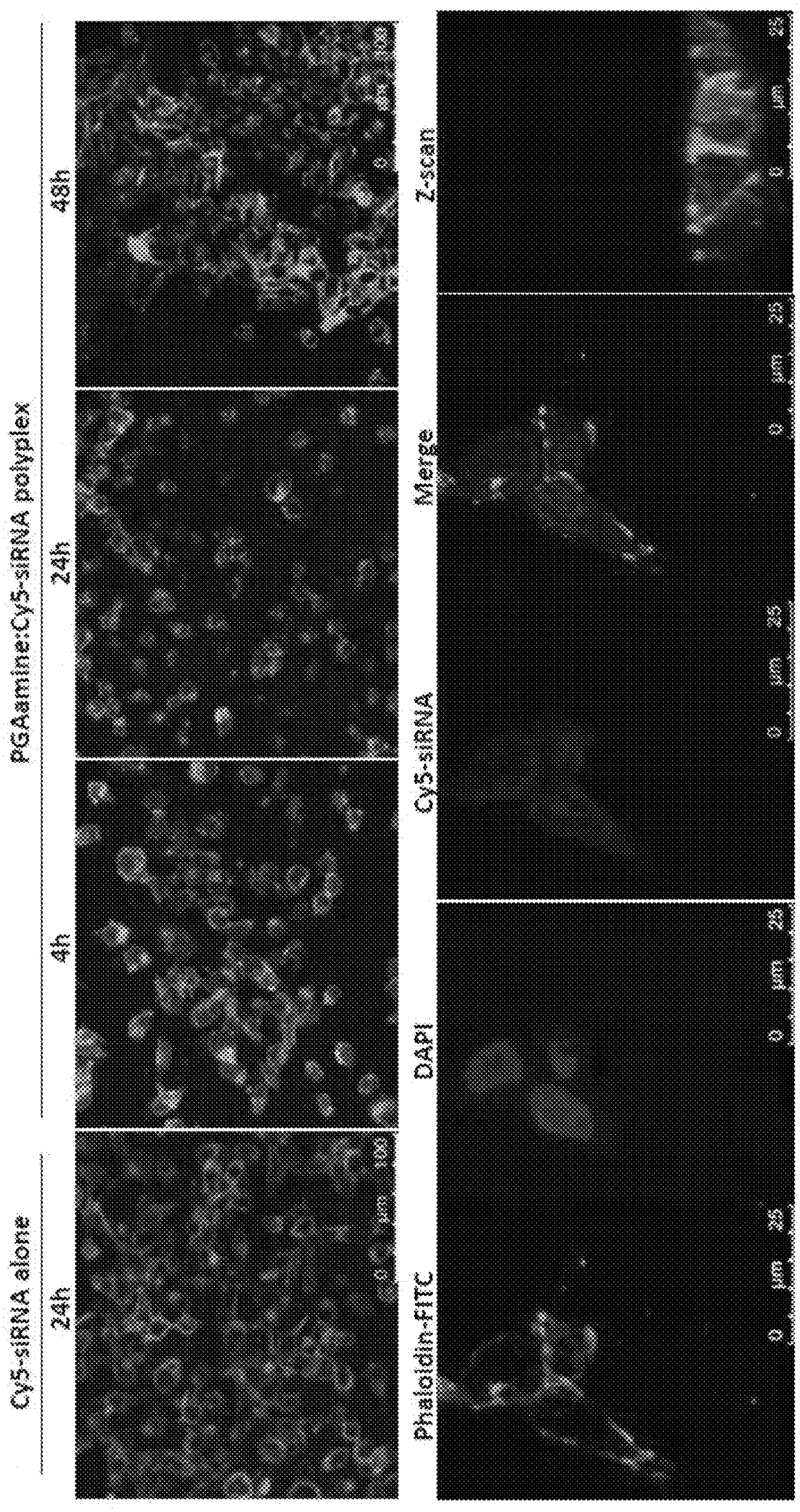
Figure 47B:
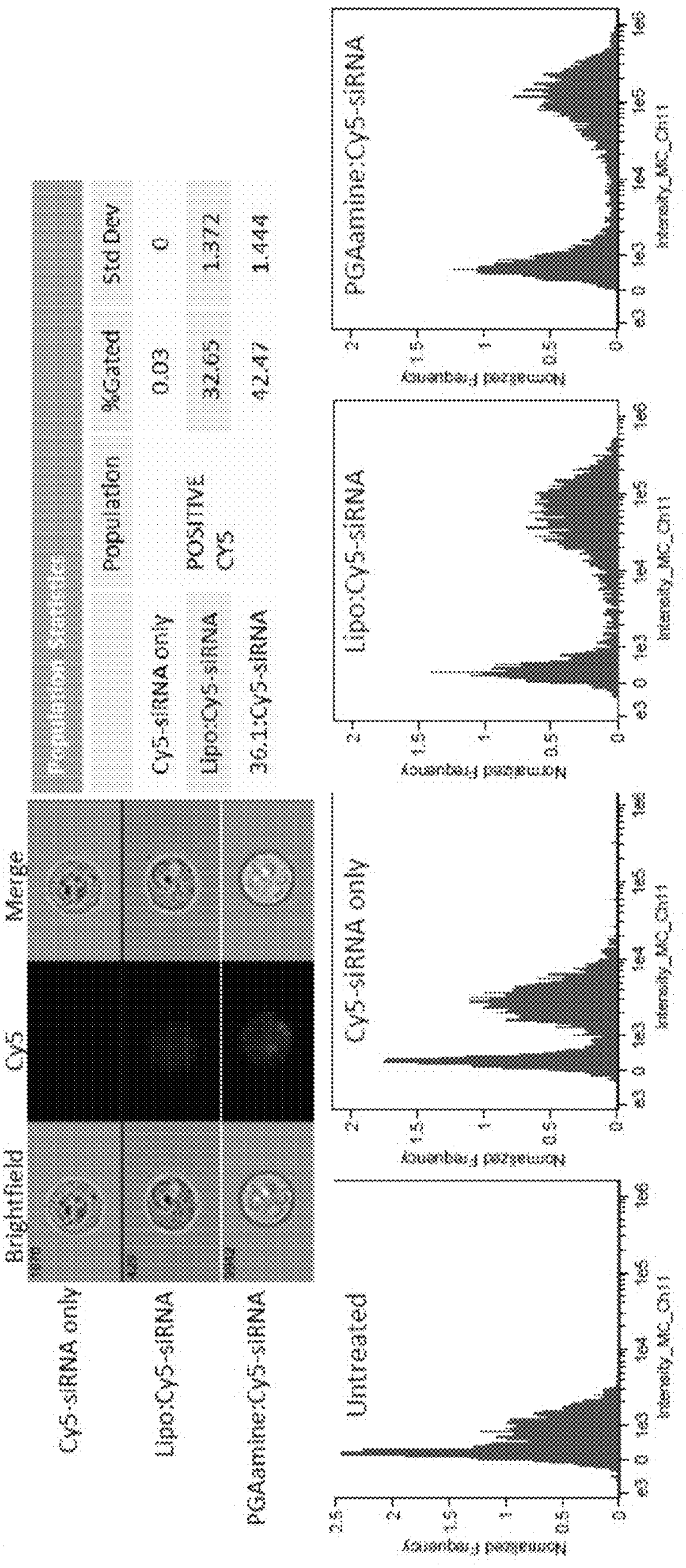

FIGS. 47A-B demonstrate the cellular internalization of PGAamine-siRNA nano-polyplexes into pancreatic cancer cells. MiaPaCa2 cells were seeded on cover slips, incubated with Cy5-labeled siRNA (red) alone or complexed with PGAamine at N/P 2 for 4, 24 and 48 hours (FIG. 47A, upper panel) and analyzed by confocal microscopy. Cells were stained with phalloidin-FITC (green) for actin filaments and DAPI (blue) for nuclei. FIG. 47A, lower panel is a larger magnification of a representative field following 48 hours incubation with the polyplex. Internalization of Cy5-siRNA-PGAamine polyplex into live MiaPaCa2 cells using ImageStream Imaging Flow Cytometer. Live MiaPaCa2 cells were monitored 24 hours following transfection with Cy5-labeled siRNA alone or complexed with either PGAamine or Lipofectamine™2000. FIG. 47B, Left panel presents brightfield and fluorescence images. FIG. 47B, Right panel presents population statistics. FIG. 47B, Lower panel presents internalization histograms.

Figure 48A:
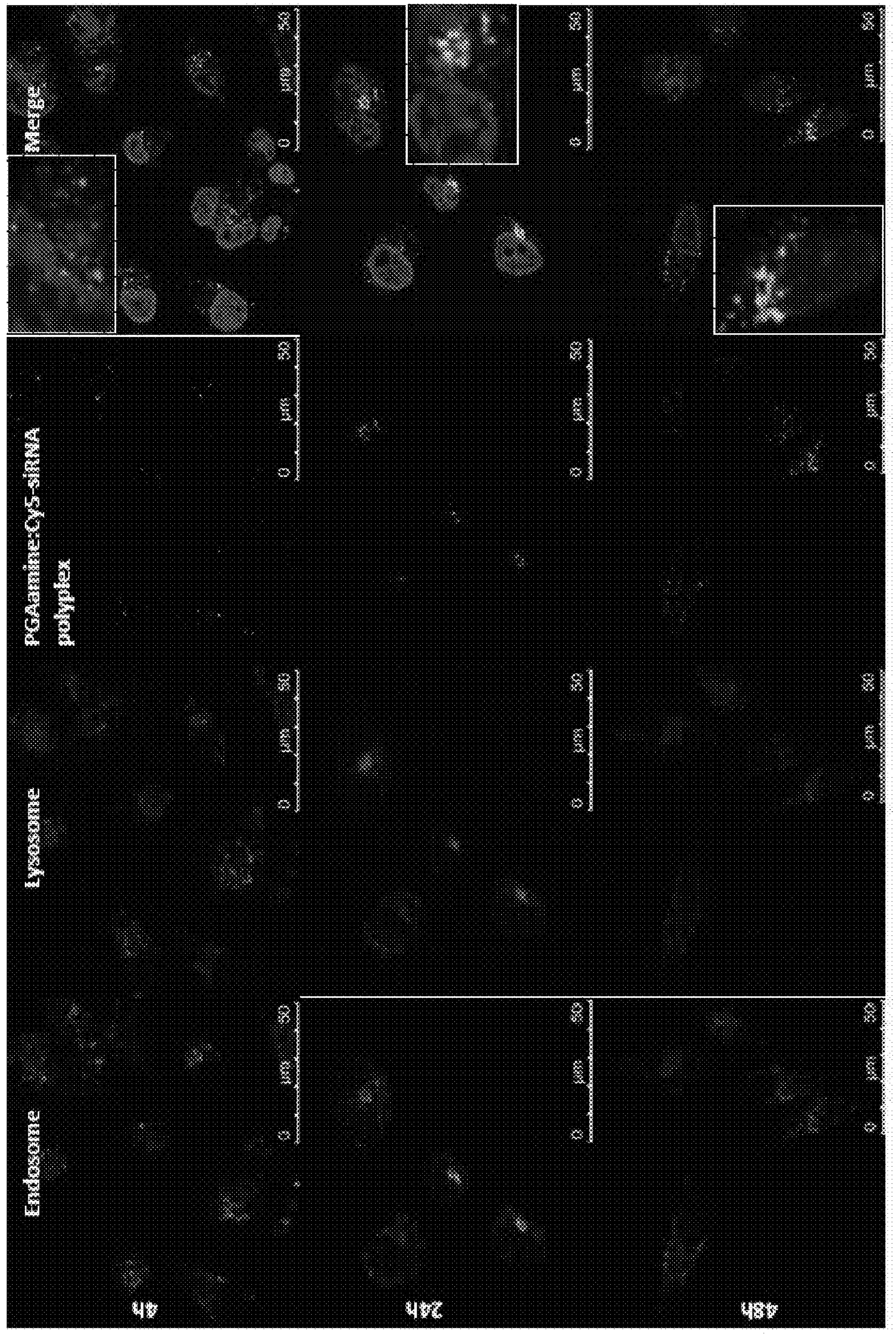
Figure 48C:
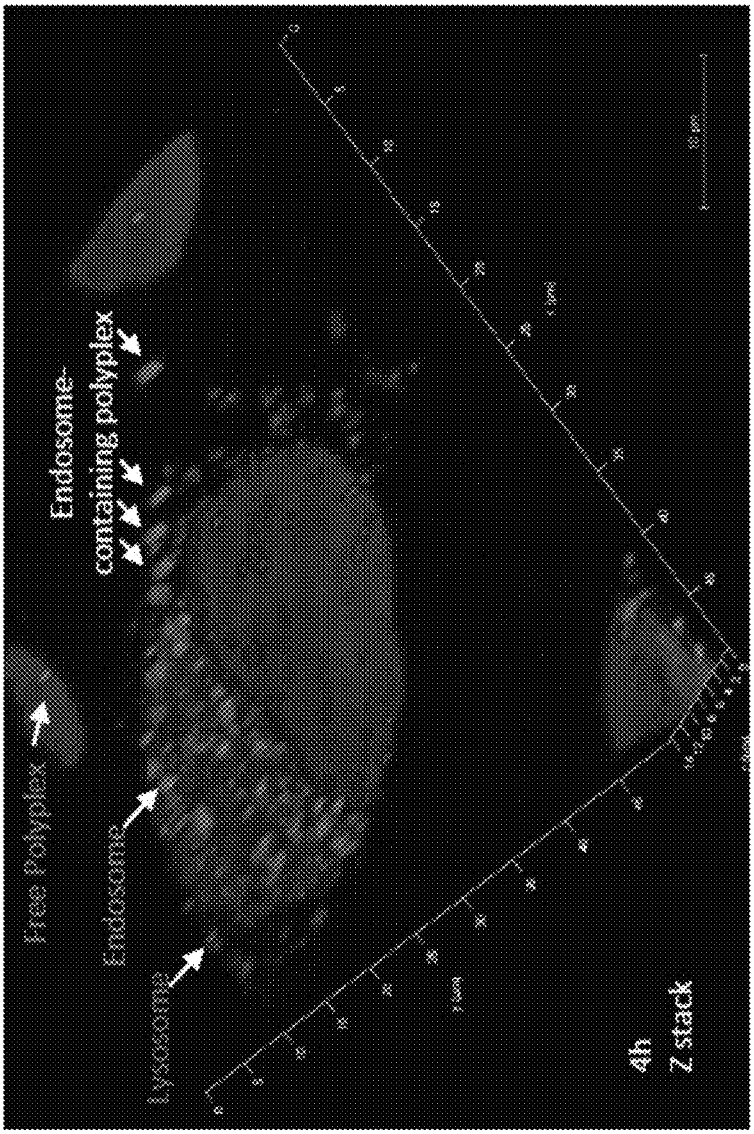
Figure 48B:
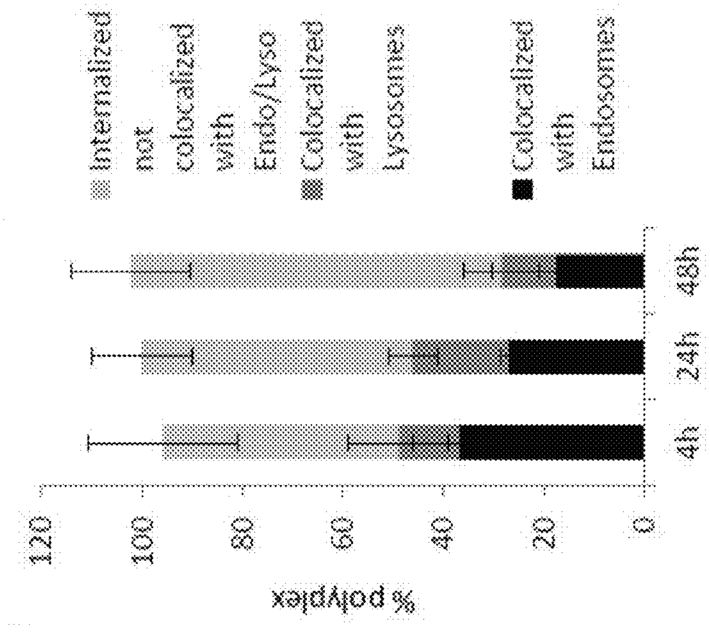

FIGS. 48A-C demonstrate the intracellular trafficking of PGAamine:Cy5-labeled siRNA polyplexes. FIG. 48A presents images of MiaPaCa2 cells incubated with PGAamine: Cy5-siRNA (100 nM siRNA, light blue) for different time points (4, 24 and 48 hours) and stained with early endosome marker EEA1 (green) or late endosome/lysosome marker LAMP1 (red). Nuclei (in blue) were stained with DAPI. FIG. 48B is a bar graph showing quantitative analysis of PGAamine:Cy5-siRNA polyplexes colocalization with EEA1 and LAMP1 4, 24 and 48 hours following polyplex incubation. Data represent mean±SD of 7 random fields. FIG. 48C presents A Z stack of 4 hours after incubation with the polyplex showing endosome-containing polyplexes. Scale bars=50 am (upper images panel-A), 10 am (lower image-C).

Figures 49A, 49B, 49C:
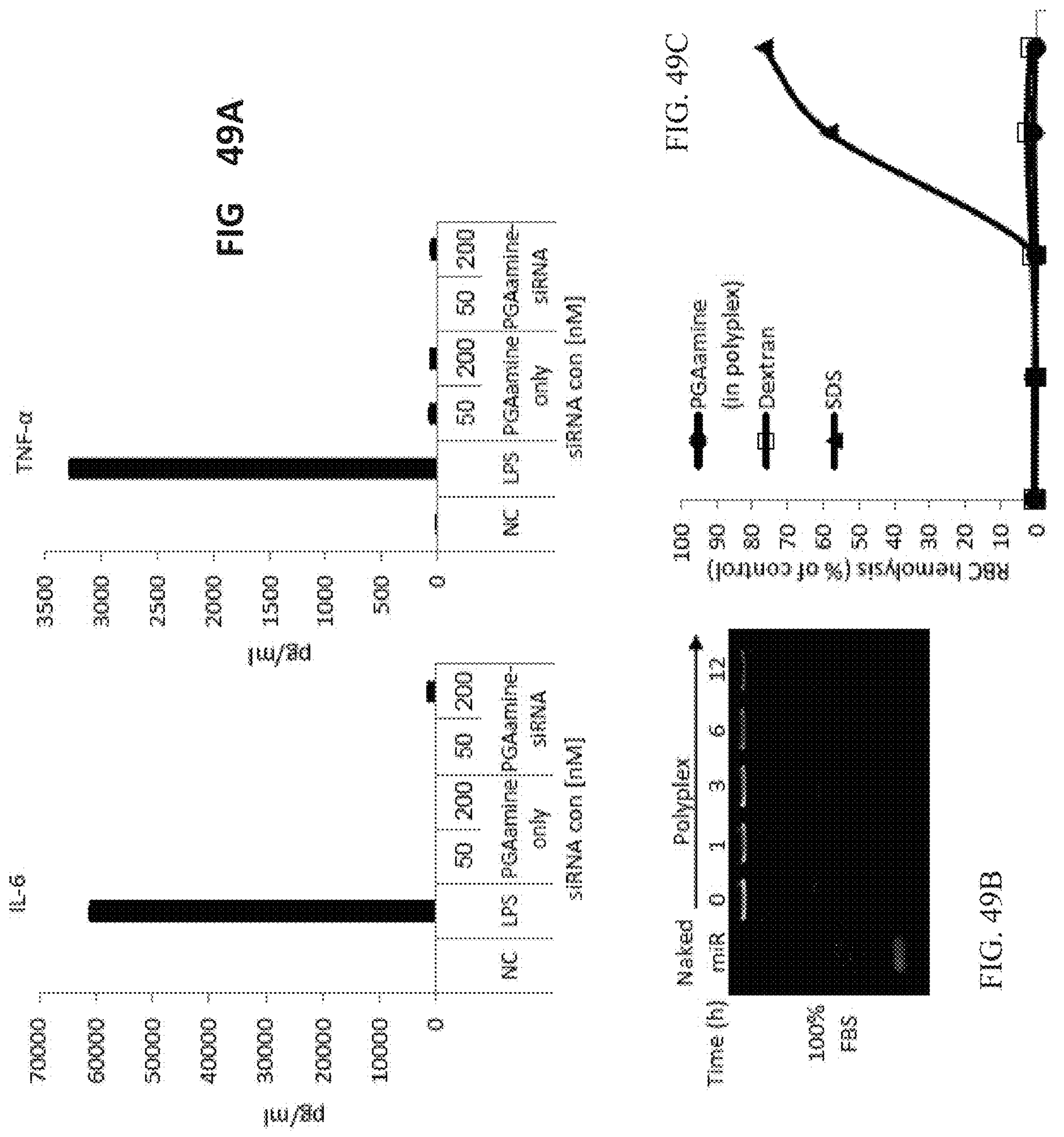

FIGS. 49A-C presents the biocompatibility of PGAamine-siRNA polyplex. FIG. 49A presents bar graphs showing data obtained when PGAamine alone or complexed with siRNA (50, 200 and 400 nM) was added to freshly isolated human PBMCs that were seeded on 12-well plates. PBMCs medium and LPS (2 μg/mL) were served as negative and positive control, respectively. Culture supernatants were collected after 24 hours and assayed for human IL-6 (left) and TNFα (right) cytokines by ELISA. FIG. 49B presents electrophoresis data of miR (35 μM) alone or complexed with PGAamine incubated in fetal bovine serum for several time points (0, 1, 3, 6 and 12 hours) at 37° C. FIG. 49C is a plot obtained in Red blood cells lysis assay of PGAamine-miR polyplexes. Results are presented as percent of hemoglobin released following 1 hour incubation with the different treatments. SDS and dextran were used as positive and negative control, respectively. Data represent mean±SD.

Figure 50D:
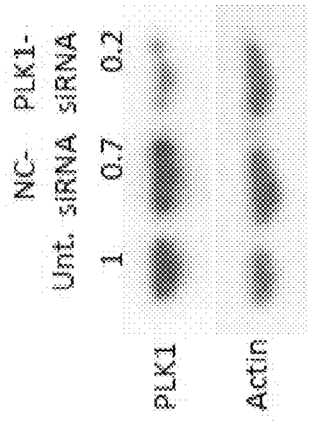
Figure 50C:
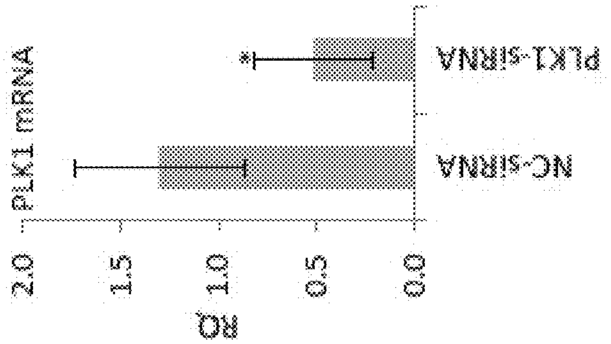
Figure 50B:
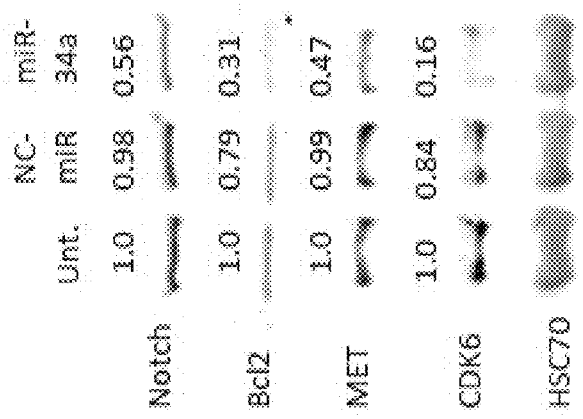
Figure 50A:
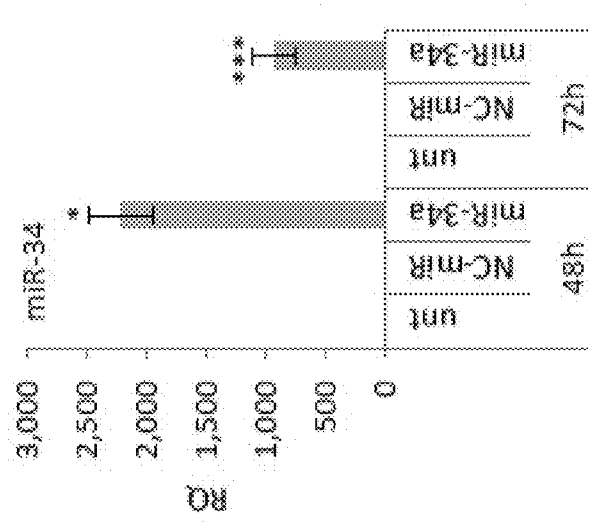

FIGS. 50A-D presents the effect of polyplexes containing miR-siRNA on MiaPaCa2 cells. FIG. 50A is a bar graph showing miR-34a levels in MiaPaCa2 cells following treatment with PGAamine polyplexes containing either miR-34a or NC-miR for 48 or 72 hours, quantified relative to U6 RNA using qRT-Real-time PCR. FIG. 50B presents protein levels of miR-34a direct target genes: CDK6, MET, Notch and Bcl-2 quantified by Western blot analysis 48 hours following treatment. Densitometric analysis is presented as percentage of band intensity compared to untreated cells. FIG. 50C is a bar graph showing PLK1 mRNA levels following transfection of PGAamine polyplexes containing either PLK1-siRNA or NC-siRNA for 24 hours, quantified relative to GAPDH RNA using qRT-Real-time PCR. FIG. 50D presents PLK1 protein levels following treatments for 48 hours.

Figure 51A:
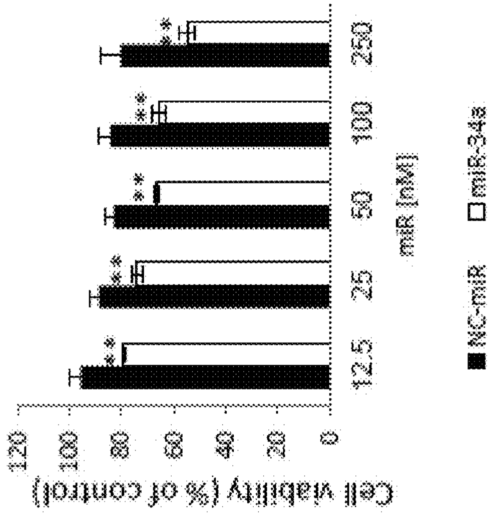
Figure 51B:
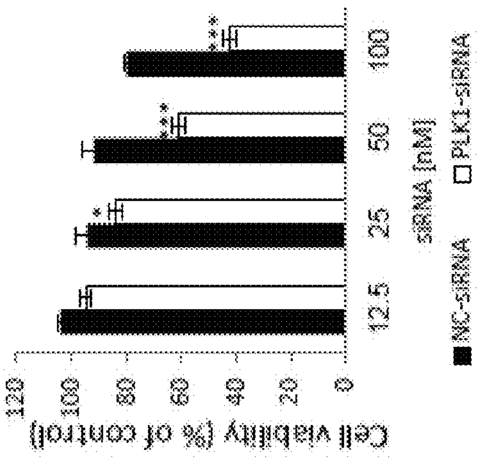
Figure 51C:
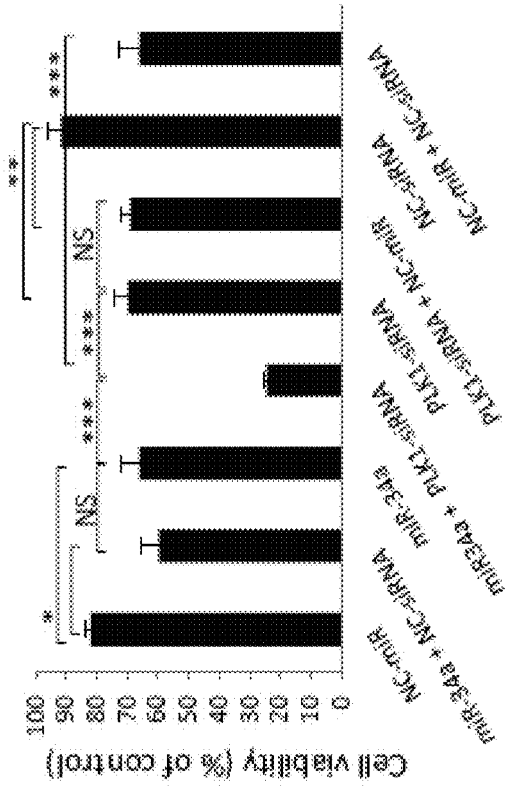
Figure 51D:
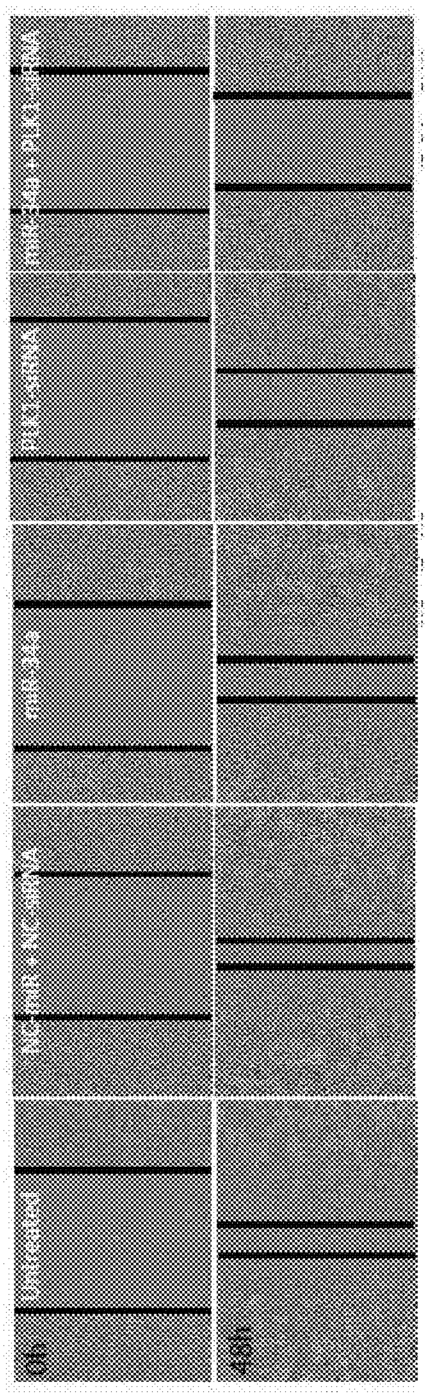
Figure 51F:
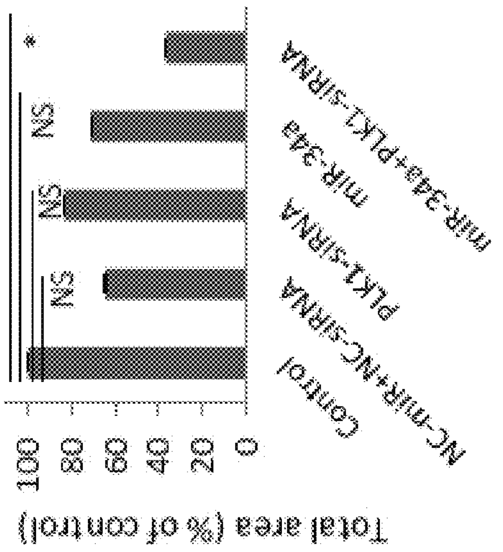
Figure 51E:
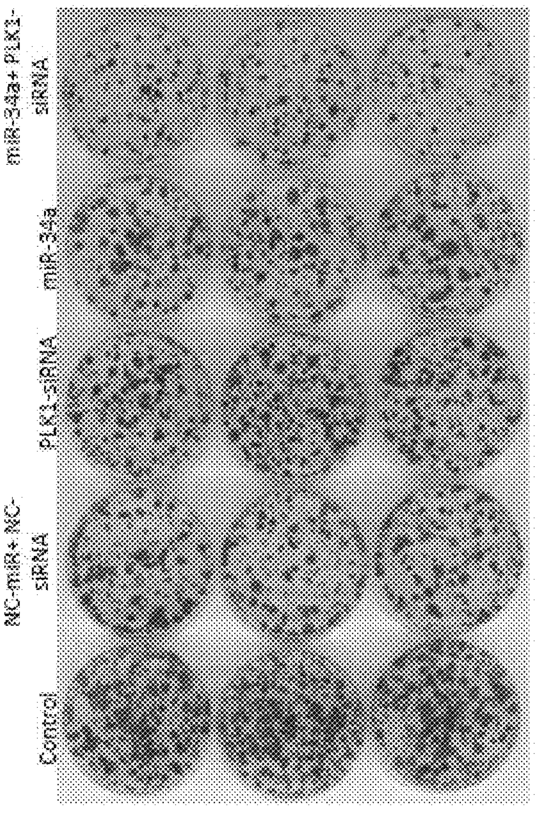
Figure 51G:
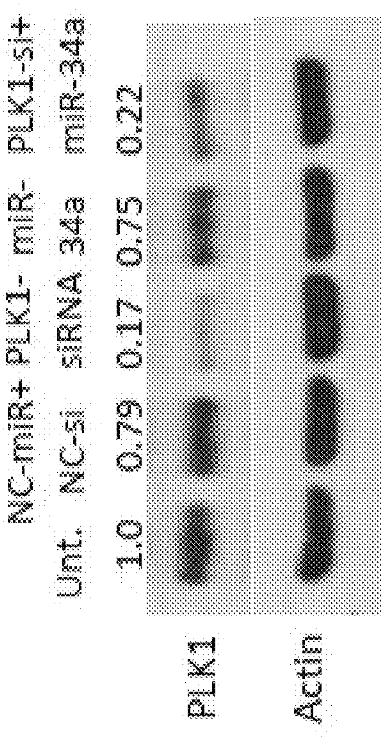

FIG. 51A-G present further data showing the effect of polyplexes containing miR-siRNA on MiaPaCa2 cells. FIGS. 51A-C show proliferation following treatment with PGAamine polyplexes containing different concentrations of miR-34a or NC-miR (FIG. 51A), PLK1-siRNA or NC-siRNA (FIG. 51B), or miR-34a (100 nM) and PLK1-siRNA (50 nM) in combination (FIG. 51C). * $P<0.05$,  $P<0.01$, * $P<0.001$ for the comparison between miR-34a and NC-miR in E and between PLK-siRNA and NC-siRNA in FIG. 51B. FIG. 51D presents images showing migration of the cells 48 hours following incubation with the same treatments. FIG. 51E-F present images showing cell survival via colony formation assay for 11 days (FIG. 51E), and quantified in a graph (FIG. 51F) as their total area, using ImageJ software. Data represent mean±SD. FIG. 51G presents PLK1 protein levels following treatments with combined treatments.

Figure 52A:
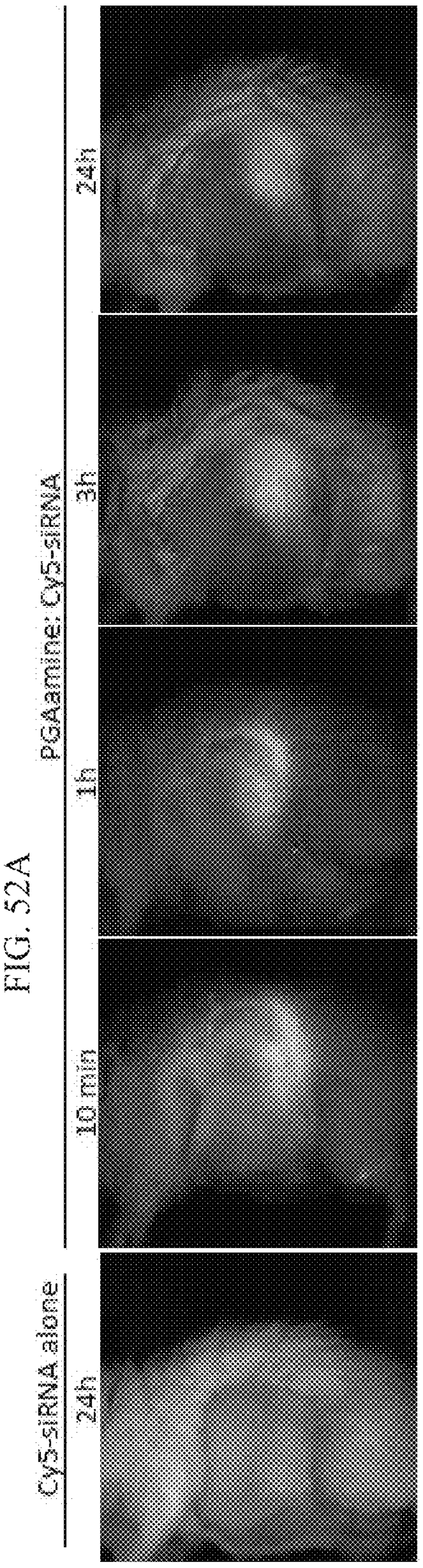
Figure 52B:
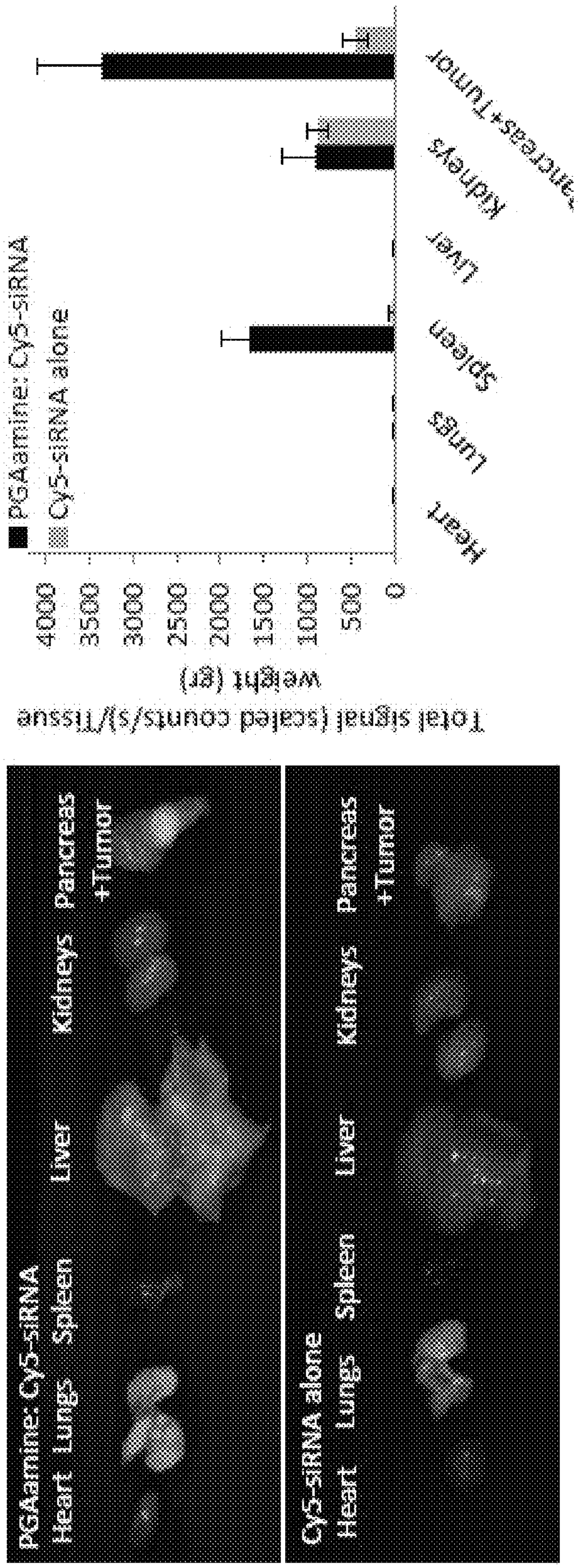
Figure 52C:
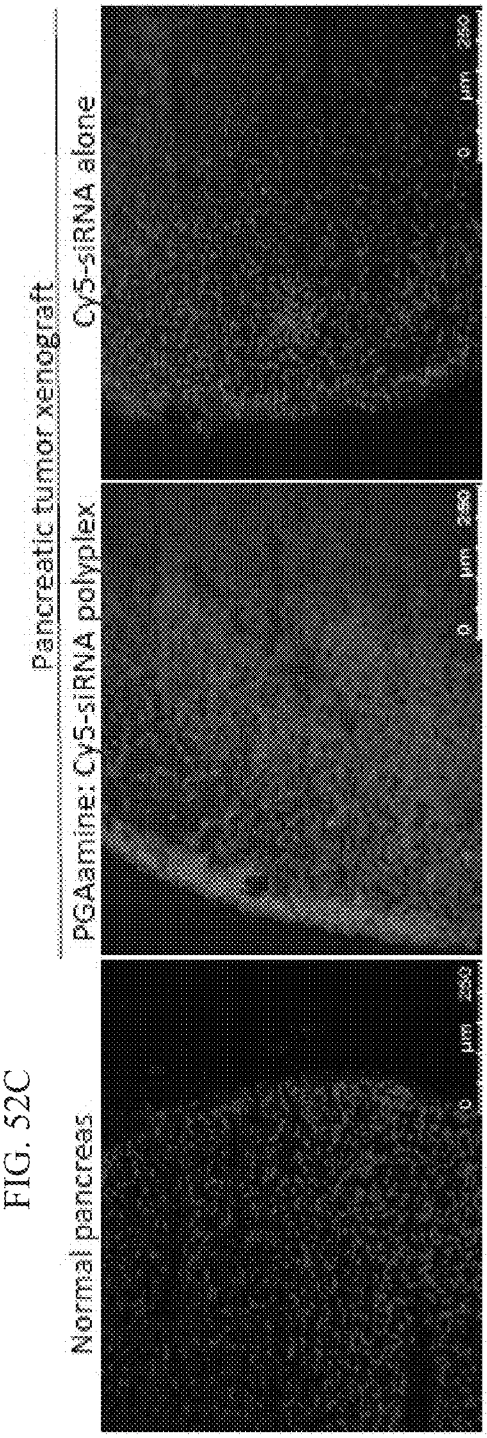
Figure 52D:
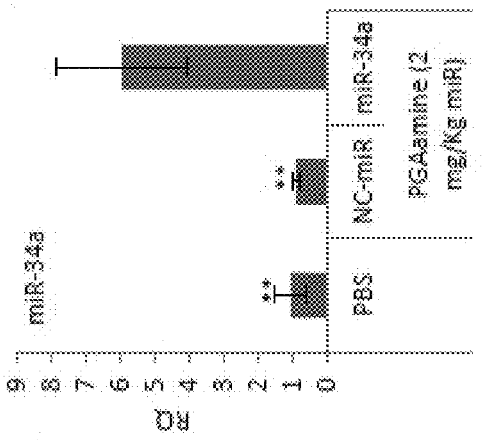
Figure 52E:
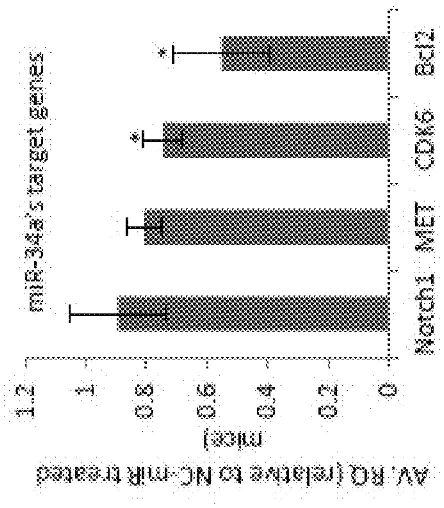

FIGS. 52A-E present the biodistribution and accumulation of PGAamine-miR-siRNA polyplexes in orthotopic pancreatic tumor-bearing mice. FIG. 52A are images showing PGAamine:Cy5-labebel siRNA polyplexes or Cy5-siRNA alone (0.5 mg/Kg siRNA dose) upon being injected intravenously to mCherry-labeled tumor-bearing mice, taken at several time points mice (n=3) by non-invasive intravital fluorescence microscopy for mCherry (red) and Cy5 (light blue) fluorescent signals. FIG. 52B presents images taken 24 hours following intravenous injection, and tumor and healthy organs resection (left), and quantification of their Cy5 fluorescent signal intensity (right). FIG. 52C presents confocal microscopy images of resected tumors embedded within OCT, cut to 10 m sections, stained with DAPI and subjected to confocal microscopy. Normal pancreas served as control. FIG. 52D is a bar graph showing relative miR-34a levels in PDAC tumors following intravenous injections (3 consecutive, once a day) of PGAamine-miR-34a or PGAamine-NC-miR (2 mg/Kg miR dose) or PBS, quantified by qRT-PCR (n=4,  $P<0.01$). FIG. 52E is a bar graph showing miR-34a target genes level following same treatments as in FIG. 52**C, quantified by qRT-PCR.

Figures 53A, 53B, 53C, 53D, 53E:
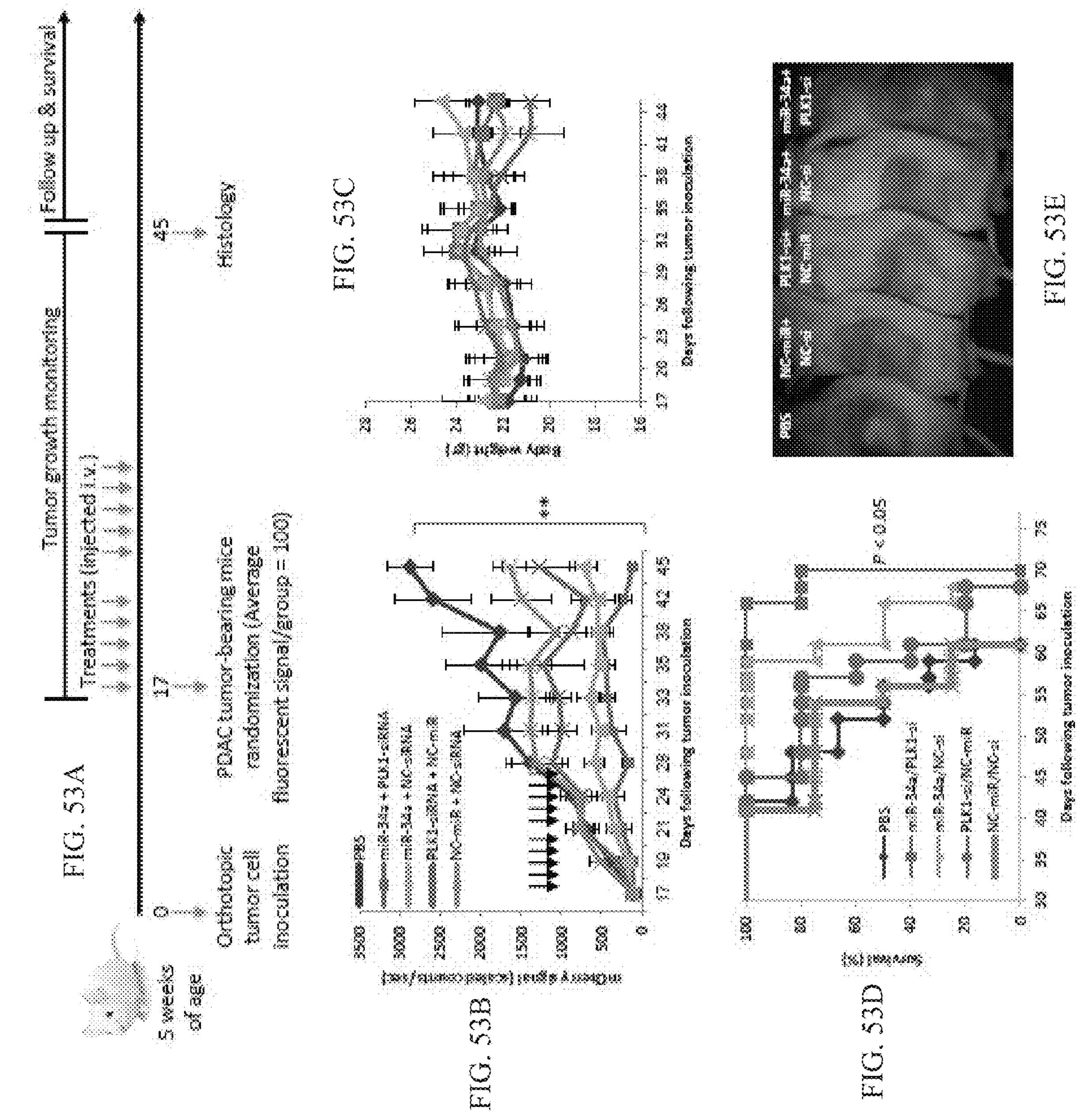
Figure 53F:
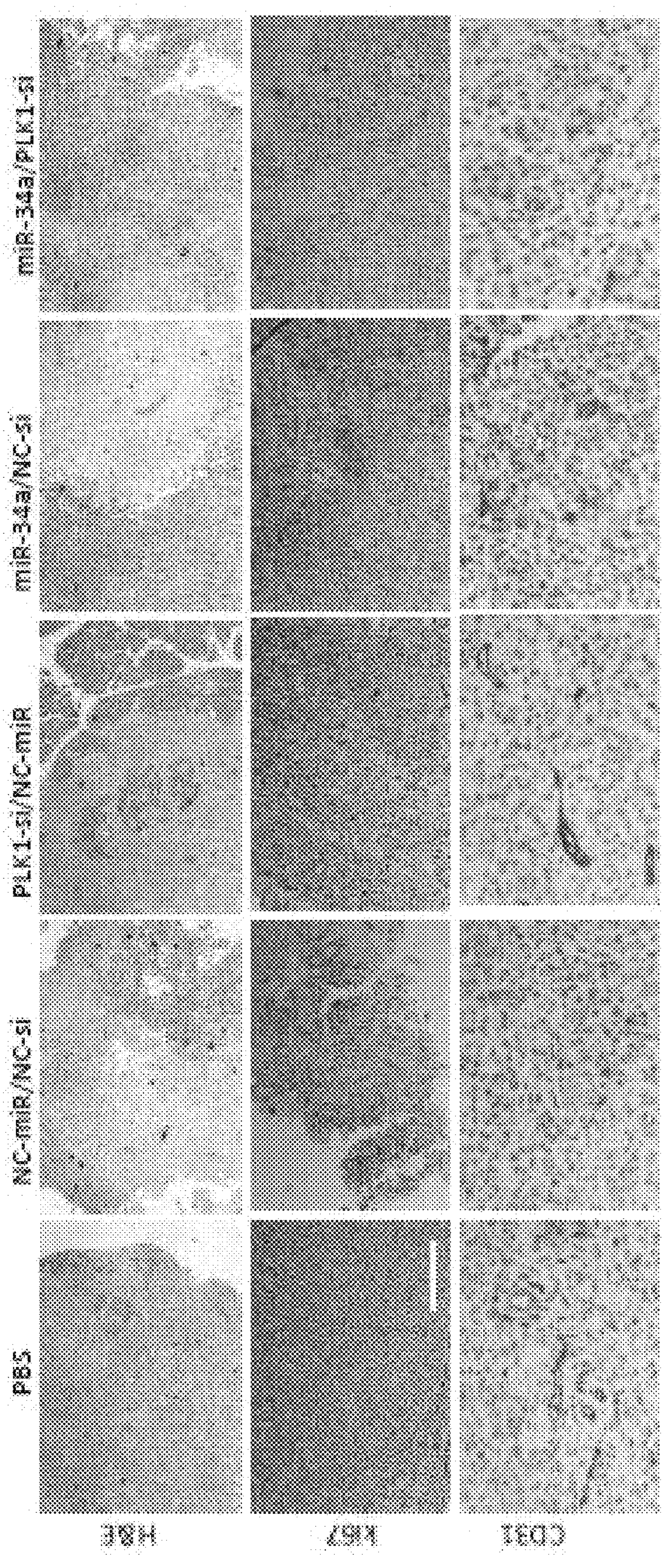

FIGS. 53A-F present In vivo anti-tumor effect of miR-siRNA combination. FIG. 53A presents the trial design used for testing miR-siRNA combination efficacy in the orthotopic PDAC model. FIG. 53B presents tumor growth curves from biweekly fluorescent measurements of tumor-bearing mice treated with PGAamine complexed with miR-34a/PLK1-siRNA, miR-34a/NC-siRNA, PLK1-siRNA/NC-miR, NC-miR/NC-siRNA or PBS (treatments are marked with arrows). P-value of miR-34a/PLK1-siRNA treatment compared to control at day 45:0.005 (n=6, 7). FIG. 53C presents comparative plots showing body weight change. FIG. 53D presents Kaplan-Meier survival graph. $P<0.05$ for the combination miR-34a/PLK1-si compared to all other treatment groups. FIG. 53E presents an image of a representative mouse from each treatment group at day 33 from tumor inoculation. FIG. 53F presents immunohistological staining H&E, Ki67 and CD31. Data represent mean±SEM.

FIGS. 54A-C presents the miR-34a (SEQ ID NO:1) binding site on MYC mRNA (SEQ ID NO:2) (FIG. 54A), PLK1 and MYC protein levels following treatments with monotherapies and their combination (FIG. 54B), and a proposed model of the synergism exhibited by the exemplary polyplexes.

DESCRIPTION OF SPECIFIC EMBODIMENTS OF THE INVENTION

The present invention, in some embodiments thereof, relates to therapy and, more particularly, but not exclusively, to novel functionalized PGA-based polymeric carriers and to uses thereof for conjugating thereto and delivering oligonucleotides, and in the treatment of medical conditions treatable by oligonucleotides, for example, medical conditions treatable by gene therapy such as gene silencing.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Currently available delivery vehicles for siRNA/miRNA offer only partial solutions. Up to date, several technologies have been tested, yet none has shown suitable safety profile and none is targeted to pathological tissue. These technologies rely on the passive accumulation by the EPR effect or on a default hepatic accumulation following systemic administration.

The present inventors have contemplated that electrostatic-based complexation between polyaminated-PGA and modified siRNA or miRNA will form therapeutically active nano-scaled polyplexes that will introduce the following list of benefits: (i) Increased stability in plasma; (ii) Specific delivery to the tumor site and accumulation of the siRNA or miRNA in the angiogenic tissue (e.g. tumor vascular bed); (iii) cellular uptake and endosomal escape that will lead the siRNA/miRNA to its active site—the mRNA in the cytoplasm; (iv) biodegradability of the polymeric backbone by cathepsin B; and (v) Prolongation of the circulating half-life of the polyplexes compared with the free siRNA/miRNA.

The present inventors have contemplated utilizing the pendant free γ-carboxyl group in the repeating L-glutamic acid units in PGA for providing functionality for attachment of various amine-containing units, to which RNA can bind by electrostatic interactions. Poly-aminated PGA is positively charged, thus can internalize to the target cell via electrostatic attraction to the negatively-charged cell membrane and provide for efficient endosomal escape via proton sponge effect.

Thus, according to some embodiments of the present invention, a polymeric delivery vehicle that interacts electrostatically with oligonucleotides such as siRNA or miRNA is provided. Targeted tumor accumulation is achieved by the Enhanced Permeability and Retention (EPR) effect—the leakiness of the tumor blood vessels that allows extravasation of nanometric macromolecules. In addition, for overcoming obstacles such as plasma aggregation and high immunogenicity, the polymer is also designed to permeate through the cell membrane via the endosome and transfer to the cytoplasm, its site of action. The polymer is degraded at the lysosome by cathepsin B which is prevalent in tumors.

The present inventors have designed, synthesized and characterized various polyaminated polyglutamic acid polymers that formed complexes with siRNA and miRNA.

Properties such as strength of complexation between the polymer and siRNA, size and charge of polyplexes, their cellular internalization, silencing activity and toxicity were investigated so as to identify advantageous modifications of the PGA pendant groups. The present inventors have identified several structural features which provide such polymers with improved capability to complex thereto and deliver siRNA and/or miRNA to the cytoplasm, compared to other polyaminated polyglutamic acid-based polymers.

The present inventors have further designed a formulation comprising the conjugates of these polyaminated polyglutamic acid polymers with ribonuclear oligonucleotides (polyplexes), while maintaining the polyplexes as discrete nanoparticles within the solution and while maintaining, and even improving, the therapeutic effect thereof.

Some embodiments of the present invention therefore relate to a polyaminated α-Poly-L-glutamic acid-based delivery system, for targeted delivery of oligonucleotides, and to polyplexes formed by associating, e.g., via electrostatic interactions, the positively charged amine moieties of the aminated PGA polymers and negatively charged oligonucleotides.

The polymer-oligonucleotide polyplexes described herein represent a novel and promising approach for tumor targeted delivery of oligonucleotides such as siRNA/miRNA. The biodegradability, non-immunogenicity and high versatility of PGA makes it an attractive carrier candidate to improve the ability of e.g., siRNA/miRNA to accumulate in the tumor environment, cross the cell membrane and exert its biological effect in a highly efficient and specific manner.

These polyplexes can be selectively activated in tumor sites due to their biodegradability by cathepsin B, an overexpressed enzyme in lysosomes of several types of tumor cells, in tumor endothelial cells and in the tumor extracellular matrix (ECM).

The polymeric delivery system described herein can be utilized therapeutically to treat all pathologies characterized by impaired siRNA or miRNA genetic regulation such as, but not limited to, cancer, viral diseases, cardiovascular diseases, metabolic diseases and neurodegenerative diseases. In addition, the polymeric delivery system can be utilized as a transfection reagent for laboratory research use.

Referring now to the drawings FIG. 3 is a schematic illustration presenting the underlying basis of some embodiments of the present invention.

FIGS. 4, 6, 8, 10 and 12 present the chemical structures of exemplary polymers according to some embodiments of the present invention, also referred to herein as Group I, II, III, IV and V polymers, respectively, and encompassed by Formula I as defined herein, and FIGS. 5, 7, 9, 11 and 13 present exemplary synthetic pathways for preparing these polymers, respectively.

FIG. 14 presents an exemplary synthetic pathway of a cross-linked co-polymer-lysine$_{(10\%)}$-γ-ethylenediamine-L-polyglutamate$_{(90\%)}$ according to some embodiments of the present invention (Polymer CL1), encompassed by Formula II, as defined herein. FIG. 15 presents an exemplary synthetic pathway of α-hexyl-amino acid-PGAamine block copolymer according to some embodiments of the present invention (Copolymer BL1), encompassed by Formula III, as defined herein.

FIGS. 16A-B, 28, 37, 39, and 41 present a characterization of the electrostatic interaction between PGAamine polymers of Groups I, II, III, IV and V, respectively and siRNA. FIGS. 43A and 44 present a characterization of the electrostatic interaction between PGAamine polymers of Formula II and III, respectively, and siRNA. The data presented in these figures show the complexation capability exhibited by the PGAamine polymers of some embodiments of the present invention.

FIGS. 18A-C, 19A-C, 32, and 47A-B, and 48A-C present the cell internalization, and intracellular localization and trafficking of exemplary PGAamine:siRNA polyplexes according to some embodiments of the present invention FIGS. 20A-C, 29, 38, 40, 42 and 43B present data demonstrating the silencing activity and in vitro toxicity of exemplary PGAamine:siRNA polyplexes according to some embodiments of the present invention.

FIGS. 21A-B and 22A-B, present the effect of exemplary PGAamine:Rac1 siRNA polyplexes according to some embodiments of the present invention on cell migration.

FIGS. 23A-C and 49A-C present data demonstrating the biocompatibility of exemplary PGAamine A:Rac1 siRNA polyplexes.

FIGS. 25A-D, 26A-D, 33A-C, 35A-C and 36A-C present in vivo data showing the effect of exemplary PGAamine A:Rac1 siRNA polyplexes on tumor growth in mice models.

FIGS. 27A-E present the effect of formulating a polyplex of a Group I polymer with a surfactant.

FIGS. 30A-D, 31A-E, and 34A-C present the effect of formulating a polyplex of a Group II polymer with glucose, using a microfluidic system.

FIGS. 45A-54C present characterization, cell internalization, silencing activity, toxicity, degradability, biocompatibility, and in vitro and in vivo anti-tumor effect of an exemplary PGAamine:miR-34a polyplex according to some embodiments of the present invention, showing a synergistic effect exhibited by combining it with a PGAamine:siRNA polyplex according to some embodiments of the present invention.

According to an aspect of some embodiments of the present invention there is provided a polymeric compound, also referred to herein interchangeably as a polymer, as described herein.

According to an aspect of some embodiments of the present invention there is provided a polymeric compound, also referred to herein interchangeably as a polymer, represented by Formula I as described herein.

According to an aspect of some embodiments of the present invention there is provided a polymeric compound, also referred to herein interchangeably as a polymer, represented by Formula Ia, Ib or Ic, as described herein.

According to an aspect of some embodiments of the present invention there is provided a polymeric compound, also referred to herein interchangeably as a polymer, represented by Formula II as described herein.

According to an aspect of some embodiments of the present invention there is provided a polymeric compound, also referred to herein interchangeably as a polymer, represented by Formula III as described herein.

According to an aspect of some embodiments of the present invention there is provided a polymeric compound, also referred to herein interchangeably as a polymer, composed of a plurality of BU(1), a plurality of BU(2), a plurality of BU(3), a plurality of BU(4), a plurality of BU(5), a plurality of BU(6), a plurality of BU(7) and/or a plurality of BU(8), as described herein. According to another aspect of some embodiments of the present invention there is provided a conjugate comprising a polymer as described herein in any of the respective embodiments, being in association with an oligonucleotide.

According to another aspect of some embodiments of the present invention, there is provided a pharmaceutical composition comprising a conjugate as described herein and a pharmaceutically acceptable carrier.

According to another aspect of some embodiments of the present invention, the conjugates, or compositions comprising same, as described herein, are used for delivering the oligonucleotides into cells, for transfecting cells, and/or in gene therapy, particularly gene silencing, as described herein.

Herein, the term "conjugate" describes a chemical entity in which two or more moieties (e.g., the polymer and the oligonucleotide) are associated to one another, as defined herein. In some embodiments, the association is via electrostatic interactions, as defined herein. In some embodiments, the electrostatic interactions are between phosphate groups of the oligonucleotide and terminal amine groups of pendant groups of the polymer.

A conjugate as described herein is also referred to herein throughout as a "polyplex".

The Polymer:

Herein throughout, the term "polymer" is also referred to herein as "polymeric compound" and describes an organic substance composed of a plurality of repeating structural units covalently connected to one another.

The repeating structural units are backbone units, which are covalently linked to one another to thereby form the polymeric backbone. The term "backbone units" is used herein to describe the portion of corresponding monomers upon polymerizing or co-polymerizing the monomers.

The term "polymer" as used herein encompasses a homopolymer, a copolymer and a mixture thereof (a blend). The term "homopolymer" as used herein describes a polymer that is made up of one type of monomers and hence is composed of homogenic backbone units. The term "copolymer" as used herein describes a polymer that is made up of more than one type of monomers and hence is composed of heterogenic backbone units.

In some embodiments, the polymer (or co-polymer) has an average molecular weight in the range of 100 Da to 800 kDa. In some embodiments, the polymer has an average molecular weight lower than 100 kDa or lower than 60 kDa. In some embodiments, the polymer's average molecular weight range is 10 kDa to 40 kDa.

Polymeric substances that have a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of a polymeric conjugate can be determined while considering the half-life in plasma, the renal clearance, and the accumulation in the tumor of the conjugate.

According to some embodiments, the polymer comprises backbone units that form a polymeric backbone of polyglutamic acid (PGA). Such polymers are also referred to herein as polymers or co-polymers deriving from PGA, or PGA-based polymers, and comprise backbone units derivable from glutamic acid.

PGA contains carboxylic functional groups as its side chains (pendant groups). PGA can be readily degraded by lysosomal enzymes such as Cathepsin B, to its nontoxic basic components, L-glutamic acid, D-glutamic acid and/or D,L-glutamic acid.

As used herein, a polyglutamic acid encompasses poly (L-glutamic acid), poly(D-glutamic acid), poly(D,L-glutamic acid), poly(L-gamma glutamic acid), poly(D-gamma glutamic acid) and poly(D,L-gamma glutamic acid). Accordingly, PGA-based polymers or copolymers can comprise backbone units derivable from D-glutamic acid, L-glutamic acid, a racemic mixture of D- and L-glutamic acid, L-gamma glutamic acid, D-gamma glutamic acid and racemic mixture of D- and L gamma glutamic acid.

In some embodiments, the PGA-based polymers or co-polymers described herein comprise at least 50% of its backbone units as derivable from glutamic acid, and optionally comprises 60, 70, 80, 90 or 100% of its backbone units as derivable from glutamic acid.

According to some embodiments, the polymer is a co-polymer that comprises a plurality of backbone units that form a polymeric backbone of polyglutamic acid (PGA), referred to herein as PGA backbone units, and a plurality of other backbone units. The other backbone units can be interlaced, or interrupt, the polymeric backbone formed of the PGA backbone units, to form a heterogenic polymeric backbone. Alternatively, the other backbone units can be included in the polymeric backbone so as to form a block co-polymer, composed of one or more polymeric backbone formed of the PGA backbone units and one or more polymeric backbones forms of the other backbone units, whereby these polymeric backbones are attached to one another alternately, in any order. Further alternatively, or in addition to any of the foregoing, the other backbone units cross-link one or more polymeric backbone units formed of the PGA backbone units.

According to the present embodiments, at least a portion of the backbone units in the polymer or co-polymer as described herein are further substituted so as to feature one or more terminal amine groups, for forming an association with an oligonucleotide, as described herein. Those backbone units that are not further substituted so as to feature an amine group are referred to herein as "free" backbone units. A PGA-based polymers or co-polymer as described herein, in which a portion of the PGA backbone units is substituted so as to feature an amine terminal group is also referred to herein interchangeably as "PGAamine polymer", "aminated PGA polymer", "PGA-based polymer", PGA aminated derivative, PGA amination derivative and simply "polymer" or "polymeric compound".

Polymers according to embodiments of the present invention comprise a plurality of backbone units covalently linked to one another, whereby the backbone units are selected from the backbone units denoted herein as BU(1), BU(2), BU(4), BU(5), BU(6), BU(7) and BU(8), as follows, provided that at least 40% of the backbone units are one or more of BU(2), BU(4), BU(5) and BU(6).

BU(1)

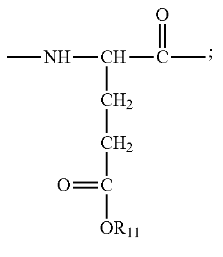

-continued

BU(2)

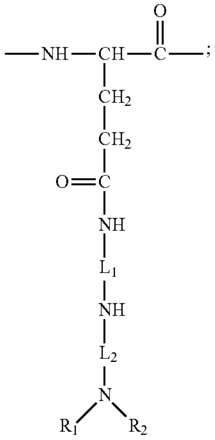

BU(3)

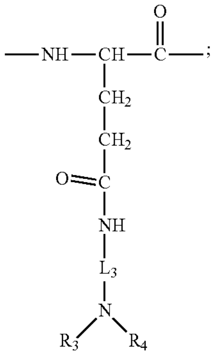

BU(4)

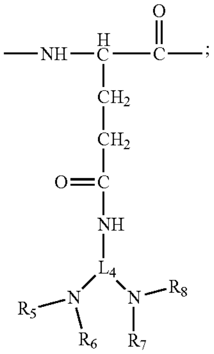

BU(5)

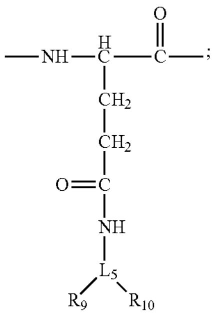

-continued

BU(6)

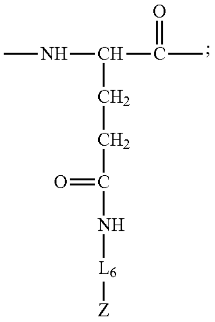

BU(7)

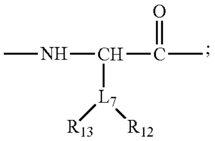

and

BU(8)

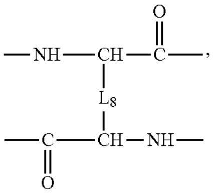

wherein:

$L_1$, $L_2$, $L_3$, $L_6$ and $L_8$ is each independently a linear linking moiety;

$L_4$ is a branched linking moiety;

$L_5$ is a linear or branched linking moiety, or is absent (depending on the nature of $R_9$ and $R_{10}$, as described in further detail hereinunder);

$L_7$ is a linear or branched linking moiety, or is absent (depending on the nature of $R_9$ and $R_{10}$, as described in further detail hereinunder);

$R_1$-$R_{13}$ are each independently selected from H, alkyl and cycloalkyl; and Z is a nitrogen-containing heterocyclic moiety.

In some embodiments, the backbone units forming a polymeric compound as described herein are covalently linked to one another so as to form a peptide (amide) bond. The backbone units forming a polymeric compound as described herein are covalently linked to one another in any order, unless indicated otherwise.

In some embodiments, a polymeric compound as described herein comprises a plurality of backbone units composed of two of the backbone units BU(1), BU(2), BU(4), BU(5), BU(6), BU(7) and BU(8) as described herein.

In some embodiments, a polymeric compound as described herein comprises a plurality of backbone units composed of three of the backbone units BU(1), BU(2), BU(4), BU(5), BU(6), BU(7) and BU(8) as described herein.

In some embodiments, a polymeric compound as described herein comprises a plurality of backbone units composed of four of the backbone units BU(1), BU(2), BU(4), BU(5), BU(6), BU(7) and BU(8) as described herein.

In some embodiments, a polymeric compound as described herein comprises a plurality of backbone units composed of five of the backbone units BU(1), BU(2), BU(4), BU(5), BU(6), BU(7) and BU(8) as described herein.

In some embodiments, a polymeric compound as described herein comprises a plurality of backbone units composed of six of the backbone units BU(1), BU(2), BU(4), BU(5), BU(6), BU(7) and BU(8) as described herein.

In some embodiments, a polymeric compound as described herein comprises a plurality of backbone units composed of seven of the backbone units BU(1), BU(2), BU(4), BU(5), BU(6), BU(7) and BU(8) as described herein.

In some embodiments, a polymeric compound as described herein comprises a plurality of backbone units composed of all of the backbone units BU(1), BU(2), BU(4), BU(5), BU(6), BU(7) and BU(8) as described herein.

In some embodiments, a polymeric compound as described herein comprises a plurality of backbone units composed of BU(1) and one or more of BU(2), BU(4), BU(5) and BU(6).

In some embodiments, a polymeric compound as described herein comprises a plurality of backbone units composed of BU(3) and one or more of BU(1), BU(2), BU(4), BU(5) and BU(6).

In some embodiments, a polymeric compound as described herein comprises a plurality of backbone units composed of BU(3) and BU(1).

In some embodiments, a polymeric compound as described herein comprises a plurality of backbone units consisting of BU(3).

In some embodiments, a polymeric compound as described herein comprises a plurality of backbone units composed of BU(3) and one or more of BU(2), BU(4), BU(5) and BU(6).

In some embodiments, a polymeric compound as described herein comprises a plurality of backbone units composed of BU(2) and BU(3).

In some embodiments, a polymeric compound as described herein comprises a plurality of backbone units composed of BU(3) and BU(5).

In some embodiments, a polymeric compound as described herein comprises a plurality of backbone units composed of BU(3) and BU(6).

In some embodiments, a polymeric compound as described herein comprises a plurality of backbone units composed of BU(3), BU(5) and BU(6).

In some embodiments, a polymeric compound as described herein comprises a plurality of backbone units composed of BU(2) and BU(5).

In some embodiments, a polymeric compound as described herein comprises a plurality of backbone units composed of BU(2), BU(3) and BU(5).

In some embodiments, a polymeric compound as described herein comprises a plurality of backbone units composed of BU(3) and BU(7).

In some embodiments, a polymeric compound as described herein comprises a plurality of backbone units composed of BU(7) and one or more of BU(2), BU(3), BU(4), BU(5) and BU(6).

In some embodiments, a polymeric compound as described herein comprises a plurality of backbone units composed of BU(8) and one or more of BU(2), BU(3), BU(4), BU(5) and BU(6).

In some of any of the embodiments described herein, $R_{11}$ is H and BU(1) represents "free" backbone units of PGA.

Herein throughout, a "linear linking moiety" describes a bi-radical linear, preferably aliphatic, group. By "bi-radical" it is meant that the linking moiety has two attachment points such that it links between two atoms or two groups. In some embodiments, the linear linking moiety is or comprises a bi-radical hydrocarbon.

By "hydrocarbon" it is meant a moiety formed of a chain of carbon atoms covalently linked to one another, and substituted mainly by hydrogen atoms. A hydrocarbon can include, for example, one or more alkyl groups, one or more alkenyl groups, one or more alkynyl groups, one or more cycloalkyl groups and/or one or more aryl groups, on any order. Preferably, the hydrocarbon includes one or more aliphatic moieties, namely, one or more alkyl groups, one or more alkenyl groups and/or one or more alkynyl groups, and, depending on the moieties forming the hydrocarbon, it is saturated or unsaturated.

In some embodiments, the hydrocarbon comprises 1 to 10 carbon atoms, preferably 2 to 10 carbon atoms, preferably 2 to 8 carbon atoms, preferably 2 to 6 carbon atoms, in its backbone chain.

The hydrocarbon, or the moieties forming the hydrocarbon, can be substituted or unsubstituted, and are preferably substituted.

In some embodiments, the hydrocarbon can be interrupted by one or more heteroatoms, such as O or S or an amine group, as described herein.

In some embodiments, the linear linking moiety is a hydrocarbon, and in some of these embodiments, the hydrocarbon is an alkyl group, preferably unsubstituted alkyl.

Herein, a bi-radical alkyl group is also referred to as alkylene.

In some embodiments, the linear linking moiety comprises one or more alkylene(s), interrupted by one or more heteroatoms such as O, S or an amine group.

In some embodiments, the linear linking moiety comprises one or more alkylene(s), interrupted by one or more amine group(s).

Hereinthroughout, a "branched linking moiety" describes a multi-radical, preferably aliphatic, group. By "multi-radical" it is meant that the linking moiety has more than two attachment points such that it links between three or more atoms or groups. In some embodiments, the branched linking moiety is or comprises a linear linking moiety as described herein in any of the respective embodiments, which is terminated by a branching unit that has at least two attachment points to two or more atoms or groups.

In some of any of the embodiments described herein, a branched linking moiety is or comprises a branching unit represented by (Rc-$C_b$Rd-Rf), wherein Rd is H or alkyl; and Rc and Rf are each independently an alkylene or absent. This branching unit has one attachment point at the carbon atom denoted as $C_b$, and additional two attachment points at the same carbon atom $C_b$ (if Rc and Rf are absent), or one attachment point at the same carbon atom $C_b$ and one at one of Rc and Rf (if one of Rc and Rf are absent), or three attachment points at the same carbon atom $C_b$ (if both Rc and Rf are absent). In some embodiments, a branched linking moiety is a branching unit represented by (Rc-$C_b$Rd-Rf), such that $C_b$ is further attached to the amide group of a respective backbone unit. In some embodiments, a branched linking moiety comprises a branching unit represented by (Rc-$C_b$Rd-Rf), and $C_b$ is attached to the amide group is a respective backbone unit via a hydrocarbon as described herein in any of the respective embodiments in the context of a linear linking moiety.

In some of any of the embodiments described herein for BU(2), $L_1$ and $L_2$ are each independently an alkylene, and in some embodiments, an unsubstituted alkylene.

In some of these embodiments, the alkylene has from 2 to 10 carbon atoms, or from 2 to 8 carbon atoms, or from 2 to 6 carbon atoms, or from 2 to 4 carbon atoms.

In some embodiments of BU(2), $L_1$ and $L_2$ are each independently an unsubstituted ethylene ($-CH_2-CH_2-$) or an unsubstituted propylene ($-CH_2-CH_2-CH_2-$). In some embodiments, $L_1$ and $L_2$ are each unsubstituted propylene (—$CH_2$—$CH_2$—$CH_2$—).

In some of any of the embodiments described herein for BU(2), at least one of $R_1$ and $R_2$ is other than H, and in some embodiments each of $R_1$ and $R_2$ is other than H. In some embodiments, $R_1$ and $R_2$ are each independently an alkyl, preferably a short alkyl, having 1 to 6, preferably 1 to 4 carbon atoms. In some embodiments, $R_1$ and $R_2$ are each methyl.

In some of any of the embodiments described herein for BU(2), in at least a portion of the BU(2) units each of $R_1$ and $R_2$ is other than H, e.g., each is methyl, and each of $L_1$ and $L_2$ is an unsubstituted alkylene, e.g., an unsubstituted propylene.

In some of any of the embodiments described herein for BU(2), in at least a portion of the BU(2) units, each of $R_1$ and $R_2$ is H, and each of $L_1$ and $L_2$ is an unsubstituted alkylene, e.g., an unsubstituted ethylene.

When a polymeric compound comprises a plurality of BU(2) backbone units, the BU(2) units can be the same or different, as described in further detail hereinbelow. When different, the BU(2) units can differ from one another by one or more of $L_1$ and $L_2$ and/or by one or more of $R_1$ and $R_2$.

In some of any of the embodiments described herein for BU(3), $L_3$ is a linear linking moiety as described herein in any of the respective embodiments. In some of any of the embodiments described herein for BU(3), $L_3$ is an alkylene, and in some embodiments, an unsubstituted alkylene. In some of these embodiments, the alkylene has from 2 to 10 carbon atoms, or from 2 to 8 carbon atoms, or from 2 to 6 carbon atoms. In exemplary embodiments, $L_3$ is an unsubstituted ethylene (—$CH_2$—$CH_2$—) or an unsubstituted propylene (—$CH_2$—$CH_2$—$CH_2$—) or an unsubstituted hexylene —$(CH_2)_6$—.

In some of any of the embodiments of BU(3), at least one of $R_3$ and $R_4$ is H, and in some embodiments, $R_3$ and $R_4$ are each H.

In exemplary embodiments of BU(3), $R_3$ and $R_4$ are each H and $L_3$ is an unsubstituted alkylene. In some of these embodiments, $L_3$ is an unsubstituted ethylene. In some of these embodiments, $L_3$ is an unsubstituted hexylene.

When a polymeric compound comprises a plurality of BU(3) backbone units, the BU(3) units can be the same or different, as described in further detail hereinbelow. When different, the BU(3) units can differ from one another by e.g., the length of $L_3$ and/or by one or more of $R_3$ and $R_4$.

In some of any of the embodiments described herein for BU(4), $L_4$ is a branched linking moiety as described herein in any of the respective embodiments. In some embodiments, $L_4$ is a hydrocarbon terminating by a branching unit (Rc-$C_b$Rd-Rf) as described herein in any of the respective embodiments. In some of these embodiments, the hydrocarbon is an alkylene, and in some embodiments an unsubstituted alkylene. In some embodiments, the hydrocarbon is an alkylene (e.g., unsubstituted) of from 1 to 10, or from 1 to 8, or from 1 to 6, or from 1 to 4, or from 1 to 2, carbon atoms is length. In exemplary embodiments, the hydrocarbon is unsubstituted methylene or unsubstituted ethylene.

In some of any of these embodiments, Rd is H.

In some of any of these embodiments, Re and Rf are each independently an alkylene, and in some embodiments each is an unsubstituted alkylene. In some embodiments, Rc and Rf are each an unsubstituted alkylene of from 1 to 10, or from 1 to 8, or from 1 to 6, or from 1 to 4, or from 1 to 2, carbon atoms is length. In exemplary embodiments, Rc and Rf are each independently an unsubstituted methylene, an unsubstituted ethylene or an unsubstituted propylene. In exemplary embodiments, Rc and Rf are each an unsubstituted ethylene.

In exemplary embodiments, $L_4$ is —$(CH_2)$—CH[$(CH_2$—$CH_2)$—$]_2$.

In some of any of the embodiments described herein for BU(4), $R_5$, $R_6$, $R_7$ and $R_8$ are each independently H or alkyl, preferably a short alkyl of 1 to 4 carbon atoms in length, preferably an unsubstituted alkyl, preferably unsubstituted methyl. In some embodiments, one or more of $R_5$, $R_6$, $R_7$ and $R_8$ is alkyl (e.g., methyl). In some embodiments, each of $R_5$, $R_6$, $R_7$ and $R_8$ is H.

When a polymeric compound comprises a plurality of BU(4) backbone units, the BU(4) units can be the same or different. When different, the BU(4) units can differ from one another by one or more of $L_4$ and $R_5$-$R_8$.

In some of any of the embodiments described herein for BU(5), $R_9$ is H and $R_{10}$ is alkyl, preferably a linear (non-branched) alkyl. In some of these embodiments, $L_5$ is absent. Alternatively, in some of these embodiments, $L_5$ is a linear linking moiety as described herein in any of the respective embodiments, and in some of these embodiments, $L_5$ is an alkylene, such that $L_5$ and $R_{10}$ together form a linear alkyl. Further alternatively, in some of these embodiments, $L_5$ is a branched linking moiety which is Rc-CRd-Rf, Rc and Rf are absent, and $L_5$ and $R_{10}$ can be regarded as forming together a linear alkyl.

In some of any of these embodiments, the alkyl (e.g., $R_{10}$, or an alkyl which $L_5$ and $R_{10}$ form together) is at least 5 atoms in length, and can be, for example, pentyl, hexyl, heptyl, or octyl, each being preferably unsubstituted.

In some of any of the embodiments described herein for BU(5), each of $R_9$ and $R_{10}$ is other than H, and in some of these embodiments each of $R_9$ and $R_{10}$ is alkyl, preferably an unsubstituted alkyl.

The alkyl according to some of these embodiments is preferably at least three carbon atoms in length, more preferably at least 5 carbon atoms in length, and can be, for example, from 3 to 10, or from 5 to 10, or from 5 to 8, or from 6 to 8, carbon atoms in length.

When each of $R_9$ and $R_{10}$ is other than H (e.g., alkyl, as described herein), $L_5$ is a branched linking moiety, as described in any one of the respective embodiments and any combination thereof.

In some embodiments, the branched linking moiety is or comprises Rc-CRd-Rf, as described herein.

In some embodiments, the branched linking moiety is Rc-CRd-Rf, as described herein, such that $L_5$ is Rc-CRd-Rf. In some of these embodiments, Rd is H.

In some embodiments, Rc and Rf are absent. In some of these embodiments of $L_5$, Rd is H, and each of $R_9$ and $R_{10}$ is alkyl, such that $L_5$, $R_9$ and $R_{10}$ can be regarded as forming together a branched alkyl. In some of these embodiments, each branch of the branched alkyl is at least 3 carbon atoms in length.

In some of any of embodiments described herein for BU(5), at least one of $R_9$ and $R_{10}$ is an alkyl being 3 or more, preferably 4 or more, carbon atoms in length.

When a polymeric compound comprises a plurality of BU(5) backbone units, the BU(5) units can be the same or different, as described in further detail hereinbelow. The BU(5) units can differ from one another by one or more of the length of an alkyl group (when formed of $L_5$ and $R_{10}$, wherein $R_9$ is hydrogen and/or when $R_9$ and $R_{10}$ are each alkyl; the nature of $R_9$ and $R_{10}$ (being the same or different, or being one or two alkyls); and the length and/or nature of the linking moiety.

In some of any of the embodiments described herein for BU(6), $L_6$ is an alkylene, preferably an unsubstituted alkylene, as described herein in any of the respective embodiments. In exemplary embodiments, $L_6$ is unsubstituted ethylene.

By “nitrogen-containing heterocyclic moiety” are encompassed heteroalicyclic and heteroaryl moieties, as defined herein, containing one or more nitrogen atoms within the cyclic ring. When Z is a heteroaryl, preferably, at least one of the nitrogen atoms does not participate in the π-electron conjugation of the aromatic system. Exemplary nitrogen-containing heterocyclic moieties include, but are not limited to, imidazole, morpholine, piperidine, piperazine, oxalidine, pyrrole, oxazole, thiazole, pyrazole, pyridine, pyrimidine, quinoline, isoquinoline and purine. Preferred moieties, according to some embodiments, include, but are not limited to, imidazole, piperazine, piperidine, and pyridine.

In exemplary embodiments, $L_6$ is ethylene and Z is imidazole.

When a polymeric compound comprises a plurality of BU(6) backbone units, the BU(6) units can be the same or different, as described in further detail hereinbelow. The BU(6) units can differ from one another by the $L_6$ linking moiety (e.g., the length of an alkylene) and/or by the Z nitrogen-containing heterocyclic moiety.

According to some of any of the embodiments described herein for BU(7), one of $R_{13}$ and $R_{12}$ is hydrogen and one is other than hydrogen. In some of these embodiments, $R_{13}$ is hydrogen and $R_{12}$ is alkyl. In these embodiments, $L_7$ is absent. Alternatively, $L_7$ is a linear linking moiety, and in some embodiments it is an alkylene, as described herein. In these embodiments $L_7$ and $R_{12}$ form together a linear alkyl. The alkyl, according to these embodiments, is preferably of 2 to 10 carbon atoms in length, more preferably 2 to 8, or 2 to 6, or 2 to 4, carbon atoms in length.

In alternative embodiments, $R_{12}$ and $R_{13}$ are each independently an alkyl, and $L_7$ is a branched linking moiety as described herein in any of the respective embodiments and any combination thereof. In some of these embodiments, $L_7$ is Rc-CRd-Rf, Rd is H and Rc and Rf are absent. In some of these embodiments, $R_{12}$ and $R_{13}$ are each independently an alkyl of from 1 to 8 or from 1 to 6, or from 1 to 4 carbon atoms in length.

When a polymeric compound comprises a plurality of BU(7) backbone units, the BU(7) units can be the same or different. The BU(7) units can differ from one another by, for example, $R_{12}$ and/or $R_{13}$, and/or by $L_7$.

According to some of any of the embodiments described herein, the BU(8) backbone units, when present, are cross-linked units, which cross-link polymeric chains in the polymeric compounds. These units can be interlaced, as single backbone units or as blocks (comprising a plurality of such units covalently attached to one another), between blocks composed of one or more of BU(2), BU(3), BU(4), BU(5), BU(6) and/or BU(7), according to the present embodiments.

The BU(8) units, when present, are covalently linked to at least two polymeric chains by means of two or more of the amine and carboxyl groups therein.

In some embodiments, when a BU(8) unit is included in the polymeric compound, the polymer can be represented by Formula II:

Formula II

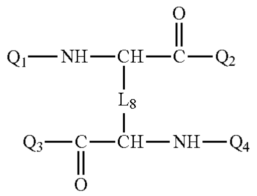

wherein:

$Q_1$ and $Q_4$ are each independently selected from an N-terminus group, as defined herein and a polymeric chain comprising a plurality of one or more of BU(1), BU(2), BU(3), BU(4), BU(5), BU(6) and BU(7) backbone units; and $Q_2$ and $Q_3$ are each independently selected from an C-terminus group, as defined herein and a polymeric chain comprising a plurality of one or more of BU(1), BU(2), BU(3), BU(4), BU(5), BU(6) and BU(7) backbone units, provided that at least one of $Q_1$, $Q_2$, $Q_3$ and $Q_4$ comprises a plurality of one or more of BU(2), BU(3), BU(4), and BU(6) backbone units.

In some of the embodiments of Formula II, at least one, at least two, at least three, or all of $Q_1$, $Q_2$, $Q_3$ and $Q_4$ comprises a plurality of BU(2) backbone units.

In some of any of the embodiments of BU(8), $L_8$ is a linear (non-branched) linking moiety, as described herein in any of the respective embodiments. In some embodiments, $L_8$ is or comprises a hydrocarbon, as described herein, interrupted by one or more heteroatoms, preferably one or more nitrogen atoms.

In exemplary embodiments, $L_8$ is a hydrocarbon composed of alkylene and alkenylene groups, interrupted by one or more nitrogen atoms. In some embodiments, $L_8$ is formed upon reacting two cross-linkable groups with a suitable bi-functional, cross-linking agent, and is the product of such a reaction. In exemplary embodiments, $L_8$ is formed upon reacting aminoalkylene cross-linkable groups with a dialdehyde compound (e.g., glutaraldehyde), and as such, $L_8$ is an alkylene chain interrupted by corresponding Schiff bases formed upon the cross-linking reaction. $L_8$ can alternatively be an alkylene chain interrupted by any other moieties formed upon interaction between cross-linkable groups and a corresponding cross-linking agent or moieties. Additional, non-limiting examples of cross-linkable groups and cross-linking moieties formed therefrom include, disulfide bonds formed upon cross-linking thiolated amino acids such as, but not limited to, cysteine, cysteamine. Cross-linking agents or moieties that can be included for forming cross-links between amine and/or thiol groups include, but are not limited to, succinimidyl 3-(2-pyridyldithio)propionate), azide-phosphine crosslinkers; disuccinimidyl glutarate (DSG); Bis(sulfosuccinimidyl) suberat; click chemistry reagents; Genipin. Any other cross-linkable groups and corresponding cross-linking agents are contemplated for forming $L_8$.

In some of any of the embodiments described herein, a polymeric compound as described herein can be regarded as featuring a peptide-like backbone chain, in which the backbone units are linked to one another via a peptide (amide) bond.

The groups at the N-terminus and at the C-terminus of such peptide-like backbone chain can be an amine, at the N-terminus, and hydroxy, at the C-terminus, reflecting the amine and carboxylic acid groups of the respective monomers used to form the polymeric backbone, and which are positioned at the N-terminus and the C-terminus of the polymeric compound, respectively.

In some embodiments, the N-terminus group is modified by replacing one or both hydrogens of the terminal amine by one or more substituents. Such substituents can be, for example, alkyl, cycloalkyl, aryl, acyl, carboxylate, as well as any of the substituents described in the context of an amide group hereinunder.

In exemplary embodiments, the N-terminus group is an amine in which one of the hydrogens is substituted by an alkyl. In some embodiments, the alkyl is at least 3, or at least 4 carbon atoms in length. In some embodiments, the alkyl is from 4 to 18 carbon atoms in length. The alkyl can be linear or branched alkyl, and is preferably a linear alkyl.

In some embodiments, the C-terminus group is modified by replacing the hydroxy group of the carboxylic acid by an alkoxy, aryloxy, alkyl, cycloalkyl, amine or a nitrogen-containing heterocyclic group, as these terms are defined herein, such that the modified C-terminus group is a carboxylate, a ketone, or an amide.

According to some of any of the embodiments described herein, and any combination thereof, a polymeric compound as described herein comprises a plurality of backbone units composed of one or more of BU(2), BU(3), BU(4) and BU(6), optionally in combination with backbone units BU(5) and/or BU(1).

Polymers according to embodiments of the present invention can be collectively represented by Formula I:

$R_1$-$R_{11}$ are each independently selected from H, alkyl and cycloalkyl, as defined herein and as described in any one of the respective embodiments and any combination thereof;

$L_1$, $L_2$, $L_3$ and $L_6$ is each independently a linear (non-branched) linking moiety, as defined herein and as described in any one of the respective embodiments and any combination thereof;

$L_4$ is a branched linking moiety, as defined herein and as described in any one of the respective embodiments and any combination thereof, for BU(4);

$L_5$ is a linear linking moiety or a branched linking moiety, or is absent, as defined herein and as described in any one of the respective embodiments and any combination thereof, for BU(5); and Z is a nitrogen-containing heterocylic moiety, as described in any one of the respective embodiments and any combination thereof, for BU(6), provided that at least one of x, y and z is other than 0.

In some of any of the embodiments described herein, each of x, y, z, u and v, representing the mol % of BU(2), BU(3), BU(4), BU(5) and BU(6), as described in any of the respective embodiments, respectively, when other than 0, independently ranges from 10 to 100%, or from 10 to 80%, including any subranges and intermediate values therebetween.

By "mol %" it is meant the mol fraction of a backbone unit relative to 1 mol of the polymer, multiplied by 100.

Thus, for example, 50 mol % of BU(3) units describes a polymer composed of 100 backbone units, whereby 50 of its Formula I

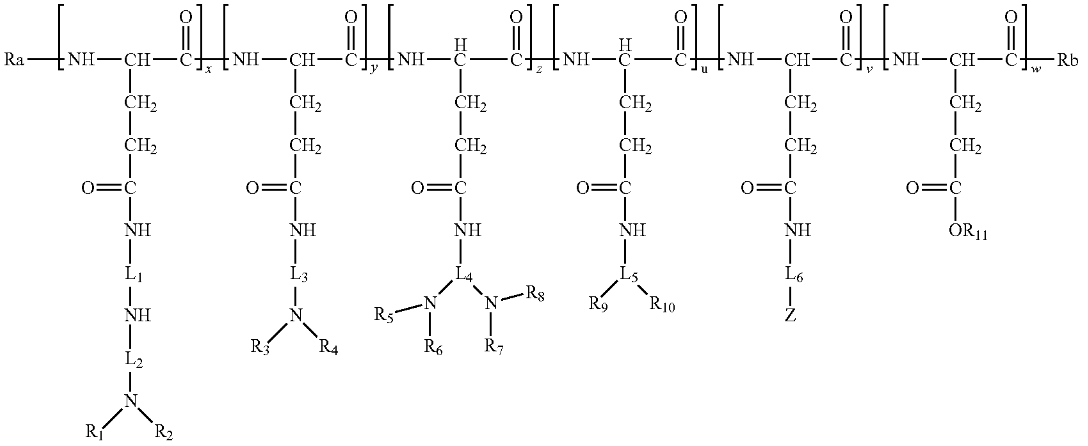

wherein:

x, y, z, u, v and w each independently represents the mol % of the respective backbone unit, such that x+y+z+u+v+w=100 mol %, wherein x+y+z+u+v≥40 mol %;

Ra is selected from hydrogen (in case an N-terminus group is amine) and alkyl, preferably an alkyl (linear or branched) of at least 4 carbon atoms in length, representing an alkyl substituent of an N-terminus amine, as described herein);

Rb is selected from hydroxyl (in case a C-terminus group is carboxylic acid), alkoxy (in case a C-terminus group is a carboxylate), amine (in case a C-terminus group is an amide) and pyrrolidinone (in case a C-terminus group is amide formed with a nitrogen-containing heterocyclic group);

backbone unit are BU(3) and the other 50 backbone units are units of one or more of BU(1), BU(2), BU(4), BU(5) and BU(6).

In other words, 50 mol % of BU(3) units describes a polymer composed of 100 PGA backbone units, in which 50 backbone units are substituted by an —NH-$L_3$-$NR_3R_4$ moiety.

In some of any of the embodiments described herein, w, which represents the mol % of BU(1) is 0, such that 100% of the backbone units feature PGA pendant groups that are further substituted, namely, 100% of the backbone units are BU(2), BU(3), BU(4), BU(5) and/or BU(6) backbone units, according to the present embodiments.

In some of any of the embodiments described herein, the polymer comprises a plurality of BU(3) backbone units, such that y in Formula I, which represents the mol % of BU(3), is other than 0. In some of any of the embodiments in which y is other than 0, $R_3$ and $R_4$ are each H.

In some of any of the embodiments in which y is other than 0, $L_3$ is an unsubstituted alkylene being 2 to 10, or 2 to 8, or 2 to 6, carbon atoms in length.

In some of any of the embodiments described herein, y ranges from 50 to 100 mol %, or from 60 to 100 mol %, or from 70 to 100 mol %. In some embodiments, y is about 100 mol %, such that the polymeric compound consists of BU(3) backbone units. In some of these embodiments, $R_3$ and $R_4$ are each hydrogen. In some of these embodiments, $L_3$ is ethylene. See, for example, Polymer A in FIG. 4. In some of these embodiments, $L_3$ is hexylene. See, for example, Polymer B in FIG. 4. Polymers in which y is other than 0 and $R_3$ and $R_4$ are each hydrogen comprise backbone units featuring a pendant group that terminates by a primary amine.

In some embodiments, in at least a portion of the plurality of BU(3) backbone units, one or both of $R_3$ and $R_4$ is other than H (hydrogen). In some of these embodiments, $R_3$ and $R_4$ are each methyl. Polymers in which y is other than 0 and $R_3$ and $R_4$ are each other than H comprise backbone units featuring a pendant group that terminates by a tertiary amine. In some of these embodiments, $R_3$ is H and $R_4$ is methyl. Polymers in which y is other than 0 and one of $R_3$ and $R_4$ is other than H comprise backbone units featuring a pendant group that terminates by a secondary amine.

In exemplary embodiments, $R_3$ and $R_4$ are each methyl and $L_3$ is an alkylene, preferably an unsubstituted alkylene being 2 to 6 carbon atoms in length. In some of these embodiments y is about 100 mol %, such that the polymeric compound consists of BU(3) backbone units featuring pedant groups that terminate by a tertiary amine. See, for example, Polymer C in FIG. 4.

In some embodiments, in a portion of the BU(3) backbone units $R_3$ and $R_4$ are each hydrogen, according to any of the respective embodiments described herein, and in another portion of the BU(3) backbone units $R_3$ and $R_4$ are each alkyl such as methyl, according to any of the respective embodiments described herein. In some of these embodiments y is about 100 mol %, such that the polymeric compound consists of two types of BU(3) backbone units. See, for example, Polymers D and E in FIG. 4. The mol ratio of BU(3) units featuring a primary amine and of BU(3) featuring a tertiary amine can be from 1:99 to 99:1, including any intermediate values and subranges therebetween.

In some embodiments, in a portion of the BU(3) backbone units $R_3$ and $R_4$ are each hydrogen, according to any of the respective embodiments described herein, and in another portion of the BU(3) backbone one of $R_3$ and $R_4$ is an alkyl such as methyl, according to any of the respective embodiments described herein. In some of these embodiments y is about 100 mol %, such that the polymeric compound consists of two types of BU(3) backbone units. The mol ratio of BU(3) units featuring a primary amine and of BU(3) featuring a secondary amine can be from 1:99 to 99:1, including any intermediate values and subranges therebetween.

In some of any of the embodiments described herein, the polymer comprises a plurality of BU(2) backbone units, such that x in Formula I, which represents the mol % of BU(2), is other than 0.

In some of any of the embodiments described herein, x, which represents the mol % of BU(2), is at least 40 mol %, and at least one of $R_1$ and $R_2$, preferably each, is other than H.

In some of any of the embodiments described herein, x, which represents the mol % of BU(2), ranges from 50 to 100 mol %, or from 60 to 100 mol %, or from 70 to 100 mol %, including any intermediate values and subranges therebetween. In some of any of the embodiments in which x is other than 0, in at least a portion of the plurality of the BU(2) backbone units, one or more of, and preferably each of, $R_1$ and $R_2$ is alkyl, for example, a $C_{1-4}$ alkyl such as methyl.

In some of any of the embodiments in which x is other than 0, $L_1$ and $L_2$ are each alkylene, and in some embodiments $L_1$ and $L_2$ are each ethylene.

In some of any of the embodiments in which x is other than 0, x is about 100%.

In some of these embodiments, all the BU(2) units are such that $R_1$ and $R_2$ are each an alkyl, as described herein. See, for example, polymer F in FIG. 4.

In some of these embodiments, at least 50%, or at least 60% or at least 70% or more of the BU(2) units (at least 50%, or 60% or 70% of y) are units in which each of $R_1$ and $R_2$ is alkyl, for example, methyl, and in the remaining units one or both of $R_1$ and $R_2$ is H. See, for example, Polymer I in FIG. 4.

Polymers in which x is other than 0 and $R_1$ and $R_2$ are each hydrogen comprise backbone units featuring a pendant group that comprises a secondary amine and terminates by a primary amine.

Polymers in which x is other than 0 and one of $R_1$ and $R_2$ is other than hydrogen comprise backbone units featuring a pendant group that comprises a secondary amine and terminates by a secondary amine.

Polymers in which x is other than 0 and $R_1$ and $R_2$ are each other than hydrogen comprise backbone units featuring a pendant group that comprises a secondary amine and terminates by a tertiary amine.

In some of any of the embodiments described herein, the polymer comprises a plurality of BU(2) units and a plurality of BU(3) units, as described herein in any of the respective embodiments. In some of these embodiments, x+y is about 100%.

In some of these embodiments, x is at least 40 mol %, and at least one of $R_1$ and $R_2$, preferably each, is other than H. In some of these embodiments, y is lower than 40 mol %, and can also be 0.

In some of any of the embodiments described herein, the polymer comprises a plurality of BU(2) units, wherein in a first portion of the BU(2) units at least one of $R_1$ and $R_2$, preferably each, is other than H, as described herein, and in another portion of the BU(2) units, each of $R_1$ and $R_2$ is H. In some of these embodiments, the first portion of the BU(2) units in which at least one of $R_1$ and $R_2$, preferably each, is other than H is at least 50%, or at least 60%, or at least 70%, of x. In some of these embodiments, x is about 100%. See, for example, Polymer I.

Polymers composed of BU(2) and/or BU(3) backbone units featuring a terminal primary amine, optionally in combination with BU(1) units, are also referred to herein as Group I polymers.

Polymers composed of BU(2) and/or BU(3) backbone units featuring a terminal secondary or tertiary amine, optionally in combination with BU(5) and/or BU(1) units, and further optionally in combination with BU(2) and/or BU(3) backbone units featuring a terminal primary amine, are also referred to herein as Group V polymers.

In some of any of the embodiments described herein, u, which represents the mol % of BU(5) backbone units in the polymer, is other than 0, such that the polymer comprises backbone units featuring alkyl pendant groups. In some of these embodiments, at least one of x, y, z and v is other than 0, such that at least a portion of the backbone units are BU(2), BU(3), BU(4) and/or BU(6).

In some of any of the embodiments described herein, u is at least 40 mol %.

In some of any of the embodiments described herein, u ranges from 40 to 50 mol %, including any intermediate values and subranges therebetween.

In some of any of the embodiments described herein, u is at least 40 mol % and y is other than 0. See, for example, Polymers K, M, O and P, in FIG. 6, and Polymers V and W in FIG. 10.

In some of these embodiments, y ranges from 60 to 50 mol %, respectively, including any intermediate values and subranges therebetween. That is, for example, u and y together are 100 mol %, and, for example, when u is 40 mol %, y is 60 mol %, when u is 45 mol %, y is 55 mol %, etc.

In some of any of the embodiments described herein, u is at least 40 mol % and x is other than 0. In some of these embodiments, x is at least 40 mol %. See, for example, Polymer X in FIG. 12.

In some of any of the embodiments described herein, u is at least 40 mol % and both x and y are other than 0. In some of these embodiments, x is at least 40 mol %. See, for example, Polymer Y in FIG. 12.

In some of any of the embodiments described herein for u other than 0, in at least a portion of, or in all of, the plurality of the BU(5) units, $R_9$ is H and $R_{10}$ is alkyl, as described herein in any of the respective embodiments.

In some of any of the embodiments described herein for u other than 0, in at least a portion of, or in all of, the plurality of the BU(5) units, each of $R_9$ and $R_{10}$ is alkyl, as described herein in any of the respective embodiments.

The alkyl in these embodiments can be of 3 to 10, or 5 to 10, or 5 to 8, or 6 to 8, carbon atoms in length.

In some of any of embodiments described herein, when u is other than 0, at least one of $R_9$ and $R_{10}$ is an alkyl being 3 or more, preferably 4 or more, carbon atoms in length, and at least one of x, y, z and v is other than 0.

In some of any of embodiments described herein, when u is other than 0, a first portion of the plurality of the BU(5) units can be such that one of $R_9$ and $R_{10}$ is hydrogen, as described herein in any of the respective embodiments, and a second portion of the plurality of BU(5) units is such that each of $R_9$ and $R_{10}$ is other than hydrogen, as described herein in any of the respective embodiments.

Polymers comprising a plurality of BU(5) backbone units in which one of $R_9$ and $R_{10}$ is hydrogen, in combination with BU(3) units featuring terminal primary amine, and optionally in combination with BU(1) units, are also referred to herein as Group II polymers.

Polymers comprising a plurality of BU(5) backbone units in which each of $R_9$ and $R_{10}$ is other than hydrogen, in combination with one or more of BU(2) and BU(3), and optionally in combination with BU(1) units, are also referred to herein as Group IV polymers.

In some of any of the embodiments described herein, the polymer comprises a plurality of BU(6) units such that v, which represents the mol % of BU(6) units in the polymer, is other than 0.

In some of these embodiments, v is at least 20, or at least 30 mol %.

In some of any of the embodiments where v is other than 0, and u is at least 20, or at least 30 mol %, such that the polymer comprises, or consists of, a plurality of BU(6) units and a plurality of BU(5) units.

In some of any of the embodiments where v is other than 0, at least one of x, y and z is other than 0, such that the polymer consists of, or comprises, a plurality of BU(6) units in combination with a plurality of BU(2), BU(3) and/or BU(4) units, and optionally further comprises a plurality of BU(5) units.

In some of these embodiments, y is other than 0, such that the polymer consists or comprises a plurality of BU(6) units and a plurality of BU(3) units. In some of these embodiments, u is at least 20, or at least 30 mol %. See, for example, Polymers Q and R, in FIG. 8.

In some of any of these embodiments, y ranges from 40 to 80 mol %, preferably from 40 to 60 mol %.

In some of these embodiments, y is other than 0, and u is other than 0, such that the polymer consists or comprises a plurality of BU(6) units, a plurality of BU(3) units and a plurality of BU(5) units. In some of these embodiments, u is at least 20, or at least 30 mol %. In some of any of these embodiments, y ranges from 40 to 60 mol %. In some of these embodiments, u ranges from 20 to 40 mol %. See, for example, Polymers S and T, in FIG. 8.

In some of any of the embodiments described herein, Z is a nitrogen-containing heteroaryl, for example, imidazole.

Polymers composed of BU(6), optionally in combination with BU(2), BU(3), BU(4) and/or BU(5), and further optionally in combination with BU(1) units, are also referred to herein as Group III polymers.

In some of any of the embodiments described herein, the polymer comprises a plurality of BU(4) backbone units, as described herein in any of the respective embodiments, optionally in combination with a plurality of backbone units of one or more of BU(2), BU(3), BU(5) and/or BU(6), and further optionally in combination with BU(1). In some of these embodiments, z, which represents the mol % of BU(4) units, at least 20%, or at least 30%, or at least 40%.

In some embodiments, the polymers described and exemplified herein in embodiments of Formula I are constructed of a PGA backbone and pending functional moieties (pendant groups) attached to the backbone via the carboxylic groups, preferably via an amide bond. The pendant groups can comprise primary, secondary and/or tertiary amines (as in BU(2) and BU(3) units), heterocyclic moieties (as in BU(6) units), linear and/or branched alkyls (as in BU(5) units), and/or branched alkyls terminating by primary., secondary and/or tertiary amines (as in BU(4) units).

In exemplary embodiments, a polymeric compound represented by Formula I as described herein is represented by Formula Ia as follows:

Formula Ia

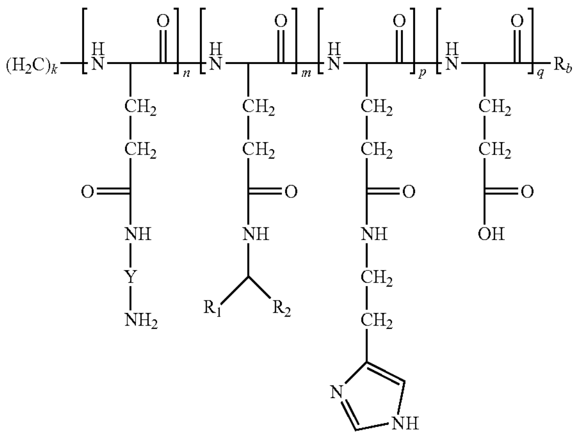

wherein, in some embodiments:

Y is $(CH_2)a$, and a is an integer of from 2 to 6;

$R_1$ is H;

$R_2$ is $(CH_2)bCH_3$, and b is an integer of from 4 to 8, and, in some embodiments, Y is $(CH_2)a$, and a is an integer of from 2 to 6;

$R_1$ and $R_2$ are each independently $(CH_2)bCH_3$, wherein b is an integer of from 2 to 5, and wherein for each of these embodiments, n, m, p and q represent the mol % of exemplary BU(3) units (n), exemplary BU(5) units (m), exemplary BU(6) units (p) and exemplary BU(1) units (q), whereas n ranges from 40 to 100%, m ranges from 0 to 45%, p ranges from 0 to 30%, and q ranges from 0 to 60%.

In some embodiments, n, m, p and q correspond to y, u, v and q in Formula I, respectively, as described herein in any of the respective embodiments.

In some of any of these embodiments, k is 4-18, and $(CH_2)k$ is an exemplary Ra group, as defined herein for Formula I.

In some of any of these embodiments, Rb is as described herein for Formula I.

In some embodiments, polymers represented by Formula Ia comprise, as a pendant group of some backbone units, a linear alkyl amine moiety bearing 2-6 carbon atoms, wherein a mol % (n) of backbone units bearing such a pendant group is 40-100 mol %; and may further comprise as a pendant group of another portion of the backbone units a linear alkyl moiety of 6-10 carbons or branched alkyl moieties of 8-14 carbons, wherein a mol % (m) of backbone units bearing such a pendant group is 0-45%; and/or a pendant group comprising an imidazole ring conjugated via ethylene or another alkylene to the carboxylic acid of another portion of backbone units, wherein a mol % (p) of backbone units bearing such a pendant group is 0-30%; and wherein the remaining backbone units feature a carboxylic acid-containing pendant group of PGA, wherein a mol % (q) of backbone units bearing such a pendant group is 0-60%.

In exemplary embodiments, a polymeric compound represented by Formula I as described herein is represented by Formula Ib as follows:

Formula Ib

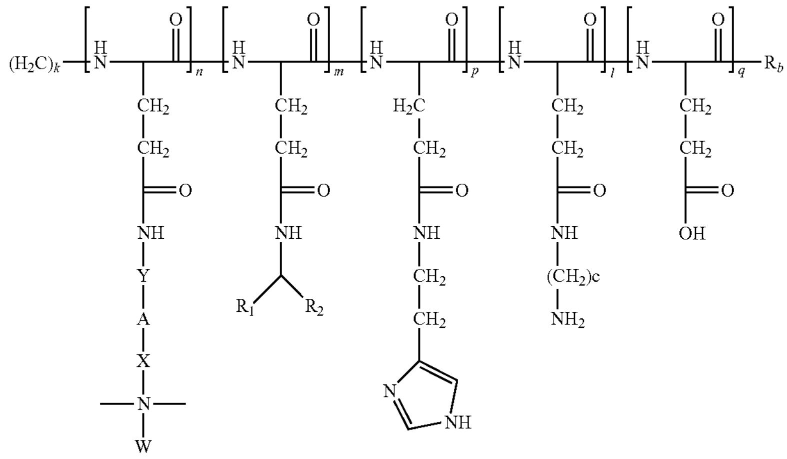

wherein:

Y is $(CH_2)a$, and a is an integer of from 2 to 10;

X$=$$(CH_2)a'$, and a' is an integer of from 2 to 10;

W is H or $CH_3$;

$R_1$ is $(CH_2)bCH_3$, and b is an integer of from 4 to 8;

$R_2$ is H or is $(CH_2)bCH_3$, and b is an integer of from 4 to 8;

C is an integer of from 2 to 6; and

A is N or $CH_2$, and wherein for each of these embodiments, n, m, p, 1 and q represent the mol % of exemplary BU(2) and/or BU(3) units (n), exemplary BU(5) units (m), exemplary BU(6) units (p), exemplary BU(3) units (1), and exemplary BU(1) units (q), whereas n ranges from 40 to 100%, m ranges from 0 to 45%, p ranges from 0 to 30%, 1 ranges from 0 to 30%, and q ranges from 0 to 60%.

In some embodiments, n, m, p, 1 and q correspond to x, u, v, y and q, respectively, in Formula I, as described herein in any of the respective embodiments.

In some of any of these embodiments, k is 4-18, and $(CH_2)k$ is an exemplary Ra group, as defined herein for Formula I.

In some embodiments, polymers represented by Formula Ib comprise, comprise, as a pendant group of some backbone units thereof, a linear alkyl chain bearing 4-20 carbon atoms terminated by a secondary or tertiary amine, and optionally featuring an additional secondary amine at the middle of the alkyl chain, wherein a mol % (n) of backbone units bearing such a pendant group is 40-100%; and may further comprise, as a pendant group of another portion of the backbone units, a linear alkyl moiety of 6-10 carbons or branched alkyl moiety of 4-7 carbons in case of short (4-6 carbons) alkyl chain in the first moiety, wherein a mol % (m) of backbone units bearing such a pendant group is 0-45%; and/or a pendant group comprising an imidazole ring conjugated via ethylene or other alkylene to the carboxylic acid groups of another portion of backbone units, wherein a mol % (p) of backbone units bearing such a pendant group is 0-30%; and/or as a pendant group of another portion of the backbone units, a linear alkyl amine moiety of 2-6 carbons, wherein a mol % (1) of backbone units bearing such a pendant group is 0-50%; and wherein the remaining backbone units feature a carboxylic acid-containing pendant group of PGA, wherein a mol % (q) of backbone units bearing such a pendant group is 0-60%.

In exemplary embodiments, a polymeric compound represented by Formula I as described herein is represented by Formula Ic as follows:

Formula Ic

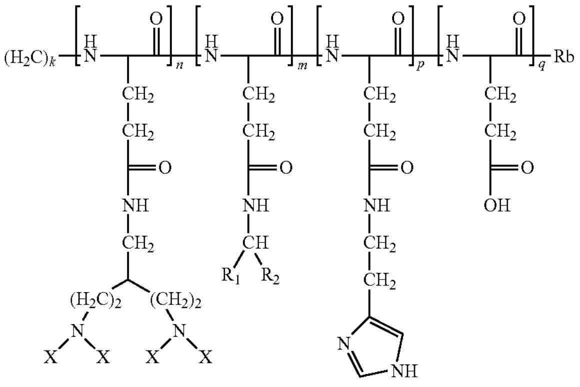

wherein, in some embodiments:

X is independently H or $CH_3$;

$R_1$ is $(CH_2)bCH_3$, and b is an integer ranging from 4 to 8; and $R_2$ is H, and in some embodiments:

X is H or $CH_3$;

$R_1$ and $R_2$ are each independently $(CH_2)bCH_3$, and b is an integer of from 2 to 5, and, in some embodiments:

X is H or $CH_3$;

$R_1$ is $(CH_2)_2NH(CH_2)_5CH_3$; and $R_2$ is H, and, wherein, for each of these embodiments, n, m, p and q represent the mol % of exemplary BU(4) units (n), exemplary BU(5) units (m), exemplary BU(6) units (p), and exemplary BU(1) units (q), whereas n ranges from 40 to 100%, m ranges from 0 to 45%, p ranges from 0 to 30%, and q ranges from 0 to 60%.

In some embodiments, n, m, p and q correspond to z, u, v, and q, respectively, in Formula I, as described herein in any of the respective embodiments.

In some embodiments, polymers represented by Formula Ic comprise, as a pendant group of some backbone units thereof, a branched alkyl amine bearing either primary, secondary or tertiary terminal amines, wherein a mol % (n) of backbone units bearing such a pendant group is 40-100% rate; and may optionally further comprises, as a pendant group of another portion of the backbone units, a linear or branched alkyl chain bearing 6-14 carbon atoms with or without a secondary amine at the middle of the alkyl chain, wherein a mol % (m) of backbone units bearing such a pendant group is 0-45%; and/or as a pendant group, an imidazole ring conjugated via ethylene or another alkylene to the carboxylic acid of another portion of the backbone units, wherein a mol % (p) of backbone units bearing such a pendant group is 0-30%; and wherein the remaining backbone units feature a carboxylic acid-containing pendant group of PGA, wherein a mol % (q) of backbone units bearing such a pendant group is 0-60%.

In some embodiments, the polymers represented by Formula Ia, Ib or Ic have an N-terminus unit of linear alkyl bearing 4-18 carbons.

In some of any of the embodiments described herein for Formulae I, Ia, Ib and Ic, the polymer comprises BU(3) backbone units, at a mol % (x or a variable corresponding thereto) of at least 40%, and at least one, and preferably both, of $R_1$ and $R_2$ is other than H. In some of these embodiments, if the polymer further comprises BU(2) backbone units, the mol % of BU(2) units (y or a variable corresponding thereto) is lower than 40%.

In some of any of the embodiments described herein for Formulae I, Ia, Ib and Ic, the polymer comprises BU(5) backbone units, and at least one of $R_9$ and $R_{10}$ is an alkyl being more than 3 carbon atoms in length, as described herein in any of the respective embodiments. In any of these embodiments, at least one of x, y, z and v, or variables corresponding thereto, is other than 0.

In some of any of the embodiments described herein for Formulae I, Ia, Ib and Ic, when the polymer comprises BU(6) backbone units, it comprises also a plurality of BU(5) units, such that v and u, or any of the variables corresponding thereto, is other than 0, as described herein in any of the respective embodiments.

In some of any of the embodiments described herein for Formulae I, Ia, Ib and Ic, the polymer comprises BU(4) backbone units, at a mol % (z or a variable corresponding thereto) of at least 40%.

In some of any of the embodiments described herein, the polymers described herein are collectively represented by Formula I*:

Formula I*

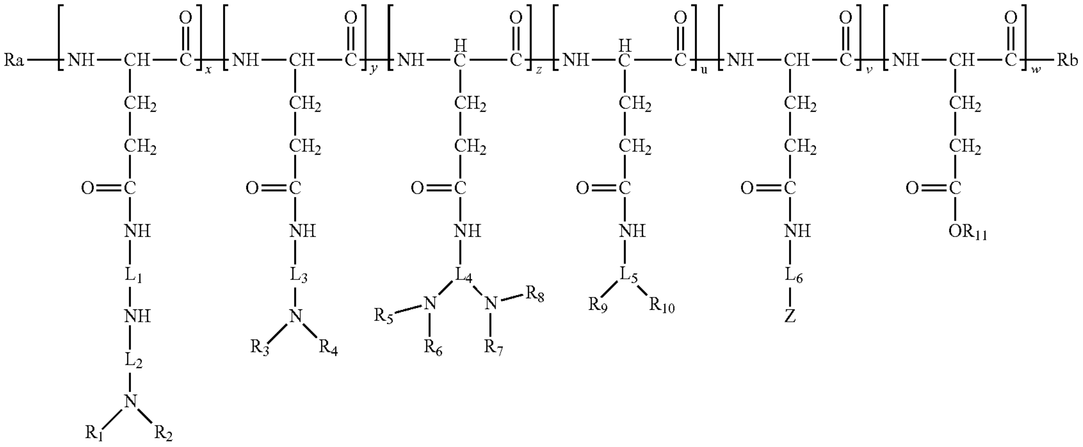

wherein:

x, y, z, u, v and w each independently represents the mol % of the respective backbone unit, such that x+y+z+u+v+w=100 mol %, wherein x+y+z+u+v≥40 mol %;

Ra is selected from hydrogen (in case an N-terminus group is amine) and alkyl, preferably an alkyl (linear or branched) of at least 4 carbon atoms in length, representing an alkyl substituent of an N-terminus amine, as described herein), as described herein for any of the respective embodiments of Formula I, Ia, Ib and/or Ic;

Rb is selected from hydroxyl (in case a C-terminus group is carboxylic acid), alkoxy (in case a C-terminus group is a carboxylate), amine (in case a C-terminus group is an amide) and pyrrolidinone (in case a C-terminus group is amide formed with a nitrogen-containing heterocyclic group), as described herein for any of the respective embodiments of Formula I, Ia, Ib and/or Ic;

$R_1$-$R_{11}$ are each independently selected from H, alkyl and cycloalkyl, as defined herein and as described in any one of the respective embodiments and any combination thereof for any of Formula I, Ia, Ib and/or Ic;

$L_1$, $L_2$, $L_3$ and $L_6$ is each independently a linear (non-branched) linking moiety, as defined herein and as described in any one of the respective embodiments and any combination thereof for Formula I;

$L_4$ is a branched linking moiety, as defined herein and as described in any one of the respective embodiments and any combination thereof, for BU(4), and for Formula I;

$L_5$ is a linear linking moiety or a branched linking moiety, or is absent, as defined herein and as described in any one of the respective embodiments and any combination thereof, for BU(5), and for Formula I; and Z is a nitrogen-containing heterocylic moiety, as described in any one of the respective embodiments and any combination thereof, for BU(6), and for Formula I, provided that:

(i) x is at least 40 mol %, y is lower than 40 mol %, and at least one of $R_1$ and $R_2$ is other than H; or (ii) when u is other than 0, at least one of $R_9$ and $R_{10}$ is an alkyl being more than 3 carbon atoms in length, and at least one of x, y, z and v is other than 0; or (iii) when v is other than 0, u is other 0; or (iv) z is greater than 40 mol %.

Exemplary polymers according to some embodiments of the present invention include Polymers A-Y, as shown in the Examples section and in FIGS. 4, 6, 8, 10 and 12.

Exemplary polymers according to some embodiments of the present invention include Polymer A, Polymer B, Polymer F, Polymer I, Polymer K, Polymer M, Polymer O, Polymer P, and Polymer T.

In some embodiments, Exemplary polymers according to some embodiments of the present invention include Polymer F, Polymer I, Polymer K, Polymer M, Polymer O, Polymer P, and Polymer T, as described herein.

According to an aspect of some embodiments of the present invention there are provided processes of preparing the polymers of Formula I as described herein. The processes are generally effected by coupling PGA to a respective amine-containing moiety, as described herein.

Any coupling agent useful in forming peptide bonds is contemplated. One or more types of coupling agents can be used, depending on the type(s) of the amine to be conjugated.

Exemplary coupling agents include, without limitation, CDI and DIC.

Cross-Linked Polymers:

In some embodiments of the present invention, there is provided a polymer as described herein in any of the respective embodiments, which further comprises BU(8) units as described herein, in any of the respective embodiments. Such polymers are cross-linked polymers (co-polymers), and can be collectively represented by Formula II, as described herein:

Formula II

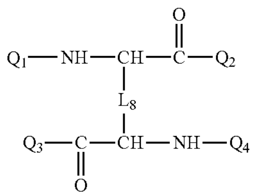

wherein:

$Q_1$ and $Q_4$ are each independently selected from an N-terminus group, as defined herein and a polymeric chain comprising a plurality of one or more of BU(1), BU(2), BU(3), BU(4), BU(5), BU(6) and BU(7) backbone units; and $Q_2$ and $Q_3$ are each independently selected from an C-terminus group, as defined herein and a polymeric chain comprising a plurality of one or more of BU(1), BU(2), BU(3), BU(4), BU(5), BU(6) and BU(7) backbone units, provided that at least one of $Q_1$, $Q_2$, $Q_3$ and $Q_4$ comprises a plurality of one or more of BU(2), BU(3), BU(4), and BU(6) backbone units.

In some embodiments, one or more of $Q_1$, $Q_2$, $Q_3$ and $Q_4$ is a polymeric chain that corresponds to any one of the polymers of Formula I, Ia, Ib, Ic or I*, as described herein in any of the respective embodiments, such that a polymer represented by one of these Formulae is a cross-linked polymer.

In some of any of the embodiments described herein for Formula II, the mol % of the BU(8) in the cross-linked polymer ranges from 1 to 20%, and the mol % of the other backbone units (e.g., of BU(1), BU(2), BU(3), BU(4), BU(5), BU(6) and/or BU(7)) ranges from 99 to 80%, respectively.

In some of any of the embodiments described herein for Formula II, BU(8) represents cross-linked lysine moieties, such that $L_8$ is formed upon cross-linking the terminal amine group of one lysine with a terminal amine group of another lysine. Alternatively, BU(8) can be a cross-linked form of any other amino acid featuring an amine-containing pendant groups. When amine-containing pendant groups are cross-linked by, for example, a dialdehyde such as glutaraldehyde, $L_8$ represents a cross-linking moiety that comprises two Schiff base moieties linking alkylene chains. Alternatively, BU(8) can be any of the other cross-linked amide acids as described herein.

An exemplary polymer of Formula II, referred to herein as Polymer PL1, is depicted in FIG. 14. As shown therein, a cross-linked polymer featuring a cross-linked polylysine (1-20%)-L-polyglutamate (99-80%) polymeric backbone is prepared and then can be functionalized as described herein so to feature pendant groups as in BU(2), BU(3), BU(4), and/or BU(6), optionally in combination with pendant groups as in BU(1) and/or BU(5).

In Polymer CL1, the cross-linked polylysine is attached to polymeric backbones comprising or consisting of BU(3) units featuring a terminal primary amine.

Co-Polymers:

In some embodiments of the present invention, there is provided a polymer as described herein in any of the respective embodiments, which further comprises BU(7) units as described herein, in any of the respective embodiments.

In some of these embodiments, the polymer comprises a plurality of backbone units selected from BU(1), BU(2), BU(3), BU(4), BU(5), and/or BU(6), and a plurality of BU(7) backbone units, as described herein in any of the respective embodiments.

In some embodiments, at least 40 mol % of the backbone units are selected from BU(2), BU(3), BU(4), and/or BU(6).

In some embodiments, the polymer is arranged as a block-copolymer comprising at least one block comprising a plurality of BU(1), BU(2), BU(3), BU(4), BU(5), and/or BU(6), and at least one block comprising BU(7) backbone units.

In some embodiments, a total mol % of the BU(2), BU(3), BU(4), BU(5), and/or BU(6) is at least 60%.

Such polymers can alternatively be collectively represented by Formula III, as described herein:

$$[Qa]m\text{-}[M]p \qquad \text{Formula III}$$

wherein:

M comprises one or more BU(7) backbone units as defined herein in any of the respective embodiments;

Qa comprises one or more (e.g., a plurality) of backbone units selected from BU(1), BU(2), BU(3), BU(4), BU(5), and/or BU(6), and optionally BU(8), as described herein for any of the embodiments Formula I, Ia, Ib, Ic and II, and any combination thereof, p, which represents the total mol % of BU(7) units ranges from 20 to 40; and m, which represents the total mol % of BU(1), BU(2), BU(3), BU(4), BU(5), and/or BU(6), and optionally BU(8, ranges from 60 to 80, respectively, provided that Qa comprises a plurality of one or more of BU(2), BU(3), BU(4), and BU(6) backbone units.

In some embodiments, Qa and m are such that the total mol % of the BU(2), BU(3), BU(4), and BU(6) backbone units, whichever present, is at least 40%.

In some embodiments, Qa and m are as described herein for polymers of Formula I, Ia, Ib or Ic, in any of the respective embodiments and any combination thereof.

The BU(7) units and the backbone units of Qa can be arranged in the polymeric backbone in any order, as is known in the art for co-polymers.

In some embodiments, the BU(7) backbone units can be interlaced randomly within the backbone units composing Qa.

In some embodiments, the BU(7) and backbone units of Qa are arranged as a block co-polymer, comprising one or more clusters of the backbone units composing Qa and one or clusters of BU(7) backbone units.

For example, the block co-polymer can be arranged as follows:

$$[M']g\text{-}[Qa']h\text{-}[M']f\text{-}[Q'a']i$$

wherein:

M' is a block comprising a plurality of BU(7) backbone units;

Qa' is a block comprising a plurality of backbone units as described herein for Formula I, Ia, Ib, or Ic;

g and f represent the mol % of each M' block, h and i represent the mol % of each Qa' block, g ranges from 0 to 40;

f ranges from 0 to 40;

h ranges from 40 to 80; and i ranges from 0 to 40, such that g+f ranges from 20 to 40 and h+i ranges from 60 to 80, and g+h+f+1=100.

Thus, for example, g can be 20-40, h can be 80-60, respectively, and f and i are each 0. Alternatively, g is 10-20, h is 60-80, and f is 10-20. Further alternatively, g is 0, h is 30-40, f is 20-40, and i is 30-40. Any other values are contemplated.

The block copolymer can include more than 2 Qa' blocks and/or more than 2 M' blocks.

When two or more blocks of Qa' are present, the blocks of Qa' can include the same or different composition of backbone units, and in some embodiments, each of the Qa' blocks is the same.

In some embodiments, each Qa' block comprises one type of backbone units (for example, one type of BU(2), BU(3), BU(4) or BU(6), or two or more types, as described herein for any of the embodiments of Formula I.

In some embodiments, each of the Qa' blocks consists of BU(3) backbone units, and in some of these embodiments, the BU(3) backbone units feature a primary terminal amine.

When two or more M' blocks are present, the M' blocks can include the same or different composition of BU(7) backbone units, and in some embodiments, each of the M' blocks is the same.

In some embodiments, a M' block comprises one type of BU(7) backbone units, or two or more types.

The BU(7) units can be, for example, any of the naturally occurring amino acid bearing an alkyl pendant group (e.g., alanine, valine, leucine, isoleucine), or can be a synthetic amino acid.

In some embodiments, a copolymer of Formula III comprises a block co-polymer of α-alkyl-amino acid (20-40%) and L-polyglutamate (80-60%) backbone in which the glutamate units include one or more of BU(1), BU(2), BU(3), BU(4), BU(5), and/or BU(6), and optionally BU(8), as described herein for any of the embodiments Formula I, Ia, Ib, Ic and II, and any combination thereof.

In some embodiments, block copolymers of Formula III can be represented by Formula IIIa:

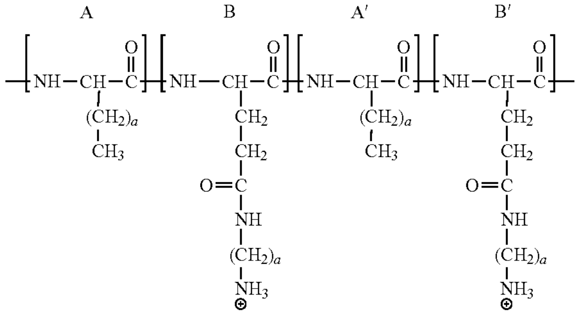

Formula III a = 0, 3 - 17
A = 20-40%, B = 60-80%
A = 10-20%, B = 60-80%, A' = 10–20%
B = 30-40%, A = 40-20%, B' = 30–40% wherein A, B, A' and B' represent the mol % of the respective backbone units in each block.

Polymers of Formula III are also referred to herein as Polymers of Group V.

Polymers of Formula III can be prepared by co-polymerizing a plurality of glutamate units and a plurality of BU(7) (or precursors thereof) under conditions that form a respective block-copolymer, and thereafter modifying some or all of the glutamate units to provide the respective BU(2), BU(3), BU(4), BU(5), and/or BU(6) backbone units, as described herein for polymers of Formula I.

If the Qa or Qa' comprises BU(8) units, such units are co-polymerized with the glutamate and BU(7) units.

The Conjugate:

A conjugate as described herein comprises a polymer as described herein in any one of the respective embodiments and any combination thereof, including any of the block co-polymers and cross-linked polymers and any of the respective embodiments thereof, in association with an oligonucleotide, as described herein.

By "association", "associated with" and any grammatical diversion of these terms, it is meant that that the oligonucleotide and the polymer are linked to one another via one or more chemical and/or physical interactions.

In some embodiments, the oligonucleotide is complexed to the polymer, and the conjugate is therefore referred to herein interchangeably as a polyplex.

In some embodiments, the association is by electrostatic interactions, or bonds, formed between the amine moieties and optionally other nitrogen-containing moieties (e.g., imidazole) in the polymer and the negatively charged groups of the oligonucleotide.

In some embodiments, the electrostatic interactions are between terminal amine groups or other terminal nitrogen-containing moieties (e.g., imidazole) of the polymer and phosphate groups of the oligonucleotide.

N/P ratio is the ratio between phosphate groups of the oligonucleotide and terminal amines of the pendant groups of the PGA backbone. For example: 5 N/P means 5 terminal nitrogen groups for each phosphate group (can be also written as 5:1 ratio).

In some embodiments, this N/P ratio between a number of the terminal amine groups and a number of the phosphate groups ranges from 15:1 to 1:1, or from 10:1 to 1:1, or from 5:1 to 1:1.

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions.

In some embodiments, the oligonucleotide is an RNA nucleotide. In some embodiments, the oligonucleotide is an RNA silencing agent.

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene.

As used herein, the term "RNA silencing agent" refers to an RNA which is capable of specifically inhibiting or "silencing" the expression of a target gene. In certain embodiments, the RNA silencing agent is capable of silencing mRNA in a cell. In some embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The term "siRNA" refers to small inhibitory RNA duplexes (generally between 18-30 basepairs) that induce the RNA interference (RNAi) pathway.

Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to some embodiments, the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

It will be appreciated that the RNA silencing agent of some embodiments of the invention need not be limited to those molecules containing only RNA, but further encompasses chemically-modified nucleotides and non-nucleotides.

A conjugate as described herein can comprise one or more types of an oligonucleotide in association therewith. In some embodiments, the conjugate comprises two oligonucleotides that act in synergy. Exemplary such oligonucleotides are as described in Example 8 hereinbelow. In some of these embodiments, the conjugate comprises a siRNA and a mi-RNA, for example, as exemplified in Example 8 hereinbelow.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

A conjugate as described herein can further comprise other moieties associated therewith, such as, but not limited to, a labeling agent, as described herein, a targeting moiety, an additional therapeutically active agent, and any other moiety, as desired. In some embodiments, the additional moiety is attached to the conjugate via chemical bonds (e.g., covalent bonds), for example, to one or more of the backbone units, or to one or more of the termini of the polymeric backbone.

In some embodiments, the additional moiety is a cell-penetrating peptide. Exemplary peptides include those described in Milletti Drug Discov Today. 2012; 17:850-60, TAT peptides as described, for example, in Frankel et al. Cell. 1988; 55:1189-93, TAT-like structures as described, for example, in Bersani et al. Bioconjugate chemistry. 2012; 23:1415-25, and mitochondria-disrupting peptides, as described, for example, in Javadpour et al. Journal of medicinal chemistry. 1996; 39:3107-13. Such cell-penetrating peptides may promote cellular uptake of the conjugates. Any other moiety that promotes cellular uptake is also contemplated.

As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

Targeting moieties or agents suitable for use in the context of the present embodiments include ligands of cell-surface receptors expressed in tumor cells.

Exemplary moieties or agents include, without limitation, an arginine-glycine-aspartate (RGD) peptide, fibronectin, folate, galactose, an apolipoprotein, insulin, transferrin, a fibroblast growth factor (FGF), an epidermal growth factor (EGF), and an antibody. In an embodiment, the targeting agent can interact with a receptor selected from $\alpha_v,\beta_3$-integrin, folate, asialoglycoprotein, a low-density lipoprotein (LDL), an insulin receptor, a transferrin receptor, a fibroblast growth factor (FGF) receptor, an epidermal growth factor (EGF) receptor, and an antibody receptor. In some embodiments, the arginine-glycine-aspartate (RGD) peptide can be cyclic (fKRGD). NCAM targeting moieties are also contemplated. Bisphosphonates such as alendronate are also contemplated.

As used herein, the phrase "labeling agent" describes a detectable moiety or a probe. Exemplary labeling agents which are suitable for use in the context of the these embodiments include, but are not limited to, a fluorescent agent, a radioactive agent, a magnetic agent, a chromophore, a bioluminescent agent, a chemiluminescent agent, a phosphorescent agent and a heavy metal cluster.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}$Tc, $^{18}$F, $^{131}$I and $^{125}$I., The term "magnetic agent" describes a substance which is attracted to an externally applied magnetic field. These substances are commonly used as contrast media in order to improve the visibility of internal body structures in Magnetic Resonance Imaging (MRI). The most commonly used compounds for contrast enhancement are gadolinium-based. MRI contrast agents alter the relaxation times of tissues and body cavities where they are present, which, depending on the image weighting, can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process The term "chemiluminescent agent" describes a substance which emits light as the result of a chemical reaction.

The phrase "fluorescent agent" refers to a compound that emits light at a specific wavelength during exposure to radiation from an external source. Exemplary such labeling agents include agents that emit light at the Near IR range (e.g., cyanines).

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

Uses:

The conjugates described herein can be used for delivering the oligonucleotide into a cell, thus for transfecting a cell.

By "cell" are encompassed prokaryotic or eukaryotic cells, preferably animal cells, mammalian cells, and human cells.

The conjugates described herein are designed to release the oligonucleotide in the cell.

The conjugate is such that the oligonucleotide is releasably associated with the polymer.

In some embodiments, the conjugates as described herein are for use in gene therapy, particularly, gene silencing.

In some embodiments, the conjugates described herein are for use in silencing a gene in a cell.

In some embodiments, the conjugates described herein are for use in the treatment of medical conditions treatable by gene silencing, as described herein.

In some embodiments, the conjugates described herein are for use in the treatment of medical conditions characterized by impaired siRNA and/or miRNA genetic regulation.

Exemplary medical conditions treatable by the conjugates as described herein include, but are not limited to cancer (e.g., solid tumors), viral infections and diseases, cardiovascular diseases, metabolic diseases, neurodegenerative diseases, autoimmune diseases such as rheumatoid arthritis, and genetic diseases and disorders.

Exemplary genes to be targeted by the silencing therapy described herein include, but are not limited to, cancer-related such as K-ras, Rac1, Plk1, c-myc, bcr/abl, c-myb, c-fms, c-fos and cerb-B, growth factor genes (e.g., genes encoding epidermal growth factor and its receptor, fibroblast growth factor-binding protein), matrix metalloproteinase genes (e.g., the gene encoding MMP-9), adhesion-molecule genes (e.g., the gene encoding VLA-6 integrin), tumor suppressor genes (e.g., bcl-2 and bcl-X1), angiogenesis genes, and metastatic genes; rheumatoid arthritis-related genes include, for example, genes encoding stromelysin and tumor necrosis factor; viral genes include human papilloma virus genes (related, for example, to cervical cancer), hepatitis B and C genes, and cytomegalovirus (CMV) genes (related, for example, to retinitis). Numerous other genes relating to these diseases or others are also contemplated.

According to an aspect of some embodiments of the present invention there is provided a use of the conjugates described herein in the manufacture of a medicament for delivering the oligonucleotide to a cell, and/or for silencing a gene in a cell, and/or for use in gene therapy or gene silencing, as described herein. The medicament can be a pharmaceutical composition as described herein.

According to an aspect of some embodiments of the present invention there is provided a method of delivering an oligonucleotide to a cell, and/or for silencing a gene in a cell, and/or for treating a medical condition treatable by gene therapy or gene silencing as described herein, which is effected by contacting the cell with a conjugate as described herein in any of the respective embodiments.

The contacting can be effected in vivo, ex-vivo or in vivo. When the contacting is in vivo, the method comprises administering to a subject in need thereof (e.g., in which silencing a gene is beneficial) a conjugate as described herein in any of the respective embodiments.

The contacting can be effected by any method known in the art.

In some of any of the embodiments described herein for the methods and uses of the conjugates, two or more conjugates are utilized, each conjugate comprises a different oligonucleotide is association with the polymer.

In some of these embodiments, one conjugate comprises a siRNA and one conjugate comprises a mi-RNA, for example, miRNA as exemplified in the Examples section that follows. In some embodiments, the two or more oligonucleotides associated with the two or more polymers act in synergy.

Pharmaceutical Compositions:

According to some of any of the embodiments described herein there is provided a pharmaceutical composition comprising a conjugate as described herein in any of the respective embodiments, and a pharmaceutically acceptable carrier.

In some embodiments, the pharmaceutical composition is for use in any of the methods and uses described herein.

According to some embodiments of the present invention a pharmaceutical composition comprising the conjugate as described herein comprises an aqueous carrier.

A pharmaceutical composition as described herein is also referred to as a formulation.

According to some embodiments, the conjugate is in a form of a plurality of particles (e.g., nanoparticles) dispersed in the carrier.

According to some embodiments, the carrier further comprises a dispersing agent.

According to some embodiments, the carrier further comprises glucose.

According to some embodiments, the dispersing agent is selected so as to prevent aggregation of the nanoparticles and/or to maintain the discrete particles of the conjugate in the composition.

According to some embodiments, the dispersing agent is selected so as to obtain and maintain nanoparticles featuring an average particle size (diameter) of said particles is lower than 1 micron, or lower than 500 nm or lower than 300 nm, or lower than 200 nm and/or PDI lower than 1, or lower than 0.5, or lower than 0.3.

In some embodiments, for conjugates in which the polymer features amine-containing groups (e.g., primary amine-containing groups, such as PGAamine A), the dispersing agent is a surfactant, such as Tween®. Other surfactants are also contemplated.

In some embodiments, a concentration of the surfactant ranges from 0.1% to 40% by volume, of the total volume of the composition.

In some embodiments, a concentration of the surfactant ranges from 0.1 to 10, or from 0.1 to 40 mol %, relative to the conjugate.

In some embodiments, for conjugates in which the polymer features amine-containing pendant groups and alkyl-containing pendant groups, the dispersing agent can be a polyethylene glycol and/or a glucose (for isotonicity) as described herein.

In some embodiments, a concentration of the PEG ranges from 1 to 20%, or from 5 to 15%, or is about 10%, by volume, of the total volume of the composition.

In some embodiments, a MW of the PEG is at least 400 grams/mol.

In some embodiments, a concentration of the glucose ranges from 1 to 20%, or from 1 to 15%, or from 1 to 10%, by volume, of the total volume of the composition.

In some embodiments, for conjugates in which the polymer features amine-containing pendant groups and alkyl-containing pendant groups, the composition is prepared by means of a microfluidic system.

According to an aspect of some embodiments of the present invention there is provided a pharmaceutical composition comprising a pharmaceutically acceptable carrier, e.g., an aqueous carrier, and a conjugate which comprises a polymer represented by Formula I, as described herein in any of the respective embodiments, and an oligonucleotide associated with said polymer, wherein the conjugate is in a form of particles dispersed in said carrier, and wherein an average particle size (in diameter) of said particles is lower than 1 micron, or lower than 500 nm or lower than 300 nm, or lower than 200 nm; and/or a PDI of said particles is lower than 1, or lower than 0.5, or lower than 0.3.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the conjugate (polyplex) accountable for the biological effect, as described herein.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions.

Pharmaceutical compositions suitable for use in context of some embodiments of the invention include compositions wherein the active ingredients are contained in an amount effective to achieve the intended purpose. More specifically, a therapeutically effective amount means an amount of active ingredient (a conjugate as described herein) effective to prevent, alleviate or ameliorate symptoms of a disorder (e.g., as described herein) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The composition may further comprise an additional therapeutically active agent usable in treating an indicated condition, as described herein.

General:

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

It is expected that during the life of a patent maturing from this application many relevant RNA silencing agents will be developed and the scope of the term "RNA silencing agent" is intended to include all such new technologies a priori.

As used herein the term "about" refers to ±10%, or to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

As used herein, the term "alkyl" describes an aliphatic hydrocarbon including straight chain and branched chain groups. Preferably, the alkyl group has 1 to 20 carbon atoms, and more preferably 1 to 10 carbon atoms. Whenever a numerical range; e.g., "1 to 10", is stated herein, it implies that the group, in this case the alkyl group, may contain 1 carbon atom, 2 carbon atoms, 3 carbon atoms, etc., up to and including 10 carbon atoms. In the context of the present invention, a "long alkyl" is an alkyl having at least 10 carbon atoms in its main chain (the longest path of continuous covalently attached atoms). In the context of the present invention, a "medium alkyl" is an alkyl having from 5 to 9 carbon atoms in its main chain (the longest path of continuous covalently attached atoms). A short alkyl therefore has 4 or less main-chain carbons. The alkyl can be substituted or unsubstituted. When substituted, the substituent can be, for example, an alkyl, an alkenyl, an alkynyl, a cycloalkyl, an aryl, a heteroaryl, a halide, an amine, a hydroxyl, a thiol, an alkoxy and a thioalkoxy, as these terms are defined herein.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl is a linking group, it is also referred to herein as "alkylene" or "alkylene chain".

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, hydroxy, alkoxy and thioalkoxy. Representative examples are piperidine, piperazine, tetrahydrofurane, tetrahydropyrane, morpholino and the like.

Piperidine and piperazine are exemplary nitrogen-containing heterocylic.

The term "hydroxy", as used herein, refers to an —OH group.

The term "alkoxy" refers to a —OR' group, were R' is alkyl, aryl, heteroalicyclic or heteroaryl.

As used herein, the term "amine" describes a —NR'R" group where each of R' and R" is independently hydrogen, alkyl, cycloalkyl, heteroalicyclic, aryl or heteroaryl, as these terms are defined herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents, as described hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples of nitrogen-containing heterocyclics include imidazole, thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

The term "alkylene" as used herein describes a —(CR'R")f-, wherein R' and R" are as described herein, and f is an integer from 1 to 20, or from 1 to 10.

The term "thiol" describes a —SH group.

The term "thioalkoxy" describes both an —S-alkyl group, and an —S-cycloalkyl group, as defined herein.

The term "cyano" describes a —C≡N group.

The term "carbonyl" describes a —C(=O)—R' group, where R' is hydrogen, alkyl, cycloalkyl, aryl, heteroaryl (bonded through a ring carbon) or heteroalicyclic (bonded through a ring carbon) as defined herein.

The term "thiocarbonyl" describes a —C(=S)—R' group, where R' is as defined herein.

The term "O-carbamyl" describes an —OC(=O)—NR'R" group, where R' is as defined herein and R" is hydrogen, alkyl, cycloalkyl, aryl, heteroaryl (bonded through a ring carbon) or heteroalicyclic (bonded through a ring carbon) as defined herein.

The term "N-carbamyl" describes an R'OC(=O)—NR"— group, where R' and R" are as defined herein.

The term "O-thiocarbamyl" describes an —OC(=S)—NR'R" group, where R' and R" are as defined herein.

The term "N-thiocarbamyl" describes an R"OC(=S)NR'— group, where R' and R" are as defined herein.

The term "amide" describes a —C(=O)—NR'R" group, where R' and R" are as defined herein.

The term "carboxy" describes a —C(=O)—O—R' groups, where R' is as defined herein. When R' is H, this term is also referred to herein as carboxylic acid. When R' is alkyl, cycloalkyl or aryl, this term is also referred to herein as carboxylate.

The term "sulfonyl" group describes an $—S(=O)_2—R'$ group, where R' is as defined herein.

The term "halogen" or "halo" describes fluoro, chloro, bromo or iodo atom.

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

Herein, the phrase "therapeutically active agent" is also referred to herein as "drug".

The polymeric moieties described herein may possess asymmetric carbon atoms (optical centers) or double bonds; the racemates, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The polymeric moieties described herein can exist in unsolvated forms as well as solvated forms, including hydrated forms. In general, the solvated forms are equivalent to unsolvated forms and are encompassed within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

As used herein, a "reactive group" describes a chemical group that is capable of reacting with another group so as to form a chemical bond, typically a covalent bond. Optionally, an ionic or coordinative bond is formed.

A reactive group is termed as such if being chemically compatible with a reactive group of an agent or moiety that should be desirably attached thereto. For example, a carboxylic group is a reactive group suitable for conjugating an agent or a moiety that terminates with an amine group, and vice versa.

A reactive group can be inherently present in the monomeric units forming the backbone units, or be generated therewithin by terms of chemical modifications of the chemical groups thereon or by means of attaching to these chemical groups a spacer or a linker that terminates with the desired reactive group.

By "cancer" are encompassed any solid or non-solid cancer and/or cancer metastasis, including, but is not limiting to, tumors of the gastrointestinal tract (colon carcinoma, rectal carcinoma, colorectal carcinoma, colorectal cancer, colorectal adenoma, hereditary nonpolyposis type 1, hereditary nonpolyposis type 2, hereditary nonpolyposis type 3, hereditary nonpolyposis type 6; colorectal cancer, hereditary nonpolyposis type 7, small and/or large bowel carcinoma, esophageal carcinoma, tylosis with esophageal cancer, stomach carcinoma, pancreatic carcinoma, pancreatic endocrine tumors), endometrial carcinoma, dermatofibrosarcoma protuberans, gallbladder carcinoma, Biliary tract tumors, prostate cancer, prostate adenocarcinoma, renal cancer (e.g., Wilms' tumor type 2 or type 1), liver cancer (e.g., hepatoblastoma, hepatocellular carcinoma, hepatocellular cancer), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, serous ovarian cancer, ovarian sex cord tumors, cervical carcinoma, uterine cervix carcinoma, small-cell and non-small cell lung carcinoma, nasopharyngeal, breast carcinoma (e.g., ductal breast cancer, invasive intraductal breast cancer, sporadic; breast cancer, susceptibility to breast cancer, type 4 breast cancer, breast cancer-1, breast cancer-3; breast-ovarian cancer), squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, hereditary adrenocortical carcinoma, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute—megakaryoblastic, monocytic, acute myelogenous, acute myeloid, acute myeloid with eosinophilia, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm, predisposition to myeloid malignancy, acute nonlymphocytic leukemia), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor (invasive), plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma, gastric cancer, fibrosarcoma, glioblastoma multiforme; multiple *glomus* tumors, Li-Fraumeni syndrome, liposarcoma, lynch cancer family syndrome II, male germ cell tumor, mast cell leukemia, medullary thyroid, multiple meningioma, endocrine neoplasia myxosarcoma, paraganglioma, familial nonchromaffin, pilomatricoma, papillary, familial and sporadic, rhabdoid predisposition syndrome, familial, rhabdoid tumors, soft tissue sarcoma, and Turcot syndrome with glioblastoma.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials

All chemicals and solvents were A.R. or HPLC grade. Chemical reagents were purchased from Sigma-Aldrich (Israel) and Merck (Israel). O-benzyl protected glutamic acid (H-Glu(OBzl)-OH) were purchased from Chemimpex (Israel). HPLC grade solvents were from Biolab (Israel). All tissue culture reagents were purchased from Biological Industries Ltd (Beit Haemek, Israel), unless otherwise indicated.

All tissue culture reagents were purchased from Biological Industries Ltd (Beit Haemek, Israel), unless otherwise indicated.

EGFP siRNA, Rac1 siRNA, Cy5-labeled Rac1 siRNA, Plk1 siRNA sequences were obtained from collaborators.

Methods

Aminated PGA polymers were prepared as described in Example 1 hereinunder.

$^{1}H$-Nuclear Magnetic Resonance (NMR):

NMR spectroscopy was performed by 400 MHz Avacne, Bruker (Karlshruhe, Germany) system. PGAamine was dissolved in $D_2O$.

Gel Permeation Chromatography (GPC):

GPC Max VE2001 system (Viscotek) was used for size analysis of the OBz-PGA, equipped with VE3580 RI detector and OmniSEC 4.7 software. 4 columns of Styragel (Waters), HR 4, 3, 1, 0.5 were used in a raw. Chromatographic conditions: flow: 0.5 ml/min, isocratic DMF supplemented with 0.1 M LiBr. 3 OBz-PGA standards (Alamanda, 11 KDa, 22 KDa and 44 KDa) were used for size calibration.

Electrophoretic Mobility Shift Assay (EMSA):

Evaluation of siRNA: polymer complexation in molar ratios between 1:1 to 15:1 (N/P ratios) was performed as follows: 50 pmol of siRNA and increasing amount of polymer were diluted in RNase free water, mixed together and left to form complexes at room temperature for 20-30 minutes. DNA loading buffer was added to the samples, and the solution was loaded on a 2% agarose gel supplemented with ethidium bromide. A voltage of 100 volts was applied for 30 minutes. Sample's run was evaluated under UV light.

Zeta Potential Determination:

The zeta-potential measurements were performed using a ZetaSizer Nano ZS instrument with an integrated 4 mW He—Ne laser (λ=633 nm; Malvern Instruments Ltd., Malvern, Worcestershire, UK). PGAamine:siRNA samples were prepared by dissolving 1 mg of polymer and the indicated amount of siRNA (diluted from 20 μM Rac1-siRNA in RNase free water solution) in 1 ml of 15 mM phosphate buffer, pH=7.4. All measurements were performed at 25° C. using folded capillary cell (DTS 1070) for zeta-potential measurements.

Dynamic Light Scattering:

The hydrodynamic radius and PDI measurements were performed using either a ZetaSizer Nano ZS instrument with an integrated 4 mW He—Ne laser (λ=633 nm; Malvern Instruments Ltd., Malvern, Worcestershire, UK), or Vasco DLS (Nano Instruments Ltd. Cordouan Technologies, Pessac, France), equipped with a 657 nm laser. Data analysis was performed according to cumulants analysis. All measurements were performed at 25° C.

Nanoparticles Tracking Analysis (NTA):

Polyplexes for NTA were prepared as followed: PGAamine polymer was dissolved in DDW to 0.1 mg/mL solution. RNA was added at the indicated N/P ratio from a 20 μM solution in DDW. NTA Analysis was performed using a NanoSight NS300 (Malvern Instruments Ltd., Malvern, Worcestershire, UK), equipped with a sCMOS camera and a 532 nm laser. Data analysis was performed using NTA 3.1 software. Each sample was measured for 60 seconds at 3 different fields, measurements were taken at room temperature.

Multi Static Light Scattering (MALS):

Molecular weight and polydispersity analysis were performed on Agilent 1200 series HPLC system (Agilent Technologies) equipped with a multi angle light scattering detector (Dawn Heleos, Wyatt), using Shodex Kw404-4F column (Showa Denko America, Inc.) in PBS, flow 0.3 mL/minute for the polyglutamic acid. For the Polypexes, Shodex SB-803 HQ column was used in 0.5 M AcOH and 0.2 M sodium nitrate at flow 0.5 mL/min.

Scanning Electron Microscope:

Polymer solution at 0.1 mg/mL was mixed with siRNA solution at the indicated N/P ratio and incubated at room temperature for 20 minutes. Samples were filtered to remove large aggregates, dropped on a silicon wafer and blotted with cellulose paper.

SEM images were taken by Quanta 200 FEG Environmental SEM (FEI, Oregon, USA). Diameters were measured by measureIT software, Gaussian distribution was fitted using OriginPro software.

Transmission Electron Microscopy (TEM and Cryo-TEM).

Polymer solution was mixed with siRNA solution at 1.5 N/P ratio and 1.5 mg/kg equivalent siRNA concentration in 5% glucose solution. Polymer solution was prepared at the same concentration in 5% glucose solution. The resulting solutions were diluted in DDW to 0.5 mg/mL concentration, dropped on TEM GRID and negatively stained with uranyl acetate (for TEM imaging) or frozen (for Cryo-TEM imaging). TEM images were taken using JEM 1200EX TEM (JEOL Ltd., Tokyo, Japan). Cryo-TEM images were taken using Tecnai 12 TWIN TEM (FEI, Oregon, USA). Radiuses were measured by measureIT software and represent the average of 3 fields, 40 particles per field.

Flow Cytometry (FACS).

HeLa and SKOV-3 cells were seeded onto 6 wells plate at 200,000 cells/well densities. Following 24 h, cells were treated with PGAamine: Rac1 Cy5-labeled siRNA for 4 h. Cells were washed twice with PBS, and harvested with phenol red free Trypsin. 3 mL of 5% FBS in PBS solution were added, and the samples were centrifuged for 7 min at 1100 rpm. Supernatant was discharged, and cells pellets were suspended in 500 μL of 5% FBS in PBS solution. Fluorescence was read at 635 nm using FACSCalibur™ flow cytometer (BD Biosciences, Heidelberg, Germany).

Confocal:

Cells uptake of the PGAamine:Cy5-Rac1 siRNA polyplexes was followed using Leica SP5 confocal imaging systems (X60 Magnification). HeLa cells were treated with polyplexes of PGAamines A to I and Cy5-Rac1 siRNA for various time courses. The cells were fixed with 4% paraformaldehyde and stained with mouse anti EEA1 (BD) and with rabbit anti LAMP1 (Cell signaling) primary antibodies, and then with Goat anti mouse IgG-FITC and Goat anti rabbit IgG-Rhodamine secondary antibodies.

Luciferase Reporter Assay:

In vitro silencing of Rac gene/PLK1 gene by siRac1-polyplex/siPLK1-polyplex was evaluated using psiCHECK reporter assay (Promega Cat No. E1960 Madison, Wisconsin, USA). psiCHECK™-2-based (Promega) construct was prepared for the evaluation of the target activity of Rac1/Plk1. One copy of a consensus target sequence of Rac1/PLK1 was cloned into the multiple cloning site located downstream of the *Renilla* luciferase translational stop codon in the 3'-UTR region.

HeLa cells ($1\times10^6$) were seeded in 10 cm dishes and were incubated in a 37° C., 5% $CO_2$ incubator for 24 hours. Each cell-containing plate was transfected with 4 μg Rac1-psiCHECK™-2-based plasmids using 4 μL Lipofectamine® 2000 (Life Technologies, Grand Island, NY). Following 5 hours, cells were re-seeded in 96-wells plate at final concentration of 4000 cells per well and incubated overnight.

Cells expressing siRNA reporter plasmid were transfected with Rac1/Plk1 siRNA or eGFP/Luciferase siCtrl either complexed with PGA cationic carrier or with Lipofectamine® 2000 as a control (100, 250, or 500 nM siRNA;) or left untreated.

After 72 hours, medium was removed completely from cells and the cells were lysed for 20 minutes in room temperature in gentle rocking by the addition of 50 μL/well 1× Luciferase lysis solution. *Renilla* and firefly luciferase activities were measured in each of the wells of the 96-wells plate, using Dual-Luciferase® Assay kit (Promega Corporation, Wisconsin, USA) according to manufacturer procedure. Aliquots of 10 μL of cell lysate from each sample were transferred to a 96-well white plate. Forty L of Luciferase substrate (LARII) was added to each extract and firefly luciferase activity was measured by luminescence microplate Reader (Mithras LB 940 Multimode Microplate Reader, Berthold Technologies, Germany), then 40 μL of Stop&Glo Reagent was added to each of the samples and *Renilla* luciferase activity was measured immediately afterwards. The *Renilla* luciferase activity is expressed as the percentage of the normalized activity value (*Renilla* luciferase/firefly luciferase) in the tested sample relative to the normalized value obtained in cells transfected with the corresponding psiCHECK™-2 plasmid only (no siRNA or polyplex).

Cells Viability Assay:

HeLa cells were plated onto a 96-well plate (4000 cells/well) in DMEM supplemented with 10% FBS, 2 mM L-glutamine and incubated for 24 hours (37° C.; 5% $CO_2$). Then, cells were transfected with siRNA complexed with PGAamine in various N/P ratios, at 100-500 nM-Rac1/EGFP siRNA concentration or 50 nM Rac1/EGFP siRNA transfected by Lipofectamine™ 2000 as positive control. Following 72 hours amount of viable cells was assessed by modified 3-(4,5-dimethylthiazol-2-yl)-2,5-diphenyltetrazolinium bromide (MTT) assay. Thirty L of 3 mg/ml MTT solution in PBS were added to the wells and incubated for 4-6 hours, the medium was then replaced by 200 μL of dimethyl sulfoxide (DMSO) to dissolve the formazan crystals formed, incubated for 20 minutes at 37° C. Absorbance of the solution was measured at 560 nm by SpectraMax® M5 plate reader (molecular devices). Percent of viable cells was normalized to the viability of non-treated cells (100% viability).

Heparin Displacement Assay.

The relative strength of complexation of PGAamine: siRNA polyplexes was evaluated by measuring the release of siRNA in the presence of heparin. PGAamine:siRNA polyplexes were prepared as described herein. Polyplex solutions were incubated in the presence of 0.01-0.35 IU of heparin/50 pmol siRNA for 15 minutes. DNA loading buffer was added to the samples, and the samples were loaded on a 2% agarose gel supplemented with ethidium bromide. A voltage of 100 volts was applied for 15-30 minutes. Sample's run was evaluated under UV light.

Monolayer Wound Healing Assay.

To study the ability of PGAamine:siRac1 polyplex to inhibit the migration of SKOV-3 cells, IncuCyte ZOOM® Live Cell Imaging system (Essen BioScience, Ann Arbor, Michigan, USA) was used.

SKOV-3 cells were plated onto a 96-well ImageLock tissue culture plate (Essen BioScience, Ann Arbor, Michigan, USA) (30,000 cells/well) in DMEM supplemented with 10% FBS, 2 mM L-glutamine and incubated for 24 hours (37° C.; 5% CO2). Using WoundMaker™, a precise gap was made in each well of 96-wells plate, dislodged cells were washed with DMEM medium. Next, cells were treated with 500 nM siRNA (Rac1 or Ctrl) complexed with PGAamine, with siRac1 only or left untreated with medium only. The plate was placed in IncuCyte ZOOM™ incubator and phase contrast images were taken at regular intervals over a course of 19 hours by IncuCyte ZOOM™ CellPlayer using 10× objective. Relative Wound Density (RWD) accounts for the background density of the wound at the initial time point, and for changes in both the density of the cell (outside the wound region) and the wound region. This parameter is calculated and graphically presented by the IncuCyte™ Software.

Plasma Stability Assay.

The stability of siRac1-polyplex in plasma was evaluated by incubating the polyplexes in whole mouse plasma/fetal bovine serum (FBS) for 0.25-24 hours. Following incubation, the samples were divided to two; one half was incubated for additional 15 minutes with heparin (0.21 IU of heparin/35 pmol siRNA) and the other was incubated in Ultra-Pure Water (UPW) for additional 15 minutes. Next, the samples were loaded on 2% agarose gel and electrophoresis was performed at 100 V for 15-30 minutes. The gel was stained with ethidium bromide solution for siRNA visualization under UV light. As control, naked siRNA at the same concentration as in the polyplexes was loaded into the gel.

Hemolysis Assay:

Rat red blood cells (RBC) solution (2% wt/wt) was incubated with serial dilutions of PGAamine:siRac1 polyplex for 1 hour at 37° C. Dextran (Mw 70 kDa, Sigma) or PBS were used as negative controls, whereas 1% wt/vol solution of Triton X-100 or SDS as positive control. Following centrifugation, the supernatants were transferred to a new plate and absorbance was measured at 550 nm using a SpectraMax® M5e plate reader (Molecular Devices LLC., Sunnyvale, California, USA).

Skov-3 Cells Migration Assay:

Cells migration assay was performed using modified 8 μm Boyden chambers. Prior to migration assay, Skov-3 cells were transfected with PGAamine:Rac1 siRNA polyplexes for 48 hours in 6-well plate (150,000 cells/well) in DMEM+ 20% FCS, 1% Hepes 1 M, 1% sodium pyruvate, 100 μg/mL Penicillin 100 U/mL Streptomycin, 2 mM L-glutamine. Then cells were washed and added without polyplexes to the upper chamber of the transwell (100,000 cells/well) in 100 μL of DMEM without FBS. Two hours later, cells were allowed to migrate to the underside of the chamber for another 20 hours, in the presence or absence of FBS (20% v/v) in the lower chamber. Cells were then fixated with ice-cold methanol and stained (Hema 3 Stain System). Next the stained and migrated cells were imaged using Nikon TE2000E inverted microscope by ×6 objective, brightfield illumination. Migrated cells from captured images were counted using NIH image software (ImageJ). Percent of migrated cells was normalized to migrated cells toward FBS alone (no siRNA transfection).

Western Blot Analysis:

MDA-MB-231 and MCF-7 cells were seeded in 6 wells plate at a density of 100,000 cells/well. After 24 hours, cells were treated with 250 nM of plk1/luciferase siRNA formulated with PGAamine or plk1 siRNA alone. Following 48 hours, cells were harvested and ran on an acryl amide gel under 120 V for about 2 hours. Gels were transferred to nitrocellulose membrane under 80 mA current for overnight. Membrane was blocked with 5% skim milk for 1 hour, reacted with rabbit anti-plk1 antibody (cell signaling) (1:500 in TBST) and mouse anti HSP70 antibody (Santa Cruz Biotechnology, Dallas, Texas, US) (1:40000) for over-night at 4° C., and then with Goat anti Rabbit and Goat anti mouse secondary antibodies (both at 1:10,000 in TBST) for 1 hour. Blots were developed using ECL kit (Thermo Fisher Scientific, Waltham, Massachusetts, US) according to the manufacturer's protocol.

Growth Inhibition of MDA-MB-231 and MCF-7 Cells:

MDA-MB-231 cells were seeded in a 24 well plate at a density of 100,000 cells/well, while MCF-7 cells were seeded at a density of 70,000 cells/well. After 24 hours of incubation, cells were treated with PGAamine:Plk1 siRNA or PGAamine:Luciferase siRNA polyplexes in concentrations of 100, 250 and 500 nM. After 72 hours, cells were harvested and counted using coulter counter.

Maximum Tolerated Dose:

PGAamine:Rac1 siRNA polyplexes at N/P ratio of 5 (A, F and I) or 10 (B), at siRNA concentrations of 1-10 mg/kg were injected intravenously (i.v.) to BALB/c mice, at 400 μL/mouse. Mice were monitored for signs of toxicity up to 24 hours post injection.

MTD of PGAamine:Rac1 siRNA Polyplexes at 3, 5 and 10 N/P Ratios and of Alkylated PGAamine:Rac1 siRNA Polyplexes at 2 N/P:

PGAamine:Rac1 siRNA polyplexes at 3, 5 and 10 N/P ratio at siRNA concentrations of 2-10 mg/kg were injected i.v. to BALB/c mice, at 200 μL/mouse. Alkylated PGAamine:Rac1 siRNA polyplexes at 2 N/P ratio at siRNA concentrations of 8 and 15 mg/kg were injected i.v. to BALB/c mice, at 200 μL/mouse. Mice were monitored for signs of toxicity 24 hours post injection.

Anti-Cancer Efficacy of PGAamine:Plk1 siRNA/miR34a Polyplexes in Skov-3 mCherry-Labeled Orthotopic Tumor Bearing Nu/Nu Mice:

Nu/nu female mice were inoculated intraperitoneally (i.p.) with $6\times10^6$ mCherry-labeled Skov-3 human ovarian adenocarcinoma cells. Seven days post inoculation mice were monitored for tumor formation using CRI™ Maestro non-invasive intravital imaging system, according to the fluorescent measurements mice were randomized (n=7-8 mice/group). Tumor bearing mice were injected i.p. with polymer:siRNA (Plk1 or Luciferase) or polymer: miR (miR-34a or NC miR) formulations (9 q.o.d. injections of 8 mg/kg siRNA or miRNA equivalent dose), saline was injected to control mice (same treatment schedule).

Body weight and tumor progression was monitored twice a week. CRI Maestro™ non-invasive fluorescence imaging system was used to follow tumor progression of mice bearing mCherry-labeled tumors. Mice were anesthetized using ketamine (100 mg/kg) and xylazine (12 mg/kg) injected s.c. and placed inside the imaging system. Multi-spectral image-cubes were acquired through 550-800 nm spectral range in 10 nm steps using excitation (575-605 nm) and emission (645 nm longpass) filter set. Mice autofluorescence and undesired background signals were eliminated by spectral analysis and linear unmixing algorithm. At termination, tumors were dissected and weighed. Data is expressed as mean±standard error of the mean (s.e.m.).

Accumulation and Silencing Activity of PGAamine:siRac1/siLuc Polyplexes in A549 Lung Carcinoma SC Tumor Bearing Nu/Nu Mice:

Nu/nu female mice were subcutaneously (SC) inoculated with $4\times10^6$ A549 human lung carcinoma cells. When tumors reached 100 $mm^3$ in size, twenty days post inoculation, mice were randomized (n=8 mice/group) and divided in a way that 1 group was used for PK study and the other for accumulation and silencing study. For PK study tumor bearing mice were injected once with PGAamine:siRac1 polyplexes or free siRac1 (4 mg/kg siRNA equivalent dose). Blood samples were collected at 0, 10, 30 minutes and 1, 2 and 24 hours, organs and tumors were collected as well at final time point. RAC 1 mRNA levels analysis in the RNA prepared from all frozen tumor tissues and cells were measured using qPCR. For siRNA detection the tissue was lysed and siRNA quantity examined by stem and loop qPCR technique.

PGAamine:siRac1 polyplex, PGAamine:siLuc polyplex Rac1 siRNA alone (4 mg/kg siRNA-equivalent dose) or saline were administered in 3 sequential IV injections (~24 hours interval) in female nu/nu mice bearing SC lung tumors (n=8). Mice were euthanized 24 hours following the 3rd injection. Tumors were collected for analysis and were homogenized and lyophilized. Then, tissue lysates were prepared by placing the samples in 0.25% Triton X-100. The quantity of siRac1 was evaluated by stem-loop qPCR method using SYBR Green on Applied Biosystem 7300 PCR System.

Biodistribution of PGAamine:siRac1-Cy5 in mCherry Labelled MDA-MB-231 Mammary Adenocarcinoma Intramammary Tumor Bearing Nu/Nu Mice:

MDA-MB-231 cells were infected with the mCherry retroviral particles media, and 48 hours following the infection, mCherry positive cells were selected by puromycin resistance. Nu/nu female mice were intramammary inoculated with $1.5\times10^6$ mCherry MDA-MB-231 human breast carcinoma cells. When tumors reached 100 $mm^3$ in size, 12 mice were injected with 1.5 mg/kg of PGAamine:siRac1-Cy5 and images were taken at specific time point (0, 3, 6 and 24 hours) with CRI™ Maestro non-invasive intravital imaging system. Mice were anesthetized using ketamine (100 mg/kg) and xylazine (12 mg/kg) injected s.c, and placed inside the imaging system. Multispectral image-cubes were acquired through 590-750 nm spectral range in 10 nm steps using excitation (605 nm) and emission (635 nm) filter set. Mice auto fluorescence and undesired background signals were eliminated by spectral analysis and the Maestro™ linear unmixing algorithm. After imaging, 3 mice at each time point were euthanized and organs resected to collect the images in the same conditions as reported above.

Accumulation and Silencing Activity of PGAamine:siRac1/siLuc Polyplexes in MDA-MB-231 Mammary Adenocarcinoma Intramammary Tumor Bearing Nu/Nu Mice:

Nu/nu female mice were intramammary inoculated with $1.5\times10^6$ MDA-MB-231 human breast carcinoma cells. When tumors reached 100 $mm^3$ in size, twenty days post inoculation, mice were randomized (n=5 mice/group) and injected IV every day for 3 days with PGAamine:siRac1 polyplex, PGAamine:siLuc polyplex (1.5 mg/kg siRNA-equivalent concentration) or 5% glucose. Mice were euthanized 24 hours following the third injection. Tumors were collected for analysis and were homogenized and lyophilized. Then, tissue lysates were prepared by placing the samples in 0.25% Triton X-100. The quantity of siRac1 was evaluated by stem-loop qPCR method using SYBR Green on Applied Biosystem 7300 PCR System.

Example 1

Aminated PGA Polymers

General Syntheses of Polymers of Formula I

Aminated PGA polymers A to I (FIG. 4) were synthesized using a coupling reagent (e.g., CDI) to conjugate an amine moiety to the pending carboxylic groups of the PGA backbone, as shown in FIG. 5. Efficient chemical conjugation obtained by CDI reagent have allowed 100% substitution of the carboxylic groups using only 1.1 equivalents of the amination reagent, while DIC coupling reagent yielded 80-90% substitution degree with 5 equivalents of amination reagent (data not shown). Whenever an amine moiety containing primary terminal amine was conjugated, the amine was Boc-protected and subsequent acidic deprotection was performed (polymers A, B, D, E, G, H, I) (see, FIGS. 4 and 5). When two different moieties were conjugated on the same backbone, the two different reagents with different molarities were mixed together and conjugated at the same manner with CDI coupling reagent (polymers D, E, G, I).

The amine moieties conjugated to each polymeric backbone have varied in size and functionality: while Polymer A was conjugated to "short" side chain terminated by primary amine, Polymer B was conjugated to longer side chain. Polymer C was conjugated to side chain terminated by tertiary amine, which may increase the complexation strength with siRNA and decrease the N/P ratio of their complete complexation. Successful siRNA delivery depends on fine tuning between strong and stable complexation with the ability to release the siRNA to the cytoplasm before reaching the lysosome [Rejman, Bragonzi et al. 2005; Scomparin, Polyak et al. 2015)]. Polymers D and E were conjugated with two different moieties, each terminated by either primary or tertiary amine. This may achieve strong binding between the polymer and siRNA while maintain buffering capabilities ((Boussif, Lezoualc'h et al. 1995)). The effect of side chain's length on the size of these obtained polyplexes was evaluated by using either "short" (Polymer D) or longer (Polymer E) side chains. Polymer F was conjugated with a side chain bearing the two amine functionalities, combining terminal tertiary amine and medial secondary amine on the same side chain. In Polymer G, a combination of the latter side chain structure with side chain terminated by primary amine is present. Polymer H includes functionalities of primary and secondary amine on single side chain and Polymer I features a combination with tertiary and secondary amine on single side chain at a hybrid system.

Alkyl moiety-bearing aminated PGA polymers J to P (FIG. 6) were synthesized using CDI coupling reagent to conjugate in parallel ethylenediamine and alkyl moieties on the pending carboxylic groups of the PGA backbone, as shown in FIG. 7. The molar ratios in Boc-ethylenediamine and alkylamine solution have determined the percentage of loading of the different moieties, as shown in FIGS. 6 and 7. Molecular weight of each polymer J to P (see, Table A below) was analyzed using SLS.

Imidazole-bearing aminated PGA polymers Q and R (FIG. 8, upper panel) were synthesized using CDI coupling reagent to conjugate in parallel ethylenediamine and imidazole moieties on the pending carboxylic groups of the PGA backbone, as shown in FIG. 9. The molar ratios in Boc-ethylenediamine and histamine dihydrochloride solution have determined the percentage of loading of the different moieties, as illustrated in FIGS. 8 and 9.

Imidazole-bearing alkylated PGAamine polymers S and T (FIG. 8, lower panel) were synthesized using CDI coupling reagent to conjugate in parallel ethylenediamine, histamine dihydrochloride and Alkylamine moieties on the pending carboxylic groups of the PGA backbone. The molar ratios of Boc-ethylenediamine, histamine dihydrochloride and alkylamine have determined the percentage of loading of the different moieties, as illustrated in FIGS. 8 and 9.

Dialkylated PGAamine polymers U, V and W (FIG. 10) were synthesized using CDI coupling reagent to conjugate in parallel Dialkylamine and ethylenediamine moieties on the pending carboxylic groups of the PGA backbone, as shown in FIG. 11. The molar ratios in Boc-ethylenediamine and Dialkylamine solution have determined the percentage of loading of the different moieties, as illustrated in FIGS. 10 and 11.

PGAamine polymers that bear amine moiety with tertiary and secondary amines and an alkyl moiety X and Y (FIG. 12) were synthesized using CDI coupling reagent to conjugate in parallel alkylamine and the amination moieties on the pending carboxylic groups of the PGA backbone, as shown in FIG. 13. The molar ratios in amination moieties and alkylamine solution have determined the percentage of loading of the different moieties, as illustrated in FIGS. 12 and 13.

Synthesis of PGAamines A-I (Group I; BU(2) and/or BU(3) Backbone Units)

Preparation of γ-Ethylenediamine-L-Polyglutamate (A)

To a solution of poly-α-glutamic acid (50 mg, 0.38 mmol per monomer) in dry DMF (1 ml) was added a solution of Carbodiimidazole (75 mg, 0.46 mmol) in dry DMF (1 ml). The reaction, mixture was stirred for 1.5 hours, at 25° C., under Argon atmosphere. Tributylamine (94 μl, 0.39 mmol) was added and the reaction left to stir for 5 more minutes at the same conditions. A solution of Boc-Ethylenediamine (0.42 mmol) in dry DMF (1.5 mL) was added and the reaction mixture was stirred for additional 2 hours at the starting conditions. A solution of Carbodiimidazole (133 mg, 0.82 mmol) in dry DMF (1 mL) was added and the reaction mixture was stirred at 25° C., under Argon for additional 12 hours. DMF was removed under reduced pressure and the remaining oily residue was dissolved in water (40 mL) and freeze dried. The resulting solid was dissolved in DCM (5 mL) and Trifluoroacetic acid (5 mL) was added at 0° C. The mixture was stirred at 25° C. for 10 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH=5.5, then freeze dried. The remaining solid was dissolved in double distilled water (20 mL) and dialyzed for 48 hours at 4° C. (total of 8 L of double distilled water). The aqueous phase was collected and freeze dried to receive a white powder as a trifluoraoacetic salt, with a 41% yield. $^1H$ NMR ($D_2O$; 400 MHz): δ 4.32 (1H, s), 3.45 (2H, s), 3.27 (2H, s), 2.36 (2H, s), 2.05, (1H, s), 1.94 (1H, s).

Preparation of γ-Hexydiamino-L-Polyglutamate (B)

To a solution of poly-α-glutamic acid (50 mg, 0.38 mmol per monomer) in dry DMF (1 mL) was added a solution of Carbodiimidazole (192 mg, 1.20 mmol) in dry DMF (1 mL). The reaction mixture was stirred for 1.5 hours at 25° C., under nitrogen atmosphere. Tributylamine (92 μL, 0.39 mmol) was added and the reaction left to stir for 5 more minutes at the same conditions. A solution of Boc-1, 6-diaminohexane (1.96 mmol) in dry DMF (1 mL) was added and the reaction mixture was stirred for additional 12 hours at the starting conditions. DMF was removed under reduced pressure and the remaining oily residue was dissolved in water (40 mL) and freeze dried. The resulting solid was dissolved in DCM (5 mL) and Trifluoroacetic acid (5 mL) was added at 0° C. The mixture was stirred at 25° C. for 10 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 5.5, then freeze dried. The remaining solid was dissolved in double distilled water (20 mL) and dialyzed for 48 hours at 4° C. (total of 8 L of double distilled water). The aqueous phase was collected and freeze dried to receive a white powder as a trifluoroacetic salt, with a 31% yield. $^1H$ NMR ($D_2O$; 400 MHz): δ 4.26 (1H, s), 3.13 (2H, s), 2.93 (2H, s), 2.32 (2H, s), 2.08, (1H, s), 1.97 (1H, s), 1.61 (2H, s), 1.47 (2H, s), 1.32 (4H, s).

Preparation of γ-3-Dimethylamino-1-Propylamino-L-Polyglutamate (C)

To a solution of poly-α-glutamic acid (51 mg, 0.39 mmol per monomer) in dry DMF (1 mL) was added a solution of Carbodiimidazole (201 mg, 1.24 mmol) in dry DMF (1.5 mL). The reaction, mixture was stirred for 1.5 hours, at 25° C., under nitrogen atmosphere. Tributylamine (92 μL, 0.39 mmol) was added and the reaction left to stir for 5 more minutes at the same conditions. A solution of 3-(dimethylamine)-1-propylamine (3.98 mmol) in dry DMF (1 mL) was added and the reaction mixture was stirred for additional 12 hours at the starting conditions. Double distilled water (40 mL) was added and the mixture was treated with 10% HCl solution to pH of 2.5. The reaction mixture was extracted with $CHCl_3$ (2×40 mL) and diethyl ether (50 mL). The aqueous phase was collected and treated with a 10% NaOH solution to pH of 7, then freeze dried. The remaining solid was dissolved in double distilled water (20 mL) and dialyzed for 72 hours at 4° C. (total of 12 L of double distilled water). The aqueous phase was collected and freeze dried to receive a white powder as a chloride salt, with a 45% yield. $^1H$ NMR ($D_2O$; 400 MHz): δ 4.29 (1H, s), 3.25 (2H, s), 3.01 (2H, s), 2.81 (6H, s), 2.33, (2H, s), 2.05-1.90 (2H, bs), 1.90 (2H, s).

Preparation of γ-3-Dimethylamino-1-propylamino-ethylendiamino-L-polyglutamate (D)

To a solution of poly-α-glutamic acid (50 mg, 0.38 mmol per monomer) in dry DMF (1 mL) was added a solution of Carbodiimidazole (70 mg, 0.43 mmol) in dry DMF (1 mL). The reaction mixture was stirred for 1 hour, at 25° C., under nitrogen atmosphere. Tributylamine (92 μL, 0.39 mmol) was added and the reaction left to stir for 5 more minutes at the same conditions. A solution of 3-Dimethylamine-1-propylamine (0.12 mmol) in dry DMF (1 mL) was added and the reaction mixture was stirred for additional 1 hour at the starting conditions. A solution of Boc-ethylenediamine (0.31 mmol) in dry DMF was added and the reaction mixture was stirred for additional 2 hours at the starting conditions. A solution of Carbodiimidazole (125 mg, 0.477 mmol) in dry DMF (0.7 mL) was added and the reaction mixture was stirred for additional 12 hours at the starting conditions. DMF was removed under reduced pressure. Double distilled water (40 mL) was added and the reaction mixture was freeze dried. The resulting solid was dissolved in DCM (5 mL) and Trifluoroacetic acid (5 mL) was added at 0° C. The mixture was stirred at 25° C. for 20 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 5.5, then freeze dried. The remaining solid was dissolved in double distilled water (20 mL) and dialyzed for 48 hours at 4° C. (total of 8 L of double distilled water). The aqueous phase was collected and freeze dried to receive a white powder as a trifluoroacetic salt, with a 22% yield.

$^{1}$H NMR ($D_2O$; 400 MHz): δ 4.20 (1H, s), 4.04 (0.3H, s) 3.37 (2H, s), 3.15 (1H, s), 3.02 (2H, s), 2.76, (3H, s), 2.26 (3H, s), 1.98-1.81 (4H, bs).

Preparation of γ-6-Dimethylaminohexyl-diamino-hexane-L-polyglutamate (E)

To a solution of poly-α-glutamic acid (41 mg, 0.32 mmol per monomer) in dry DMF (2 ml) was added a solution of Carbodiimidazole (56 mg, 0.34 mmol) in dry DMF (1 mL). The reaction, mixture was stirred for 1 hour at 25° C., under nitrogen atmosphere. Tributylamine (83 μl, 0.32 mmol) was added and the reaction left to stir for 5 more minutes at the same conditions. A solution of 6-Dimethylhexyamine (0.09 mmol) in dry DMF (1 mL) was added and the reaction mixture was stirred for additional 1 hour at the starting conditions. A solution of Boc-diaminohexane (0.26 mmol) in dry DMF (1.5 mL) was added and the reaction mixture was stirred for additional 1 hour at the starting conditions. A solution of Carbodiimidazole (103 mg, 0.63 mmol) in dry DMF (1 mL) was added and the reaction mixture was stirred for additional 12 hours at the starting conditions. DMF was removed under reduced pressure. Double distilled water (40 mL) was added and the reaction mixture was freeze dried. The resulting solid was dissolved in DCM (5 mL) and Trifluoroacetic acid (5 mL) was added at 0° C. The mixture was stirred at 25° C. for 20 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 5.5, then freeze dried. The remaining solid was dissolved in double distilled water (20 mL) and dialyzed for 48 hours at 4° C. (total of 8 L of double distilled water). The aqueous phase was collected and freeze dried to receive a white powder as a trifluoroacetic salt, with a 32% yield. $^{1}$H NMR ($D_2O$; 400 MHz): δ 4.16 (1H, s), 3.03 (3H, s), 2.86 (1H, s), 2.73 (1H, s), 2.22 (2H, s), 1.98-1.86 (2H, bs), 1.53 (3H, s), 1.98 (3H, s), 1.23 (1H, s).

Preparation of γ-6-Dimethylaminohexyl-diamino-hexane-L-polyglutamate (F)

To a solution of poly-α-glutamic acid (40 mg, 0.31 mmol per monomer) in dry DMF (1 mL) was added a solution of Carbodiimidazole (60 mg, 0.37 mmol) in dry DMF (1 mL). The reaction, mixture was stirred for 1 hour at 25° C., under nitrogen atmosphere. Tributyl (73 μL, 0.31 mmol) was added and the reaction left to stir for 5 more minutes at the same conditions. A solution of Dimethyldipropylenetriamine (0.34 mmol) in dry DMF (2 mL) was added and the reaction mixture was stirred for additional 2 hours at the starting conditions. A solution of Carbodiimidazole (106 mg, 0.65 mmol) in dry DMF (2 mL) was added and the reaction mixture was stirred for additional 12 hours at the starting conditions. Double distilled water (40 mL) was added and the reaction mixture was treated with 10% HCl solution to pH of 4. The reaction mixture was extracted with DCM (2×50 mL) and diethyl ether (50 mL). The aqueous phase was collected and treated with a 10% NaOH solution to reach pH of 5.5, then freeze dried. The oil residue was dissolved in double distilled water (20 mL) and dialyzed for 48 hours at 4° C. (total of 6 L of double distilled water) and additional 12 hours at 25° C. (total of 2 L). The aqueous phase was collected and freeze dried to receive a white powder as a chloride salt, with a 35% yield. $^{1}$H NMR ($D_2O$; 400 MHz): δ 4.27 (1H, s), 3.19 (3H, s), 2.59 (4H, s), 2.41 (2H, s), 2.33 (2H, s), 2.23 (6H, s), 2.08-1.97 (2H, bs), 1.67 (4H, s).

Preparation of γ-Dimethyldipropylenetriamine-di-aminohexane-L-polyglutamate (G)

To a solution of poly-α-glutamic acid (41 mg, 0.32 mmol per monomer) in dry DMF (1 mL) was added a solution of Carbodiimidazole (57 mg, 0.34 mmol) in dry DMF (1 mL). The reaction, mixture was stirred for 2 hours, at 25° C., under nitrogen atmosphere. Tributyamine (83 μL, 0.32 mmol) was added and the reaction left to stir for 5 more minutes at the same conditions. A solution of 6-Dimethyl-dipropylenetriamine (0.13 mmol) in dry DMF (1 mL) was added and the reaction mixture was stirred for additional 1 hour at the starting conditions. A solution of Boc-diamino-hexane (0.22 mmol) in dry DMF (1 mL) was added and the reaction mixture was stirred for additional 1 hour at the starting conditions. A solution of Carbodiimidazole (105 mg, 0.65 mmol) in dry DMF (1 mL) was added and the reaction mixture was stirred for additional 12 hours at the starting conditions. DMF was removed under reduced pressure. Double distilled water (40 mL) was added and the reaction mixture was freeze dried. The resulting solid was dissolved in DCM (5 mL) and Trifluoroacetic acid (5 mL) was added at 0° C. The mixture was stirred at 25° C. for 15 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 5.5, then freeze dried. The remaining solid was dissolved in double distilled water (20 mL) and dialyzed for 48 hours at 4° C. (total of 8 L of double distilled water), then 24 hours at 25°

C. (total of 4 L of double distilled water). The aqueous phase was collected and freeze dried to receive a white powder as a trifluoroacetic salt, with a 36% yield. $^1H$ NMR ($D_2O$; 400 MHz): δ 4.32-4.10 (1H, bs), 3.18-1.29 (16H, m).

Preparation of γ-2, 2-iminodiethylamino-L-polyglutamate (H)

To a solution of poly-α-glutamic acid (47 mg, 0.36 mmol per monomer) in dry DMF (1 mL) was added a solution of Carbodiimidazole (67 mg, 0.41 mmol) in dry DMF (1 mL). The reaction, mixture was stirred for 1 hour, at 25° C., under nitrogen atmosphere. Tributylamine (87 μL, 0.36 mmol) was added and the reaction left to stir for 5 more minutes at the same conditions. A solution of Boc-2, 2-iminodiethylamine (0.43 mmol) in dry DMF (1.5 mL) was added and the reaction mixture was stirred for additional 1 hour at the starting conditions. A solution of Carbodiimidazole (124 mg, 0.77 mmol) in dry DMF (1 mL) was added and the reaction mixture was stirred for additional 12 hours at the starting conditions. DMF was removed under reduced pressure. Double distilled water (40 mL) was added and the reaction mixture was freeze dried. The resulting solid was dissolved in DCM (5 mL) and Trifluoroacetic acid (5 mL) was added at 0° C. The mixture was stirred at 25° C. for 10 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 5.5, then freeze dried. The remaining solid was dissolved in double distilled water (20 ml) and dialyzed for 48 hours at 4° C. (total of 8 L of double distilled water), then 8 hours at 25° C. (total of 2 L of double distilled water). The aqueous phase was collected and freeze dried to receive a white powder as a trifluoroacetic salt, with a 42% yield.

$^1H$ NMR ($D_2O$; 400 MHz): δ 4.23 (1H, s), 3.49 (2H, s), 3.33-3.22 (6H, m), 3.1 (1H, s), 2.27 (2H, s), 2.01-1.91 (2H, bs).

Preparation of γ-2, 2-iminodiethylamino-dimethy-dipropylenetriamino-L-polyglutamate (I)

To a solution of poly-α-glutamic acid (40 mg, 0.31 mmol per monomer) in dry DMF (1 mL) was added a solution of Carbodiimidazole (67 mg, 0.41 mmol) in dry DMF (1 mL). The reaction, mixture was stirred for 1 hour at 25° C., under nitrogen atmosphere. Tributylamine (74 μL, 0.31 mmol) was added and the reaction left to stir for 5 more minutes at the same conditions. A solution of Boc-2, 2-iminodiethylamine (0.1 mmol) in dry DMF (1 mL) was added and the reaction mixture was stirred for additional 1 hour at the starting conditions. A solution of dimethydipropylenetriamine (0.24 mmol) in dry DMF (1 mL) was added and the reaction mixture was stirred for additional 1 hour at the starting conditions. A solution of Carbodiimidazole (100 mg, 0.62 mmol) in dry DMF (1 mL) was added and the reaction mixture was stirred for additional 12 hours at the starting conditions. DMF was removed under reduced pressure. Double distilled water (40 ml) was added and the reaction mixture was freeze dried. The resulting solid was dissolved in DCM (5 mL) and Trifluoroacetic acid (5 mL) was added at 0° C. The mixture was stirred at 25° C. for 10 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 5.5, then freeze dried. The remaining solid was dissolved in double distilled water (20 ml) and dialyzed for 48 hours at 4° C. (total of 8 L of double distilled water), then 12 hours at 25° C. (total of 2 L of double distilled water). The aqueous phase was collected and freeze dried to receive a white powder as a trifluoroacetic salt, with a 30% yield. $^1H$ NMR ($D_2O$; 400 MHz): δ 4.12 (1H, s), 3.07-3.74 (15H, m).

Synthesis of Alkylated PGAamines (Group II Polymers; BU(3) and BU(5) Featuring a Linear Alkyl Backbone Units)

Preparation of γ-aminohexane$_{(20\%)}$-diamin-oethane$_{(80\%)}$-L-polyglutamate (J)

To a solution of poly-α-glutamic acid (71 mg, 0.55 mmol per monomer) in dry DMF (2 mL) was added a solution of Carbodiimidazole (101 mg, 0.62 mmol) in dry DMF (1.2 mL). The reaction, mixture was stirred for 1.5 hours at 25° C., under Argon atmosphere. Tributylamine (1.3 mL, 0.55 mmol) was added and the reaction left to stir for 5 more minutes at the same conditions. A solution of Hexylamine (12.4 mg, 0.12 mmol) and Boc-ethylenediamine (83 mg, 0.52 mmol) in dry DMF (2 mL) was added and the reaction mixture was stirred for additional 3 hours at the starting conditions. A solution of Carbodiimidazole (178 mg, 1.1 mmol) in dry DMF (1.5 mL) was added and the reaction mixture was stirred for additional 12 hours at the starting conditions. DMF was removed under reduced pressure. Double distilled water (40 mL) was added and the reaction mixture was freeze dried. The resulting solid was dissolved in DCM (5 mL) and Trifluoroacetic acid (5 mL) was added at 0° C. The mixture was stirred at 25° C. for 10 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 7.3 then freeze dried. The left solid was dissolved in double distilled water (20 mL) and dialyzed for 48 hours at 4° C. (total of 8 L of double distilled water). The aqueous phase was collected and freeze dried to receive a white powder as a trifluoroacetic salt, with a 44% yield. $^1H$ NMR ($D_2O$; 400 MHz): δ 4.26 (1H, s), 3.42 (1.5H, s), 3.06 (2H, s), 2.33 (2H, s), 1.97 (2H, s), 1.40 (0.5H, s), 1.20 (1.5H, s), 0.78 (0.5H, s).

Preparation of γ-aminohexane$_{(45\%)}$-diamin-oethane$_{(55\%)}$-L-polyglutamate (K; SE36)

To a solution of poly-α-glutamic acid (56 mg, 0.43 mmol per monomer) in dry DMF (2.5 mL) was added a solution of Carbodiimidazole (86 mg, 0.53 mmol) in dry DMF (0.7 mL). The reaction, mixture was stirred for 1.5 hours at 25° C., under Argon atmosphere. Tributylamine (1 mL, 0.43 mmol) was added and the reaction left to stir for 5 more minutes at the same conditions. A solution of Hexylamine (19 mg, 0.19 mmol) and Boc-ethylenediamine (42 mg, 0.26 mmol) in dry DMF (2 mL) was added and the reaction mixture was stirred for additional 2 hours at the starting conditions. A solution of Carbodiimidazole (146 mg, 0.9 mmol) in dry DMF (1 mL) was added and the reaction mixture was stirred for additional 12 hours at the starting conditions. DMF was removed under reduced pressure. Double distilled water (40 ml) was added and the reaction mixture was freeze dried. The resulting solid was dissolved in DCM (5 mL) and Trifluoroacetic acid (5 mL) was added at 0° C. The mixture was stirred at 25° C. for 10 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 5 then freeze dried. The left solid was dissolved in double distilled water (20 mL) and dialyzed for 48 hours at 4° C. (total of 8 L of double distilled water). The aqueous phase was collected and freeze dried to receive a white powder as a trifluoroacetic salt, with a 53% yield. $^1$H NMR ($D_2O$; 400 MHz): δ 4.15 (1H, s), 3.36 (1.5H, s), 3.06 (1H, s), 2.99 (2H, s), 2.26 (2H, bs), 1.90 (2H, bs), 1.33 (1H, s), 1.12 (3H, s), 0.71 (2H, s).

Preparation of γ-aminooctane$_{(20\%)}$-diaminoethane$_{(80\%)}$-L-polyglutamate (L)

To a solution of poly-α-glutamic acid (50 mg, 0.39 mmol per monomer) in dry DMF (2 mL) was added a solution of Carbodiimidazole (75 mg, 0.46 mmol) in dry DMF (1 mL). The reaction, mixture was stirred for 1.5 hours at 25° C., under Argon atmosphere. Tributylamine (92 μL, 0.39 mmol) was added and the reaction left to stir for 5 more minutes at the same conditions. A solution of Octylamine (14 mg, 0.11 mmol) and Boc-ethylenediamine (54 mg, 0.34 mmol) in dry DMF (3 mL) was added and the reaction mixture was stirred for additional 2 hours at the starting conditions. A solution of Carbodiimidazole (125 mg, 0.77 mmol) in dry DMF (1 mL) was added and the reaction mixture was stirred for additional 12 hours at the starting conditions. DMF was removed under reduced pressure. Double distilled water (40 mL) was added and the reaction mixture was freeze dried. The resulting solid was dissolved in DCM (5 mL) and Trifluoroacetic acid (5 mL) was added at 0° C. The mixture was stirred at 25° C. for 10 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 6 then freeze dried. The left solid was dissolved in double distilled water (20 mL) and dialyzed for 48 hours at 4° C. (total of 8 L of double distilled water). The aqueous phase was collected and freeze dried to receive a white powder as a trifuoroactic salt, with a 52% yield. $^1$H NMR ($D_2O$; 400 MHz): δ 4.30 (1H, s), 3.46 (1H, s), 3.10 (2H, s), 2.36 (2H, bs), 2.02 (2H, bs), 1.44 (0.5H, s), 1.22 (3H, s), 0.82 (1H, s).

Preparation of γ-aminooctane$_{(40\%)}$-diaminoethane$_{(60\%)}$-L-polyglutamate (M)

To a solution of poly-α-glutamic acid (42 mg, 0.32 mmol per monomer) in dry DMF (2 mL) was added a solution of Carbodiimidazole (58 mg, 0.45 mmol) in dry DMF (1 mL). The reaction, mixture was stirred for 1.5 hours at 25° C., under Argon atmosphere. Tributylamine (76 μL, 0.32 mmol) was added and the reaction left to stir for 5 more minutes at the same conditions. A solution of Octylamine (20 mg, 0.16 mmol) and Boc-ethylenediamine (34 mg, 0.21 mmol) in dry DMF (3 ml) was added and the reaction mixture was stirred for additional 2 hours at the starting conditions. A solution of Carbodiimidazole (105 mg, 0.65 mmol) in dry DMF (1 ml) was added and the reaction mixture was stirred for additional 12 hours at the starting conditions. DMF was removed under reduced pressure. Double distilled water (40 mL) was added and the reaction mixture was freeze dried. The resulting solid was dissolved in DCM (5 mL) and Trifluoroacetic acid (5 mL) was added at 0° C. The mixture was stirred at 25° C. for 10 minutes then evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH of 6 then freeze dried. The left solid was dissolved in double distilled water (20 mL) and dialyzed for 48 hours at 4° C. (total of 8 L of double distilled water). The aqueous phase was collected and freeze dried to receive a white powder as a trifuoroactic salt, with a 61% yield. $^1$H NMR ($D_2O$; 400 MHz): δ 4.23 (1H, s), 3.39 (1H, s), 3.03 (1.5H, s), 2.28 (2H, bs), 1.99 (2H, bs), 1.35 (2H, s), 1.13 (5H, s), 0.72 (1.5H, s).

Preparation of γ-aminobutyl (40%)-ethylenediamine (60%)-L-polyglutamate (N)

To a solution of poly-α-glutamic acid (40 mg, 0.31 mmol per monomer) in dry DMF (3 mL) was added a solution of Carbodiimidazole (56 mg, 0.35 mmol) in dry DMF (2 mL). The reaction mixture was stirred for 1.5 hours, at 25° C., under Argon atmosphere. Tributylamine (0.1 mL, 0.69 mmol) was added and the reaction left to stir for 10 more minutes at the same conditions. A solution of Boc-ethylenediamine (32 mg, 0.20 mmol) and butylamine (10 mg, 0.14 mmol) in dry DMF (2.5 mL) was added and the reaction mixture was stirred for additional 3 hours at the starting conditions. A solution of Carbodiimidazole (107 mg, 0.66 mmol) in dry DMF (2 mL) was added and the reaction mixture was left at the starting conditions for additional 12 hours. DMF was removed under reduced pressure and the left oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was hereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 5.7, then freeze-dried. The obtained solid was dissolved in DD water (20 mL) and dialyzed for 48 hours at 4° C. (total of 8 L of DD water). The aqueous phase was collected and freeze-dried to obtain a white powder as a trifluoroacetic salt, with 49% yield.

$^1$H NMR ($D_2O$; 400 MHz): δ=4.26 (1H, s), 3.44 (1H, s), 2.35 (2H, bs), 1.93 (2H, bs), 1.41 (1H, bs), 1.26 (1H, bs), 0.83 (1.6H, t).

Preparation of γ-aminopentyl (40%)-ethylenediamine (60%)-L-polyglutamate (O)

To a solution of poly-α-glutamic acid (47 mg, 0.36 mmol per monomer) in dry DMF (3 mL) was added a solution of Carbodiimidazole (66 mg, 0.41 mmol) in dry DMF (2 mL). The reaction mixture was stirred for 1.5 hours, at 25° C., under Argon atmosphere. Tributylamine (85 μL, 0.36 mmol) was added and the reaction left to stir for 10 more minutes at the same conditions. A solution of Boc-ethylenediamine (38 mg, 0.24 mmol) and pentylamine (14 mg, 0.16 mmol) in dry DMF (2.5 mL) was added and the reaction mixture was stirred for additional 3 hours at the starting conditions. A solution of Carbodiimidazole (119 mg, 0.72 mmol) in dry DMF (1.5 mL) was added and the reaction mixture was left at the starting conditions for additional 12 hours. DMF was removed under reduced pressure and the left oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 6.5, then freeze-dried. The obtained solid was dissolved in DD water (20 mL) and dialyzed for 48 hours at 4° C. (total of 8 L of DD water). The aqueous phase was collected and freeze dried to obtain a white powder as a trifluoroacetic salt, with 39% yield.

$^1$H NMR ($D_2O$; 400 MHz): δ 4.27 (1H, s), 3.45 (1.5H, s), 3.07 (2.5H, s), 2.35 (2H, bs), 1.99 (2H, bs), 1.42 (1.3H, s), 1.23 (2.5H, s), 0.81 (1.75H, bs).

Preparation of γ-aminoheptyl (40%)-ethylenediamine (60%)-L-polyglutamate (P)

To a solution of poly-α-glutamic acid (47 mg, 0.36 mmol per monomer) in dry DMF (3 mL) was added a solution of Carbodiimidazole (66 mg, 0.41 mmol) in dry DMF (2 mL). The reaction mixture was stirred for 1.5 hours, at 25° C., under Argon atmosphere. Tributylamine (85 μL, 0.36 mmol) was added and the reaction left to stir for 10 more minutes at the same conditions. A solution of Boc-ethylenediamine (38 mg, 0.24 mmol) and heptylamine (18.4 mg, 0.16 mmol) in dry DMF (2.5 mL) was added and the reaction mixture was stirred for additional 3 hours at the starting conditions. A solution of Carbodiimidazole (119 mg, 0.72 mmol) in dry DMF (1.5 mL) was added and the reaction mixture was left at the starting conditions for additional 12 hours. DMF was removed under reduced pressure and the left oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 6.5, then freeze-dried. The obtained solid was dissolved in DD water (20 mL) and dialyzed for 48 hours at 4° C. (total of 8 L of DD water). The aqueous phase was collected and freeze dried to obtain a white powder as a trifluoroacetic salt, with 41% yield.

The molecular weights of Polymers J-P are presented in Table A below.

TABLE A

| Sample PGAamine/siRNA | molecular weight (g/mol) |
|---|---|
| J | 11835 |
| K | 10560 |
| L | 14332 |
| M | 16475 |
| N | 11,070 |
| O | 14,090 |
| P | 42,010 |

Synthesis of Imidazolated PGAamines (Group III polymers composed of BU(6) and BU(3) backbone units)

Preparation of γ-ethylenediamine (80%)-histamine (20%)-L-polyglutamate (Q) (BU(6) and BU(3))

To a solution of poly-α-glutamic acid (47 mg, 0.36 mmol per monomer) in dry DMF (3 mL) was added a solution of Carbodiimidazole (69 mg, 0.42 mmol) in dry DMF (2 mL). The reaction mixture was stirred for 1.5 hours, at 25° C., under Argon atmosphere. Tributylamine (85 μL, 0.36 mmol) was added and the reaction left to stir for 10 more minutes at the same conditions. A solution of Boc-ethylenediamine (0.27 mmol), histamine dihydrochloride (0.08 mg) and tributylamine (120 μL) in dry DMF (5 mL) was added and the reaction mixture was stirred for additional 3 hours at the starting conditions. A solution of Carbodiimidazole (120 mg, 0.72 mmol) in dry DMF (2 mL) was added and the reaction mixture was left at the starting conditions for additional 12 hours. DMF was removed under reduced pressure and the left oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 5.5, then freeze-dried. The obtained solid was dissolved in DD water (20 mL) and dialyzed for 48 hours at 4° C. (total of 8 L of DD water). The aqueous phase was collected and freeze-dried to obtained a white powder as a trifluoroacetic salt, with 30% yield.

$^1$H NMR ($D_2O$; 400 MHz): δ 7.6 (0.25H, S), 6.7 (0.25H, S), 4.16 (1H, s), 3.33 (2H, s), 2.97 (1.5H, s), 2.62 (0.5H, s), 2.22-2.14 (2H, bs), 1.91-1.75 (2H, bs).

Preparation of γ-Histamine (10%)-Aminohexyl (30%)-Ethylenediamino(60%)-L-Polyglutamate (S) (BU(6), BU(3) and BU(5))

To a solution of poly-α-glutamic acid (44 mg, 0.34 mmol per monomer) in dry DMF (3 mL) was added a solution of Carbodiimidazole (62 mg, 0.38 mmol) in dry DMF (2 mL). The reaction mixture was stirred for 1.5 hours, at 25° C., under Argon atmosphere. Tributylamine (81 μL, 0.56 mmol) was added and the reaction left to stir for 10 more minutes at the same conditions. A solution of histamine dihydrochloride (7 mg, 0.04 mmol), Boc-ethylenediamine (36 mg, 0.22 mmol), hexylamine (12 mg, 0.12 mmol) and tributylamine (64 μL, 0.44 mmol) in dry DMF (3 mL) was added and the reaction mixture was stirred for additional 3 hours at the starting conditions. A solution of Carbodiimidazole (110 mg, 0.68 mmol) in dry DMF (1.5 mL) was added and the reaction mixture was left at the starting conditions for additional 12 hours. DMF was removed under reduced pressure and the remaining oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 6, then freeze-dried. The obtained solid was dissolved in DD water (20 mL) and dialyzed for 48 hours at 4° C. (total of 8 L of DD water). The aqueous phase was collected and freeze-dried to obtain a white powder as a trifluoroacetic salt, with 48% yield.

$^1$H NMR ($D_2O$; 400 MHz): δ 7.68 (0.1H, bs), 6.88 (0.1H, bs), 4.26 (1H, bs), 3.44 (1.2H, s), 3.07 (1.7H, s), 2.73 (0.2H, s), 2.35 (2H, bs), 2.05 (2H, bs), 1.40 (0.6H bs), 1.22 (2H, bs), 0.80 (1H, s).

Preparation of γ-Histamine (30%)-Aminohexyl (30%)-Ethylenediamino (40%)-L-Polyglutamate (T) (BU(6), BU(3) and BU(5))

To a solution of poly-α-glutamic acid (42 mg, 0.32 mmol per monomer) in dry DMF (2.5 mL) was added a solution of Carbodiimidazole (64 mg, 0.39 mmol) in dry DMF (1.5 mL). The reaction mixture was stirred for 1.5 hours, at 25° C., under Argon atmosphere. Tributylamine (0.1 mL, 0.69 mmol) was added and the reaction left to stir for 10 more minutes at the same conditions. A solution of hexyamine (11 mg, 0.11 mmol), Boc-ethylenediamine (22 mg, 0.14 mmol), histamine dihydrochloride (19 mg, 0.12 mmol) and tributylamine (100 μL, 0.69 mmol) in dry DMF (3.5 mL) was added and the reaction mixture was stirred for additional 3 hours at the starting conditions. A solution of Carbodiimidazole (109 mg, 0.67 mmol) in dry DMF (1.5 mL) was added and the reaction mixture was left at the starting conditions for additional 12 hours. DMF was removed under reduced pressure and the remaining oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 6.3, then freeze-dried. The left solid was dissolved in DD water (20 mL) and dialyzed for 48 hours at 4° C. (total of 8 L of DD water). The aqueous phase was collected and freeze-dried to afford a white powder as a trifluoroacetic salt, with 43% yield.

$^1H$ NMR ($D_2O$; 400 MHz): δ 7.73 (0.25H, bs), 6.90 (0.25H, bs), 4.23 (1H, bs), 3.44-3.37 (1.3H, bs), 3.08 (1.3H, s), 2.72 (0.6H, s), 2.34-2.29 (2H, bs), 2.05 (2H, bs), 1.38 (0.5H bs), 1.19 (2H, bs), 0.79 (1H, s).

Synthesis of Dialkylated PGAamines (Group IV Polymers Composed of BU(3) and BU(5) Featuring Branched Alkyl Backbone Units)

Preparation of γ-Aminoundecyl (20%)-Ethylenediamine (80%)-L-Polyglutamate (U)

To a solution of poly-α-glutamic acid (34 mg, 0.26 mmol per monomer) in dry DMF (2.5 mL) was added a solution of Carbodiimidazole (47 mg, 0.28 mmol) in dry DMF (1.5 mL). The reaction mixture was stirred for 2 hours, at 25° C., under Argon atmosphere. Tributylamine (0.1 mL, 0.69 mmol) was added and the reaction left to stir for 10 more minutes at the same conditions. A solution of undecylamine (14 mg, 0.08 mmol) and tributylamine (32 μL, 0.22 mmol) in dry DMF (1 mL) was added and the reaction mixture was stirred for additional 3 hours at the starting conditions. A solution of Boc-ethylenediamine (33 mg, 0.21 mmol) in dry DMF (1 mL) was added and the reaction mixture was stirred for additional 2 hours. A solution of Carbodiimidazole (85 mg, 0.52 mmol) in dry DMF (1 mL) was added and the reaction mixture was left at the starting conditions for additional 12 hours. DMF was removed under reduced pressure and the remaining oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 6, then freeze-dried. The obtained solid was dissolved in DD water (20 mL) and dialyzed for 48 hours at 4° C. (total of 8 L of DD water). The aqueous phase was collected and freeze-dried to afford a white powder as a trifluoroacetic salt, with 42% yield.

$^1H$ NMR (D2O; 400 MHz): δ 4.28 (1H, bs), 3.70 (0.15H, s), 3.45 (1.5H, s), 3.09 (1.5H, s), 2.35 (2H, bs), 2.06 (2H, bs), 1.21 (2.6H, bs), 0.81 (1.2H, s).

Preparation of γ-aminoundecyl (40%)-ethylenediamine (60%)-L-polyglutamate (V)

To a solution of poly-α-glutamic acid (32 mg, 0.25 mmol per monomer) in dry DMF (2.5 mL) was added a solution of Carbodiimidazole (45 mg, 0.27 mmol) in dry DMF (1.5 mL). The reaction mixture was stirred for 2 hours, at 25° C., under Argon atmosphere. Tributylamine (0.1 mL, 0.69 mmol) was added and the reaction left to stir for 10 more minutes at the same conditions. A solution of undecylamine (27 mg, 0.15 mmol) and tributylamine (64 μL, 0.44 mmol) in dry DMF (1 mL) was added and the reaction mixture was stirred for additional 2 hours at the starting conditions. A solution of Boc-ethylenediamine (32 mg, 0.21 mmol) in dry DMF (1 mL) was added and the reaction mixture was stirred for additional 2 hours. A solution of Carbodiimidazole (81 mg, 0.5 mmol) in dry DMF (1 mL) was added and the reaction mixture was left at the starting conditions for additional 12 hours. DMF was removed under reduced pressure and the remaining oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 6.8, then freeze-dried. The obtained solid was dissolved in DD water (20 mL) and dialyzed for 48 hours at 4° C. (total of 8 L of DD water). The aqueous phase was collected and freeze-dried to afford a white powder as a trifluoroacetic salt, with 37% yield.

$^1H$ NMR (D2O; 400 MHz): δ 4.27-4.25 (1H, bs), 3.72 (0.2H, s), 3.45 (1.2H, s), 3.08 (1.2H, s), 2.35-1.94 (4H, bs), 1.20 (6H, bs), 0.80 (2.5H, s).

Preparation of γ-1-aminopropybutyl (40%)-ethylenediamine (60%)-L-polyglutamate (W)

To a solution of poly-α-glutamic acid (33 mg, 0.26 mmol per monomer) in dry DMF (2.5 mL) was added a solution of Carbodiimidazole (46 mg, 0.28 mmol) in dry DMF (1.5 mL). The reaction mixture was stirred for 2 hours, at 25° C., under Argon atmosphere. Tributylamine (0.1 mL, 0.69 mmol) was added and the reaction left to stir for 10 more minutes at the same conditions. A solution of 1-propylbutylamine (10 mg, 0.09 mmol) in dry DMF (1 mL) was added and the reaction mixture was stirred for additional 3 hours at the starting conditions. A solution of Boc-ethylenediamine (26 mg, 0.16 mmol) in dry DMF (1 mL) was added and the reaction mixture was stirred for additional 2 hours. A solution of Carbodiimidazole (84 mg, 0.52 mmol) in dry DMF (1 mL) was added and the reaction mixture was left at the starting conditions for additional 12 hours. DMF was removed under reduced pressure and the remaining oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 6.3, then freeze-dried. The obtained solid was dissolved in DD water (20 mL) and dialyzed for 48 hours at 4° C. (total of 8 liter of DD water). The aqueous phase was collected and freeze-dried to afford a white powder as a trifluoroacetic salt, with 37% yield.

$^1$H NMR (D2O; 400 MHz): δ 4.26 (1H, bs), 3.74 (0.3H, s) 3.45 (1H, s), 3.08 (1H, s), 2.35 (2H, bs), 2.07 (2H, bs), 1.41-1.24 (4H, s), 0.81 (3H, t).

Syntheses of PGAamine Polymers Bearing Amine Moiety with Secondary and Tertiary Amines and an Alkyl Moiety (Group V Polymers, Composed of BU(2) and/or BU(3) Backbone Units Featuring a Secondary or Tertiary Amine and BU(5) Units)

Preparation of γ-Aminohexyl (40%)-Dimethyldipropylenetriamino (60%)-L-Polyglutamate (X)

To a solution of poly-γ-glutamic acid (180 mg, 1.39 mmol per monomer) in dry DMF (12 mL) was added a solution of Carbodiimidazole (259 mg, 1.60 mmol) in dry DMF (3 mL). The reaction mixture was stirred for 2 hours, at 25° C., under Argon atmosphere. Tributylamine (0.4 mL, 2.76 mmol) was added and the reaction left to stir for 10 more minutes at the same conditions. A solution of dimethyldipropylenetriamine (135 mg, 0.85 mmol) and hexylamine (60 mg, 0.59 mmol) in dry DMF (2 mL) was added and the reaction mixture was stirred for additional 4 hours at the starting conditions. A solution of Carbodiimidazole (452 mg, 2.79 mmol) in dry DMF (3 mL) was added and the reaction mixture was left at the starting conditions for additional 12 hours. DMF was removed under reduced pressure and the remaining oily residue was dissolved in water (40 mL) and freeze-dried. The residue was dissolved in DD water (40 mL) and the mixture was treated with a 10% HCl to adjust the pH to 4.5. The aqueous phase was then extracted with DCM (40 mL) and Diethylether (40 mL). The aqueous phase was then collected and treated with 10% NaOH solution to adjust the pH to 6.5 and then freeze-dried. The obtained solid was dissolved in DD water (20 mL) and dialyzed for 48 hours at 4° C. (total of 8 L of DD water) and at 25° C. for additional 12 hours. The aqueous phase was collected and freeze-dried to afford a white powder as a chloride salt, with 40% yield.

$^1$H NMR ($D_2O$; 400 MHz): δ 4.25 (1H, bs), 3.20-3.11 (2H, bs), 2.82 (2H, bs), 2.53 (2H, bs), 2.31 (1H, bs), 1.87-1.76 (3H, bs), 1.42 (0.5H, s), 1.22 (2H, s), 0.81 (1H, s).

Preparation of γ-Dimethyldipropylenetriamino (40%)-Aminohexyl (40%)-Ethylenediamino (20%)-L-Polyglutamate (Y)

To a solution of poly-γ-glutamic acid (105 mg, 0.81 mmol per monomer) in dry DMF (7 mL) was added a solution of Carbodiimidazole (149 mg, 0.92 mmol) in dry DMF (3 mL). The reaction mixture was stirred for 2 hours, at 25° C., under Argon atmosphere. Tributylamine (0.2 mL, 1.38 mmol) was added and the reaction left to stir for 10 more minutes at the same conditions. A solution of dimethyldipropylenetriamine (52 mg, 0.33 mmol), Boc-ethylenediamine (28 mg, 0.18 mmol) and hexylamine (34 mg, 0.34 mmol) in dry DMF (7 mL) was added and the reaction mixture was stirred for additional 4 hours at the starting conditions. A solution of Carbodiimidazole (262 mg, 1.62 mmol) in dry DMF (3 mL) was added and the reaction mixture was left at the starting conditions for additional 12 hours. DMF was removed under reduced pressure and the remaining oily residue was dissolved in water (40 mL) and freeze-dried. The resulting solid was dissolved in DCM (5 mL) and Trifluoroacetic acid (5 mL) was added at 0° C. The mixture was stirred at 25° C. for 10 minutes, and was thereafter evaporated under reduced pressure. The oily residue was dissolved in DD water (40 mL) and the aqueous phase was extracted with DCM (2×50 mL) and diethyl ether (50 mL). The aqueous phase was collected and treated with a 10% NaOH solution to adjust the pH to 6, then freeze-dried. The obtained solid was dissolved in DD water (20 mL) and dialyzed for 48 hours at 4° C. (total of 8 L of DD water) and then for 12 hours at 25° C. The aqueous phase was collected and freeze-dried to afford a white powder as a trifluoroacetic salt, with 18% yield.

$^1$H NMR ($D_2O$; 400 MHz): δ 4.26 (1H, bs), 3.3-2.82 (6H, bm), 2.32-1.82 (4H, bm), 1.42 (0.5H, s), 1.22 (3H, s), 0.81 (1.5H, s).

Synthesis of Cross Linked PGAamines of Formula II

Crosslinked PGAamine polymers are synthesized from a co-polymer of L-PGA and backbone units featuring a cross-linkable group (e.g., lysine backbone units), using a suitable cross-linking agent to cross link the cross-linkable moieties. Then a coupling reagent is used to conjugate amination moieties to the pending carboxylic groups of the glutamic acid units, as exemplified in FIG. 14 for Polymer CL1.

Preparation of Polymer CL1

Preparation of Cross Linked Co-Polymer-Lysine$_{(10\%)}$-L-Polyglutamate$_{(90\%)}$ A solution of co-polymer-lysine$_{(10\%)}$-L-polyglutamate$_{(90\%)}$ (98 mg) in DDW (3 mL) was treated with a solution of 10% NaOH to reach a clear solution (pH=12), then a solution of 5% glutaraldehye (6.5 μL) in DDW was added and the reaction mixture was stirred for 12 hours, at 25° C. DDW (20 mL) was added and the reaction mixture was treated with 10% TFA solution in DDW to pH=7 and then freeze dried. The remaining solid was dissolved in double distilled water (20 mL) and dialyzed for 72 hours at 4° C. (total of 8 L of double distilled water). The aqueous phase was collected and freeze dried to receive a white powder. The solid was dissolved in DDW (3 mL) and treated with 10% HCl solution to pH=1. The mixture was kept for 1 hour at 25° C. The solid was isolated by centrifugation (4500 rpm, 5 minutes at 4° C.), washed with DDW and then freeze dried to afford a white powder at a 43% yield.

The polymer was analyzed by static light scattering technique, using agilent 1200 series HPLC system (Agilent Technologies) equipped with a multi angle light scattering detector (Dawn Heleos, Wyatt) and Shodex Kw404-4F column (Showa Denko America, Inc.). Molecular weight and PDIs derived from the analysis indicate $2.97\times10^4$ grams/mol and around 1.2, respectively.

Preparation of cross linked co-polymer-lysine$_{(10\%)}$-γ-ethylenediamine-L-polyglutamate$_{(90\%)}$ A solution of cross linked co-polymer-lysine$_{(10\%)}$-L-polyglutamate$_{(90\%)}$ (35 mg) in dry DMF (3 ml) was added to a solution of Carbodiimidazole (63 mg) in dry DMF (2 ml). The reaction mixture was stirred for 2 hours, at 25° C., under Argon atmosphere. Tributylamine (94 μl, 0.39 mmol) was added and the reaction was left to stir for 5 more minutes at the same conditions. A solution of Boc-Ethylenediamine (66 mg) in dry DMF (1.2 mL) was added and the reaction mixture was stirred for additional 3 hours at the starting conditions. A solution of Carbodiimidazole (92 mg) in dry DMF (1 mL) was added and the reaction mixture was stirred at 25° C., under Argon for additional 12 hours. DMF was removed under reduced pressure and the remaining oily residue was dissolved in water (40 mL) and freeze dried. The resulting solid was dissolved in DCM (5 mL) and Trifluoroacetic acid (5 mL) was added at 0° C. The mixture was stirred at 25° C. for 10 minutes and thereafter evaporated under reduced pressure. The reaction mixture was treated with a 10% NaOH solution to reach pH=7.0, then freeze dried. The remaining solid was dissolved in double distilled water (20 mL) and dialyzed for 48 hours at 4° C. (total of 8 liters of double distilled water). The aqueous phase was collected and freeze dried to afford a white powder as a trifluoraoacetic salt, at a 73% yield. $^1$H NMR ($D_2O$; 400 MHz): δ 4.17 (1H, s), 3.32 (2H, s), 2.95 (2H, s), 2.22 (2H, s), 1.91-1.80 (2H, bs).

Synthesis of PGAamine-Containing Block Copolymers of Formula III

Block co-polymer are synthesized by preparing a block copolymer of L-polyglutamate and an amino acid derivative featuring an alkyl pendant group. A CDI coupling agent was thereafter used to conjugate amination moieties on the pending carboxylic groups of the glutamic acid units, as exemplified in FIG. 15.

Synthesis of α-Hexyl-Amino-PGAamine Block Co-Polymer (Co-Polymer BL1)

Preparation of Co-Polymer-D,L-α-Hexyl-Amino Acid$_{(20\%)}$-L-Polyglutamate$_{(80\%)}$ To a solution of 4-Oxazolidinepropanoic acid, 2,5-dioxo-, phenylmethyl ester (507 mg, 1.88 mmol) in dry DCM (20 mL) was added hexylamine (1.2 μL) and the reaction mixture was stirred for 8 days, at 12° C., under Argon. A solution of 4-hexyl-2,5-Oxazolidinedione (232 mg, 1.25 mmol) in dry DCM (15 mL) was added and the reaction mixture was stirred for 3 more days, at 12° C., under Argon atmosphere, then decanted to a cold diethyl ether (200 mL) and kept at −12° C. for 12 hours. The obtained solid was isolated by centrifugation (4500 rpm, 5 minutes, 4° C.) and dried under reduced pressure. The residual solid was dissolved in TFA (6 mL), a solution of 33% HBr in AcOH (6 mL) was added and the reaction mixture was stirred for 1 hour at 25° C. The reaction mixture was thereafter decanted to cold diethyl ether (80 mL) and kept at −12° C. for 12 hours. The solid was isolated by centrifugation and dried under reduced pressure to afford the intermediate copolymer at a yield of 48%.

Preparation of Co-Polymer-D,L-α-Hexyl-Amino Acid$_{(20\%)}$-γ-Ethylenediamine-L-Polyglutamate $_{(80\%)}$ To a solution of co-polymer-D,L-α-hexyl-amino acid-L-polyglutamate (29 mg, 0.11 mmol) in dry DMF (6 mL) was added a solution of Carbodiimidazole (42 mg, 0.26 mmol) in dry DMF (1 ml). The reaction, mixture was stirred for 2 hours, at 25° C., under Argon atmosphere. Tributylamine (0.1 mL, 0.4 mmol) was added and the reaction was left to stir for 5 more minutes at the same conditions. A solution of Boc-Ethylenediamine (54 mg, 0.34 mmol) in dry DMF (1 mL) was added and the reaction mixture was stirred for additional 4 hours at the starting conditions. A solution of Carbodiimidazole (74 mg, 0.46 mmol) in dry DMF (1 mL) was added and the reaction mixture was stirred at 25° C., under Argon for additional 12 hours. DMF was then removed under reduced pressure and the remaining oily residue was dissolved in water (40 mL) and freeze dried. The resulting solid was dissolved in DCM (5 mL) and Trifluoroacetic acid (7 mL) was added at 0° C. The mixture was stirred at 25° C. for 10 minutes and thereafter evaporated under reduced pressure. The oily residue was dissolved in double distilled water (40 mL) and the aqueous phase was extracted with DCM (2×50 mL) and diethyl ether (50 mL). The aqueous phase was collected and treated with a 10% NaOH solution to reach pH=5, then freeze dried. The remaining solid was dissolved in double distilled water (20 mL) and dialyzed for 72 hours at 4° C. (total of 8 L of double distilled water). The aqueous phase was collected and freeze dried to receive a white powder as a trifluoraoacetic salt.

$^1$H NMR (D20; 400 MHz): δ 4.17 (1H, s), 3.32 (1.6, s), 2.95 (1.8H, s), 2.23 (2H, s), 1.92, (2H, bs), 1.1 (0.7H, bs), 0.6 (0.6H, bs).

$^1$H-NMR Characterization of the Amination Products:

The various products of the amination synthesis illustrated in FIGS. 5, 7, 9, 11, 13, 14 and 15 were characterized by $^1$H-NMR. $D_2O$ was used as a solvent. The data of the obtained $^1$H-NMR spectra are presented hereinabove for each polymeric compound.

Example 2

Group I PGAamine Polymers and siRNA Polyplexes Thereof

Characterization of the PGA Precursor Used for PGAamine Polymers A-I Synthesis:

The precursor PGA polymers were analyzed by static light scattering technique, using agilent 1200 series HPLC system (Agilent Technologies) equipped with a multi angle light scattering detector (Dawn Heleos, Wyatt) and Shodex Kw404-4F column (Showa Denko America, Inc.) molecular weight and PDIs were derived from the analysis, and have ranged between 6300 to 8500 g/mol and around 1.2 respectively. The number of monomers per polymer was calculated according to the molecular weight obtained by SLS measurement.

Table 1 below presents the Molecular weight, polydispersity index and calculated number of monomers of the PGA precursor used for PGAamine polymer synthesis as analyzed by SLS (Table 1 presents a characterization of an exemplary PGA precursor used in the synthesis of PGAamine polymers A-I, according to some embodiments of the present invention).

TABLE 1

| polymer | molecular weight of the precursor PGA (g/mol) | PDI of the precursor PGA | Calculated number of monomers |
|---|---|---|---|
| A | 8470 | 1.226 | 66 |
| B | 6315 | 1.208 | 49 |
| C | 6315 | 1.208 | 49 |

TABLE 1-continued

| polymer | molecular weight of the precursor PGA (g/mol) | PDI of the precursor PGA | Calculated number of monomers |
|---|---|---|---|
| D | 6719 | 1.198 | 52 |
| E | 6719 | 1.198 | 52 |
| F | 6719 | 1.198 | 52 |
| G | 6719 | 1.198 | 52 |
| H | 6719 | 1.198 | 52 |
| I | 6719 | 1.198 | 52 |

Characterization of the Electrostatic Interaction Between PGAamine Amination Derivatives and siRNA:

Complex formation of PGAamines A-I with siRNA was investigated by gel electrophoresis mobility shift assay (EMSA) (FIG. 16A). The optimum terminal nitrogen/phosphate (N/P) ratio for each complex was inferred from the retardation of siRNA mobility in agarose gel. In order to evaluate the complexation strength in light of the addition of tertiary terminal amine moiety, heparin displacement assay was applied (FIG. 16B). The polyanion heparin is an established indicator for the strength of complexation between cationic polymers and oligonucleotides.

Both polymers A and B have shown complete complexation starting from 2 N/P ratio. Polymer C has also complexed with siRNA at 2 N/P ratio, indicating that branching of the terminal amine did not affect the minimal complexation ratio.

The Strength of the complexation of polyplex C (tertiary terminal amine) was higher than that of polyplex A (primary terminal amine), as indicated by the higher amount of the anion heparin required in order to displace the siRNA from its binding to the polymer (0.075 IU heparin/50 pmol siRNA compared with only 0.025 IU required in polyplex A. This stronger complexation was also approved by the decreased intensity of the ethidium bromide fluorescence at 10 N/P ratio shown in the EMSA of polyplex C. This phenomena results from exclusion of ethidium bromide for its intercalation sites with siRNA by the strong affinity of the oligonucleotides to the polymer [A. J. Geall, I. S. Blagbrough, *Journal of pharmaceutical and biomedical analysis* 22, 849-859 (2000); published online EpubJun]. The combination of two different side chains on one polymer: one ends with tertiary amine and the other with primary amine seems to result in lower affinity towards siRNA and higher minimal complexation ratio, as indicated for Polymers D and E. Polymer E with the longer side chains had slightly better complexation qualities exhibiting 3 N/P ratio minimal complexation ratio compared to 5 N/P minimal complexation ratio obtained by polymer D. Adding a secondary amine to moieties ending by tertiary amine have restored the complexation qualities, as shown by complexation properties of polymers F and G that exhibited minimal complexation ratios of 1 and 2 N/P respectively. The addition of a secondary amine, aimed to increase buffering capabilities, strengthened the complexation with siRNA, as demonstrated by heparin displacement assay performed on polymer F indicating that the siRNA was not displaced even in the presence of 0.25 IU heparin (FIG. 16B). Adding a secondary amine to side chain that ends with primary amine (polymer H) had affected the complexation strength and charge neutralization of the polyplexes.

The EMSA image shows that minimal neutralization of charge was obtained only at 10 N/P ratio. This relatively low surface charge of polyplex H at 5 N/P ratio was further approved by zeta potential analysis (see, Table 2 below).

Complexation qualities were restored again when the latter side-chain moiety was combined with additional moiety that bears tertiary terminal amine and secondary amine, as indicated by Polymer I. This structure resulted in minimal complexation ratio of 1 N/P, indicating strong attraction between PGAamine polymer to siRNA.

Size and Charge Characterization of PGAamine:Rac1 siRNA Polyplexes:

Zeta potential analysis of the various PGAamine:siRNA polyplexes was performed in order to assess the surface charges of the polyplexes.

Zeta potentials and hydrodynamic radiuses were obtained by Zetasizer ZS at 633 nm wavelength and by NS300 at 532 nm respectively. SEM images were obtained by Quanta 200 FEG Environmental SEM.

Table 2 below presents the Zeta potential, hydrodynamic diameter values and Diameter as imaged by SEM of PGAamine:siRNA polyplexes at selected N/P ratios.

TABLE 2

| Sample PGAamine/ siRNA | N/P ratio | Zeta potential (mV) | Hydrodynamic Diameter (nm) | Size diameter by SEM (nm) |
|---|---|---|---|---|
| A | 5 | 25.4 ± 4.85 | 91.72 ± 36 | 155 |
| B | 10 | 17.5 ± 7.42 | 147.21 ± 59.76 | 100 |
| C | 5 | 3.71 ± 6.47 | 72.7 ± 29.49 | 93 |
| D | 5 | 0.914 ± 3.39 | 178.57 ± 72.62 | 106 |
| E | 5 | 6.8 ± 2.96 | 200.71 ± 89.13 | 79 |
| F | 5 | 15.3 ± 4.42 | 241.8 ± 101.5 | 148 |
| G | 5 | 4.13 ± 3.47 | 84.73 ± 32.49 | 72 |
| H | 5 | 0.415 ± 3.55 | 39.83 ± 12.14 | 122 |
| I | 5 | 18.9 ± 4.62 | 97.44 ± 33.7 | 142 |

Zeta potentials of the 5 N/P ratio polyplexes A, C, D, E, F, G, H and I and of 10 N/P ratio polyplex B have ranged between 0 to 25 mV. Polyplexes A and B, that bear side chain moieties with primary terminal amine, had relatively high zeta potentials of 25.4±4.85 and 17.5±7.42 mV, respectively. The transition to tertiary terminal amine resulted in reduced zeta potential as indicated by the charge of polyplex C (3.71±6.47 mV). Combining both tertiary and primary terminal amine side chains on one backbone did not restore the high zeta potential, as indicated by charges of polyplexes D and E (0.914±3.39 and 6.8±2.96 mV, respectively). Vast addition of secondary amines to the tertiary amine-bearing moieties has resulted in increased surface charge (polyplex F with 15.3±4.42 mV). Polyplex G with the low percentage of secondary amines had lower surface charge (4.13±3.47 mV), while the addition of a secondary amine to a terminal primary amine backbone resulted in almost neutral zeta potential (H, 0.415±3.55 mV). Polyplex I with high percentage of tertiary terminal amines and secondary amines had also high positive charge of 18.9±4.62 mV.

The zeta potential of higher N/P ratio polyplexes was further tested and the data is summarized in Table 4 below. The increase in N/P ratio generally resulted in increased zeta potential.

The size and morphology of the polyplexes were evaluated using DLS and SEM (see, Table 2 above and FIG. 17). Diameters have ranged between 69 to 155 nm according to SEM, and between 40 to 240 nm according to DLS, reflecting supramolecular assemblies of polymers and siRNA molecules.

Particles at this size range are assumed to selectively accumulate in the tumor tissue due to the enhanced permeability and retention (EPR) effect [Scomparin et al, *Biotech-*

*nology advances,* 33, 1294-1309 (2015); published online EpubApr 25 (10.1016/j.biotechadv.2015.04.008].

Higher N/P ratio polyplexes were measured for their hydrodynamic diameter using Vasco DLS, and the obtained data is presented in Table 3 below. Polyplexes have either increased their size or remained at nearly similar size with the increase in N/P ratio.

TABLE 3

| Polyplex | N/P ratio | Diameter ± SD (nm) |
|---|---|---|
| C | 10 | 85 ± 47 |
| | 15 | 189 ± 96 |
| | 25 | 135 ± 72 |
| D | 10 | 332 ± 192 |
| | 15 | 286 ± 148 |
| | 25 | 523 ± 303 |
| | 50 | NA (Aggregated) |
| E | 10 | 167 ± 99 |
| | 15 | 158 ± 90 |
| | 25 | 251 ± 143 |
| G | 10 | 82 ± 33 |
| | 15 | 90 ± 51 |
| H | 10 | 33 ± 16 |
| | 15 | 29 ± 16 |
| | 25 | 46 ± 24 |
| | 50 | 146 ± 69 |
| | 100 | 299 ± 161 |

Table 4 below presented the Zeta potential values of high N/P ratio polyplexes as obtained by zetasizer ZS.

TABLE 4

| Polyplex | N/P ratio | Zeta potential ± SD (mV) |
|---|---|---|
| C | 10 | 2.62 ± 3.47 |
| | 15 | 3.14 ± 3.72 |
| | 25 | 4.94 ± 4.46 |
| D | 10 | 3.94 ± 2.83 |
| | 15 | 19.6 ± 3.50 |
| | 25 | 24.1 ± 4.32 |
| | 50 | 24.7 ± 4.10 |
| E | 10 | 9.51 ± 4.33 |
| | 15 | 13.9 ± 3.94 |
| | 25 | 16.4 ± 4.01 |
| G | 10 | 14.6 ± 4.95 |
| | 15 | 15 ± 4.11 |
| H | 10 | 4.14 ± 3.95 |
| | 15 | 5.65 ± 3.92 |
| | 25 | 6.42 ± 3.13 |
| | 50 | 5.66 ± 3.96 |
| | 100 | 7.95 ± 4.08 |

Membrane Crossing and Intracellular Trafficking of PGAamine:siRNA Polyplexes:

One of the major obstacles in the therapeutic usage of siRNA is their poor cellular penetration [A. Scomparin, D. Polyak, A. Krivitsky, R. Satchi-Fainaro, *Biotechnology advances,* 33, 1294-1309 (2015); published online EpubApr 25 (10.1016/j.biotechadv.2015.04.008]. The ability of PGAamine polymers to assist membrane-crossing of siRNA was evaluated using confocal microscopy and the obtained data is presented in FIGS. 18A-B. HeLa cells were transfected with polymers A-I polyplexed with Cy5-conjugated Rac1 siRNA at 5 N/P ratio (polymers A, C, D, E, F, I) or 10 N/P ratio (polymer B) for 4 hours. Internalization of siRNA was indicated by the appearance of punctuate cy5-marked structure. This pattern have appeared in wells treated with polyplexes A, B, F and I. Lower Cy5 signal was observed at wells treated with the G polyplex.

Polyplexes A, B, F and I were further tested for their intracellular trafficking, and the obtained data is presented in FIGS. 19A-C.

In previous works in which the internalization mechanisms and intracellular trafficking of cationic polymers were studied, both Macropinocytosis, Clathrin-mediated endocytosis (CME) and Caveole-mediated endocytosis (CvME) were indicated as possible parallel routes for cellular internalization of polyplexes [Hess et al., *Biochimica et biophysica acta* 1773, 1583-1588 (2007); Xiang ET AL., *Journal of controlled release: official journal of the Controlled Release Society* 158, 371-378 (2012)].

To distinguish the CME from the other pathways, ammonium chloride, a cytosolic acidification agent was used [Xiang et al., 2012 (supra); Ofek et al., *FASEB journal: official publication of the Federation of American Societies for Experimental Biology* 24, 3122-3134 (2010)].

FIG. 19A shows that the internalization of polyplexes A and F was inhibited due to ammonium chloride treatment, thus indicating that the internalization of these polyplexes is attributed mostly to the CME pathway.

Colocalization with late lysosomes was further evaluated using the specific marker LAMP-1 [Xiang et al., 2012 (supra)], as shown in FIG. 19B.

FIG. 19C shows that all four polyplexes A, B, F and I exhibited a time-dependant increase in co-localization with lysosomes, suggesting all four polyplexes reach the lysosomes and accumulate there.

Although all 3 possible pathways (macropinocytosis, CME and CvME) fuse with the lysosome, the silencing activity of cationic polyplexes is traditionally attributed to their ability to escape the endosome and locate at the cytoplasm by an endosomal buffering mechanism formally termed "the proton sponge effect" [Boussif et al., *Proceedings of the National Academy of Sciences of the United States of America* 92, 7297-7301 (1995)].

Regardless of the escape mechanism, the cytoplasm is the site of activity for the siRNA, and at least some portion of it should locate there in order to efficiently silence gene's expression.

Silencing Activity of PGAamine:Rac1 siRNA Polyplexes:

To further evaluate the silencing potential of the PGAamine polymers as delivery vehicles of siRNA, dual luciferase reporter assay was implied (see, FIG. 20A). HeLa and SKOV-3 cells were treated with polyplexes A-I for 72 hours and evaluated for Rac1-mRNA knockdown. Some silencing activity (lower than 0.5-fold) was exhibited by polyplexes C, D, E, G and H at 5 N/P ratio in both cell lines. Silencing activity (more than 0.5-fold silencing) was found with polyplexes A and F in HeLa cells and with polyplexes A, B, F and I in SKOV-3 cells, while high silencing activity was obtained by polyplexes B and I (0.60 and 0.54-fold silencing at 250 nM concentration, 0.96 and 0.81-fold silencing at 500 nM concentration, respectively) in HeLa cells. Altogether, silencing pattern in both cell lines was similar, indicating the active polyplexes to be A, B, F and I. These results correlate with the internalization ability of the polyplexes. These findings may show that the limiting step to successful silencing is the ability to penetrate into cells.

To better evaluate the performance of the polyplexes, linear PEI and lipofectamine as positive control nanocarriers for transfection were used. HeLa and SKOV-3 cells were treated with 50 nM of the commercial transfection reagents jetPRIME and lipofectamine (marked PEI and lipo respectively in FIG. 20A) for 72 hours according to the manufacturer's protocol. As shown in FIG. 20A, lipofectamine was efficient but cytotoxic (<60% cell viability), while HeLa cells responded well to the PEI nanocarrier by silencing to almost 0.1 fold of the original luciferase expression level. SKOV-3 cells, however, were less sensitive to treatment with 50 nM siRNA carried by PEI. Higher concentration (100 nM) was required in order to obtain effective silencing, but was accompanied by increased cytotoxicity. Cell viability studies showed that the toxicity of the PGAamine polyplexes described herein was strongly related to the cellular internalization ability and to a positive surface charge, with some variability within the active polyplexes between the two cell lines. The less active polyplexes at 5 N/P ratio were all nontoxic and retained more than 78% viability. The high toxicity of the active polyplexes can be attributed to their high positive charge (zeta potential of each was higher than 15 mV).

The studies herein focused on N/P ratios of either 5 or 10, since these are the most applicable ratios for the polymer based delivery system. As, in some embodiments, about 100% of the functional pendent groups of the PGA are modified, each added amine unit means an additional monomer. Higher N/P ratios, therefore, result in large amounts of polymer administered only as a delivery vehicle.

The silencing activity of polymers that were not active at 5 or 10 N/P ratios at increasing ratios up to 100 N/P was tested. The increase was limited to the point of indicated toxicity, that is, viability reduction to less than 0.75-fold (see, FIGS. 20B and 20C). Less than 0.5-fold activity of these polymers in HeLa cells was obtained only by G polyplex at 15 N/P ratio, alongside high toxicity. G polymeric structure features a terminal tertiary amine with additional secondary amine at the low rate of 40%, and demonstrated low cellular internalization ability at 5 N/P.

While evaluating the activity of the polyplexes on SKOV-3 cells, it was found that polyplexes C and G exhibited silencing activity at 15 N/P ratio, while E polyplex was active at the higher 25 N/P ratio. Except for polyplex G evaluated on SKOV-3 cell line, all other polyplexes that were active at the high N/P ratios (15 N/P and more) were also toxic at the relevant concentrations.

To further evaluate the biological silencing activity of polyplexes A-I, a transwell migration assay on SKOV-3 cells was performed using 20% FBS-containing serum as incentive for migration and Rac1 siRNA as migration inhibitor. Rac1 is a member of the Rho small GTPase proteins family and its role in cell motility in embryonic development and tumor invasiveness is well established. Recently, its role in epithelial-mesenchymal transition (EMT) towards migration and metastasis of cancer cells was demonstrated, placing Rac1 as an attractive anti-cancer target.

Inhibition of migration obtained following 48 hours of treatment with A, B, F and I polyplexes composed of PGAamine and Rac1 siRNA, while polyplexes containing eGFP control siRNA were unable to inhibit cell migration. FIG. 21A demonstrates the inhibition of migration obtained by 72 hours treatment with A, B, F and I polyplexes composed of PGAamine polymers and Rac siRNA, while polyplexes containing EGFP control siRNA were unable to inhibit the cell's migration. FIGS. 21B and 21C show that polyplexes C, D, E, G and H composed of PGAamine polymers and Rac1 siRNA were unable to inhibit serum-induced migration of SKOV-3 cells.

Inhibition of serum-induced migration of SKOV-3 cells is the result of downregulation of Rac1 mRNA induced by our PGAamine:Rac1 siRNA A, B, F and I polyplexes. These results support the data obtained in the Dual luciferase assay and confocal cellular internalization analysis: polymers A, B, F and I had the ability to assist siRNA cellular internalization, and to downregulate gene's expression.

Inhibition of Cellular Motility by PGAamine A:Rac1 siRNA Polyplexes:

The ability of PGAamine A:siRac1 polyplex to inhibit cells' motility by Rac1 knockdown was evaluated in thin-layer wound healing assay. IncuCyte ZOOM® live cell imaging showed that PGAamine A:siRac1 polyplex inhibited the migration of SKOV-3 cells by 35% as opposed to control treatments, as presented in FIGS. 22A-B.

Plasma Stability and Immune- and Hemo-Compatibility in Ex Vivo Blood Compartment:

The ability of the siRNA-polymer complex to stay intact in the blood was evaluated by incubating PGAamine A:siRac1 polyplex in 100% mouse plasma for up to 24 hours. Plasma-polyplex mixtures were then loaded on 2% agarose gel and electrophoresis was performed to assess the amount of siRNA released from the polyplex. No release of siRNA was seen following incubation of the polyplex in plasma as implied by the absence of free-siRNA running towards the cathode (see, FIG. 23A, left gel). Presence of complexed-siRNA in polyplexes at tested time points, following plasma incubation, was confirmed using heparin displacement assay (see, FIG. 23A, right gel). Heparin is a polyanion that competes with siRNA on electrostatic binding to polyaminated polymers, thus may lead to polyplex disassembly. Since heparin is a major component of the extracellular matrix in many tissues and it is a protein component of human serum, polyplex's integrity was evaluated following its interaction with it. As depicted in FIG. 23C, siRNA was gradually displaced by heparin concentration of 0.17 IU of heparin/50 pmol siRNA to fully displacement from the PGAamine A-siRNA polyplex at heparin concentration of 25 IU/50 pmol siRNA. The lowest concentration at which displacement of siRNA from the complex occurred was equal to 85,000 IU/100 mL, while the average heparin levels in human plasma are well below at 15 IU/100 mL.

The interactions of PGAamine:siRNA polyplex with blood compartment were tested using a series of ex vivo assays.

Hematocompatibility of PGAamine A:siRac1 polyplex was assessed by measuring red blood cells (RBC) lysis. The concentrations of PGAamine:siRac1 polyplex used were the relevant in vivo concentrations, adjusted to dilution in the mouse blood volume (0.417 mg/mL polymer is equivalent to 8 mg/kg siRNA for 25 g mouse with 2 mL blood volume). The results are depicted in FIG. 23B and show that the extent of hemolysis caused by the polyplex is similar to that of negative controls (e.g. PBS and Dextran), which makes this polyplex safe for IV administration.

Measurement of PGAamine A:Rac1 siRNA Polyplex-Mediated Immune Response:

Complement activation following treatment with PGAamine A:Rac1 siRNA 5 N/P ratio polyplex was evaluated by quantification of the complement terminal complex SC5b-9 present in human plasma, and the results are presented in FIGS. 24A-C. As shown in FIG. 24A, levels of SC5b-9 complex in the presence of the polymer alone (PGAamine A) or the polyplexes (A:Rac1 siRNA 5 N/P ratio) at the tested concentrations, were similar to the levels of human plasma complement terminal complex in negative control samples.

Furthermore, the effect of a polymer alone or in complex with siRNA on cytokines secretion and interferon responsive genes on normal human peripheral blood mononuclear cells (PBMCs) was evaluated and the results are presented in FIG. 24B. There was no indication of IL-6 secretion following the incubation of the polyplexes with PBMCs, compared with the secretion of the cytokine following incubation with positive and negative controls. TNF-α secretion from PBMCs following incubation with either 200 nM or 400 nM A (with or without complexation to siRNA) have ranged from 760 pg/ml to 1041 pg/ml, with no dose response, which are 11% to 30% of the positive control.

The effect of PGAamine A:Rac1 siRNA polyplex on inflammatory genes expression was also assessed (FIG. 24C). Levels of IFN responsive genes IFIT1, MX1, OAS1 and ISG15 were higher following treatment with 400 nM PGAamine A:Rac1 siRNA 5 N/P ratio polyplexes than with 400 nM polymer only, and were between 49% to 78% of the levels following CLO75 positive control treatment. Treatment with 20 nM A alone have raised the expression of IFIT1 to 102% of the CLO75 positive control. There was high variability of gene expression between the two positive controls-CLO75 and LPS, when LPS had very little effect on the expression of the inflammatory genes that was only slightly higher than the expression following negative control treatment.

In Vivo Toxicity of PGAamine:Rac1 siRNA Polyplexes

Maximum tolerated dose (MTD) of A, B, F and I polyplexes was performed by evaluating the viability of BALB/c mice following single IV (intravenous) injection.

Table 5 below presents the maximum tolerated dose of polyplexes A, B, F and I at N/P ratios of 5 (polymers A, F and I) or 10 (polymer B) for in vivo treatments injected i.v. to BALB/c mice at 400 μL/mouse dose. The MTD of polyplex A was the highest—above 8 mg/kg, polyplexes F and B were tolerated at above 6 mg/kg and polyplex I exhibited MTD of 1 mg/kg.

TABLE 5

| Polymer | siRNA dose [mg/kg] | Polymer dose [mg/kg] |
|---|---|---|
| A | 8 | 35.2 |
| B | 6 | 49.1 |
| F | 8 | 36.6 |
| I | 1 | 5.7 |

Activity of PGAamine:siRNA Polyplex Evaluated Following IP or IV Administration in Human and Murine In Vivo Models:

The accumulation of PGAamineA:Rac1 siRNA polyplexes at N/P 5 in tumor tissue was assessed after 3 sequential intraperitoneal (IP) injections (about 24 hours interval), in the orthotopic Skov-3 human ovarian carcinoma model in athymic nude female mice. Followed by collection of tumors 24 hours post the 3rd injection and analyzes for accumulation of Rac1 siRNA. The results indicate 8-fold and 2.75-fold increase in Rac1 siRNA tumor accumulation following treatment with A:Rac1 siRNA polyplexes compared to treatment with saline or siRNA alone, respectively (see, FIG. 25A). In addition, collected tumor tissue were analyzed for Rac1 gene knock-down by A:Rac1 siRNA polyplexes. Results indicate decrease of 38% and 44% in murine Rac1 mRNA levels in tumors of mice treated with A:Rac1 siRNA 5 N/P ratio polyplexes compared to saline or Rac1 siRNA injected mice, respectively (see, FIG. 25B). These finding were verified by RACE products in tumor tissues of mice treated with the polyplex (see, FIG. 25C).

Furthermore, C57 mice bearing subcutaneous LLC tumors were treated via the tail vein (IV) with PGAamineA: Rac1 siRNA polyplexes at N/P 5 as described above. The analyzes of collected tumor tissues showed Rac1 gene knockdown of 47% in PGAamineA:Rac1 siRNA polyplexes treated mice compared to saline treated mice (see, FIG. 25D).

Anti-Cancer Efficacy of PGAamine:Plk1 siRNA Polyplexes in Skov-3 mCherry-Labeled Orthotopic Tumor Bearing Nu/Nu Mice:

The potential of PGAamine-based polyplex to inhibit tumor growth of ovarian carcinoma was tested. The Plk1 gene was selected as a target with the PGAamine:siPlk polyplex. Deregulation of Plk1 was shown to be responsible for mitotic defects, by affecting cell cycle checkpoints, thus resulting in aneuploidy and tumorigenesis. Overexpression of Plk1 was observed in many cancerous tissues, including ovarian carcinoma and was shown to correlate with tumor stage, grade and poor patient prognosis. Since Plk1 is considered as a “proto-oncogene”, inhibition of Plk1 is effective treatment for cancers.

In vivo anticancer efficacy of Plk1 siRNA complexed with A PGAamine was evaluated in nu/nu mice bearing orthotopic intraperitoneal tumors of mCherry-labeled SKOV-3 human ovarian adenocarcinoma cells. Following 9 every other day intraperitoneal injections of PGAamine:siRNA polyplexes (8 mg/kg siRNA) (as shown in FIG. 26A), siPlk1 polyplex inhibited the growth of ovarian tumors for 30 days after the last injection resulting in 87% inhibition of tumor growth compared to saline-treated mice (p=0.005) and 73% inhibition of tumor growth compared to siCtrl-treated mice (p=0.005) (see, FIG. 26C). Furthermore, 33% of the siPlk-treated mice survived on day 170, while control mice (saline and luciferase siRNA-treated mice) died during 57 days of the study (see, FIG. 26D).

Example 3

Alkylated PGAamine Polymers (Group II) and siRNA Polyplexes Thereof

Characterization of the Electrostatic Interaction Between Alkylated PGAamine Derivatives and siRNA:

For each of polymers J-M, complex formation with siRNA was investigated by gel electrophoresis mobility shift assay (EMSA), and the obtained data is presented in FIG. 28. Existence of complexation and the optimum nitrogen/phosphate (N/P) ratio for each complex was inferred from the retardation of siRNA mobility in agarose gel.

Polymer J fully complexed with siRNA from 2 N/P ratio and on as indicated by reversing the migration of siRNA towards the negative electrode. Polymer K was forming polyplexes from 1.5 N/P ratio and on, as indicated by the partial inhibition of migration compared to free siRNA. Zeta potential measurements of K:siRNA in 1.5 N/P ratio showed slightly negative charge of the complex (−2.56±3.79 mV), that further resulted in partial migration towards the positively charged electrode. The reduction in ethidium bromide fluorescence at the higher ratios indicates the strong affinity between siRNA and the polymer resulting in exclusion of ethidium bromide from its attachment to the siRNA. Similar phenomenon is illustrated in polymers L and M, when fluorescence of ethidium bromide is decreased with the increase of N/P ratio. Lowest full complexation ratios of polymers L and M with siRNA are 1 and 2, respectively.

Both polymers N and O are fully complexed with siRNA at N/P ratio 2 and above as indicated by reversed migration of siRNA towards the anode. Polymer P fully complexed with siRNA from 3 N/P ratio, reduction in the band’s strength in 5, 8 and 10 N/P might indicate strong affinity between polymer and siRNA and the resulting ethidium-bromide exclusion.

Silencing Activity of Alkylated PGAamine:Rac1 siRNA Polyplexes:

Evaluation of the silencing activity of polymers J-P when forming polyplexes with siRNA was done by Dual luciferase assay as described hereinabove and the results are presented in FIG. 29. More than 50% silencing activity was indicated by polyplexes J, K, L, M and O at different ratios and RNA concentration: polymer J when complexed with Rac1 siRNA at 5 N/P ratio and 250 nM concentration, polymer K when complexed with Rac1 siRNA at 2 or 3 N/P ratio and 500 nM concentration or at 5 N/P ratio and 250 and 500 nM siRNA concentrations, polymer L when complexed at 3 or 5 N/P ratios and 250 nM siRNA concentration, polymer M at complex with Rac1 siRNA at 3 N/P ratio and 100 or 250 nM concentration and at 5 N/P ratio at 100 nM concentration, and polymer O when complexed with Rac1 siRNA at 2 N/P ratio and 500 nM siRNA concentration and at 3 N/P ratio at 250 and 500 nM concentration. Highly effective silencing activity (more than 80%) was indicated by polyplexes of J:siRNA at 5 N/P ratio and siRNA concentration of 500 nM, and at 8 and 10 N/P ratios at concentrations of 250 and 500 nM concentrations. Polyplexes of Polymer K:siRNA at 2, 3 and 5 N/P ratios have also silenced Rac1 siRNA expression to more than 80% extent at concentrations of 100 and 250 nM while retaining high cells viability (more than 80%). Polymer L complexed with siRNA at 5 N/P ratio and 500 nM concentration caused more than 80% Rac1 siRNA silencing, but also around 40% viability reduction.

Polyplex O at 2 N/P ratio and 100 and 250 nM concentrations, 3 N/P ratio at 100 nM concentration and 5 N/P ratio at 100, 250 and 500 nM concentrations have also demonstrated higher than 80% silencing activity, mostly with retained more than 80% viability, toxic N/P ratios and concentrations that have demonstrated 25%-35% percent reduction in viability were 3 N/P ratio at 250 nM concentration and 5 N/P ratio at 100 and 250 nM concentration.

K:siRNA, M:siRNA and O:siRNA polyplexes have shown interesting phenomenon of decreased silencing efficiency with increasing N/P ratios and treatment concentrations, that might be explained by alterations in supramolecular rearrangement.

Polyplex P have demonstrated moderate (more than 50%) silencing activity at 3 N/P ratio and concentration of 250 and 500 nM siRNA and at 5 N/P ratio at concentrations 100 and 250 nM siRNA and high silencing activity (more than 80%) at 2 N/P and concentrations 100, 250 and 500 nM, 3 N/P ratio and concentration of 100 nM siRNA and 5 N/P and 500 nM siRNA concentration.

Polyplex N:siRNA at 2, 3 or 5 N/P ratio have shown no silencing activity, due to its short 4 carbon alkyl moiety, demonstrating the lower limit required (side chain of 5 carbons) for the length of the alkyl-side chain of the PGAamine polyplexes constructed of polymers bearing 40% alkyl-moiety and 60% ethylene-diamine moiety in order to have in-vitro silencing activity by dual-luciferase assay.

These data indicate that the optimal percentage of the alkyl-moiety in terms of silencing activity is around 40%, as demonstrated by improved silencing activity of polyplexes K, O, P and M comparing to J and L (20% alkyl). For the length of the alkyl moiety, it is demonstrated that the alkyl chain should have more than 4 carbons, as shown by lack of silencing activity demonstrated by polyplex N compared to good silencing activity demonstrated by polyplexes K, O and P (6, 5 and 7 carbons respectively). Good silencing activity was demonstrated also by polyplexes containing PGAamine polymers bearing 8 and 9 carbon chains as an alkyl moiety (data not shown).

In Vivo Toxicity of Alkylated PGAamine K:Rac1 siRNA Polyplexes at 2 N/P Ratios:

To determine the in vivo toxicity of K:Rac1 siRNA polyplexes at 2 N/P ratios, the viability of BALB/c mice following single i.v. injection at 200 μL/mouse dosage of alkylated PGAamine K polymer complexed with Rac1 siRNA was tested. The mice were viable following 8 and 15 mg/kg siRNA dosage. Data is presented in Table 6.

Example 4

Imidazole-Bearing PGAamine Polymers (Group III) and siRNA Polyplexes Thereof Characterization of the Electrostatic Interaction Between Imidazole-Bearing PGAamine Derivatives and siRNA:

For each of polymers Q-T, complex formation with siRNA was investigated by gel electrophoresis mobility shift assay (EMSA), and the obtained data is presented in FIG. 37. Existence of complexation and the optimum nitrogen/phosphate (N/P) ratio for each complex was inferred from the retardation of siRNA mobility in agarose gel. Polymers Q and R exhibited full complexation with siRNA at N/P ratio of 3, although a "tail" toward the cathode might imply that anionic particles are formed. Polymers S and T complex fully with siRNA at N/P ratio of 3. Although complexation is formed at higher N/P ratio, no retardation toward the anode is seen.

Silencing Activity of Imidazolated PGAamine:Rac1 siRNA Polyplexes:

Evaluation of the silencing activity of polymers Q-T when forming polyplexes with siRNA was done by Dual luciferase assay as described hereinabove and the results are presented in FIG. 38. Both polyplexes composed of polymers Q and R and Rac1 siRNA at 2, 3 and 5 N/P ratios (polymer Q) and 3, 5 and 8 N/P ratios (polymer R) had no indicated silencing activity. Polymer S at 5 N/P ratio with Rac1 siRNA and 500 nM concentration exhibited 78% silencing activity along with 30% viability reduction, and had no silencing activity at 2 and 3 N/P ratios and 100, 250 or 500 nM siRNA concentration. Polyplex T, composed of polymer T and Rac1 siRNA at 5 and 8 N/P ratios have demonstrated high (more than 90%) silencing activity at concentrations 100, 250 and 500 nM of Rac siRNA, along with medial toxicity (retained 70% viability).

Altogether when determining the desired properties of imidazolated PGAamine polymers as a delivery vehicle to siRNA, based on silencing activity properties, it is indicated that polymers containing imidazole ring and ethylenediamine moiety exclusively are inactive, while the addition of an alkyl moiety restore the silencing activity, only in case that the imidazole moiety rate exceeding 10% (in this case 30% of imidazole ring along with 40% ethylenediamine and 30% of alkyl moiety).

Branched Alkyl-Bearing PGAamine Polymers and siRNA Polyplexes Therewith

Characterization of the Electrostatic Interaction Between Branched Alkyl-Bearing PGAamine Derivatives and siRNA:

For each of polymers U-W, complex formation with siRNA was investigated by gel electrophoresis mobility shift assay (EMSA), and the obtained data is presented in FIG. 39. Existence of complexation and the optimum nitrogen/phosphate (N/P) ratio for each complex was inferred from the retardation of siRNA mobility in agarose gel. Polymer U fully complexed with siRNA at N/P ratio of 5, with full complexation at higher N/P ratios. Polymers V and W exhibited full complexation with siRNA in N/P ratio 5 and 3, respectively.

Silencing Activity of Dialkylated PGAamine:Rac1 siRNA Polyplexes:

Evaluation of the silencing activity of polymers U-W when forming polyplexes with siRNA was done by Dual luciferase assay as described hereinabove and the results are presented in FIG. 40. Polyplex U composed of U polymer and Rac1 siRNA had moderate (more than 50%) silencing activity at 5 N/P ratio and 500 nM concentration. MTT indicates retaining of high viability (more than 80%) at this ratio and concentration. Polyplex V composed of polymer V and Rac1 siRNA at 5 N/P had moderate to high silencing activity (between 60% to 80%) at concentrations of 50, 100 150, 250 and 500 nM siRNA. Polyplex W composed of polymer W and Rac1 siRNA at 5 N/P had moderate (more than 50%) silencing activity at concentrations of 50-500 nM siRNA. By comparison between the silencing activities of polymers U and V, it is seen that improved performance is obtained with more than 20% of the dialkyl moiety. When comparing silencing activities of V and W polymers, it is seen that improved performance is obtained by polymers bearing longer-chain dialkyl moieties-11 carbon chains (polymer V) had better activity than 7 carbon chain (polymer W).

Characterization of the Electrostatic Interaction Between X and Y PGAamine Derivatives and siRNA:

For each of polymers X and Y, complex formation with siRNA was investigated by gel electrophoresis mobility shift assay (EMSA), and the obtained data is presented in FIG. 41. Existence of complexation and the optimum nitrogen/phosphate (N/P) ratio for each complex was inferred from the retardation of siRNA mobility in agarose gel. Both polymers X and Y have fully complexed with siRNA at 2 N/P ratio with full complexation at higher N/P ratios.

Silencing Activity of X and Y PGAamine:siRNA Polyplexes:

Evaluation of the silencing activity of polymers X and Y when forming polyplexes with siRNA was done by Dual luciferase assay as described hereinabove and the results are presented in FIG. 42. Polyplex X had moderate (more than 50%) silencing activity at 5 N/P ratio and 500 nM concentration and at 8 N/P ratio and 250 nM concentration, both with low toxicity, and high silencing activity (more than 80% silencing) at N/P ratio of 8 and 500 nM siRNA concentration, with high toxicity of more than 50% cellular growth inhibition. Polyplex Y at 3 N/P had moderate silencing activity (more than 50%) at 250 and 500 nM concentrations and at 5 N/P ratio and 100 nM concentration and high silencing activity (more than 80%) at 5 N/P ratio and 250 and 500 nM concentrations, along with high toxicity of less than 60% viability. All together it seems that there is no additional advantage for adding an alkyl group to polymers bearing amine-moiety with secondary and tertiary amines (comparing X and F polyplexes) or to polymers bearing amine-moiety with secondary and tertiary amines and ethylene diamine moiety (polyplex Y was much more toxic than I although more active at 250 nM concentration and 5 N/P ratio). When comparing silencing activity of polymers composed ethylenediamine moiety and alkyl moiety to polymers bearing amine-moiety with secondary and tertiary amines and an alkyl moiety (for example X and Y to K, polymers bearing only ethylenediamine and alkylamine had better activity than the others.

Example 5

Characterization of the Electrostatic Interaction Between Cross-Linked PGAamine (Group IV) and siRNA Complex formation between Polymer CL1, as described herein, and siRNA was investigated by gel electrophoresis mobility shift assay (EMSA), and the obtained data is presented in FIG. 43A. Existence of complexation and the optimum nitrogen/phosphate (N/P) ratio for each complex was inferred from the retardation of siRNA mobility in agarose gel. Polymer Z fully complexed with siRNA at 3 N/P ratio.

Silencing Activity of CL1:siRNA Polyplexes:

Evaluation of the silencing activity of Polymer CL1 when forming polyplex with siRNA was done by Dual luciferase assay as described hereinabove and the results are presented in FIG. 43B. Polyplex CL1 had high and specific silencing activity at 3 N/P ratio and 250 nM concentration, at 5 N/P ratio and 100 nM concentration and at 10 N/P ratio and 100 nM concentration. Non-specific silencing activity along with cellular toxicity was demonstrated at 3 N/P ratio and 500 nM concentration and at 5 and 10 N/P ratios following treatment with 250 and 500 nM siRNA concentrations.

Example 6

Characterization of the Electrostatic Interaction Between PGAamine-Containing Block Copolymer (Group V) and siRNA Complex formation between Co-polymer BL1 and siRNA was investigated by gel electrophoresis mobility shift assay (EMSA), and the obtained data is presented in FIG. 44. Existence of complexation and the optimum nitrogen/phosphate (N/P) ratio for the complex was inferred from the retardation of siRNA mobility in agarose gel. Polymer a fully complexed with siRNA at 5 N/P ratio.

Example 7

Formulations

Formulation of PGAamineA:siRNA Polyplex:

Following physicochemical characterization of Polymer A:siRNA polyplexes in low concentrations and pure water, Malvern zetasizer ZS DLS measurements have revealed problematic physicochemical profile. The polyplexes had high tendency to aggregate forming microparticles with diameter of 5218±633.3 nm and very high polydispersity (PDI=1.0) (FIG. 27A). The hydrodynamic radius and morphology of PGAamine A:siRNA polyplexes presented in Table 2 and FIG. 17 were obtained by Vasco DLS and SEM, both methods are much less sensitive to heterogeneity of the solution compared to Malvern zetasizer ZS DLS. In Malvern zetasizer ZS DLS measurement the smaller-sized populations are masked by the aggregates, as demonstrated in FIG. 27A. The polyplexe's aggregation tendency have even increased in physiological solution and at high concentrations needed for in vivo administration. This aggregation tendency is a known characteristic of cationic polyplexes and is a recognized obstacle in their clinical translation [Scomparin et al. 2015, supra]. IV injection of microparticles will result in high toxicity [Nicholas et al. Nanotechnology in Therapeutics: Current Technology and Applications. Current Technology and Applications: Amazon(dot) com.].

A formulation of Polymer A:siRNA polyplex was therefore designed in order to maintain stable and discrete nanoparticles. It was uncovered that the addition of 0.2%-10% (molar ratio with the polymer) Tween®20 assisted in maintaining discrete polymer particles in aqueous solution. Polyplexes constructed from polymers that were first dissolved in 0.2 and 2% Tween® solution (molar ratio) and siRNA at 5 N/P ratio have demonstrated size homogeneity and narrower dispersity (PDI=0.323) as analyzed by Malvern zetasizer ZS and imaged in FIG. 27B. Activity of these polyplexes by dual luciferase assay revealed more than 50% silencing obtained at 5 N/P already at 50 and 100 nM concentrations along with low toxicity (retained more than 80% viability). High toxicity was demonstrated at the active concentrations of 250 and 500 nM. The size of the nanoparticles was however too small (5.9±1.501 nm) to retain prolonged blood circulation (FIG. 27D).

In view of these results, the N/P ratio of the polyplexes was decreased in order to optimize structural features of the polyplexes. Polyplexes dissolved first in 0.2% Tween® and then complexed with siRNA at 2 N/P ratio have demonstrated micellar-like structure with hydrodynamic radius of 173.3±60.51 nm and narrow polydispersity (PDI=0.213), as analyzed by Malvern zetasizer ZS and presented in FIG. 27C. Polymers at this size are known to maintain prolonged blood-circulation and targeted accumulation in tumors due to the EPR effect [Scomparin et al., 2015, supra].

Thus, it has been demonstrated that the addition of 0.2-10% surfactant to PGAamines not bearing an alkyl-moiety assists in forming ordered discrete and around 100 nm diameter sized polyplexes when assembled manually at 2 N/P ratio with oligonucleotides.

Formulation of Polymer K:siRNA Polyplex

Physicochemical characteristics of Polymer K:siRNA polyplexes have suffered from strong aggregation tendency and heterogeneity as described above regarding Polymer A:siRNA polyplexes. DLS measurements have revealed size of 2786±454.9 nm and high polydispersity of 1.0 (FIG. 30A).

In order to improve these characteristics a formulation of Polymer K:siRNA polyplexes was designed. For improved distribution, controlled assembly was used via a microfluidic system. This system introduces the two solutions (polymer solution and siRNA solution) on a very thin interface, to thereby prevent aggregates that stem from high local concentrations of polymer or siRNA during bulk interaction when the two solutions are mixed manually. Both siRNA and PGAamine polymers are water soluble and gave nice 28.11±7.35 nm particles when assembled via the microfluidic system in water (FIG. 30B). The microfluidic system (the Nanoassemblr™ Benchtop Instrument) is manufactured by precision nanosystems (Vancouver BC, Canada). The instrument runs tow solutions from separate syringes and brings them together on a thin interface. The volume of the syringes can be 1, 3, 5 or 10 mL. maximum volume per rum is 15 mL (the size of a falcon tube). The interface volume is smaller than 20 mL. The pace of injection can vary from 2 to 12 mL/min. the dimensions of the instrument: 31×23×38 cm (W×D×H). A 1:1 volume ratio (the two tubes run at the same pace), total of 12 mL/min pace, 1, 3 or 5 mL syringes, were used.

The resulting solution however cannot be injected IV as is, and therefore 10% glucose solution was added to the polymer prior to assembly in order to obtain a 5% glucose concentration at the final injectable polyplex solution. Since DLS measurements revealed size dependency in both N/P ratio and component's concentrations (see, Table 5 above), N/P ratio was reduced to 1.5 and concentration to 1.5 mg/kg. This solution has maintained the narrow polydispersity and the desired diameter of 43±12 nm (see, FIG. 30C, and Table 7 below).

This injectable polyplex mixture was further evaluated for its morphology using TEM and Cryo-TEM, and shown in FIGS. 31A-D. The obtained images show the morphology of K polymer Vs. the morphology of the obtained K:siRNA 1.5 N/P ratio polyplexes.

Table 7 below presents a screen of N/P ratios and concentrations Vs. the obtained size of the formed polyplexes. siRNA was mixed with PGAamine K at the indicated N/P ratios and concentrations via a microfluidic chip. Size and PDI were measured by Zetasizer ZS.

Further activity assays were performed using the above formulation of PGAamine K, as follows.

Time Course Cellular Internalization of Formulated 1.5 N/P Ratio K:Cy5-Rac1 siRNA Polyplexes:

The uptake of PGAamine:Cy5-Rac1 siRNA 1.5 N/P ratio polyplexes was assessed by confocal microscopy, as shown in FIG. 32. MDA-MB-231 mammary adenocarcinoma cells were treated with our polyplexes for 30 minutes to 48 hours. Actin cytoskeleton filamentous were stained with phalloidin-conjugated FITC. The appearance of Cy5 punctuate structures inside cells following 4 hours of treatment and the time course increase in stains, indicate time-dependent internalization of Cy5-Rac1 siRNA to cells, that was assisted by our polymeric vehicle. The lack of capability of the Cy5-Rac1 siRNA to penetrate to cells without the delivery vehicle, is indicated by lack of Cy5-punctuate signal in cells treated with Cy5-Rac1 siRNA alone (without a carrier), even following 48 hours of treatment.

Downregulation of Plk1 Expression and Inhibition of the Proliferation of MDA-MB-231 and MCF-7 Cells The PGAamine K:Plk1 siRNA polyplexes were evaluated for their in vitro silencing activity using the artificial test system of Dual luciferase reporter, on both MDA-MB-231 and MCF-7 mammary adenocarcinoma cells and the obtained data is shown in FIGS. 33A-B. Cells were initially transfected with the psicheck plasmid containing *Renilla* luciferase gene under the regulation of Plk1 siRNA binding sequence and Firefly luciferase normalizing gene. Cells were than treated with 50, 100 and 250 nM polyplexes prepared at N/P ratio of 1.5. Luciferase-bearing polyplexes served as a negative control to evaluate non-specific effects of our polyplexes on gene's expression. Plk1 siRNA polyplexes silenced the expression of Plk1 gene to less than 0.5 fold, while no significant non-specific effect was observed at these concentrations (luciferase polyplexes retained around 1 and 0.7 fold of the original Plk1 expression in MCF-7 and MDA-MB-231 cells respectively). However, the commercial tranfection reagent Lipofectamine® 2000 that used as a positive control, demonstrated significant non-specific silencing to around 0.4 fold of the original expression levels in MDA-MB-231 cells, while the specific Plk1 silencing was very efficient and silenced luciferase fluorescence to around 0.01 fold of the original level. Plk1 siRNA alone was unable silence gene's expression in each of the cell lines tested.

In order to evaluate the ability of the plk1 polyplexes to downregulate inherent protein's expression, the expression of Plk1 protein in MDA-MB-231 and MCF-7 cells following treatment with K:siPlk1 polyplexes was further tested by Western Blot analysis. Representative blot is shown on the left of FIG. 33B, while the quantification of 3 repeats appears on the right of FIG. 33B. It was found that K:siPlk1 polyplexes downregulated Plk1 protein expression to 0.65 and 0.36 folds of the expression in MDA-MB-231 and MCF-7 cells respectively, while treatment with Plk1 siRNA alone was unable to downregulate the protein's expression in both cell lines. Non-specific effect of PGAamine:luciferase siRNA was demonstrated to some extant in MCF-7 cells, but its effect (0.6 fold downregulation) was much smaller than that of the targeted Plk1 polyplex (0.36 folds).

To demonstrate the ability of PGAamine K:siPlk1 polyplexes to inhibit mammary cancer cells growth, the effect of PGAamine K:Plk1 siRNA polyplexes treatment on the viability of MDA-MB-231 and MCF-7 cells was tested. Culture cells were treated with 50, 100 and 250 nM of siRNA for 72 hours. Cells were then trypsinized and counted. Number of cells was normalized to untreated cells. PGAamine K:plk1 siRNA treatment reduced the number of cells to 0.77, 0.66 and 0.53 folds of untreated cells in MCF-7 cells using 50, 100 and 250 nM concentrations respectively, and to 0.45, 0.26 and 0.31 folds of untreated cells in MDA-MB-231 cells using the same concentrations. Non-specific effect on the viability of cells was demonstrated in MDA-MB-231 cells, when PGAamine K:luciferase siRNA polyplexes reduced cells number to 0.84, 0.63 and 0.61 folds of the number of untreated cells. This non-specific effect, however, was weaker than the effect of the targeted PGAamine K:Plk1 siRNA polyplex on MDA-MB-231 cells (see, FIG. 33C).

Stability and Toxicity of K:siRNA Polyplexes.

K:siRNA polyplexes were evaluated for their compatibility to biological fluids. FIG. 34A demonstrates the partial release of free siRNA with the addition of 0.01 heparin IU per 50 pmol siRNA and the complete replacement of the siRNA in the complex with the addition of 0.1 heparin IU per 50 pmol siRNA.

The stability of PGAamineK:siRNA polyplexes in serum was also tested. Polyplexes were prepared at 1.5 N/P ratio and 1.5 mg/kg concentration and incubated with full FBS for the time course indicated above the gel image (see, FIG. 34B). The complexes were stable at 2 hours and started to release free siRNA at 4 hours, and by 6 hours the complexes were fully degraded, as indicated by the appearance of a single band at the same line with free siRNA.

PGAamine K:siRNA polyplexes were further tested for their biocompatibility by an ex vivo red blood cell lysis assay (FIG. 34C). Polyplexes were incubated in Rat red blood cells 2% solution following by a measurement of the hemolysis ratio by the absorbance of the released hemoglobin. The results indicate PGAamine K:siRNA polyplexes caused no hemolysis up to 1,000 μg/mL PGAamine equivalent dose (about 25 folds of the equivalent polymer dose used for the following in vivo experiments), similarly to dextran negative control and the lower concentrations of SDS, while the higher concentrations of SDS, from 40 μg/mL and on, caused increased hemolysis.

K:Rac1 siRNA Polyplexes Accumulation in MDA-MB-231 Mammary Tumors and Silencing of Rac1 mRNA:

To further evaluate the ability of PGAamine to facilitate tumor accumulation of siRNA following systemic IV administration, the levels of siRNA in MDA-MB-231 mammary tumors were quantified using RT-PCR. 5 Nu/Nu tumor bearing mice were treated with 1.5 mg/kg PGAamine K:siRNA polyplexes for 3 sequential days, following by tumors resection on day 4.

The results demonstrate about 8 fold accumulation of Rac1 siRNA in mice treated with PGAamine K:Rac1siRNA polyplexes, while no Rac1 siRNA accumulation was noted in the tumors of mice treated with PGAamine:luciferase siRNA polyplexes (see, FIG. 35D).

To validate specific mRNA silencing in MDA-MB-231 tumor-bearing mice following the PGAamine K:Rac1 siRNA treatment regimen, both human-source (the tumor cells) and murine-source (the surroundings) mRNA levels of Rac1 were quantified. Both murine and human Rac1 mRNA levels were silenced to 0.04 and 0.08 folds respectively. Significant non-specific effect of luciferase siRNA was detected, with silencing to 0.43 and 0.59 folds in human and murine Rac1 mRNA levels respectively. See, FIG. 35E.

In order to follow the biodistribution of the polyplexes, PGAamine K:Cy5-Rac1 siRNA polyplexes were injected IV to 5 mCherry-labeled MDA-MB-231 mammary tumors bearing mice. Twenty four hours following a single injection of 1.5 mg/kg siRNA dose, mice were imaged and then organs were resected and quantified for Cy5 fluorescence. Due to the proximity in the absorbance and emission spectra of Cy5 and mCherry, a valid quantification of Cy5-siRNA tumor accumulation was not possible by this method, but tumor accumulation can be generally seen in FIG. 35A. Distribution of Cy5-siRNA to other organs demonstrated about 1100 signal intensity in the kidneys, probably due to renal excretion of polyplexes, and low signal from lungs (about 15). The rest of the organs: liver, heart and spleen demonstrated no detectable Cy5-Rac1 signal intensity. See, FIGS. 35B and 35C.

To demonstrate the targeted accumulation of PGAamine K:siRNA in an additional in vivo model, the polyplexes were IV injected at 4 mg/kg dose to A549 lung carcinoma SC tumor bearing mice. As shown in FIGS. 36A-C, Rac1siRNA demonstrated about 20 fold accumulation compared to mice treated with PBS only. mRNA silencing was less efficient in this case, though, demonstrating significant silencing to less than 0.6 folds, while murine Rac1 mRNA was not silenced following PGAamine:Rac1siRNA treatment.

PK measurements performed on the A549 tumor model revealed rapid clearance from plasma with a decrease to about 4% of the initial plasma level within 30 minutes, and to about 0.7% within 2 hours (see, FIG. 36C). This amount, however, was about 3.5 fold of siRNA levels in plasma of mice treated with non-formulated siRNA (without a delivery vehicle). At 24 hours only the low concentration of 0.23 nM was detected in plasma.

The significant accumulation of siRNA in tumors despite the rapid plasma clearance, indicates an efficient and fast tumor uptake.

Example 8

PEGamineK Polyplexes Bearing SiRNA and mRNA for Treating Pancreatic Cancer

The amphiphilic aminated poly(α)-glutamic acid (PGA) biodegradable polymeric nanocarrier (PGAamine) described herein was harnessed to provide a miRNA-siRNA combination treatment to target in parallel distinct molecular pathways activated in pancreatic cancer. siRNA was used to silence Polo-like kinase 1 (PLK1), a highly conserved serine-threonine kinase that is elevated in pancreatic ductal adenocarcinoma (PDAC), and miR-34a was introduced as a tumor suppressor miRNA which is downregulated in this cancer.

It was found that PGAamine-mediated delivery of PLK1-siRNA and miR-34a combination, effectively suppressed growth, clonogenicity and migration of human (MiaPaCa, Panc01, BxPC3), murine (Panc02) and transgenic (KrasLSL.G12D/+; p53R172H/+; PdxCretg/+(or KPC)) PDAC cells in vitro. Systemic administration of the polymer-miRNA-siRNA nano-sized polyplex to orthotopically-inoculated pancreatic tumors showed no toxicity and selective accumulation at the tumor site. This combination resulted in a synergistic antitumor effect and greater therapeutic efficacy than either monotherapies alone, suggesting an enhanced anticancer effect by inhibiting several key oncogenic pathways, amongst them a common target of PLK1 and miR-34a, myc.

Physico-Chemical Optimization of PGAamine K:miR-siRNA Nanoplexes:

Aminated poly(α)-glutamic acid (PGA) polymeric nanocarrier (PGAamine K) was synthesized by subsequently conjugating ethylenediamine and alkylamine moieties to the pending carboxylic groups of the PGA backbone, as described hereinabove for Polymer K. The resulting polymer (see, FIG. 6) consisted of 55% positively charged aminated side chains and 45% hydrophobic alkylated side chains.

To verify the ability of the polymer to form an electrostatic-based interaction with miRNA and siRNA, Nitrogen/Phosphate (N/P) ratios of polymer and miRNA-siRNA were incubated and the retardation of the small RNAs mobility on agarose gel was analyzed using electrophoretic mobility shift assay (EMSA).

Positively-charged PGAamine was able to bind miRNA-siRNA and neutralize their negative charge with an optimal N/P ratio of 2 (FIG. 45A). The reduction in ethidium bromide fluorescence at high N/P ratio, 4, might indicate strong affinity between the small RNAs and the polymer, resulting in a reduced ethidium bromide intercalation.

The neutralization of the negatively charged miRNA-siRNA pair following mixture with the cationic carrier PGAamine was confirmed by surface charge measurements (zeta potential) of the polyplex and found to be almost neutral (4.68±3 mV, FIG. 45B). These polyplexes exhibited rounded structures readily visible in high-resolution transmission electron microscopy (TEM, FIG. 45C) of approximately 150 nm in diameter, which was also confirmed by dynamic light scattering (DLS) measurements (189.79±11 nm).

Following cellular internalization, the small RNA oligonucleotides are expected to be released from the polyplex into the cytoplasm. Therefore, the ability of the polyplex to release miR-34a in increased amounts of the polyanion heparin using gel electrophoresis was tested (see, FIG. 45D). Partial release was obtained already at 0.01 heparin units while full release was obtained at 1 heparin unit.

The capability of the PGAamine-containing polyplex to release miRNA following incubation with cathepsin B, a thiol-dependent protease, which degrade PGA and is highly expressed in most tumor tissues, was attested. A gradual miRNA release from PGAamine-miR-34a polyplexes over time was observed following incubation with cathepsin B (2 Units/mg polymer, FIG. 46A).

The level of cathepsins activity (particularly cathepsin B) in pancreatic tumor xenograft tissues was profiled. For this purpose, Cy5-labeled GB123 activity based probe was used. As a control for specificity of labeling, a potent active-site cathepsin inhibitor GB111-$NH_2$ was used prior to incubation with the Cy5-labeled GB123 probe. As depicted in the fluorescent microscopy images, high expression levels of active cathepsins were found in the pancreatic tumor tissue. On the other hand, no considerable expression was observed in the normal adjacent tissue, as well as in the negative control (FIG. 46B).

Cellular Internalization of PGAamine-siRNA Nano-Polyplexes:

The ability of Cy5-labeled siRNA complexed with PGAamine to internalize into human MiaPaCa2 PDAC cells was tested. Confocal images of cellular uptake kinetics for cells incubated with Cy5-siRNA-PGAamine polyplexes for 4, 24 and 48 hours are depicted in FIG. 47A, upper panel, showing that the siRNA was taken up by cells at 4 hours with a maximum peak of cellular uptake at 48 hours. Larger magnification of cells at 24 hours following incubation with the polyplexes, detected the Cy5-labeled siRNA intracellularly with a predominant accumulation in the cytoplasm (FIG. 47A, lower panel).

To evaluate the cellular localization of the polyplex and to eliminate optical artifacts, z-scan (FIG. 47A, lower panel, right) was captured and analyzed. The siRNA was found to be located at the same focal plane as the nuclei, confirming its intracellular uptake.

Further examination of cellular internalization of siRNA-PGAamine polyplex was performed in live MiaPaCa2 cells using the ImageStream multispectral imaging flow cytometer. Live cells were monitored 24 hours after transfection, using Cy5-labeled siRNA (FIG. 47B). Flow cytometry statistic data showed that PGAamine (3.5 μg $mL^{-1}$) was capable of delivering Cy5-siRNA (100 nM) into 42.47±1.4% of the cancer cells (Cy5 positive), as compared to cells treated with Cy5-siRNA alone with only 0.03% Cy5 positive cells (FIG. 47B). Transfection using Lipofectamine™ 2000 served as positive control for siRNA internalization with 32.65±1.3% Cy5 positive cells.

The amount of cells that internalized the polyplex was shown also by the internalization histograms, FIG. 47B lower panel).

The intracellular uptake was investigated and it was found that the two distinct cell morphologies of MiaPaCa2 possess different pattern of siRNA uptake. According to the ATCC, MiaPaCa2 cells have two morphologies: One is attached epithelial cells and the other is floating rounded cells. It was found that the attached, larger cell population in size (R4) internalized Cy5-siRNA-PGAamine polyplexes, while the smaller in size cell populations (R3 and R2) did not (data not shown). The same intracellular uptake pattern was observed using Lipofectamine™ 2000 as a transfection reagent, indicating that in live MiaPaCa2 cells siRNA uptake is achieved mostly by the adherent large cell population.

The transfection efficiency into other pancreatic cancer cell lines, using Cy5-labeled PGAamine, was investigated. Flow cytometry data showed that polyplexes (3.5 μg $mL^{-1}$ Cy5-PGAamine complexed with 100 nM siRNA) were able to transfect 86.64±4.4% of KPC cells, 97.43±3.07% of Panc02 cells, 46.76±2.7% of Panel cells and 93.78±4.6% of BxPC3 cells (data not shown).

Nano-Polyplexes Cellular Trafficking:

Further insight into the trafficking and intracellular distribution of PGAamine-siRNA polyplex was gained by confocal microscopy analysis (see, FIGS. 48A-C). MiaPaCa2 cells were incubated with polyplexes containing PGAamine and Cy5-labeled siRNA for 4, 8, 24 and 48 hours. To visualize endocytic compartments, the cells were immunostained for early endosome antigen 1 (EEA1) and for lysosome-associated membrane protein 1 (LAMP1). EEA1, a coiled-coil protein which acts as a Rab5 effector to mediate docking of early endosomes, was used as a marker for early endocytic compartments. LAMP1, which is an integral membrane protein with a highly N-glycosylated luminal domain, was used as a marker for late endocytic compartments, specifically late endosomes and lysosomes. Confocal images revealed that, after 48 hours incubation, the majority of the internalized polyplexes were not colocalized with early endosomes or with late endosomal/lysosomal compartments (FIG. 48A). Furthermore, the percentage of polyplexes that were not in colocalization with early and late endosomal/lysosomal compartments was gradually increased over time (from 47% to 73%, see, FIGS. 48A and 48B). In contrast, the percentage of polyplexes which colocalized with early endosome was decreased over the same period of time (from 36% to 17%, FIGS. 48A and 48B). This might be explained by a time dependent release of polyplexes from early endosomes into the cytoplasm. Co-localization of polyplexes with lysosomes was relatively low (about 10%) and hardly changed during this time course. Endosomes, lysosomes, endosome-containing polyplex and free polyplex, 4 hours following incubation, are depicted in FIG. 48C.

Biocompatibility of PGAamine-siRNA Polyplexes:

In order to evaluate the safety profile of PGAamine K as a nanocarrier, an ex vivo cytokines induction assay was performed using human PBMCs, which determined the secretion level of important inflammatory cytokines, IL-6 and TNF-α, as a model for the innate immune response. For this purpose, freshly isolated PBMCs were seeded in 6-well plates and treatments of PGAamine alone or complexed with several concentration of siRNA (40, 200 and 400 nM) was added to the PBMCs. Following 24 hours of incubation, supernatants of the cells were collected and human IL-6 and TNFα cytokines were measured by ELIZA.

Neither PGAamine alone nor PGAamine-siRNA polyplex induce elevated secretion of the cytokines tested (see, FIG. 49A). As a positive control, the Toll-like receptor 4 natural ligand, lipopolysaccharides (LPS), that induced secretion of high levels of both TNF-α and IL-6, was used.

Stability of polyplex was tested in vitro in 100% fetal bovine serum (FBS). There was no release of miRNA from polyplexes up to 12 hours of incubation. Moreover, PGAamine polymer stabilized miR-34a against serum degradation for a much longer time (12 hours) compared to the naked miR-34a (see, FIG. 49B). Biocompatibility was also assessed by measuring red blood cell (RBC) lysis. PGAamine concentrations used (1-10,000 μg/mL) were the relevant in vivo concentrations, adjusted to dilution in the mouse blood volume (1.5 mL). The results clearly showed that at these concentrations the nano-polyplexes did not cause hemolysis ex vivo and are therefore suitable for i.v. administration (see, FIG. 49C). Sodium dodecyl sulfate (SDS) was used as a positive control and dextran was used as a negative control.

To determine the in vivo toxicity and maximum tolerated dose (MTD) of PGAamine-miRNA polyplexes, the viability of Balb/c mice was tested and monitored for a period of 5 weeks, following a single intravenous injection of the polyplex at various miRNA dosages (6, 8, 10 and 12 mg/kg). The mice were viable following all miRNA dosages that were injected, up to 12 mg/kg siRNA-equivalent dose (see, Table 8 below).

TABLE 8

| N/P ratio | siRNA dose [mg/kg] | miRNA dose [mg/kg] | Total small RNA dose [mg/kg] | Polymer dose [mg/kg] | survival |
|---|---|---|---|---|---|
| 2 | 3 | 3 | 6 | 16.07 | + |
| | 2 | 2 | 4 | 10.7 | + |

TABLE 8-continued

| N/P ratio | siRNA dose [mg/kg] | miRNA dose [mg/kg] | Total small RNA dose [mg/kg] | Polymer dose [mg/kg] | survival |
|---|---|---|---|---|---|
| | 2 | 1 | 2 | 5.3 | + |
| | 0.5 | 0.5 | 1 | 2.6 | + |

The polyplexes effect on mouse normal pancreas and on glucose levels in mouse blood was assessed. Following 3 sequential i.v. injections of PGAamine-miR-34a (2 mg/kg miRNA dose) polyplexes or PBS, blood glucose levels were measured from the mice tail and pancreas was resected, embedded in paraffin and stained with Hematoxylin and Eosin. No differences in normal pancreas morphology as well as in blood glucose levels were observed between PBS treated and polyplex treated mice (data not shown).

In Vitro Efficacy of miRNA-siRNA Delivery and their Combination Effect:

To confirm in vitro miRNA and siRNA delivery efficacy, PGAamine polymer carrying separately, miR-34a or PLK1-siRNA, at the optimal N/P ratio of 2, was applied to cultured MiaPaCa2 cells and the levels of the miR and its target genes as well as the levels of PLK1 mRNA and protein were quantified using real-time qRT-PCR and western blot analyses.

There was a significant elevation in miR-34a levels following transfection with the PGAamine-miR-34a polyplexes compared to the untreated cells and NC-miR-treated cells, with a 929 fold change increase after 72 hours, as shown in FIG. 50A. miR-34a delivered by PGAamine was active and potently down-regulated its target genes: Notch1, CDK6, Bcl2 and MET at the protein level (see, FIG. 50B). Downregulation of the targeted proteins ranged between 44% and 84%.

Transfection with NC-miR had no significant effect on the expression levels of the investigated target genes. Transfection of cells with PGAamine-PLK1-siRNA polyplexes was also efficient and silenced PLK1 by 50% and 80% at mRNA and protein levels, respectively (see, FIGS. 50C and 50D).

The ability of miR-34a and PLK1-siRNA, complexed with a PGAamine nanocarrier, to affect the tumorigenisity of pancreatic cancer cells was tested. Cells were transfected with serial concentrations of PGAamine-polyplexes containing miR-34a or PLK1-siRNA alone and viable cells were counted by Coulter Counter. Both, miR-34a alone (see, FIG. 51A) and PLK1-siRNA alone (see, FIG. 51B), significantly reduced the viability of MiaPaCa2 cells in a dose dependent manner (up to 49% at 250 nM miRNA concentration and up to 58% at 100 nM siRNA concentration) compared with the NC-miR/NC-siRNA and with the untreated cells. The combination treatment of miR-34a and PLK1-siRNA (FIG. 51C) showed synergistic reduction in cell viability as analyzed using the additive model.

Cell migration was studied using a wound closure assay in which cells were allowed to grow in a 96-well ImageLock plate until confluency and a wound was created using a 96-pin woundmaking tool (WoundMaker™). The cells were then incubated with the PGAamine-miR-siRNA polyplexes and wound closure was monitored using IncuCyte® ZOOM Live-Cell Analysis System.

Cells treated with NC-miR and NC-siRNA together and cells that left untreated, closed the wound almost completely (about 80%) within 48 hours (see, FIG. 51D). Cells treated with miR-34a and PLK-siRNA separately showed almost full or partial closure of the wound over this time frame, whereas cells treated with the combination closed only 50% of the wound (a reduction of 30% compared to the untreated cells and to the NC-miR+NC-siRNA treated cells).

The effect on growth and survival of pancreatic cancer cells was assessed also using clonogenic assay. MiaPaCa2 and KPC cells were transfected with miR-34a or PLK1-siRNA (100 nM) separately or combined using PGAamine K for 24 hours. Transfected cells were seeded in 35 mm plates in triplicates for 8-10 days and stained with crystal violet to determine the number of surviving colonies. miR-34a-PLK1-siRNA combination (100 nM each) reduced the number and size of surviving colonies of the pancreatic cancer cells (by 64%) compared to the untreated cells (FIGS. 51E and 51F). It was also verified at protein level that PLK1 was downregulated in the single treatment as well as in the combination one (FIG. 51G).

To validate the synergistic effect of miR-34a-PLK1-siRNA combination treatment using the PGAamine nanocarrier, its effect on the murine pancreatic cancer cell line, KPC was studies. It was found that although, only PLK1-siRNA alone and not miR-34a alone significantly reduced the viability of KPC cells, the combination treatment of both of the small RNA oligonucleotides showed synergistic reduction in cell viability as analyzed using the additive model (data not shown). In addition, KPC cells treated with the combination closed only 33% of the wound compared to the untreated cells and to the NC-miR/NC-siRNA treated cells that closed the wound almost completely (data not shown). miR-34a/PLK1-siRNA combination reduced the number and size of surviving colonies of the KPC cells (by 72%) compared to the untreated cells (data not shown). These results indicate that PGAamine carrying miR-34a-PLK1-siRNA combination could inhibit pancreatic cancer cells growth, migration and survival effectively.

Biodistribution and Tumor Accumulation of PGAamine-siRNA Polyplexes in Mice:

To assess whether PGAamine nanocarrier exhibit preferable accumulation at the tumor site once injected systemically, an orthotopic pancreatic cancer mouse model was developed by injecting mCherry-labeled MiaPaCa2 cells into the pancreas of SCID mice. First, cells were infected with a pQC-mCherry retroviral vector, as previously described. Then, mCherry-labeled cells were injected orthotopically to the pancreas and tumor growth rate was monitored by fluorescence using a non-invasive intravital imaging system (CRI Maestro™). Two weeks post injection, tumors were observed with increase in signal until day 31 (data not shown). mCherry fluorescent signal was found only in the pancreas (data not shown).

To study the pharmacokinetics profile of nano-polyplexes, mice bearing orthotopic mCherry-labeled tumors (with a fluorescent signal of about 1000 scaled counts/s) were administered via the tail vein with PGAamine-Cy5-siRNA polyplexes (0.5 mg/Kg siRNA, 100 μl) or with Cy5-siRNA alone and imaged at 10 minutes, 1, 3 and 24 hours thereafter in the Maestro.

As shown in FIG. 52A, the polyplex (light blue) demonstrated accumulation in the tumor site (in red) over time up to 24 hours, as shown by the Cy5 fluorescent signal coming from the intact mouse. When only Cy5-siRNA was injected, no accumulation was observed in the intact mouse.

For biodistribution examination, tumors were and healthy organs (heart, lungs, liver, kidneys and spleen) were resected from mice, 24 hours following intravenous administration of Cy5-labeled siRNA alone or complexed with PGAamine and measured Cy5 fluorescent intensity. As shown in FIG. 52B, the polyplex showed high localization in the tumor and relatively low accumulation in the kidneys, spleen, heart, lungs and liver. Cy5-labeled siRNA alone was accumulated mainly in the kidneys and for relatively small amounts in the tumor.

Quantification of Cy5 component revealed a 5-fold increase in total signal (scaled counts/sec)/tissue weight of the siRNA complexed with PGAamine compared to siRNA alone at the tumor site (see, FIG. 52B, graph). There was no significant difference in the heart, lungs, liver and kidneys localization between the two treatments. Further confocal analysis of OCT samples prepared from the resected tumors confirmed that the polyplex accumulated in the PDAC tumor (see, FIG. 52C).

In addition, the vasculature functionality and morphology of the pancreatic cancer tumor from the orthotopic xenograft mouse model was evaluated. It showed enlarged unorganized leaky blood vessels as compared to normal pancreas (data not shown).

The accumulation of miR-34a in the orthotopic PDAC tumors following 3 sequential IV injections of PBS or polyplex formulated with miR-34a or NC-miR (n=4 mice per group, 2 mg/kg miR dose) was further tested. As shown in FIG. 52D, miR-34a levels were 6 fold higher in isolated tumors from mice treated with PGAamine-miR-34a polyplex, compared with mice treated with either PBS or PGAamine-NC-miR.

miR-34a target genes levels, from the same isolated tumors, were quantified by Real-Time RT-PCR. In tumors from miR-34a-treated mice, Bcl2, CDK6, MET and Notch1 levels were reduced by 45, 25, 20 and 11% relative to NC-miR treated mice (see, FIG. 52E). These data suggest that PGAamine nanocarrier successfully delivered two therapeutic small RNA oligonucleotides into PDAC tumors.

In Vivo Anti-Tumor Effect of miR-siRNA Combination:

To determine the therapeutic effects of combined miR-34a and PLK1-siRNA delivery in vivo, tumor-bearing mice, 14 weeks following cells inoculation, were randomized into four treatment groups (n=6/7 mice per group): (i) miR-34a/PLK1-siRNA, (ii) miR-34a/NC-siRNA, (iii) PLK1-siRNA/NC-miR, and (iv) NC-miR/NC-siRNA, and a group treated with PBS. Mice were IV injected with a total small RNA dose of 3.0 mg/kg every day, five consecutive times, for two rounds with a 3 days break between them.

Tumor growth monitoring using intravital fluorescent imaging revealed that miR-34a/PLK1-siRNA combination therapy induced pancreatic tumor regression, inhibiting tumor growth to an average of 3.85% (11.3±39 scaled counts/sec, P<0.01) compared to tumors treated with PBS (see, FIG. 53B). The monotherapies of miR-34a/NC-siRNA and PLK1-siRNA/NC-miR inhibited tumor growth to an average of 25% (733.0±168 scaled counts/sec) and 44.25% (1278.0±459 scaled counts/sec) respectively (see, FIG. 53B).

During this efficacy study, at day 33 from tumor inoculation, an image of representative mouse from each treatment group was taken in the CRI-Maestro, in which the differences in tumor signal can be seen (see, FIG. 53E). This suggests that targeted combination RNA therapy using miR-34a and PLK1-siRNA elicit a potent antitumor response inhibiting tumor cell proliferation and angiogenesis (FIG. 53F).

All animals tolerated small RNA therapy well, with no significant weight loss observed after administration of all treatments (see, FIG. 53C).

The effects of the treatments on blood counts and chemistry were also studied. For that, blood was withdrawn from PBS and PGAamine-small RNA oligonucleotides-treated mice, on day 23 from treatment initiation. All treatments did not affect either blood counts (data not shown) or blood chemistry parameters (see, Table 9 below). Survival of mice treated with the combination was significantly (P<0.05) prolonged compared to all other treatment groups (see, FIG. 53D).

What is claimed is:

1. A polymer comprising a plurality of backbone units selected from BU (3) and BU (5), wherein said BU (3) and BU (5) backbone units are represented by:

BU(3)

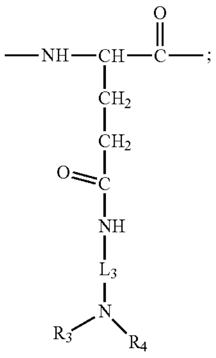

; and

BU(5)

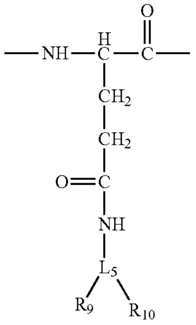

wherein:

$L_3$ is an unsubstituted ethylene;

$R_3$ and $R_4$ are each H;

$L_5$ is a branched linking moiety and each of $R_9$ and $R_{10}$ is an unsubstituted alkyl of from 5 to 10 carbon atoms in length, wherein said linking moiety is Rc-CRd-Rf, each of Rc and Rf is absent and Rd is H;

from 20 to 40 mol % of said backbone units are said BU (5) units; and from 60 to 80 mol % of said backbone units are said BU (3) units, and wherein a total mol % of said BU (5) units and said BU (3) units is 100 mol %.

2. A polymer comprising a plurality of backbone units selected from BU (3) and BU (5), wherein said BU (3) and BU (5) backbone units are represented by:

BU(3)

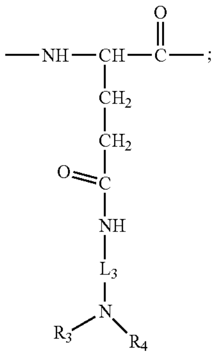

; and

BU(5)

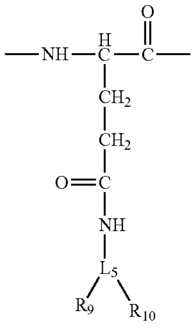

wherein:

$L_3$ is an unsubstituted ethylene;

$R_3$ and $R_4$ are each H; and $L_5$, $R_9$ and $R_{10}$ are such that either $L_5$ and $R_{10}$ form together a linear unsubstituted alkyl of more than 5 carbon atoms in length, and $R_9$ is H; or $L_5$ is a branched linking moiety and each of $R_9$ and $R_{10}$ is an unsubstituted alkyl of from 5 to 10 carbon atoms in length, wherein said linking moiety is Rc-CRd-Rf, each of Rc and Rf is absent and Rd is H, wherein:

45 mol % of said backbone units are said BU (5) units, 55 mol % of said backbone units are said BU (3) units, and $L_5$, $R_9$ and $R_{10}$ are such that $L_5$ and $R_{10}$ form together said linear unsubstituted alkyl of more than 5 carbon atoms in length, and $R_9$ is H; or 40 mol % of said backbone units are said BU (5) units, 60 mol % of said backbone units are said BU (3) units, and $L_5$, $R_9$ and $R_{10}$ are such that $L_5$ and $R_{10}$ form together said linear unsubstituted alkyl of more than 5 carbon atoms in length, and $R_9$ is H; or 20 mol % of said backbone units are said BU (5) units, 80 mol % of said backbone units are said BU (3) units, and $L_5$ is a branched linking moiety and each of $R_9$ and $R_{10}$ is an unsubstituted alkyl of from 5 to 10 carbon atoms in length, wherein said linking moiety is Rc-CRd-Rf, each of Rc and Rf is absent and Rd is H;

40 mol % of said backbone units are said BU (5) units, 60 mol % of said backbone units are said BU (3) units, and $L_5$ is a branched linking moiety and each of $R_9$ and $R_{10}$ is an unsubstituted alkyl of from 5 to 10 carbon atoms in length, wherein said linking moiety is Rc-CRd-Rf, each of Rc and Rf is absent and Rd is H.

3. A conjugate comprising the polymer of claim 1, and an RNA silencing agent associated therewith.

4. A pharmaceutical composition comprising the conjugate of claim 1, and a pharmaceutically acceptable carrier.

5. The composition of claim 4, wherein the conjugate is in a form of a plurality of particles dispersed in said carrier.

6. A method of silencing a gene in a cell, the method comprising contacting the cell with the conjugate of claim 3.

7. A method of treating a medical condition treatable by silencing a gene, in a subject in need thereof, the method comprising administering to the subject the composition of claim 4.

8. A conjugate comprising the polymer of claim 2, and an RNA silencing agent associated therewith.

9. A pharmaceutical composition comprising the conjugate of claim 2, and a pharmaceutically acceptable carrier.

10. The composition of claim 9, wherein the conjugate is in a form of a plurality of particles dispersed in said carrier.

11. A method of silencing a gene in a cell, the method comprising contacting the cell with the conjugate of claim 8.

12. A method of treating a medical condition treatable by silencing a gene, in a subject in need thereof, the method comprising administering to the subject the composition of claim 9.

* * * * *